US012582684B2

(12) United States Patent
Krishnan et al.

(10) Patent No.: US 12,582,684 B2
(45) **Date of Patent: *Mar. 24, 2026**

(54) COMPOSITIONS AND METHODS FOR THE TREATMENT OF WOUNDS, DISORDERS, AND DISEASES OF THE SKIN

(71) Applicant: Krystal Biotech, Inc., Pittsburgh, PA (US)

(72) Inventors: Suma Krishnan, Pittsburgh, PA (US); Pooja Agarwal, Mars, PA (US)

(73) Assignee: Krystal Biotech, Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/342,284

(22) Filed: Jun. 27, 2023

(65) Prior Publication Data

US 2023/0414686 A1 Dec. 28, 2023

Related U.S. Application Data

(63) Continuation of application No. 18/060,515, filed on Nov. 30, 2022, now Pat. No. 11,865,148, which is a continuation of application No. 17/529,161, filed on Nov. 17, 2021, now abandoned, which is a continuation of application No. 16/598,982, filed on Oct. 10, 2019, now Pat. No. 11,185,564, which is a continuation of application No. 16/177,153, filed on Oct. 31, 2018, now Pat. No. 10,441,614, which is a continuation of application No. 15/851,488, filed on Dec. 21, 2017, now Pat. No. 10,155,016, which is a continuation of application No. 15/393,151, filed on Dec. 28, 2016, now Pat. No. 9,877,990.

(60) Provisional application No. 62/320,316, filed on Apr. 8, 2016.

(51) Int. Cl.
| | |
|---|---|
| *A61K 35/763* | (2015.01) |
| *A61K 9/00* | (2006.01) |
| *A61K 9/06* | (2006.01) |
| *A61K 38/17* | (2006.01) |
| *A61K 38/39* | (2006.01) |
| *A61K 47/38* | (2006.01) |
| *A61K 48/00* | (2006.01) |
| *C07K 14/78* | (2006.01) |
| *C12N 9/02* | (2006.01) |

(52) U.S. Cl.
CPC .......... *A61K 35/763* (2013.01); *A61K 9/0014* (2013.01); *A61K 38/1748* (2013.01); *A61K 38/39* (2013.01); *A61K 48/005* (2013.01); *C07K 14/78* (2013.01); *C12N 9/0071* (2013.01); *C12Y 114/11004* (2013.01); *A61K 9/06* (2013.01); *A61K 47/38* (2013.01); *C12N 2710/16643* (2013.01)

(58) Field of Classification Search
CPC .. A61K 35/763; A61K 38/1748; A61K 38/39;
A61K 48/005; A61K 9/0014; A61K 9/06;
A61K 47/38; A61K 38/443; C07K 14/78;
C12N 9/0071; C12N 2710/16643; C12Y
114/11004; A61P 35/00; A61P 17/16;
A61P 17/04; A61P 17/02; A61P 17/00
See application file for complete search history.

(56) References Cited

U.S. PATENT DOCUMENTS

| | | | |
|---|---|---|---|
| 5,658,724 | A | 8/1997 | Deluca et al. |
| 5,672,344 | A | 9/1997 | Kelley et al. |
| 5,998,174 | A | 12/1999 | Glorioso et al. |
| 6,106,826 | A | 8/2000 | Brandt et al. |
| 6,719,982 | B1 | 4/2004 | Coffin et al. |
| 6,846,670 | B2 | 1/2005 | Schwartz et al. |
| 6,887,490 | B1 | 5/2005 | Jahoda et al. |
| 7,531,167 | B2 | 5/2009 | Glorioso et al. |
| 9,314,505 | B2 | 4/2016 | Wise et al. |
| 9,877,990 | B2 | 1/2018 | Krishnan et al. |
| 10,155,016 | B2 | 12/2018 | Krishnan et al. |
| 10,174,341 | B2 | 1/2019 | Glorioso et al. |

(Continued)

FOREIGN PATENT DOCUMENTS

| | | |
|---|---|---|
| CN | 102 212 559 | 4/2014 |
| EP | 3377637 | 9/2018 |

(Continued)

OTHER PUBLICATIONS

Goins WF, Lee KA, Cavalcoli JD, O'Malley ME, DeKosky ST, Fink DJ, Glorioso JC. Herpes simplex virus type 1 vector-mediated expression of nerve growth factor protects dorsal root ganglion neurons from peroxide toxicity. J Virol. Jan. 1999;73(1):519-32. (Year: 1999).*

(Continued)

*Primary Examiner* — Rachel B Gill

(74) *Attorney, Agent, or Firm* — The Webb Law Firm

(57) ABSTRACT

Provided herein are pharmaceutical compositions comprising one or more polynucleotides suitable for enhancing, increasing, augmenting, and/or supplementing the levels of Collagen alpha-1 (VII) chain polypeptide and/or Lysyl hydroxylase 3 polypeptide and/or Keratin type I cytoskeletal 17 polypeptide in a subject. Also provided herein are pharmaceutical compositions and methods of use for providing prophylactic, palliative, or therapeutic relief of a wound, disorder, or disease of the skin in a subject, including a subject having, or at risk of developing, one or more symptoms of epidermolysis bullosa.

18 Claims, 17 Drawing Sheets
(7 of 17 Drawing Sheet(s) Filed in Color)
Specification includes a Sequence Listing.

(56) References Cited

U.S. PATENT DOCUMENTS

| | | | |
|---|---|---|---|
| 10,441,614 B2 | 10/2019 | Krishnan et al. | |
| 10,525,090 B2 | 1/2020 | Krishnan et al. | |
| 11,185,564 B2 | 11/2021 | Krishnan et al. | |
| 2002/0187163 A1* | 12/2002 | Johnson | A61K 38/162 |
| | | | 424/229.1 |
| 2003/0082142 A1 | 5/2003 | Coffin et al. | |
| 2003/0190637 A1* | 10/2003 | Hovnanian | C07K 14/8135 |
| | | | 435/6.1 |
| 2004/0253606 A1 | 12/2004 | Aziz et al. | |
| 2005/0255085 A1* | 11/2005 | Fong | A61P 35/04 |
| | | | 435/456 |
| 2007/0066552 A1* | 3/2007 | Clarke | A61K 9/0014 |
| | | | 424/440 |
| 2008/0095819 A1* | 4/2008 | Gourdie | A61P 29/00 |
| | | | 514/1.2 |
| 2008/0299182 A1 | 12/2008 | Zhang | |
| 2010/0041737 A1* | 2/2010 | Naldini | A61P 13/00 |
| | | | 435/325 |
| 2010/0081707 A1 | 4/2010 | Ali et al. | |
| 2010/0330112 A1* | 12/2010 | Long | A61K 39/245 |
| | | | 424/185.1 |
| 2011/0212530 A1 | 9/2011 | Baltimore et al. | |
| 2012/0148627 A1* | 6/2012 | Terman | A61K 39/46447 |
| | | | 424/281.1 |
| 2013/0034586 A1* | 2/2013 | Mohr | A61P 35/00 |
| | | | 435/236 |
| 2013/0295076 A1 | 11/2013 | Kolattukudy et al. | |
| 2013/0331547 A1 | 12/2013 | Hall et al. | |
| 2014/0256798 A1 | 9/2014 | Osborn et al. | |
| 2014/0288155 A1 | 9/2014 | Hovnanian et al. | |
| 2014/0341877 A1 | 11/2014 | Kolattukudy | |
| 2015/0038556 A1 | 2/2015 | Heartlein et al. | |
| 2015/0352191 A1 | 12/2015 | South et al. | |
| 2016/0153000 A1 | 6/2016 | Glorioso et al. | |
| 2016/0250267 A1 | 9/2016 | Uchida et al. | |
| 2016/0324934 A1 | 11/2016 | Angel et al. | |
| 2017/0096684 A1 | 4/2017 | Alton et al. | |
| 2017/0143780 A1* | 5/2017 | Zitvogel | A61K 35/28 |
| 2017/0290866 A1 | 10/2017 | Krishnan et al. | |
| 2017/0319693 A1 | 11/2017 | Koizumi et al. | |
| 2018/0256748 A1* | 9/2018 | Angel | A61M 37/0015 |
| 2018/0339004 A1* | 11/2018 | Greenberg | C12N 15/113 |
| 2018/0353614 A1 | 12/2018 | Peters | |
| 2019/0160122 A1 | 5/2019 | Krishnan et al. | |
| 2019/0276845 A1 | 9/2019 | Glorioso et al. | |
| 2019/0328644 A1 | 10/2019 | Krishnan et al. | |
| 2020/0061209 A1 | 2/2020 | Bennett et al. | |
| 2020/0101123 A1 | 4/2020 | Krishnan et al. | |
| 2020/0199618 A1 | 6/2020 | Krisky et al. | |
| 2021/0040172 A1 | 2/2021 | Cascio et al. | |
| 2022/0273737 A1 | 9/2022 | Krishnan et al. | |
| 2023/0149486 A1 | 5/2023 | Krishnan | |

FOREIGN PATENT DOCUMENTS

| | | |
|---|---|---|
| WO | WO 1999/064094 | 12/1999 |
| WO | WO 2000/040734 | 7/2000 |
| WO | WO 2013/121202 | 8/2013 |
| WO | WO 2015/009952 | 1/2015 |
| WO | WO 2015/117021 | 8/2015 |
| WO | WO 2016/191684 | 12/2016 |
| WO | WO 2017/165806 | 9/2017 |
| WO | WO 2017/165813 | 9/2017 |
| WO | WO 2017/176336 | 10/2017 |
| WO | WO 2019/200163 | 10/2019 |
| WO | WO 2019/210219 | 10/2019 |
| WO | WO 2020/006486 | 1/2020 |

OTHER PUBLICATIONS

Acland et al., "Gene therapy restores vision in a canine model of childhood blindness," Nat Genet. (2001) 28(1):92-5.

Aldawsari et al., "Progress in Topical siRNA Delivery Approaches for Skin Disorders," Curr Pharm Des. (2015) 21(31): 4594-4605.

Ali et al., "Gene therapy for inherited retinal degeneration," Br J Ophthalmol. (1997) 81(9):795-801.

Andtbacka et al., "Talimogene Laherparepvec Improves Durable Response Rate in Patients With Advanced Melanoma," J Clin Oncol. (2015) 33(25): 2780-2788.

Armstrong, M. "Krystal gets more skin in the epidermolysis bullosa game." Vantage. Mar. 5, 2019.

Armstrong, M. "Krystal gets a flying start in epidermolysis bullosa gene therapy" Vantage. Oct. 17, 2018.

Bastian et al., "Herpes simplex virus type 1 immediate-early protein ICP22 is required for VICE domain formation during productive viral infection." J Viral. Mar. 2010;84(5):2384-94. doi: 10.1128/JVI.01686-09. Epub Dec. 23, 2009.

Boehmer et al., "Herpes Virus Replication," IUBMB Life (2003) 55(1):13-22.

Brehm et al., "Immunogenicity of herpes simplex virus type 1 mutants containing deletions in one or more alpha-genes: ICP4, ICP27, ICP22, and ICP0," Virology (1999) 256(2): 258-69.

Burton et al., "Gene delivery using herpes simplex virus vectors." DNA Cell Biol. Dec. 2002;21(12):915-936.

Chamorro et al., "Gene Editing for the Efficient Correction of a Recurrent COL7A1 Mutation in Recessive Dystrophic Epidermolysis Bullosa Keratinocytes", Molecular Therapy—Nucleic Acids, vol. 5, 2016, pp. 1-13.

Choate et al., "Transglutaminase 1 delivery to lamellar ichthyosis keratinocytes," Human Gene Therapy (1996) 7:2247-2253.

Christiano AM. Collagen, type VII, alpha 1 (epidermolysis bullosa, dystrophic, dominant and recessive) [Homo sapiens]. NCBI Reference Sequence: NP_000085.1. Dep. Mar. 19, 1999.

Clinicaltrials.gov. NCT03536143: Topical Bercolagene Telserpavec (KB103) Gene Therapy to Restore Functional Collagen VII for the Treatment of Dystrophic Epidermolysis Bullosa (GEM-1). May 24, 2018.

Clinicaltrials.gov. NCT04047732: Topical KB105 Gene Therapy for the Treatment of TGM1-deficient Autosonnal Recessive Congenital Ichthyosis (ARCI). Aug. 7, 2019.

Clinicaltrials.gov. NCT04214002: The Natural History of Wounds in Patients with Dystrophic Epidermolysis Bullosa (DEB). Dec. 30, 2019.

Communication pursuant to Article 94(3) EPC for EP 16826873.8, dated Apr. 17, 2019, 7 pages.

Periphagen, Complaint in PeriphaGen v. Krystal Biotech, Filed May 1, 2020 in the Western District of Pennsylvania (96 pgs).

Deluca et al., "Isolation and Characterization of Deletion Mutants of Herpes Simplex Virus Type 1 in the Gene Encoding Immediate-Early Regulatory Protein ICP4", Journal Of Virology, (1985) 56(2): 558-570.

Di et al., "Phase I study protocol for ex vivo lentiviral gene therapy for the inherited skin disease, Netherton syndrome," Hum Gene Ther Clin Dev. (2013) 24(4):182-190.

Dingwell et al., "The Herpes Simplex Virus gE-gI Complex Facilitates Cell-to-Cell Spread and Binds to Components of Cell Junctions," J Virol. (1998) 72(11): 8933-8942.

Eming SA, Krieg T, Davidson JM. Gene therapy and wound healing. Clin Dermatol. Jan.-Feb. 2007;25(1):79-92.

Eming et al., "Gene transfer in tissue repair: status, challenges and future directions," Exp Opin Biol Ther (2004) 4(9):1373-1386.

Farasat et al., "Novel transglutaminase-1 mutations and genotype-phenotype investigations of 104 patients with autosomal recessive congenital ichthyosis in the USA," J Med Genet (2009) 46(2):103-111.

Final Office Action received for U.S Appl. No. 15/393,151, mailed on Aug. 31, 2017, 13 pages.

Fink et al., "Gene therapy for pain: Results of a Phase I clinical trial," Ann Neurol (2011) 70(2):207-212.

Fraefel et al., "In vivo gene transfer to the rat retina using herpes simplex virus type 1 (HSV-1)-based amplicon vectors," Gene Ther. (2005) 12(16):1283-8.

Geller et al., "An efficient deletion mutant packaging system for defective herpes simplex virus vectors: potential applications to human gene therapy and neuronal physiology," Proc Natl Acad Sci U S A. (1990) 87(22): 8950-8954.

(56) References Cited

OTHER PUBLICATIONS

Georgiadis et al., "Lentiviral Engineered Fibroblasts Expressing Codon-Optimized COL7A1 Restore Anchoring Fibrils in RDEB", Journal of Investigative Dermatology, (2016) 136: 284-292.

Glorioso JC. "Herpes simplex viral vectors: late bloomers with big potential." Hum Gene Ther. (2014) 25(2): 83-91.

Goins et al. "Engineering HSV-1 Vectors for Gene Therapy," Methods Mol Biol (2014) 1144: 63-79.

Goins et al. "Generation of replication-competent and -defective HSV vectors," Cold Spring Harb Protoc. May 1, 2011;2011(5): 512-519; pdb.prot5615.

Gorell et al., "Gene therapy for skin diseases," Cold Spring Harb Perspect Med (2014) 4:a015149.

Goto et al., "Fibroblasts Show More Potential as Target Cells than Keratinocytes in COL7A1 Gene Therapy of Dystrophic Epidermolysis Bullosa", Journal of Investigative Dermatology, (2006) 126: 766-772.

Grant, Kyle, "Production and Purification of Highly Replication Defective Hsv-1 Based Gene Therapy Vectors", Doctoral Dissertation, University of Pittsburgh, 2008, 137 pages.

Gurevich et al. 759 "Successful in vivo col. 7A1 gene delivery and correction of recessive dystrophic epidermolysis bullosa (RDEB) skin using an off the shelf HSV-1 vector (KB103)." J Invest Derm. vol. 138, Iss. 5 Supp. May 2018, p. S129. Available online Apr. 19, 2018.

Heikkinen et al., "Diremerization of human lysyl hydroxylase 3 (LH3) is mediated by the amino acids 541 547," Matrix Biology (2010) 30(1):27-33.

Hennig et al., "HEK293-based production platform for y-retroviral (self-inactivating) vectors: application for safe and efficient transfer of COL7A1 cDNA". Hum Gene Ther Clin Dev. Dec. 2014;25(4):218-28.

International Preliminary Report on Patentability received for PCT Patent Application No. PCT/US2016/068974, mailed on Oct. 18, 2018, 11 pages.

International Search Report and Written Opinion received for PCT Patent Application No. PCT/US2016/068974, mailed on May 18, 2017, 18 pages.

Invitation to Pay Additional Fee received for PCT Patent Application No. PCT/US2016/068974, mailed on Mar. 27, 2017, 8 pages.

Kim et al., "Microneedles for Drug and Vaccine Delivery", Advanced Drug Delivery Reviews, vol. 64, 2012, pp. 1547-1568.

Kohlhapp et al., Molecular Pathways: Mechanism of Action for Talimogene Laherparepvec, a New Oncolytic Virus Immunotherapy, Clinical Cancer Research (2015) 22(5):1048-1054.

Kopecki et al., "Commentary: New advances in the development of therapies for treating inherited skin fragility disorders," Wound Practice and Research (2015) 23(4): 184, Dec. 5, 2015.

Krisky et al., "Deletion of multiple immediate-early genes from herpes simplex virus reduces cytotoxicity and permits long-term gene expression in neurons," Gene Ther. (1998) 5(12):1593-603.

Krisky et al., "Development of herpes simplex virus replication-defective multigene vectors for combination gene therapy applications," Gene Ther (1998) 5(110):1517-1530.

Krystal Biotech, Inc. "Krystal Biotech Announces Settlement with PeriphaGen, Inc." Mar. 15, 2022, https://ir.krystalbio.com/node/8481/pdf. (Year: 2022).

Lachmann, R. "Herpes simplex virus-based vectors," Int J Exp Pathol. (2004) 85(4): 177-190.

Lewin et al., "Gene therapy for autosomal dominant disorders of keratin," J Investig Dermatol Symp Proc. (2005) 10(1): 47-61.

Liu et al., "Herpes simplex virus mediated gene transfer to primate ocular tissues," Exp Eye Res. (1999) 69(4):385-95.

Lu et al., "Topical Application of Viral Vectors for Epidermal Gene Transfer", J Invest Dermatol. (1997) 108(5): 803-808.

Ma et al., "Efficacy of Herpes Simplex Virus Vector Encoding V the Human Preproenkephalin Gene for Treatment of Facial Pain in Mice," J aral Facial Pain Headachce (2016) 30(1):42-50.

Marconi et al., "HSV as a Vector in Vaccine Development and Gene Therapy." In: Madame Curie Bioscience Database [Internet]. Austin (TX): Landes Bioscience; 2000-2013. 30 pages.

Marconi et al., "Replication-defective herpes simplex virus vectors for gene transfer in vivo," Proc Natl Acad Sci USA (1996) 93:11319-11320.

Mayr et al., "Gene Therapy for the COL7A1 Gene", Chapter 23, Intech, 2013, pp. 561-589.

McGowan et al., "Keratin 17 n ull mice exhibit age- and strain-dependent alopecia," Genes & Dev (2002) 16:1412-1422.

Messmer et al., "Ocular manifestations of keratitis-ichthyosis-deafness (KID) syndrome," Ophthalmology. (2005) 112(2):e1-6.

Miezeiewski et al., "Role of adherens junction proteins in differential herpes simplex virus type 2 infectivity in communication-competent and -deficient cell lines," Intervirology. (2012) 55(6): 465-474.

Miyagawa et al., "Herpes simplex viral-vector design for efficient transfuction of nonneuronal cells without cytotoxcity," Proc Natl Acad Sci USA (2015) 112(13):E1632-E1641.

Miyagawa et al., "Deletion of the Virion Host Shut-off Gene Enhances Neuronal-Selective Transgene Expression from an HSV Vector Lacking Functional IE Genes," Mol Ther Methods Clin Dev. (2017) 6: 79-90.

Ng et al., "Fibroblast-Derived Dermal Matrix Drives Development of Aggressive Cutaneous Squamous Cell Carcinoma in Patients with Recessive Dystrophic Epidermolysis Bullosa", Cancer Research, vol. 72, No. 14, Jul. 15, 2012, pp. 3522-3534.

Non-Final Office Action received for U.S. Appl. No. 15/393,151, mailed on Apr. 14, 2017, 13 pages.

Non-Final Office Action received for U.S. Appl. No. 15/851,488, mailed on May 14, 2018, 10 pages.

Non-Final Office Action received for U.S. Appl. No. 16/177,153, mailed on May 9, 2019, 13 pages.

Notice of Allowance received for U.S. Appl. No. 15/393,151, mailed on Dec. 6, 2017, 11 pages.

Notice of Allowance received for U.S. Appl. No. 15/851,488, mailed on Oct. 29, 2018, 11 pages.

Notice of Allowance received for U.S. Appl. No. 16/177,153, mailed on Aug. 30, 2019, 10 pages.

Ortiz-Urda et al., "Injection of Genetically Engineered Fibroblasts Corrects Regenerated Human Epidermolysis Bullosa Skin Tissue", The Journal of Clinical Investigation, vol. 111, No. 2, Jan. 2003, pp. 251-255.

Peek et al., "Herpes simplex virus infection of the human eye induces a compartmentalized virus-specific B cell response," J Infect Dis. (2002) 186(11):1539-46.

Pepose et al., "Herpes simplex viral vectors for therapeutic gene delivery to ocular tissues. Recent breakthroughs in the molecular genetics of ocular diseases," Invest Ophthalmol Vis Sci. (1994) 35(6):2662-6.

*Periphagen,Inc* v *Krystalbiotech, Inc et al.* Pennsylvania Western District Court Judge: Mark R Hornak Case #: 2:20-U cv-00646 Nature of Suit 890 ather Statutes—ather Statutory Actions Cause 18:1836(b) Civil Action to Protect Trade Secrets; Filed May 1, 2020. (Year: 2020).

Periphagen, Krystal Biotech Inc., Answer and Counterclaim in *PeriphaGen* v. *Krystal Biotech*, Filed Jun. 26, 2020 in the Western District of Pennsylvania (60 pgs).

Rahn et al., "Invasion of Herpes Simplex Virus Type 1 into Murine Epidermis: An Ex Vivo Infection Study," J Invest Dermatol. (2015) 135(12): 3009-3016.

Sabater et al., "Topical beremagene geperpavec (B-VEC) for the treatment of recurrent cicatrizing conjunctivitis in a patient with dystrophic epidermolysis bullosa," ARVO Annual Meeting, New Orleans, LA, USA, Apr. 23-27, 2023. (2023).

Salam A. "Krystal's KB103 splits experts' thoughts on potential for HSV-1 risk in dystrophic epidermolysis bullosa patients, but final Phase I/II efficacy assured." Nov. 7, 2018. Biopharm Insight.

Salameh et al., "Early events in herpes simplex virus lifecycle with implications for an infection of lifetime," Open Virol J. (2012) 6:1-6.

Salmon-Ehr et al., "Implication of Interleukin-4 in Wound Healing", Laboratory Investigation, vol. 80, No. 8, Aug. 2000, pp. 1337-1343.

(56) References Cited

OTHER PUBLICATIONS

Samaniego et al., "Persistence and Expression of the Herpes Simplex Virus Genome in the Absence of Immediate-Early Proteins", Journal of Virology, (1998) 72(4); 3307-3320.

Samaniego et al., "The herpes simplex virus immediate-early protein ICP0 affects transcription from the viral genome and infected-cell survival in the absence of ICP4 and ICP27," J Virol. (1997) 71(6): 4614-4625.

Sankar et al., "A novel role for keratin 17 in coordinating oncogenic transformation and cellular adhersion in ewing sarcoma," Molecular and Cellular Biology (2013) 33(22):4448-4460.

Shen et al., "Herpes simplex virus 1 (HSV-1) for cancer treatment," Cancer Gene Therapy (2006) 13: 975-992.

Silva et al., "Herpes Virus Amplicon Vectors", Viruses, vol. 1, 2009, pp. 594-629.

Siprashvili et al., "Long-term type VII collagen restoration to human epidermolysis bullosa skin tissue," Hum Gene Ther. Oct. 2010;21(10):1299-310.

Spencer et al., "HSV-1 vector-delivered FGF2 to the retina is neuroprotective but does not preserve functional responses," Mol Ther. (2001) 3(5 Pt 1):746-56.

Stow et al., Isolation and characterization of a herpes simplex virus type 1 mutant containing a deletion within the gene encoding the immediate early polypeptide Vmw110. J Gen Viral. Dec. 1986;67 (Pt 12):2571-85.

Sufiawati et al., "HIV-associated disruption of tight and adherens junctions of oral epithelial cells facilitates HSV-1 infection and spread," PLoS One. (2014) 9(2): e88803.

Sufiawati et al., "HIV-induced matrix metalloproteinase-9 activation through mitogen-activated protein kinase signalling promotes HSV-1 cell-to-cell spread in oral epithelial cells," J Gen Virol. (2018) 99(7): 937-947.

Theopold et al., "A novel replication-defective HSV-1 vector for regulatable gene delivery to wounds," Journal of the American College of Surgeons (2004) 199(3):57-58.

Uitto et al., "Progress toward Treatment and Cure of Epidermolysis Bullosa: Summary of the DEBRA International Research Symposium EB2015", Journal of Investigative Dermatology, vol. 136, 2016, pp. 352-358.

Wang et al., "Comparative Effectiveness of Antinociceptive Gene Therapies in Animal Models of Diabetic Neuropathic Pain", Gene Therapy, vol. 20, 2013, pp. 742-750.

Wang et al., "Updates on Gene Therapy for Diabetic Retinopathy," Curr Diab Rep. (2020) 20(7):22.

Watanabe et al., "Properties of a Herpes Simplex Virus Multiple Immediate-early Gene-Deleted Recombinant as a Vaccine Vector", Virology, vol. 357, 2007, pp. 186-198.

Watt et al., "Lysyl Hydroxylase 3 Localizes to Epidermal Basement Membrane and Is Reduced in Patients with Recessive Dystrophic Epidermolysis Bullosa", Plos One, (2015) 10(9): e0137639.

Weiss et al., "The Role of Interleukin 10 in the Pathogenesis and Potential Treatment of Skin Diseases", Journal of the American Academy of Dermatology, vol. 50, No. 5, May 2004, pp. 657-675.

White et al., "Evaluation and optimization of the administration of a selectively replicating herpes simplex viral vector to the brain by convection-enhanced delivery," Cancer Gene Ther. May 2011;18(5):358-69. doi: 10.1038/ cgt.2011.2. Epub Mar. 4, 2011.

Wolfe et al., "Engineering Herpes Simplex Viral Vectors for Therapeutic Gene Transfer", Chapter 6, Gene and Cell Therapy, 2004, pp. 103-129.

Woodley et al., "Normal and Gene-Corrected Dystrophic Epidermolysis Bullosa Fibroblasts Alone Can Produce Type VII Collagen at the Basement Membrane Zone", The Journal of Investigative Dermatology, vol. 121, No. 5, Nov. 2003, pp. 1021-1028.

Woodley, et al., "Intradermal Injection of Lentiviral Vectors Corrects Regenerated Human Dystrophic Epidermolysis Bullosa Skin Tissue in Vivo", Molecular Therapy, vol. 10, No. 2, Aug. 2004, pp. 318-326.

Wu et al., "Prolonged gene expression and cell survival after infection by a herpes simplex virus mutant defective in the immediate-early genes encoding ICP4, ICP27, and ICP22," J Virol. (1996) 70(9): 6358-6369.

Saeki et al., "Improved Helper Virus-Free Packaging System for HSV Amplicon Vectors Using an ICP27-Deleted, Oversized HSV-1 Dna in a Bacterial Artificial Chromosome." Molecular Therapy. 2001. vol. 3, No. 4, pp. 591-601.

Titeux et al., "Gene therapeutics strategies for blistering skin diseases." Drug Discovery Today: Therapeutic Strategies. 2006. vol. 3, No. 1, pp. 87-92.

Office Action from related Application KR 10-2018-7030112, dated Jan. 24, 2024.

* cited by examiner

= heterologous promoter

= Collagen alpha-1 (VII) chain polypeptide coding sequence

= regulatory elements

Figures 1C, 1D:
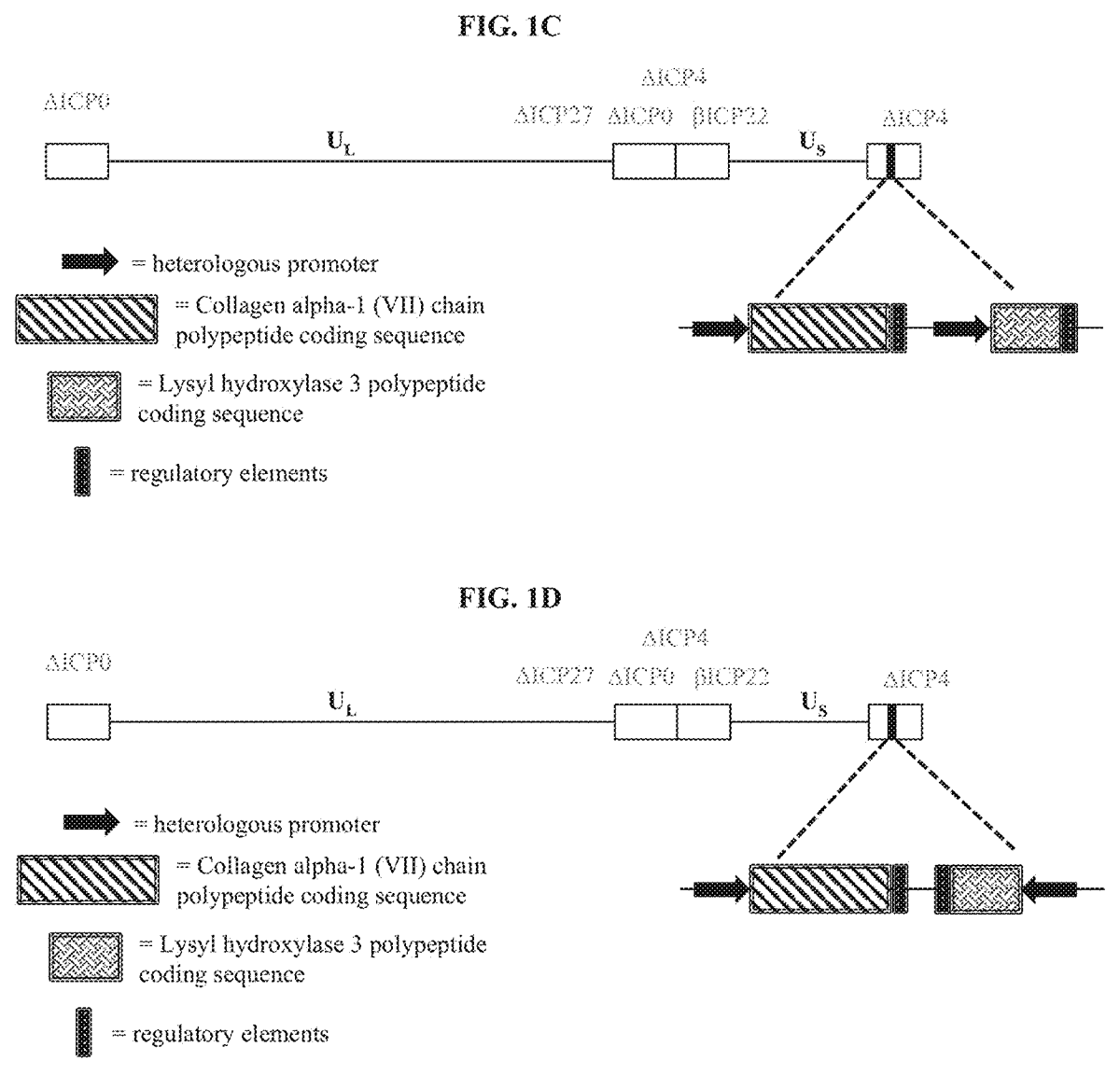

= heterologous promoter

= Collagen alpha-1 (VII) chain polypeptide coding sequence

= Lysyl hydroxylase 3 polypeptide coding sequence

= regulatory elements

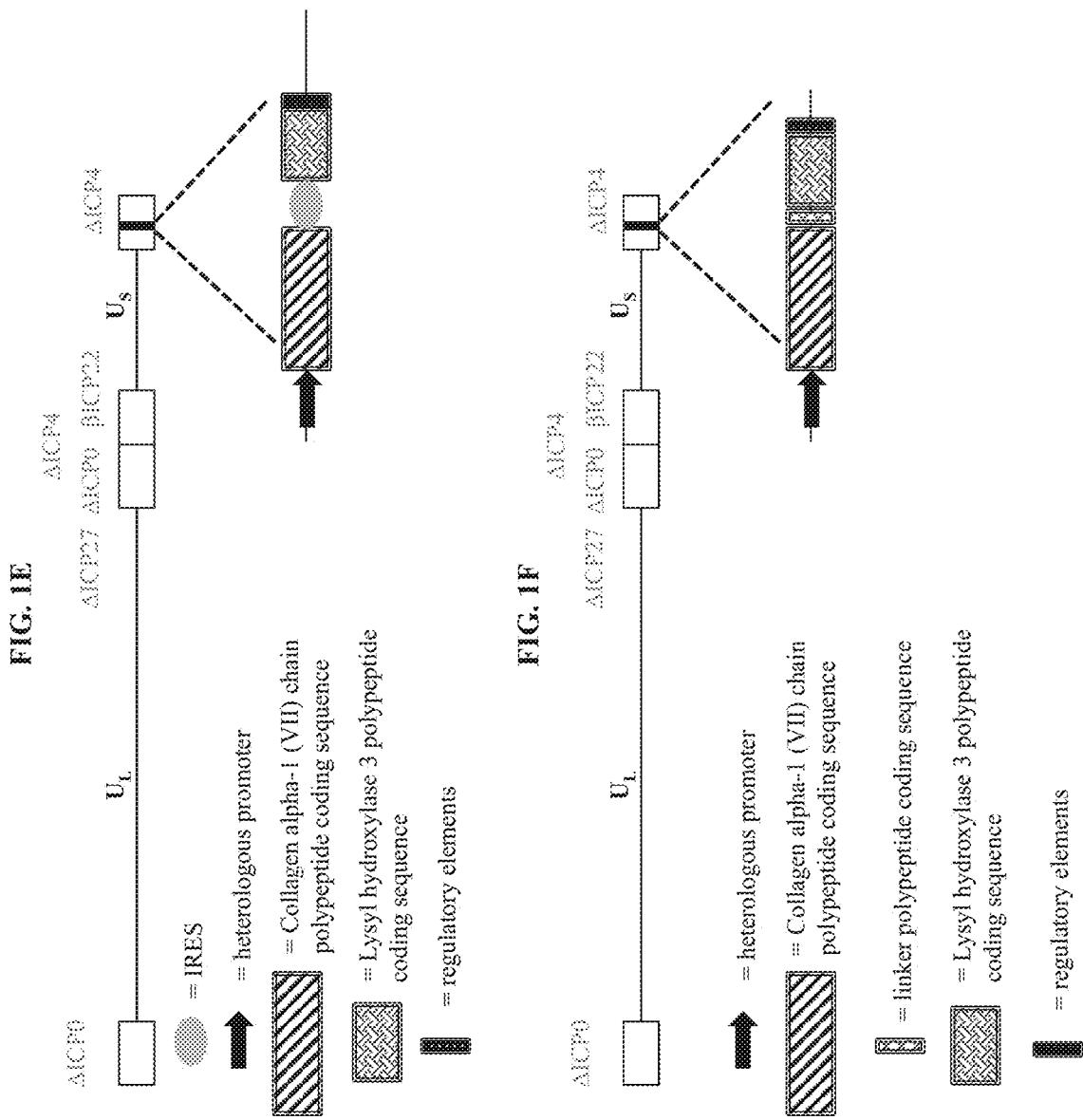

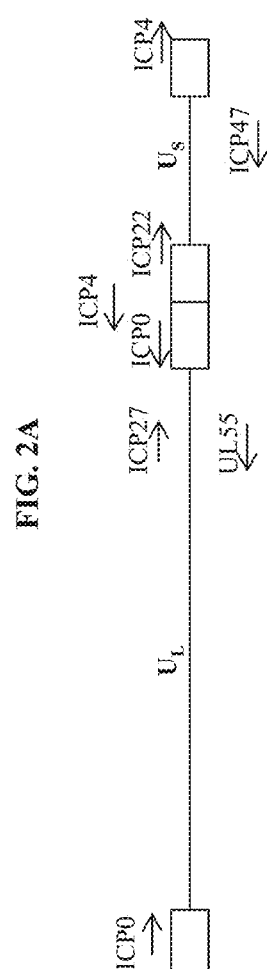
FIG. 2A
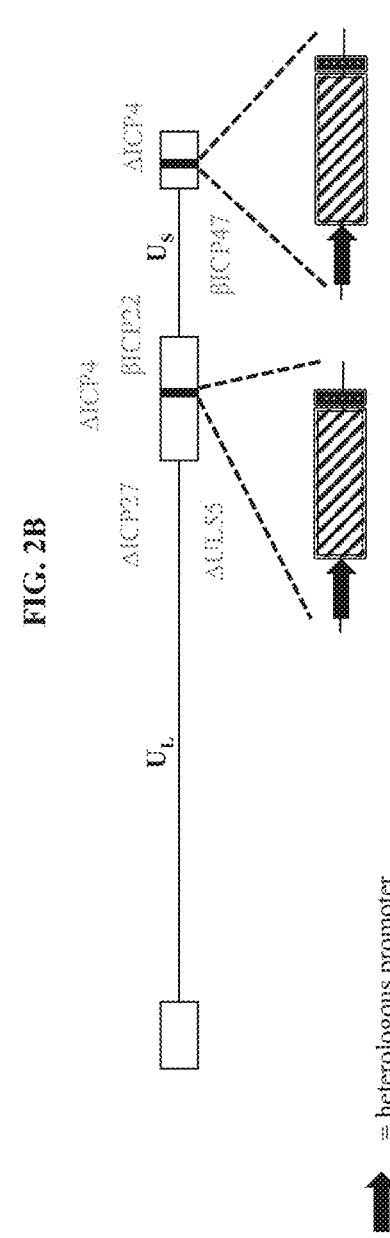
FIG. 2B
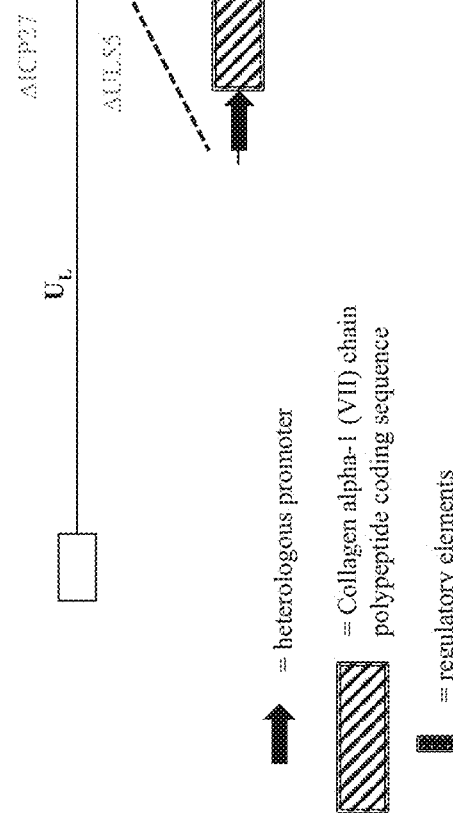
= heterologous promoter
= Collagen alpha-1 (VII) chain polypeptide coding sequence
= regulatory elements = heterologous promoter = Collagen alpha-1 (VII) chain polypeptide coding sequence = regulatory elements

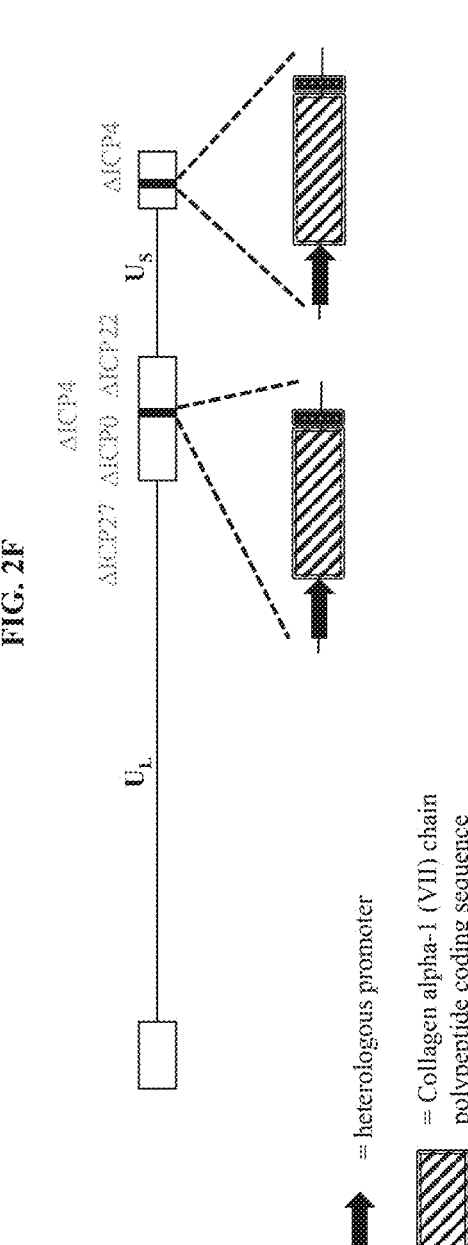

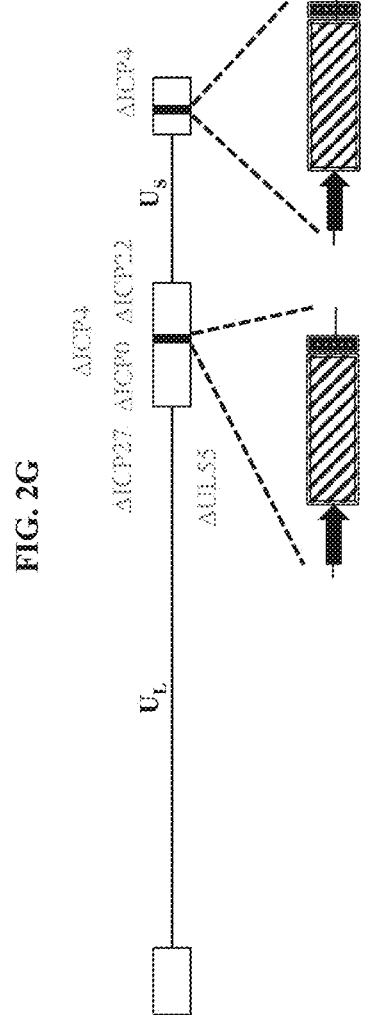
FIG. 2G
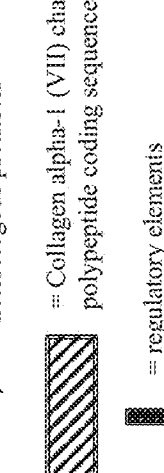
= heterologous promoter
= Collagen alpha-1 (VII) chain polypeptide coding sequence
= regulatory elements

FIG. 3

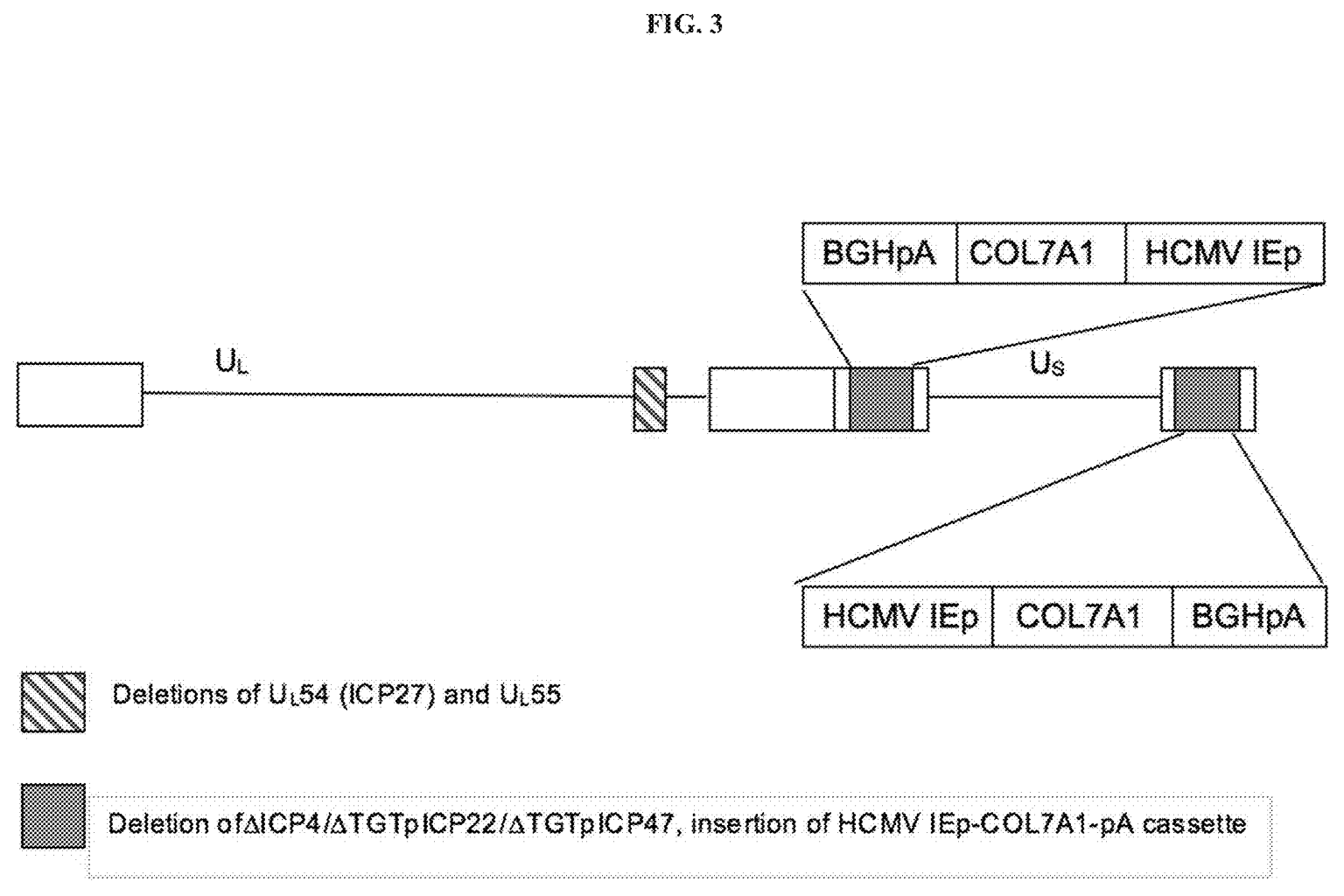

BGHpA | COL7A1 | HCMV IEp

U_S

U_L

HCMV IEp | COL7A1 | BGHpA

Deletions of U_L54 (ICP27) and U_L55

Deletion of ΔICP4/ΔTGTpICP22/ΔTGTpICP47, insertion of HCMV IEp-COL7A1-pA cassette

Col7 TRANSCRIPT AND COPY NUMBERS

FIG. 12

SEQUENCE LISTING

```
Sequence total quantity: 30
SEQ ID NO: 1            moltype = DNA  length = 8835
FEATURE                 Location/Qualifiers
source                  1..8835
                        mol_type = unassigned DNA
                        organism = Homo sapiens
SEQUENCE: 1
atgacgctgc ggcttctggt ggccgcgctc tgcgccggga tcctggcaga ggcgccccga   60
gtgcgagccc agcacaggga gagagtgacc tgcacgcgcc tttacgccgc tgacattgtg  120
ttcttactgg atggctcctc atccattggc cgcagcaatt tccgcgaggt ccgcagcttt  180
ctcgaagggc tggtgctgcc tttctctgga gcagccagtg cacagggtgt gcgctttgcc  240
acagtgcagt acagcgatga cccacggaca gagttcggcc tggatgcact tggctctggg  300
ggtgatgtga tccgcgccat ccgtgagctt agctacaagg ggggcaacac tcgcacaggg  360
gctgcaattc tccatgtggc tgaccatgtc ttcctgcccc agctggcccg acctggtgtc  420
cccaaggtct gcatcctgat cacagacggg aagtcccagg acctggtgga cacagctgcc  480
caaaggctga aggggcaggg ggtcaagcta tttgctgtgg ggatcaagaa tgctgaccct  540
gaggagctga agcgagttgc ctcacagccc accagtgact tcttcttctt cgtcaatgac  600
ttcagcatct tgaggacact actgcccctc gtttcccgga gagtgtgcac gactgctggt  660
ggcgtgcctg tgacccgacc tccggatgac tcgacctctg ctccacgaga cctggtgctg  720
tctgagccaa gcagccaatc cttgagagta cagtggacag cggccagtgg ccctgtgact  780
ggctacaagg tccagtacac tcctctgacg gggctgggac agccactgcc gagtgagcgg  840
caggaggtga acgtcccagc tggtgagacc agtgtgcggc tgcggggtct ccggccactg  900
accgagtacc aagtgactgt gattgccctc tacgccaaca gcatcgggga ggctgtgagc  960
gggacagctc ggaccactgc cctagaaggg ccggaactga ccatccagaa taccacagcc 1020
cacagcctcc tggtggcctg gcggagtgtg ccaggtgcca ctggctaccg tgtgacatgg 1080
cgggtcctca gtggtgggcc cacacagcag caggagctgg gccctgggca gggttcagtg 1140
ttgctgcgtg acttggagcc tggcacggac tatgaggtga ccgtgagcac cctatttggc 1200
cgcagtgtgg ggcccgccac ttccctgatg gctcgcactg acgcttctgt tgagcagacc 1260
ctgcgcccgg tcatcctggg ccccacatcc atcctccttt cctggaactt ggtgcctgag 1320
gcccgtggct accggttgga atggcggcgt gagactggct tggagccacc gcagaaggtg 1380
gtactgccct ctgatgtgac ccgctaccag ttggatgggc tgcagccggg cactgagtac 1440
cgcctcacac tctacactct gctggagggc cacgaggtgg ccaccctgc aaccgtggtt 1500
cccactggac cagagctgcc tgtgagccct gtaacagacc tgcaagccac cgagctgccc 1560
gggcagcggg tgcgagtgtc ctggagccca gtccctggtg ccacccagta ccgcatcatt 1620
gtgcgcagca cccaggggt tgagcggacc ctggtgcttc ctgggagtca gacagcattc 1680
gacttggatg acgttcaggc tgggcttagc tacactgtgc gggtgtctgc tcgagtgggt 1740
ccccgtgagg gcagtgccag tgtcctcact gtccgccggg agccggaaac tccacttgct 1800
gttccagggc tgcgggttgt ggtgtcagat gcaacgcgag tgagggtggc ctgggaccc 1860
```

```
gtccctggag ccagtggatt tcggattagc tggagcacag gcagtggtcc ggagtccagc    1920
cagacactgc ccccagactc tactgccaca gacatcacag ggctgcagcc tggaaccacc    1980
taccaggtgg ctgtgtcggt actgcgaggc agagaggagg ccctgctgc  agtcatcgtg    2040
gctcgaacgg acccactggg cccagtgagg acggtccatg tgactcaggc cagcagctca    2100
tctgtcacca ttacctggac cagggttcct ggcgccacag gatacaggagt ttcctggcac   2160
tcagcccacg gcccagagaa atcccagttg gtttctgggg aggccacggt ggctgagctg    2220
gatggactgg agcagatac  tgagtatacg gtgcatgtga gggcccatgt ggctggcgtg    2280
gatgggcccc ctgcctctgt ggttgtgagg actgcccctg agcctgtggg tcgtgtgtcg    2340
aggctgcaga tcctcaatgc ttccagcgac gttctacgga tcacctgggt aggggtcact    2400
ggagccacag cttacagact ggcctgdddc cggagtgaag gcggccccat gaggcaccag    2460
atactcccag gaaacacaga ctctgcagag atccggggtc tcgaaggtgg agtcagctac    2520
tcagtgcgag tgactgcact tgtctcgggac cgcgagggca cacctgtctc cattgttgtc    2580
actacgccgc ctgaggctcc gccagccctg gggacgcttc acgtggtgca gcgcggggag    2640
cactcgctga ggctgcgctg ggagccggtg cccagacgc  agggcttcct tctgcactgg    2700
caacctgagg gtggccagga acagtcccgg gtcctggggc ccgagctcag cagctatcac    2760
ctggacgggc tggagccagc gacacagtac cgcgtgaggc tgagtgtcct agggccagct    2820
ggagaagggc cctctgcaga ggtgactgcg cgcactgagt cacctcgtgt tccaagcatt    2880
gaactacgtg tggtggacac ctcgatcgac tcggtgactt tggcctggac tccagtgtcc    2940
agggcatcca gctacatcct atcctggcgg ccactcagag gccctggcca ggaagtgcct    3000
gggtccccgc agacacttcc agggatctca agctcccagc gggtgacagg gctagagcct    3060
ggcgtctctt acatcttctc cctgacgcct gtcctggatg gtgtgcgggg tcctgaggca    3120
tctgtcacac agacgccagt gtgcccccgt ggcctgggcg atgtggtgtt cctaccacat    3180
gccactcaag acaatgctca ccgtgcggag gctacgagga gggtcctgga gcgtctggtg    3240
ttggcacttg ggcctcttgg gccacaggca gttcaggttg gcctgctgtc ttacagtcat    3300
cggccctccc cactgttccc actgaatggc tcccatgacc ttggcattat cttgcaaagg    3360
atccgtgaca tgccctacat ggacccaagt gggaacaacc tgggcacagc cgtggtcaca    3420
gctcacagat acatgttggc accagatgct cctgggcgcc gccagcacgt accaggggtg    3480
atggttctgc tagtggatga acccttgaga ggtgacatat tcagccccat ccgtgaggcc    3540
caggcttctg ggcttaatgt ggtgatggttg ggaatggctg gagcggaccc agagcagctg    3600
cgtcgcttgg cgccgggtat ggactctgtc cagaccttct tcgccgtgga tgatgggcca    3660
agcctggacc aggcagtcag tggtctggcc acagccctgt gtcaggcatc cttcactact    3720
cagccccggc cagagccctg cccagtgtat tgtccaaagg gccagaaggg ggaacctgga    3780
gagatgggcc tgagaggaca agttgggcct cctggcgacc ctggcctccc gggcaggacc    3840
ggtgctcccg gcccccaggg gcccccctgga agtgccactg ccaagggcga gaggggcttc    3900
cctgagcag  atgggcgtcc aggcagccct ggccgcgcg  ggaatcctgg gacccctgga    3960
gcccctggcc taaagggctc tccagggttg cctggcccctc gtggggaccc gggagagcga    4020
ggacctcgag gcccaaaggg ggagccgggg gctcccggac aagtcatcgg aggtgaagga    4080
cctgggcttc ctgggcggaa aggggaccct ggaccatcgg gccccctgg  acctcgtgga    4140
ccactggggg acccaggacc ccgtggcccc ccagggcttc ctggaacagc catgaaggt    4200
gacaaaggcg atcgtgggga gcggggtccc cctggaccag gtgaaggtgg cattgctcct    4260
ggggagcctg ggctgccggg tcttcccgga agccctggac cccaaggccc cgttggcccc    4320
cctggaaaga aaggagaaaa aggtgactct gaggatggag ctccaggcct cccaggacaa    4380
cctgggctct cgggtgagca gggccacagg ggacctcctg gagctattgg ccccaaaggt    4440
gaccgggggct ttccaggggcc cctgggtgag gctggagaga agggcgaacg tggaccccca    4500
ggcccagcgg gatcccgggg gctgccaggg gttgctggac gtcctggagc caagggtcct    4560
gaagggccac caggacccac tggccgccaa ggagagaagg gggagcctgg tcgcctgggg    4620
gacctgcag  tggtgggacc tgctgttgct ggacccaaag gagaaaaggg agatgtgggg    4680
cccgctgggc ccagaggagc taccggagtc caagggggaac ggggcccacc cggcttggtt    4740
cttcctggag accctggccc caagggagac cctggagacc ggggtcccat tggccttact    4800
ggcagagcag gaccccccagg tgactcaggg cctcctggag agaagggaga ccctgggcgg    4860
cctggccccc caggacctgt tggcccccga ggacgagatg gtgaagttgg agagaaggt     4920
gacgagggtc ctccgggtga cccgggtttg cctggaaaag caggcgagcg tggccttcgg    4980
ggggcacctg gagttcgggg gcctgtgggt gaaaagggag accagggaga tcctggagag    5040
gatgacgaa  atggcagccc tggatcatct ggacccaagg gtgaccgtgg ggagccgggt    5100
cccccaggac ccccgggacg gctggtagac acaggccctg gccagaga  gaagggagag    5160
cctggggacc gcggacaaga gggtcctcga gggcccaagg gtgatcctgg cctccctgga    5220
gcccctgggg aaaggggcat tgaagggttt cggggacccc caggcccaca gggggaccca    5280
ggtgtccgag gcccagcagg agaaaagggt gaccggggtc ccctgggct  ggatggccgg    5340
agcggactgg atgggaaacc aggagccgct gggccctctg ggccgaatgg tgctgcaggc    5400
aaagtcgggg acccagggga gacgggcctt ccaggcctcc gtggagaaca gggcctccct    5460
ggcccctctg gtcccctgg  attaccggga aagccaggcg aggatggcaa acctggcctg    5520
aatgaaaaa  acgagaacc  tggggaccct ggagaagacg ggaggaaggg agagaaagga    5580
gattcaggcg cctctgggag agaaggtcgt gatgccccca aggtgagcg  tggagctcct    5640
ggtatccttg gaccccaggg gcctccaggc ctcccaggac cagtggcccc tcctggccag    5700
ggttttcctg gtgtcccagg aggcacgggc cccaagggtg accgtgggga gactggatcc    5760
aaaggggagc agggcctccc tggagagcgt ggcctgcgag gagagcctgg aagtgtgccg    5820
aatgtggatc ggttgctgga aactgctggc atcaaggcat ctgccctgcg ggagatcgtg    5880
gagacctggg atgagagctc tggtagcttc ctgcctgtgc ccgaacggcg tcgaggcccc    5940
aagggggact caggcgaaca ggcccccca  ggcaaggagg gcccatcg  ctttcctgga    6000
gaacgcgggc tgaagggcga ccgtggagac cctggccctc aggggccacc tggtctggcc    6060
cttgggggaga gggcccccc  cgggccttcc ggccttgccg gggagcctgg aaagcctggt    6120
attcccggc  tcccaggcag ggctggggt  gtgggagagg caggaaggcc aggagagagg    6180
ggagaacggg agagaaagg  agaacgtgga aacagggca  gagatggccc tcctggactc    6240
cctggaaccc ctggcacccc cggacccccc ggccccaagg tgtctgtgga tggaccaggt    6300
cctggactct ctgagaaaca gggaccccct ggactcaagg gtgctaaggg ggagccgggc    6360
agcaatggtg accaaggtcc caaaggagac aggggtgtgc caggcatcaa aggagaccgg    6420
ggagagcctg gaccgagggg tcaggacggc aaccccgggtc taccaggaga gcgtggtatg    6480
gctgggcctg aagggaagcc gggtctgcag ggtccaagag ccccccctgg cccagtgggt    6540
ggtcatggag accctggacc acctggtgcc ccgggtcttg ctgccctgc  aggaccccaa    6600
```

-continued

```
ggaccttctg gcctgaaggg ggagcctgga gagacaggac ctccaggacg gggcctgact   6660
ggacctactg gagctgtggg acttcctgga cccccggcc cttcaggcct tgtgggtcca    6720
caggggtctc caggtttgcc tggacaagtg ggggagacag ggaagccggg agccccaggt   6780
cgagatggtg ccagtggaaa agatggagac agagggagcc ctggtgtgcc agggtcacca   6840
ggtctgcctg gccctgtcgg acctaaagga gaacctgccc ccacgggcgc ccctggacag   6900
gctgtggtcg ggctccctgg agcaaaggga gagaagggag ccccctggagg ccttgctgga  6960
gacctggtgg gtgagccggg agccaaaggt gaccgaggac tgccaggggcc gcgaggcgag  7020
aagggtgaag ctggccgtgc aggggagccc ggagaccctg gggaagatgg tcagaaaggg   7080
gctccaggac ccaaaggttt caaggggtgac ccaggagtcg gggtcccggg ctcccctggg  7140
cctcctggcc ctccaggtgt gaagggagat ctgggcctcc ctggcctggg cggtgctcct   7200
ggtgttgttg ggtccccggg tcagacaggc cctcgaggag agatgggtca gccaggcct   7260
agtggagagc ggggtctggc aggcccccca gggagagaag gaatcccagg accctgggg    7320
ccacctggac caccggggtc agtgggacca cctggggcct ctggactcaa aggagacaag   7380
ggagaccctg gagtagggct gcctgggccc cgaggcgagc gtggggagcc aggcatccgg   7440
ggtgaagatg gccgccccgg ccaggaggga ccccgaggac tcacggggcc ccctggcagc   7500
aggggagagc gtgggggagaa gggtgatgtt gggagtgcag gactaaaggg tgacaaggga   7560
gactcagctg tgatcctggg gcctccaggc ccacggggtg ccaaggggga catgggtgaa   7620
cgagggcctc ggggcttgga tggtgacaaa ggacctcggg gagacaatgg ggaccctggt  7680
gacaagggca gcaagggaga gcctggtgac aagggctcag ccgggttgcc aggactgcgt   7740
ggactcctgg gaccccaggg tcaacctggt gcagcaggga tccctggtga cccgggatcc   7800
ccaggaaagg atggagtgcc tggtatccga ggagaaaaag gagatgttgg cttcatgggt  7860
cccccgggggcc tcaagggtga acggggagtg aagggaccct ggggccttga tggagagaag  7920
ggagacaagg gagaagctgg tccccccagcc cgcccccgggc tggcaggaca caaaggagag   7980
atgggggagc ctggtgtgcc gggccagtcg ggggcccctg gcaaggaggg cctgatcggt   8040
cccaagggtg accgaggctt tgacgggcag ccaggcccca agggtgacca gggcgagaaa   8100
ggggagggag gaaccccagg aattgggggc ttcccaggcc ccagtggaaa tgatggctct   8160
gctggtcccc cagggccacc tggcagtgtt ggtcccagag gccccgaagg acttcagggc   8220
cagaagggtg agcgaggtcc ccccggagag agagtggtgg gggctcctgg ggtccctgga   8280
gctcctggcg agagagggga gcaggggcgg ccagggcctg ccggtcctcg aggcgagaag   8340
ggagaagctg cactgacgga ggatgacatc cggggctttg tgcgccaaga gatgagtcag   8400
cactgtgcct gccagggcca gttcatcgca tctggatcac gacccctccc tagttatgct   8460
gcagacactg ccggctccca gctccatgct gtgcctgtgc tccgcgtctc tcatgcagag   8520
gaggaagagc gggtacccccc tgaggatgat gagtactctg aatactccga gtattctgtg   8580
gaggagtacc aggaccctga agctccttgg gatagtgatg accctgttc cctgccactg   8640
gatgagggct cctgcactgc ctacaccctg cgctggtacc atcgggctgt gacaggcagc   8700
acagaggcct gtcaccctt tgtctatggt ggctggtgga ggaatgccaa ccgtttttggg  8760
accccgtgagg cctgcgagcg ccgctgccca ccccgggtgg tccagagcca ggggacaggt   8820
actgcccagg actga                                                    8835
```

```
SEQ ID NO: 2          moltype = AA  length = 2944
FEATURE               Location/Qualifiers
source                1..2944
                      mol_type = protein
                      organism = Homo sapiens
SEQUENCE: 2
MTLRLLVAAL CAGILAEAPR VRAQHRERVT CTRLYAADIV FLLDGSSSIG RSNFREVRSF    60
LEGLVLPFSG AASAQGVRFA TVQYSDDPRT EFGLDALGSG GDVIRAIREL SYKGGNTRTG    120
AAILHVADHV FLPQLARPGV PKVCILITDG KSQDLVDTAA QRLKGQGVKL FAVGIKNADP    180
EELKRVASQP TSDFFFFVND FSILRTLLPL VSRRVCTTAG GVPVTRPPDD STSAPRDLVL    240
SEPSSQSLRV QWTAASGPVT GYKVQYTPLT GLGQPLPSER QEVNVPAGET SVRLRGLRPL    300
TEYQVTVIAL YANSIGEAVS GTARTTALEG PELTIQNTTA HSLLVAWRSV PGATGYRVTW    360
RVLSGGPTQQ QELGPGQGSV LLRDLEPGTD YEVTVSTLFG RSVGPATSLM ARTDASVEQT    420
LRPVILGPTS ILLSWNLVPE ARGYRLEWRR ETGLEPPQKV VLPSDVTRYQ LDGLQPGTEY    480
RLTLYTLLEG HEVATPATVV PTGPELPVSP VTDLQATELP GQRVRVSWSP VPGATQYRII    540
VRSTQGVERT LVLPGSQTAF DLDDVQAGLS YTVRVSARVG PREGSASVLT VRREPETPLA    600
VPGLRVVVSD ATRVRVAWGP VPGASGFRIS WSTGSGPESS QTLPPDSTAT DITGLQPGTT    660
YQVAVSVLRG REEGPAAVIV ARTDPLGPVR TVHVTQASSS SVTITWTRVP GATGYRVSWH    720
SAHGPEKSQL VSGEATVAEL DGLEPDTEYT VHVRAHVAGV DGPPASVVVR TAPEPVGRVS    780
RLQILNASSD VLRITWVGVT GATAYRLAWG RSEGGPMRHQ ILPGNTDSAE IRGLEGGVSY    840
SVRVTALVGD REGTPVSIVV TTPPEAPPAL GTLHVVQRGE HSLRLRWEPV PRAQGFLLHW    900
QPEGGGQEQSR VLGPELSSYH LDGLEPATQY RVRLSVLGPA GEGPSAEVTA RTESPRVPSI    960
ELRVVDTSID SVTLAWTPVS RASSYILSWR PLRGPGQEVP GSPQTLPGIS SSQRVTGLEP   1020
GVSYIFSLTP VLDGVRGPEA SVTQTPVCPR GLADVVFLPH ATQDNAHRAE ATRRVLERLV   1080
LALGPLGPQA VQVGLLSYSH RPSPLFPLNG SHDLGIILQR IRDMPYMDPS GNNLGTAVVT   1140
AHRYMLAPDA PGRRQHVPGV MVLLVDEPLR GDIFSPIREA QASGLNVVML GMAGADPEQL   1200
RRLAPGMDSV QTFFAVDDGP SLDQAVSGLA TALCQASFTT QPRPEPCPVY CPKGQKGEPG   1260
EMGLRGQVGP PGDPGLPGRT GAPGPQGPPG SATAKGERGF PGADGRPGSP GRAGNPGTPG   1320
APGLKGSPGL PGPRGDPGER GPRGPKGEPG APGQVIGGEG PGLPGRKGDP GPSGPPGPRG   1380
PLGDPGPRGP PGLPGTAMKG DKGDRGERGP PGPGEGGIAP GEPGLPGLPG SPGPQGPVGP   1440
PGKKGEKGDS EDGAPGLPGQ PGSPGEQGPR GPPGAIGPKG DRGFPGPLGE AGEKGERGPP   1500
GPAGSRGLPG VAGRPGAKGP EGPPGPTGRQ GEKGEPGRPG DPAVVGPAVA GPKGEKGDVG   1560
PAGPRGATGV QGERGPPGLV LPGDPGPKGD PGDRGPIGLT GRAGPPGDSG PPGEKGDPGR   1620
PGPPGPVGPR GRDGEVGEKG DEGPPGDPGL PGKAGERGLR GAPGVRGPVG EKGDQGDPGE   1680
DGRNGSPGSS GPKGDRGEPG PPGPPGRLVD TGPGAREKGE PGDRGQEGPR GPKGDPGLPG   1740
APGERGIEGF RGPPGPQGDP GVRGPAGEKG DRGPPGLDGR SGLDGKPGAA GPSGPNGAAG   1800
KAGDPGRDGL PGLRGEQGLP GPSGPPGLPG KPGEDGKPGL NGKNGEPGDP GEDGRKGEKG   1860
DSGASGREGR DGPKGERGAP GILGPQGPPG LPGPVGPPGQ GFPGVPGGTG PKGDRGETGS   1920
KGEQGLPGER GLRGEPGPSVP NVDRLLETAG IKASALREIV ETWDESSGSF LPVPERRRGP   1980
KGDSGEQGPP GKEGPIGFPG ERGLKGDRGD PGPQGPPGLA LGERGPPGPS GLAGEPGKPG   2040
```

```
IPGLPGRAGG VGEAGRPGER GERGEKGERG EQGRDGPPGL PGTPGPPGPP GPKVSVDEPG  2100
PGLSGEQGPP GLKGAKGEPG SNGDQGPKGD RGVPGIKGDR GEPGPRGQDG NPGLPGPERGM  2160
AGPEGKPGLQ GPRGPPGPVG GHGDPGPPGA PGLAGPAGPQ GPSGLKGEPG ETGPPGRGLT  2220
GPTGAVGLPG PPGPSGLVGP QGSPGLPGQV GETGKPGAPG RDGASGKDGD RGSPGVPGSP  2280
GLPGPVGPKG EPGPTGAPGQ AVVGLPGAKG EKGAPGGLAG DLVGEPGAKG DRGLPGPRGE  2340
KGEAGRAGEP GDPGEDGQKG APGPKGFKGD PGVGVPGSPG PPGPPGVKGD LGLPGLPGAP  2400
GVVGFPGQTG PRGEMGQPGP SGERGLAGPP GREGIPGPLG PPGPPGSVGP PGASGLKGDK  2460
GDPGVGLPGP RGERGEPGIR GEDGRPGQEG PRGLTGPPGS RGERGEKGDV GSAGLKGDKG  2520
DSAVILGPPG PRGAKGDMGE RGPRGLDGDK GPRGDNGPGD DKGSKGEPGD KGSAGLPGLR  2580
GLLGPQGQPG AAGIPGDPGS PGKDGVPGIR GEKGDVGFMG PRGLKGERGV KGACGLDGEK  2640
GDKGEAGPPG RPGLAGHKGE MGEPGVPGQS GAPGKEGLIG PKGDRGFDGQ PGPKGDQGEK  2700
GERGTPGIGG FPGPSGNDGS AGPPGPPGSV GPRGPEGLQG QKGERGPPGE RVVGAPGVPG  2760
APGERGEQGR PGPAGPRGEK GEAALTEDDI RGFVRQEMSQ HCACQGQFIA SGSRPLPSYA  2820
ADTAGSQLHA VPVLRVSHAE EEERVPPEDD EYSEYSEYSV EEYQDPEAPW DSDDPCSLPL  2880
DEGSCTAYTL RWYHRAVTGS TEACHPFVYG GCGGNANRFG TREACERRCP PRVVQSQGTG  2940
TAQD                                                              2944

SEQ ID NO: 3          moltype = DNA  length = 2217
FEATURE               Location/Qualifiers
source                1..2217
                      mol_type = unassigned DNA
                      organism = Homo sapiens
SEQUENCE: 3
atgacctcct cggggcctgg accccggttc ctgctgctgc tgccgctgct gctgcccct    60
gcggcctcag cctccgaccg gccccggggc cgagacccgg tcaacccaga gaagctgctg   120
gtgatcactg tggccacagc tgaaaccgag gggtacctgc gtttcctgcg ctctgcggag   180
ttcttcaact acactgtgcg gaccctgggc ctgggagagg agtggcgagg gggtgatgtg   240
gctcgaacag ttggtggagg acagaaggtc cggtggttaa agaaggaaat ggagaaatac   300
gctgaccggg aggatatgat catcatgttt gtggatagct acgacgtgat tctggccggc   360
agcccacag agctgctgaa gaagttcgtc cagagtggca gccgcctgct cttctctgca   420
gagagcttct gctggcccga gtgggggctg gcggagcagt accctgaggt gggcacgggg   480
aagcgcttcc tcaattctgg tggattcatc ggttttgcca ccaccatcca ccaaatcgtg   540
cgccagtgga agtacaagga tgatgacgac gaccagctgt tctacacacg gctctacctg   600
gacccaggac tgagggagaa actcagcctt aatctggatc ataagtctcg gatctttcag   660
aacctcaacg gggctttaga tgaagtggtt ttaaagtttg atcggaaccg tgtgcgtatc   720
cggaacgtgg cctacgacac gctcccatt gtggtccatg gaaacggtcc cactaagctg   780
cagctcaact acctgggaaa ctacgtcccc aatggctgga ctcctgaggg aggctgtggc   840
ttctgcaacc aggaccggag gacactcccg ggggggcagc ctccccccg ggtgtttctg   900
gccgtgtttg tggaacagcc tactccgttt ctgccccgct tcctgcagcg gctgctactc   960
ctggactatc cccccgacag ggtcacccctt ttcctgcaca caacgaggt cttccatgaa   1020
ccccacatcg ctgactcctg gccgcagctc caggaccact tctcagctgt gaagctcgtg   1080
gggccggagg aggctctgag cccaggcgag gccagggaca tggccatgga cctgtgtcgg   1140
caggaccccg agtgtgagtt ctacttcagc ctggacgccg acgctgtcct caccaacctg   1200
cagaccctgc gtatcctcat tgaggagaac aggaaggtga tcgcccccat gctgtcccgc   1260
cacggcaagc tgtggtccaa cttctggggc gccctgagcc ccgatgagta ctacgcccgc   1320
tccgaggact acgtggagct ggtgcagcgg aagcgagtgg gtgtgtggaa tgtaccctac   1380
atctcccagg cctatgtgat ccggggtgat accctgcgga tggagctgcc ccagagggat   1440
gtgttctcgg gcagtgacac agaccccggac atggccttct gtaagagctt tcgagacaag   1500
ggcatcttcc tccatctgag caatcagcat gaatttggcc ggctcctggc cacttccaga   1560
tacgacacgg agcacctgca ccccgacctc tggcagatct tcgacaaccc cgtcgactgg   1620
aaggagcagt acatccacga gaactacagc cgggccctga agggggaagg aatcgtggag   1680
cagccatgcc cggacgtgta ctggttccca ctgctgtcag aacaaatgtg tgatgagctg   1740
gtggcagaga tggagcacta cgggcagtgg tcaggcggcc ggcatgagga ttcaaggctg   1800
gctgaggct acgagaatgt gcccaccgtg gacatccaca tgaagcaggt ggggtacgag   1860
gaccagtggc tgcagctgct gcggacgtat gtggggcccca tgaccgagag cctgtttccc   1920
ggttaccaca ccaaggcgcg ggcggtgatg aactttgtgg ttcgctaccg gccagacgag   1980
cagccgtctc tgcggccaca ccacgactca tccacctttca ccctcaacgt tgccctcaac   2040
cacaaggggc tggactatga gggaggtggc tgccgcttcc tgcgctacga ctgtgtgatc   2100
tcctccccga ggaagggctg ggcactcctg cacccggcc gcctcaccca ctaccacgag   2160
gggctgccaa cgacctgggg cacacgctac atcatgtgt cctttgtcga cccctga      2217

SEQ ID NO: 4          moltype = AA  length = 738
FEATURE               Location/Qualifiers
source                1..738
                      mol_type = protein
                      organism = Homo sapiens
SEQUENCE: 4
MTSSGPGPRF LLLLPLLLPP AASASDRPRG RDPVNPEKLL VITVATAETE GYLRFLRSAE    60
FFNYTVRTLG LGEEWRGGDV ARTVGGGQKV RWLKKEMEKY ADREDMIIMF VDSYDVILAG   120
SPTELLKKFV QSGSRLLFSA ESFCWPEWGL AEQYPEVGTG KRFLNSGGFI GFATTIHQIV   180
RQWKYKDDDD DQLFYTRLYL DPGLREKLSL NLDHKSRIFQ NLNGALDEVV LKFDRNRVRI   240
RNVAYDTLPI VVHGNGPTKL QLNYLGNYVP NGWTPEGGCG FCNQDRRTLP GGQPPPRVFL   300
AVFVEQPTPF LPRFLQRLLL LDYPPDRVTL FLHNNEVFHE PHIADSWPQL QDHFSAVKLV   360
GPEEALSPGE ARDMAMDLCR QDPECEFYFS LDADAVLTNL QTLRILIEEN RKVIAPMLSR   420
HGKLWSNFWG ALSPDEYYAR SEDYVELVQR KRVGVWNVPY ISQAYVIRGD TLRMELPQRD   480
VFSGSDTDPD MAFCKSFRDK GIFLHLSNQH EFGRLLATSR YDTEHLHPDL WQIFDNPVDW   540
KEQYIHENYS RALEGEGIVE QPCPDVYWFP LLSEQMCDEL VAEMEHYGQW SGGRHEDSRL   600
AGGYENVPTV DIHMKQVGYE DQWLQLLRTY VGPMTESLFP GYHTKARAVM NFVVRYRPDE   660
QPSLRPHHDS STFTLNVALN HKGLDYEGGG CRFLRYDCVI SSPRKGWALL HPGRLTHYHE   720
```

-continued

```
GLPTTWGTRY IMVSFVDP                                                        738

SEQ ID NO: 5              moltype = DNA   length = 75
FEATURE                   Location/Qualifiers
misc_feature              1..75
                          note = Synthetic Construct
source                    1..75
                          mol_type = other DNA
                          organism = synthetic construct
SEQUENCE: 5
agggccaaga ggggcagcgg cgagggcagg ggcagcctgc tgacctgcgg cgacgtggag           60
gagaaccccg gcccc                                                           75

SEQ ID NO: 6              moltype = AA   length = 25
FEATURE                   Location/Qualifiers
REGION                    1..25
                          note = Synthetic Construct
source                    1..25
                          mol_type = protein
                          organism = synthetic construct
SEQUENCE: 6
RAKRGSGEGR GSLLTCGDVE ENPGP                                                 25

SEQ ID NO: 7              moltype = DNA   length = 66
FEATURE                   Location/Qualifiers
misc_feature              1..66
                          note = Synthetic Construct
source                    1..66
                          mol_type = other DNA
                          organism = synthetic construct
SEQUENCE: 7
ggaagcggag ctactaactt cagcctgctg aagcaggctg agacgtggga ggagaaccct           60
ggacct                                                                     66

SEQ ID NO: 8              moltype = AA   length = 22
FEATURE                   Location/Qualifiers
REGION                    1..22
                          note = Synthetic Construct
source                    1..22
                          mol_type = protein
                          organism = synthetic construct
SEQUENCE: 8
GSGATNFSLL KQAGDVEENP GP                                                    22

SEQ ID NO: 9              moltype = DNA   length = 69
FEATURE                   Location/Qualifiers
misc_feature              1..69
                          note = Synthetic Construct
source                    1..69
                          mol_type = other DNA
                          organism = synthetic construct
SEQUENCE: 9
ggaagcggac agtgtactaa ttatgctctc ttgaaattgg ctggagatgt tgagagcaac           60
cctggacct                                                                  69

SEQ ID NO: 10             moltype = AA   length = 23
FEATURE                   Location/Qualifiers
REGION                    1..23
                          note = Synthetic Construct
source                    1..23
                          mol_type = protein
                          organism = synthetic construct
SEQUENCE: 10
GSGQCTNYAL LKLAGDVESN PGP                                                   23

SEQ ID NO: 11             moltype = DNA   length = 75
FEATURE                   Location/Qualifiers
misc_feature              1..75
                          note = Synthetic Construct
source                    1..75
                          mol_type = other DNA
                          organism = synthetic construct
SEQUENCE: 11
ggaagcggag tgaaacagac tttgaatttt gaccttctca agttggcggg agacgtggag           60
tccaaccctg gacct                                                           75

SEQ ID NO: 12             moltype = AA   length = 25
FEATURE                   Location/Qualifiers
REGION                    1..25
```

```
                              note = Synthetic Construct
source                        1..25
                              mol_type = protein
                              organism = synthetic construct
SEQUENCE: 12
GSGVKQTLNF DLLKLAGDVE SNPGP                                           25

SEQ ID NO: 13                 moltype = DNA   length = 11121
FEATURE                       Location/Qualifiers
misc_feature                  1..11121
                              note = Synthetic Construct
source                        1..11121
                              mol_type = other DNA
                              organism = synthetic construct
SEQUENCE: 13
atgacgctgc ggcttctggt ggccgcgctc tgcgccggga tcctggcaga ggcgccccga   60
gtgcgagccc agcacaggga gagagtgacc tgcacgcgcc tttacgccgc tgacattgtg   120
ttcttactgg atggctcctc atccattggc cgcagcaatt tccgcgaggt ccgcagcttt   180
ctcgaagggc tggtgctgcc tttctctgga gcagccagtg cacagggtgt gcgctttgcc   240
acagtgcagt acagcgatga cccacggaca gagttcggcc tggatgcact tggctctggg   300
ggtgatgtga tccgcgccat ccgtgagctt agctacaagg ggggcaacac tcgcacaggg   360
gctgcaattc tccatgtggc tgaccatgtc ttcctgcccc agctggcccg acctggtgtc   420
cccaaggtct gcatcctgat cacagacggg aagtcccagg acctggtgga cacagctgcc   480
caaaggctga aggggcaggg ggtcaagcta tttgctgtgg ggatcaagaa tgctgaccct   540
gaggagctga agcgagttgc ctcacagccc accagtgact tcttcttctt cgtcaatgac   600
ttcagcatct tgaggacact actgcccctc gtttcccgga gagtgtgcac gactgctgtt   660
ggcgtgcctg tgacccgacc tccggatgac tcgacctctg ctccacgaga cctggtgctg   720
tctgagccaa gcagccaatc cttgagagta cagtggacag cggccagtgg ccctgtgact   780
ggctacaagg tccagtacac tcctctgacg gggctgggac agccactgcc gagtgagcgg   840
caggaggtga acgtcccagc tggtgagacc agtgtgcagc tgcggggtct ccggccactg   900
accgagtacc aagtgactgt gattgccctc tacgccaaca gcatcgggga ggctgtgagc   960
gggacagctc ggaccactgc cctagaaggg ccggaactga ccatccagaa taccacagcc   1020
cacagcctcc tggtggcctg gcggagtgtg ccaggtgcca ctggctaccg tgtgacatgt   1080
cgggtcctca gtggtgggcc cacacagcag caggagctgg gcctgggca gggttcagtg   1140
ttgctgcgtg acttggagcc tggcacggac tatgaggtga ccgtgagcac cctatttggc   1200
cgcagtgtgg ggcccgccac ttccctgatg gctcgcactg acgcttctgt tgagcagacc   1260
ctgcgcccgg tcatcctggg ccccacatcc atcctccttt cctggaactt ggtgcctgag   1320
gcccgtggct accggttgga atggcggcgt gagactggct tggagccacc gcagaaggtg   1380
gtactgccct ctgatgtgac ccgctaccag ttggatgagc tgcagccgga cactgagtac   1440
cgcctcacac tctacactct gctggagggc cacgaggtgg ccaccctgc aaccgtggtt   1500
cccactggac cagagctgcc tgtgagccct gtaacagacc tgcaagccac cgagctgccc   1560
gggcagcggg tgcgagtgtc ctggagccca gtccctggtg ccacccagta ccgcatcatt   1620
gtgcgcagca cccagggggt tgagcgacc ctggtgcttc ctgggagtca gacagcattc   1680
gacttggatg acgttcaggc tgggcttagc tacactgtgc gggtgtctgc tcgagtgggt   1740
ccccgtgagg gcagtgccag tgtcctcact gtccgccggg agccgaaac tccacttgct   1800
gttccagggc tgcgggttgt ggtgtcagat gcaacgcgag tgagggtggc ctggggaccc   1860
gtccctggag ccagtggatt tcggattagc tggagcacag gcagtggtcc ggagtccagc   1920
cagacactgc ccccagactc tactgccaca gacatcacag ggctgcagcc tggaaccacc   1980
taccaggtgg ctgtgtcggt actgcgaggc agagaggagg ccctgctgc agtcatcgtg   2040
gctcgaacgg acccactggg cccagtgagg acggtccatg tgactcaggc cagcagctca   2100
tctgtcacca ttacctggac cagggttcct ggcgccacag gatacagggt ttcctggcac   2160
tcagcccacg gcccagagaa atcccagttg gtttctgggg aggccacggt ggctgagctg   2220
gatggactgg agcagatac tgagtatacg gtgcatgtga gggcccatgt ggctggcgtg   2280
gatgggcccc ctgcctctgt ggttgtgagg actgccctg agcctgtggg tcgtgtgtcg   2340
aggctgcaga tcctcaatgc ttccagcgac gttctacgga tcacctgggt aggggtcact   2400
ggagccacag cttacagact ggcctggggc cggagtgaag cggccccat gaggcaccag   2460
atactcccag gaaacacaga ctctgcagag atccggggtc tcgaaggtgg agtcagctac   2520
tcagtgcgag tgactgcact tgtcgggga cgcgagggca cacctgtctc cattgttgtc   2580
actacgccgc ctgaggctcc gccagccctg gggacgcttc acgtggtgca gcgcggggag   2640
cactcgctga ggctgcgctg ggagccggtg cccagagcgc agggcttcct tctgcactg   2700
caacctgagg gtggccagga acagtcccgg gtcctggggc ccgagctcag cagctatcac   2760
ctggacgggc tggagccagc gacacagtac cgcgtgaggc tgagtgtcct agggccagct   2820
ggagaaggc cctctgcaga ggtgactgcg cgcactgagt cacctcgtgt tccaagcatt   2880
gaactacgtg tggtggacac ctcgatcgac tcggtgactt tggcctggac tccagtgtcc   2940
agggcatcca gctacatcct atcctggcgg ccactcagag ccctggccaa ggaagtgcct   3000
gggtccccgc agacacttcc agggatctca agctcccagc gggtgacagg gctagagcct   3060
ggcgtctctt acatcttctc cctgacgcct gtcctggatg gtgtgcgggg tcctgaggca   3120
tctgtcacac agacgccagt gtgccccgt ggcctgcgcg atgtggtgtt cctaccacat   3180
gccactcaag acaatgctca ccgtgcggag gctacgagga gggtcctgga gcgtctggtg   3240
ttggcacttg ggcctcttgg ccacaggca gttcaggttg gcctgctgtc ttacagtcat   3300
cggccctccc cactgttccc actgaatggc tccatgacc ttggcattat cttgcaaagg   3360
atccgtgaca tgcctacat ggacccaagt gggaacaacc tgggcacagc cgtggtcaca   3420
gctcacagat acatgttggc accagatgct cctgggcgcc gccagcacgt accaggggtg   3480
atggttctgc tagtggataa accctgaga ggtgacatat tcagccccat ccgtgaggcc   3540
caggcttctg ggcttaatgt ggtgatgttg ggaatggctg agcggaccc agagcagctg   3600
cgtcgcttgg cgccgggtat ggactctgtc cagaccttct tcgccgtgga tgatgggcca   3660
agcctggacc aggcagtcag tggtctggcc acagccctgt gtcaggcatc cttcactact   3720
cagccccggc cagagccctg cccagtgtat tgtccaaagg ccagaaggg ggaacctgga   3780
gagatgggcc tgagaggaca agttgggcct cctggcgacc ctgcctccc gggcaggacc   3840
```

-continued

```
ggtgctcccg gcccccaggg gcccctggga agtgccactg ccaagggcga gagggggcttc  3900
cctggagcag atgggcgtcc aggcagccct ggccgcgccg ggaatcctgg gacccctgga  3960
gcccctggcc taaagggctc tccagggttg cctggccctc gtggggaccc gggagagcga  4020
ggacctcgag gcccaaaggg ggagccgggg gctcccggac aagtcatcgg aggtgaagga  4080
cctggccttc ctgggcggaa aggggaccct ggaccatcgg gcccccctgg acctcgtgga  4140
ccactggggg acccaggacc ccgtggcccc ccagggcttc ctggaacagc catgaagggt  4200
gacaaaggcg atcgtgggga gcggggtccc cctggaccag gtgaaggtgg cattgctcct  4260
ggggagcctg ggctgccggg tcttcccgga agccctggac cccaaggccc cgttggcccc  4320
cctggaaaga aaggagaaaa aggtgactct gaggatggag ctccaggcct cccaggacaa  4380
cctgggtctc cgggtgagca gggcccacgg ggacctcctg gagctattgg ccccaaaggt  4440
gaccggggct ttccagggcc cctgggtgag gctggagaga agggcgaacg tggacccccca  4500
ggcccagcgg gatcccgggg gctgccaggg gttgctggac gtcctggagc caagggtcct  4560
gaagggccac caggacccac tggccgccaa ggagagaag gggagcctgg tcgccctggg  4620
gaccctgcag tggtgggacc tgctgttgct ggacccaaga gagaaaaggg agatgtgggg  4680
cccgctgggc ccagaggagc taccggagtc caagggaaac gggggcccacc cggcttggtt  4740
cttcctggag acccctggccc caagggagac cctggagacc ggggtcccat tggccttact  4800
ggcagagcag gacccccagg tgactcaggg cctcctggag agaagggaga ccctgggcgg  4860
cctggccccc caggacctgt tggcccccga ggacgagatg gtgaagttgg agagaaaggt  4920
gacgaggggtc ctccgggtga cccgggtttg cctggaaaaa caggcgagcg tggccttcgg  4980
ggggcacctg gagttcgggg gcctgtgggt gaaaagggag accagggaga tcctggagag  5040
gatggacgaa atggcagccc tggatcatct ggacccaagg gtgaccgtgg ggagccgggt  5100
cccccaggac ccccggggacg gctggtagac acaggacctg gagccagaga gaagggagag  5160
cctgggggacc gcggacaaga gggtcctcga gggcccaagg gtgatcctgg cctccctgga  5220
gcccctgggg aaaggggcat tgaagggtt cggggacccc caggcccaca gggggaccca  5280
ggtgtccgag gcccagcagg agaaaagggt gaccggggtc ccctgggct ggatggccgg  5340
agcggacctg atgggaaacc aggaccgcgt gggccctctg ggccgaatgg tgctgcaggc  5400
aaagctgggg acccagggag agacgggctt ccaggcctcc gtggagaaca gggcctccct  5460
ggcccctctg gtccccctgg attaccggga aagccaggcg aggatggcaa acctggcctg  5520
aatggaaaaa acgagaacc tggggaccct ggagaagacg ggaggaaggg agagaaagga  5580
gattcaggcg cctctgggag agaaggtcgt gatggcccca agggtgagcg tggagctcct  5640
ggtatccttg gaccccaggg gcctccaggc ctcccagggc cagtgggccc tcctggccag  5700
ggtttttcctg gtgtcccagg aggcacgggc cccaagggtg accgtgggga gactggatcc  5760
aaagggggagc agggcctccc tggagagcgt ggcctgcgag gagagcctgg aagtgtgccg  5820
aatgtggatc ggttgctgga aactgctggc atcaaggcat ctgccctgcg ggagatcgtg  5880
gagacctggg atgagagctc tggtagcttc ctgcctgtgc ccgaacggcg tcgaggcccc  5940
aagggggact caggcgaaca gggcccccca ggcaaggagg gccccatcgg ctttcctgga  6000
gaacgcgggc tgaagggcga ccgtggagac cctggccctc aggggccacc tggtctggcc  6060
cttggggaga ggggcccccc cgggccttcc ggccttgccg gggagcctgg aaagcctggt  6120
attcccgggc tcccaggcag ggctggggt gtgggagag caggaaggcc aggagagagg  6180
ggagaacggg gagagaaagg agaacgtgga gaacagggca gagatggccc tcctggactc  6240
cctgaaccc ctgggcccccc cggacccccct ggccccaagg tgtctgtgga tgagccaggt  6300
cctggactct ctggagaaca gggacccccct ggactcaagg gtgctaaggg ggagccgggc  6360
agcaatggtg accaaggtcc caaaggagac aggggtgtgc caggcatcaa aggagaccgg  6420
ggagagcctg gaccgagggg tcaggacggc aacccgggtc taccaggaga gcgtggtatg  6480
gctgggcctg aagggaagcc gggtctgcag ggtccaagag gcccccctgg cccagtgggt  6540
ggtcatggag accctggacc acctggtgcc ccgggtcttg ctggcctgc aggaccccaa  6600
ggaccttctg gcctgaaggg ggagcctgga gagacagacc ctccaggccg gggcctgact  6660
ggacctactg gagctgtggg acttcctgga ccccccggcc cttcaggcct tgtgggtcca  6720
caggggtctc caggtttgcc tggacaagtg ggggagacag ggaagccggg agccccaggt  6780
cgagatggtg ccagtggaaa agatggagac agagggagcc ctggtgtgcc agggtcacca  6840
ggtctgcctg gccctgtcgg acctaaagga gaacctggcc cacgggggc ccctggacag  6900
gctgtggtcg ggctccctgg agcaaaggga gagaagggag cccctggagg ccttgctgga  6960
gacctggtgg gtgagccggg agccaaaggt gaccgaggac tgccaggcc gcgaggcgag  7020
aagggtgaag ctggccgtgc aggggagccc ggagaccctg gggaagatgg tcagaaaggg  7080
gctccaggac ccaaaggttt caaggtgac ccaggagtcg gggtcccggg ctcccctggg  7140
cctcctggcc ctccaggtgt gaagggagat ctgggcctcc ctggcctgcc cggtgctcct  7200
ggtgttgttg ggttcccggg tcagacaggc cctcgaggag agatgggtca gccaggccct  7260
agtggagagc ggggtctggc aggcccccca gggagagaag gaatcccagg accctggggg  7320
ccacctggac caccgggggtc agtgggacca cctgggggcct ctggactcaa aggagacaag  7380
ggagaccctg gagtaggggt gcctgggccc cgaggcgagc gtggggagcc aggcatccgg  7440
ggtgaagatg gccgccccgg ccaggaggga cccgaggac tcacggggcc ccctggcagc  7500
aggggagagc gtgggagaa gggtgatgtt gggagtgcag gactaaaggg tgacaaggga  7560
gactcagctg tgatcctggg gcctccaggc ccacggggtg ccaaggggga catgggtgaa  7620
cgaggccctc ggggcttgga tggtgacaaa ggacctcggg gagacaatgg gaccctggt  7680
gacaagggca gcaagggaga gcctggtgac aagggctcag ccgggttgcc aggactcgct  7740
ggactcctgg gaccccaggg tcaacctggt gcagcaggga tccctggtga cccgggatcc  7800
ccaggaaagg atgggagtgcc tggtatccga ggagaaaaag gagatgttgg cttcatgggt  7860
cccccggggcc tcaagggtga cggggggagtg aagggagcct gtggccttga tggagagaag  7920
ggagacaagg agaaggtga tccccaggc cgccccgggc tggcaggaca caaaggagag  7980
atgggggagc ctggtgtgcc gggccagtcg ggggcccctg gcaaggaggg cctgatcggt  8040
cccaagggtg accgaggctt tgacgggcag ccaggcccca agggtgacca gggcgagaaa  8100
ggggagcggg gaacccagg aattggggggc ttcccaggcc ccagtggaaa tgatggctct  8160
gctggtcccca cagggccacc tggcagtgtt ggtcccagag ccccgaagg acttcagggc  8220
cagaagggtg agcgaggtcc ccccgaggag agagtggtgg ggctcctgg ggtccctgga  8280
gctcctggcg agagagggga gcagggcgg ccagggcctg ccggtcctcg aggcgagaag  8340
ggagaagctg cactgacgga ggatgacatc cggggctttg tgcgcaaga gatgagtcag  8400
cactgtgcct gccagggcca gttcatcgca tctggatcac gacccctccc tagttatgct  8460
gcagacactg ccggctccca gctccatgct gtgcctgtgc tccgcgtctc tcatgcagag  8520
gaggaagagc gggtaccccc tgaggatgat gagtactctg aatactccga gtattctgtg  8580
```

```
gaggagtacc aggaccctga agctccttgg gatagtgatg acccctgttc cctgccactg    8640
gatgagggct cctgcactgc ctacaccctg cgctggtacc atcgggctgt gacaggcagc    8700
acagaggcct gtcacccttt tgtctatggt ggctgtggag ggaatgccaa ccgttttggg    8760
acccgtgagg cctgcgagcg ccgctgccca ccccgggtgg tccagagcca ggggacaggt    8820
actgcccagg acagggccaa gaggggcagc ggcgagggca ggggcagcct gctgacctgc    8880
ggcgacgtgg aggagaaccc cggccccacc tcctcggggc ctggaccccg gttcctgctg    8940
ctgctgccgc tgctgctgcc ccctgcggcc tcagcctccg accggccccg gggccgagac    9000
ccggtcaacc cagagaagct gctggtgatc actgtggcca cagctgaaac cgaggggtac    9060
ctgcgtttcc tgcgctctgc ggagttcttc aactacactg tgcggaccct gggcctggga    9120
gaggagtggc gagggggtga tgtggctcga acagttggtg gaggacagaa ggtccggtgg    9180
ttaaagaagg aaatggagaa atacgctgac cgggaggata tgatcatcat gtttgtggat    9240
agctacgacg tgattctggc cggcagcccc acagagctgc tgaagaagtt cgtccagagt    9300
ggcagccgcc tgctcttctc tgcagagagc ttctgctggc ccgagtgggg gctggcggag    9360
cagtaccctg aggtgggcac ggggaagcgc ttcctcaatt ctggtggatt catcggtttt    9420
gccaccacca tccaccaaat cgtgcgccag tggaagtaca aggatgatga cgacgaccag    9480
ctgttctaca cacggctcta cctggaccca ggactgaggg agaaactcag ccttaatctg    9540
gatcataagt ctcggatctt tcagaacctc aacgggcttt tagatgaagt ggttttaaag    9600
tttgatcgga accgtgtgcg tatccggaac gtggcctacg acacgctccc cattgtggtc    9660
catgaaacg gtcccactaa gctgcagctc aactacctgg gaaactacgt ccccaatggc    9720
tggactcctg agggaggctg tggcttctgc aaccaggacc ggaggacact cccgggggggg    9780
cagcctcccc cccgggtgtt tctggccgtg tttgtggaac agcctactcc gtttctgccc    9840
cgcttcctgc agcggctgct actcctggac tatcccccg acagggtcac cctttttcctg    9900
cacaacaacg aggtcttcca tgaacccac atcgctgact cctggccgca gctccaggac    9960
cacttctcag ctgtgaagct cgtgggggccg gaggaggctc tgagcccagg cgaggccagg   10020
gacatggcca tggacctgtg tcggcaggac cccgagtgtg agttctactt cagcctggac   10080
gccgacgctg tcctcaccaa cctgacgacc ctgcgtatcc tcattgagga gaacaggaag   10140
gtgatcgccc ccatgctgtc ccgccacggc aagctgtggt ccaacttctg gggcgccctg   10200
agccccgatg agtactacgc ccgctccgag gactacgtgg agctggtgca gcggaagcga   10260
gtgggtgtgt ggaatgtacc atacatctcc caggcctatg tgatccgggg tgatacctg    10320
cggatggagc tgccccagag ggatgtgttc tcgggcagtg acacagacca ggacatggcc   10380
ttctgtaaga gctttcgaga caagggcatc ttcctccatc tgagcaatca gcatgaattt   10440
ggccggctcc tggccacttc cagatacgac acggagcacc tgcaccccga cctctggcag   10500
atcttcgaca accccgtcga ctggaaggag cagtacatcc acgagaacta cagccgggcc   10560
ctggaagggg aaggaatcgt ggagcagcca tgcccggacg tgtactggtt cccactgctg   10620
tcagaacaaa tgtgtgatga gctggtggca gagatgaagc actacggcca gtggtcaggc   10680
ggccggcatg aggattcaag gctggctgga ggctacgaga atgtgcccac cgtggacatc   10740
cacatgaagc aggtgggggta cgaggaccag tggctcagc tgctgcggac gtatgtgggc   10800
cccatgaccg agagcctgtt tcccggttac cacaccaagg cgcgggcggt gatgaacttt   10860
gtggttcgct accggccaga cgagcagccg tctctgccgg cacaccacga ctcatccacc   10920
ttcaccctca acgttgccct caaccacaag ggcctggact atgagggagg tggctgccgc   10980
ttcctgcgct acgactgtgt gatctcctcc ccgaggaagg gctgggcact cctgcacccc   11040
ggccgcctca cccactacca cgaggggctg ccaacgacct ggggcacacg ctacatcatg   11100
gtgtcctttg tcgacccctg a                                           11121
```

SEQ ID NO: 14          moltype = AA   length = 3706
FEATURE                Location/Qualifiers
REGION                 1..3706
                       note = Synthetic Construct
source                 1..3706
                       mol_type = protein
                       organism = synthetic construct
SEQUENCE: 14
MTLRLLVAAL CAGILAEAPR VRAQHRERVT CTRLYAADIV FLLDGSSSIG RSNFREVRSF    60
LEGLVLPFSG AASAQGVRFA TVQYSDDPRT EFGLDALGSG GDVIRAIREL SYKGGNTRTG   120
AAILHVADHV FLPQLARPGV PKVCILITDG KSQDLVDTAA QRLKGQGVKL FAVGIKNADP   180
EELKRVASQP TSDFFFFVND FSILRTLLPL VSRRVCTTAG GVPVTRPPDD STSAPRDLVL   240
SEPSSQSLRV QWTAASGPVT GYKVQYTPLT GLGQPLPSER QEVNVPAGET SVRLRGLRPL   300
TEYQVTVIAL YANSIGEAVS GTARTTALEG PELTIQNTTA HSLLVAWRSV PGATGYRVTW   360
RVLSGGPTQQ QELGPGQGSV LLRDLEPGTD YEVTVSTLFG RSVGPATSLM ARTDASVEQT   420
LRPVILGPTS ILLSWNLVPE ARGYRLEWRR ETGLEPPQKV VLPSDVTRYQ LDGLQPGTEY   480
RLTLYTLLEG HEVATPATVV PTGPELPVSP VTDLQATELP GQRVRVSWSP VPGATQYRII   540
VRSTQGVERT LVLPGSQTAF DLDDVQAGLS YTVRVSARVG PREGSASVLT VRREPETPLA   600
VPGLRVVVSD ATRVRVAWGP VPGASGFRIS WSTGSGPESS QTLPPDSTAT DITGLQPGTT   660
YQVAVSVLRG REEGPAAVIV ARTDPLGPVR TVHVTQASSS SVTITWTRVP GATGYRVSWH   720
SAHGPEKSQL VSGEATVAEL DGLEPDTEYT VHVRAHVAGV DGPPASVVVR TAPEPVGRVS   780
RLQILNASSD VLRITWVGVT GATAYRLAWG RSEGGPMRHQ ILPGNTDSAE IRGLEGGVSY   840
SVRVTALVGD REGTPVSIVV TTPPEAPPAL GTLHVVQRGE HSLRLRWEPV PRAQGFLLHW   900
QPEGGQEQSR VLGPELSSYH LDGLEPATQY RVRLSVLGPA GEGPSAEVTA RTESPRVPSI   960
ELRVVDTSID SVTLAWTPVS RASSYILSWR PLRGPGQEVP GSPQTLPGIS SSQRVTGLEP   1020
GVSYIFSLTP VLDGVRGPEA SVTQTPVCPR GLADVVFLPH ATQDNAHRAE ATRRVLERLV   1080
LALGPLGPQA VQVGLLSYSH RPSPLFPLNG SHDLGIILQR IRDMPYMDPS GNNLGTAVVT   1140
AHRYMLAPDA PGRRQHVPGV MVLLVDEPLR GDIFSPIREA QASGLNVVML GMAGADPEQL   1200
RRLAPGMDSV QTFFAVDDGP SLDQAVSGLA TALCQASFTT QPRPEPCPVY CPKGQKGEPG   1260
EMGLRGQVGP PGDPGLPGRT GAPGPQGPPG SATAKGERGF PGADGRPGSP GRAGNPGTPG   1320
APGLKGSPGL PGPRGDPGER GPRGPKGEPG APGQVIGGEG PGLPGRKGDP GPSGPPGPRG   1380
PLGDPGPRGP PGLPGTAMKG DKGDRGERGP PGPGEGGIAP GEPGLPGLPG SPGPQGPVGP   1440
PGKKGEKGDS EDGAPGLPGQ PGSPGEQGPR GPPGAIGPKG DRGFPGPLGE AGEKGERGPP   1500
GPAGSRGLPG VAGRPGAKGP EGPPGPTGRQ GEKGEPGRPG DPAVVGPAVA GPKGEKGDVG   1560
PAGPRGATGV QGERGPPGLV LPGDPGPGKD PGDRGPIGLT GRAGPPGDSG PPGEKGDPGR   1620
```

-continued

```
PGPPGPVGPR  GRDGEVGEKG  DEGPPGDPGL  PGKAGERGLR  GAPGVRGPVG  EKGDQGDPGE  1680
DGRNGSPGSS  GPKGDRGEPG  PPGPPGRLVD  TGPGAREKGE  PGDRGQEGPR  GPKGDPGLPG  1740
APGERGIEGF  RGPPGPQGDP  GVRGPAGEKG  DRGPPGLDGR  SGLDGKPGAA  GPSGPNGAAG  1800
KAGDPGRDGL  PGLRGEQGLP  GPSGPPGLPG  KPGEDGKPGL  NGKNGEPGDP  GEDGRKGEKG  1860
DSGASGREGR  DGPKGERGAP  GILGPGQPPG  LPGPVGPPGQ  GFPGPVGGTG  PKGDRGETGS  1920
KGEQGLPGER  GLRGEPGSVP  NVDRLLETAG  IKASALREIV  ETWDESSGSF  LPVPERRRGP  1980
KGDSGEQGPP  GKEGPIGFPG  ERGLKGDRGD  PGPQGPPGLA  LGERGPPGPS  GLAGEPGKPG  2040
IPGLPGRAGG  VGEAGRPGER  GERGEKGERG  EQGRDGPPGL  PGTPGPPGPP  GPKVSVDEPG  2100
PGLSGEQGPP  GLKGAKGEPG  SNGDQGPKGD  RGVPGIKGDR  GEPGPRGQDG  NPGLPGERGM  2160
AGPEGKPGLQ  GPRGPPGPVG  GHGDPGPPGA  PGLAGPAGPQ  GPSGLKGEPG  ETGPPGRGLT  2220
GPTGAVGLPG  PPGPSGLVGP  QGSPGLPGQV  GETGKPGAPG  RDGASGKDGD  RGSPGVPGSP  2280
GLPGPVGPKG  EPGPTGAPGQ  AVVGLPGAKG  EKGAPGGLAG  DLVGEPGAKG  DRGLPGPRGE  2340
KGEAGRAGEP  GDPGEDGQKG  APGPKGFKGD  PGVGVPGSPG  PPGPPGVKGD  LGLPGLPGAP  2400
GVVGFPGQTG  PRGEMGQPGP  SGERGLAGPP  GREGIPGPLG  PPGPPGSVGP  PGASGLKGDK  2460
GDPGVGLPGP  RGERGEPGIR  GEDGRPGQEG  PRGLTGPPGS  RGERGEKGDV  GSAGLKGDKG  2520
DSAVILGPPG  PRGAKGDMGE  RGPRGLDGDK  GPRGDNGDPG  DKGSKGEPGD  KGSAGLPGLR  2580
GLLGPQGQPG  AAGIPGDPGS  PGKDGVPGIR  GEKGDVGFMG  PRGLKGERGV  KGACGLDGEK  2640
GDKGEAGPPG  RPGLAGHKGE  MGEPGVPGQS  GAPGKEGLIG  PKGDRGFDGQ  PGPKGDQGEK  2700
GERGTPGIGG  FPGPSGNDGS  AGPPGPPGSV  GPRGPEGLQG  QKGERGPPGE  RVVGAPGVPG  2760
APGERGEQGR  PGPAGPRGEK  GEAALTEDDI  RGFVRQEMSQ  HCACQGQFIA  SGSRPLPSYA  2820
ADTAGSQLHA  VPVLRVSHAE  EEERVPPEDD  EYSEYSEYSV  EEYQDPEAPW  DSDDPCSLPL  2880
DEGSCTAYTL  RWYHRAVTGS  TEACHPFVYG  GCGGNANRFG  TREACERRCP  PRVVQSQGTG  2940
TAQDRAKRGS  GEGRGSLLTC  GDVEENPGPT  SSGPGPRFLL  LLPLLLLPPAA  SASDRPRGRD  3000
PVNPEKLLVI  TVATAETEGY  LRFLRSAEFF  NYTVRTLGLG  EEWRGGDVAR  TVGGGQKVRW  3060
LKKEMEKYAD  REDMIIMFVD  SYDVILAGSP  TELLKKFVQS  GSRLLFSAES  FCWPEWGLAE  3120
QYPEVGTGKR  FLNSGGFIGF  ATTIHQIVRQ  WKYKDDDDDQ  LFYTRLYLDP  GLREKLSLNL  3180
DHKSRIFQNL  NGALDEVVLK  FDRNRVRIRN  VAYDTLPIVV  HGNGPTKLQL  NYLGNYVPNG  3240
WTPEGGCGFC  NQDRRTLPGG  QPPPRVFLAV  FVEQPTPFLP  RFLQRLLLLD  YPPDRVTLFL  3300
HNNEVFHEPH  IADSWPQLQD  HFSAVKLVGP  EEALSPGEAR  DMAMDLCRQD  PECEFYFSLD  3360
ADAVLTNLQT  LRILIEENRK  VIAPMLSRHG  KLWSNFWGAL  SPDEYYARSE  DYVELVQRKR  3420
VGVWNVPYIS  QAYVIRGDTL  RMELPQRDVF  SGSDTDPDMA  FCKSFRDKGI  FLHLSNQHEF  3480
GRLLATSRYD  TEHLHPDLWQ  IFDNPVDWKE  QYIHENYSRA  LEGEGIVEQP  CPDVYWFPLL  3540
SEQMCDELVA  EMEHYGQWSG  GRHEDSRLAG  GYENVPTVDI  HMKQVGYEDQ  WLQLLRTYVG  3600
PMTESLFPGY  HTKARAVMNF  VVRYRPDEQP  SLRPHHDSST  FTLNVALNHK  GLDYEGGGCR  3660
FLRYDCVISS  PRKGWALLHP  GRLTHYHEGL  PTTWGTRYIM  VSFVDP              3706
```

```
SEQ ID NO: 15             moltype = DNA  length = 11121
FEATURE                   Location/Qualifiers
misc_feature              1..11121
                          note = Synthetic Construct
source                    1..11121
                          mol_type = other DNA
                          organism = synthetic construct
SEQUENCE: 15
atgacctcct cggggcctgg accccggttc ctgctgctgc tgccgctgct gctgccccct  60
gcggcctcag cctccgaccg gccccggggc cgagacccgg tcaacccaga gaagctgctg  120
gtgatcactg tggccacagc tgaaaccgag gggtacctgc gtttcctgcg ctctgcggag  180
ttcttcaact acactgtgcg gaccctgggc ctgggagagg agtggcgagg gggtgatgtg  240
gctcgaacag ttggtggagg acagaaggtc cggtggttaa agaaggaaat ggagaaatac  300
gctgaccggg aggatatgat catcatgttt gtggatagct acgacgtgat tctggccggc  360
agccccacag agctgctgaa gaagttcgtc cagagtgcgg gccgcctgct cttctctgca  420
gagagcttct gctggcccga gtgggggctg cgcgagcagt accctgaggt gggcacgggg  480
aagcgcttcc tcaattctgg tggattcatc ggttttgcca ccaccatcca ccaaatcgtg  540
cgccagtgga gtacaagga tgatgacgac gaccagctgt tctacacacg gctctacctg  600
gacccaggac tgaggga gaa actcagcctt aatctggatc ataagtctcg gatctttcag  660
aacctcaacg gggctttaga tgaagtggtt ttaaagtttg atcggaaccg tgtgcgtatc  720
cggaacgtgg cctacgacac gctccccatt gtggtccatg gaaacggtcc cactaagctg  780
cagctcaact acctgggaaa ctacgtcccc aatggctgga ctcctgaggg aggctgtggc  840
ttctgcaacc aggaccggag gacactcccg ggggggccagc ctccccccg ggtgtttctg  900
gccgtgtttg tggaacagcc tactccgttt ctgccccgct cctgcagcg gctgctactc  960
ctggactatc cccccgacag ggtcacccct ttcctgcaca caacgaggt cttccatgaa  1020
ccccacatcg ctgactcctg gccgcagctc caggaccact tctcagctgt gaagctcgtg  1080
gggccggagg aggctctgag cccaggcgag gccagggaca tggccatgga cctgtgtcgg  1140
caggaccccg agtgtgagtt ctacttcagc ctggacgccg acgctgtcct caccaacctg  1200
cagaccctgc gtatcctcat tgaggagaac aggaaggtga tcgcccccat gctgtcccgg  1260
cacggcaagc tgtggtccaa cttctggggc gccctgagcc ccgatgagta ctacgcccgc  1320
tccgaggact acgtggagct ggtgcagcgg aagcgagtgg gtgtgtggaa tgtaccatac  1380
atctcccagg cctatgtgat ccggggtgat accctgcgga tggagctgcc ccagaggga  1440
gtgttctcgg gcagtgacac agaccccgac atggccttct gtaagagctt ccgagacaag  1500
ggcatcttcc tccatctgag caatcagcat gaatttggcc ggctcctggc cacttccaga  1560
tacgacacgg agcacctgca ccccgacctc tggcagatct cgacaacccc cgtcgactgg  1620
aaggagcagt acatccacga gaactacagc cgggccctgg aaggggaagg aatcgtggag  1680
cagccatgcc cggacgtgta ctggttccca ctgctgtcag aacaaatgtg tgatgagctg  1740
gtggcagaga tggagcacta cggccagtgg tcaggcggcc gtcatgagga ttcaaggctg  1800
gctggaggct acgagaatgt gcccaccgtg gacatccaca tgaagcaggt ggggtacgag  1860
gaccagtggc tgcagctgct gcggacgtat gtgggcccca tgaccgagag cctgtttccc  1920
ggttaccaca ccaaggcgcg ggcggtgatg aactttgtgg ttcgctaccg ccagacgag  1980
cagccgtctc tgcggccaca ccacgactca tccacctcca cctcaacgt tgccctcaac  2040
cacaagggcc tggactatga gggaggtggc tgccgcttcc tgcgctacga ctgtgtgatc  2100
```

-continued

```
tcctccccga ggaagggctg ggcactcctg cacccaggcc gcctcaccca ctaccacgag  2160
gggctgccaa cgacctgggg cacacgctac atcatggtgt cctttgtcga ccccagggcc  2220
aagaggggca gcggcgaggg caggggcagc ctgctgacct gcggcgacgt ggaggagaac  2280
cccgccccca cgctgcggct tctggtggcc gcgctctgcg ccgggatcct ggcagaggcg  2340
ccccgagtgc gagcccagca cagggagaga gtgacctgcc gcggcctta cgccgctgac  2400
attgtgttct tactggatgg ctcctcatcc attggccgca gcaatttccg cgaggtccgc  2460
agctttctcg aagggctggt gctgcctttc tctggagcag ccagtgcaca gggtgtgcgc  2520
tttgccacag tgcagtacag cgatgaccca cggacagagt tcggcctgga tgcacttggc  2580
tctgggggtg atgtgatccg cgccatccgt gagcttagct acaagggggg caacactcgc  2640
acaggggctg caattctcca tgtggctgac catgtcttcc tgccccagct ggcccgacct  2700
ggtgtcccca aggtctgcat cctgatcaca cacgggaagt cccaggacct ggtggacaca  2760
gctgcccaaa ggctgaaggg gcagggggtc aagctatttg ctgtggggat caagaatgct  2820
gaccctgagg agctgaagcg agttgcctca cagcccacca gtgacttctt cttcttcgtc  2880
aatgacttca gcatcttgag gacactactg cccctcgttt cccggagagt gtgcacgact  2940
gctggtggcg tgcctgtgac ccgacctccg gatgactcga cctctgctcc acgagacctg  3000
gtgctgtctg agccaagcag ccaatccttg agagtacagt ggacagcggc cagtggccct  3060
gtgactggct acaaggtcca gtacactcct ctgacggggc tgggacagcc actgccgagt  3120
gagcggcagg aggtgaacgt cccagctggt gagaccaggt gcgcgctgcg gggtctccgg  3180
ccactgaccg agtaccaagt gactgtgatt gccctctacg ccaacagcat cggggaggct  3240
gtgagcggga cagctcggac cactgcccta gaagggccgg aactgaccat ccagaatacc  3300
acagcccaca gcctcctggt ggcctggcgg agtgtgccag gtgccactgg ctaccgtgtg  3360
acatggcggg tcctcagtgg tgggcccaca cagcagcagg agctgggcc tgggcagggt  3420
tcagtgttgc tgcgtgactt ggagcctggc acggactatg aggtgaccgt gagcacccta  3480
tttggccgca gtgtgggggcc cgccacttcc ctgatggctc gcactgacgc ttctgttgag  3540
cagacctgc gcccggtcat cctgggcccc acatccatcc tcctttcctg gaacttggtg  3600
cctgaggccc gtggctaccg gttggaatgg cggcgtgaca ctggcttgga gccaccgcag  3660
aaggtggtac tgccctctga tgtgaccgc taccagttgg atgggctgca gccgggcact  3720
gagtaccgcc tcacactcta cactctgctg gagggccacg aggtggccac ccctgcaacc  3780
gtggttccca ctgaccagc gctgcctgtg agccctgtaa cagacctgca agccaccgag  3840
ctgcccgggc agcgggtgcg agtgtcctga agcccagtcc ctggtgccac ccagtaccgc  3900
atcattgtgc gcagcaccca gggggttgag cggaccctgg tgcttcctgg gagtcagaca  3960
gcattcgact tggatgacgt tcaggctggg cttagctaca ctgtgcgggt gtctgctcga  4020
gtgggtcccc gtgagggcag tgccagtgtc ctcactgtcc gccgggagcc ggaaactcca  4080
cttgctgttc caggggctgcg ggttgtggtg tcagatgcaa cgcgagtgag ggtggcctgg  4140
ggaccgtcc ctggagccag tggatttcgg attagctgga gcacaggcag tggtccggag  4200
tccagccaga cactgccccc agactctact gccacagaca tcacagggct gcagcctgga  4260
accacctacc aggtggctgt gtcggtactg cgaggcagag aggagggccc tgctgcagtc  4320
atcgtggctc gaacggaccc actgggccca gtgaggacg tccatgtgac tcaggccagc  4380
agctcatctg tcaccattac ctggaccagg gttcctggcc ccacaggata caggtttccc  4440
tggcactcag cccacggccc agagaaatcc cagttggttt ctggggaggc cacggtggct  4500
gagctccatg gactggagcc agatactgag tatacggtgc atgtgagggc ccatgtggct  4560
ggcgtggatg ggcccccgc ctctgtggtt gtgaggactg ccctgagcc tgtgggtcgt  4620
gtgtcgaggc tgcagatcct caatgcttcc agcgacgttc tacggatcac ctgggtaggg  4680
gtcactggag ccacagctta cagactggcc tggggccgga gtgaaggcgg ccccatgagg  4740
caccagatac tcccaggaaa cacagactct gcagagatcc ggggtctcga aggtggagtc  4800
agctactcag tgcgagtgac tgcacttgtc ggggaccgcg agggcacacc tgtctccatt  4860
gttgtcacta cgccgcctga ggctccgcca gccctgggaa cgcttcacgt ggtgcagcgc  4920
ggggagcact cgctgaggct gcgctgggag ccggtgccca gagcgcaggg cttccttctg  4980
cactggcaac ctgagggtgg ccaggaacag tcccgggtcc tggggcccga gctcagcagc  5040
tatcacctgg acgggctgga gccagcgaca cagtaccgcg tgaggctgag tgtcctaggg  5100
ccagctggag aagggccctc tgcagaggtg actgcgcgca ctgagtcacc tcgtgttcca  5160
agcattgaac tacgtgtggt ggacacctcg atcgactcgg tgactttggc ctggactcca  5220
gtgtccaggg catccagcta catcctatcc tggcggccac tcagaggccc tggccaggaa  5280
gtgcctgggt ccccgcagac acttccaggg atctcaagct cccagcgggt gacagggcta  5340
gagcctggcg tctcttacat cttctccctg acgcctgtcc tggatggtgt gcggggtcct  5400
gaggcatctg tcacacagac gccagtgtgc ccccgtggcc tggcggatgt ggtgttccta  5460
ccacatgcca ctcaagacaa tgctcaccgt gcggaggcta cgaggagggt cctggagcgt  5520
ctggtgttgg cacttgggcc tcttgggcca caggcagttc aggttggcct gctgtcttac  5580
agtcatcggc cctccccact gttcccactg aatggctccc atgaccttgg cattatcttg  5640
caaaggatcc gtgacatgcc ctacatggac ccaagtggga acaacctggg cacagccgtg  5700
gtcacagctc acagatacat gttggcacca gatgctcctg ggcgccgcca gcacgtacca  5760
ggggtgatgg ttctgctagt ggatgaaccc ttgagaggtg acatattcag ccccatccgt  5820
gaggcccagg cttctgggct taatgtggtg atgttgggaa tggctggagc ggacccagag  5880
cagctgcgtc gcttggcgcc gggtatggac tctgtccaga ccttcttcgc cgtggatgat  5940
gggcaagcc tggaccaggc agtcagtggt ctggccacag ccctgtgtca ggcatccttc  6000
actactcagc cccggccaga gccctgccca gtgtattgtc caaagggcca gaaggggaa  6060
cctgagagag tgggcctgag aggacaagtt gggcctcctg cgaccctggg cctcccgggc  6120
aggaccggtg ctcccggccc ccagggggcc cctggaagtg ccactgccaa gggcgagagg  6180
ggcttccctg gagcagatgg gcgtccaggc agccctggcc gcgccggaaa tcctgggacc  6240
cctgagccc ctggcctaaa gggctctcca gggttgcctg gccctcgtgg ggacccggga  6300
gagcgaggac ctcgaggccc aaaggggag ccgggggctc ccggacaagt catcggaggt  6360
gaaggacctg ggcttcctgg gcggaaaggg gaccctggac catcgggccc ccctggacct  6420
cgtggaccac tgggggaccc aggaccccgt ggccccccag ggcttcctgg aacagccatg  6480
aagggtgaca aaggcgatcg tggggagcgg ggtccccctg gaccaggtga aggtggcatt  6540
gctcctgggg agcctgggct gccgggtctt cccggaagcc ctggacccca aggccccgtt  6600
ggcccccctg gaaagaaagg agaaaaaggt gactctgagg atggagctcc aggcctccca  6660
ggacaacctg ggtctccggg tgagcagggc ccacgggac ctcctggagc tattggcccc  6720
aaaggtgacc ggggcttttcc agggcccctg ggtgaggctg gagagaaggg cgaacgtgga  6780
cccccaggcc cagcgggatc ccgggggctg ccaggggttg ctggacgtcc tggagccaag  6840
```

-continued

```
ggtcctgaag ggccaccagg acccactggc cgccaaggag agaagggga gcctggtcgc   6900
cctgggacc ctgcagtggt gggacctgct gttgctggac ccaaaggaga aaagggagat   6960
gtgggccccg ctgggcccag aggagctacc ggagtccaag gggaacgggg cccaccggc    7020
ttggttcttc ctggagaccc tggccccaag ggagaccctg gagaccgggg tcccattggc   7080
cttactggca gagcaggacc cccaggtgac tcagggcctc ctggagagaa gggagacct    7140
gggcggcctg gcccccagg acctgttggc ccccgaggac gagatggtga agttggagag    7200
aaaggtgacg agggtcctcc gggtgacccg ggtttgcctg gaaaagcagg cgagcgtggc    7260
cttcgggggg cacctggagt tcggggggcct gtgggtgaaa agggagacca gggagatcct   7320
ggagaggatg gacgaaatgg cagccctgga tcatctggac ccaagggtga ccgtggggag    7380
ccgggtcccc caggacccct gggacggctg gtagacacag gacctggagc cagagagaag   7440
ggagagcctg gggaccgcgg acaagaggt cctcgagggc ccaagggtga tcctggcctc    7500
cctggagccc ctggggaaag gggcattgaa gggtttcggg gaccccccagg cccacagggg   7560
gacccaggtg tccgaggccc agcaggagaa aagggtgacc ggggtccccc tgggctggat    7620
ggccggagcg gactggatgg gaaaccagga gccgctggtc cctctgggcc gaatggtgct    7680
gcaggcaaag ctggggaccc agggagagac gggcttccag gcctccgtgg agaacagggc    7740
ctccctggcc cctctggtcc ccctggatta ccgggaaagc caggcgagga tggcaaacct    7800
ggcctgaatg gaaaaaacgg agaacctggg gaccctggag aagacgggag gaaggagag    7860
aaaggagatt caggcgcctc tgggagagaa ggtcgtgatg gcccaaggg tgagcgtgga   7920
gctcctggta tccttggacc ccagggcct ccaggcctcc cagggccagt gggccctcct    7980
ggccaggtt ttcctggtgt cccaggagc acgggcccca agggtgaccg tggggagact    8040
ggatccaaag gggagcaggg cctccctgga gagcgtggcc tgcgaggaga gcctggaagt    8100
gtgccgaatg tggatcggtt gctggaaact gctggcatca aggcatctgc cctgcgggag    8160
atcgtggaga cctgggatga gagctctggt agcttcctgc ctgtgcccga acggcgtcga    8220
ggccccaagg gggactcagg cgaacagggc cccccaggca aggagggccc catcggcttt    8280
cctggagaac gcgggctgaa gggcgaccgt ggagaccctg ccctcagggg gccacctggt    8340
ctggccettg gggagagggg cccccccggg ccttccggga ttgccgggga gcctggaaag    8400
cctggtattc ccgggctccc aggccagggct gggggtgtgg gagaggcagg aaggccagga    8460
gagaggggag aacgggggaga gaaaggagaa cgtggagaac agggcagaga tggccctcct    8520
ggactccctg gaaccctgg gcccccggga cccctggcc ccaaggtgtc tgtggatgag    8580
ccaggtcctg gactctctgg agaacaggga cccctggc tcaagggtgc taaggggga    8640
ccgggcagca atggtgacca aggtcccaaa ggagacaggg gtgtgccagg catcaaagga    8700
gaccggggag agcctggacc gaggggtcag gacggcaacc cgggtctacc aggagagcgt    8760
ggtatggctg ggcctgaagg gaagccgggt ctgcagggtc caagaggccc cctggccca    8820
gtgggtggtc atggagaccc tggaccacct ggtgcccgg gtcttgctgg ccctgcagga    8880
ccccaaggac cttctggcct gaaggggga cctggagaca caggacctcc aggacgggcg   8940
ctgactggac ctactggagc tgtgggactt cctggacccc ccggcccttc aggccttgtg    9000
ggtccacagg ggtctccagg tttgcctgga caagtggggg agacagggaa gccgggagcc    9060
ccaggtcgag atggtgccag tggaaaagat ggagacagag ggagccctgg tgtgccaggg   9120
tcaccaggtc tgcctggccc tgtcggacct aaaggagaac ctggccccac ggggcccct    9180
ggacaggctg tggtcgggct ccctggagca aagggagaga agggagcccc tggaggcctt    9240
gctggagacc tggtcgggtga gccgggagcc aaaggtgacc gaggactgcc agggccgcga    9300
ggcgagaagg gtgaagctgg ccgtgcaggg gagcccggag accctgggga agatggtcag    9360
aaagggacg caggacccaa aggtttcaag ggtgacccag gagtcgggt ccggggctcc    9420
cctgggcctc ctggccctcc agtgtgaag ggagatctgg gcctccctgg cctgcccggt    9480
gctcctggtg ttgttgggtt cccgggtcag acagccctc gaggagagat gggtcagcca    9540
ggccctagtg gagagcgggg tctggcaggc cccccaggga gagaaggaat cccaggaccc    9600
ctggggccac ctggaccacc ggggtcagtg ggaccacctg gggcctctgg actcaaagga    9660
gacaagggag accctggagt aggggctgcct gggccccga gcgagcgtgg ggagccaggc    9720
atccggggtg aagatggccg ccccggccag gagggacccc gaggactcac gggggcccct    9780
ggcagcaggg gagagcgtgg ggagaaggt gatgttggga gtgcaggact aaagggtgac    9840
aagggagact cagctgtgat cctggggcct ccaggcccac gggtgccaa ggggggacatg    9900
ggtgaacgag ggcctcgggg cttggatggt gacaaaggac ctcggggaga caatgggac    9960
cctggtgaca agggcagcaa gggagagcct ggtgacaagg gctcagccgg gttgccagga   10020
ctgcgtggac tcctgggacc ccagggtcaa cctggtgcag cagggatccc tggtgacccg    10080
ggatccccag gaaaggatgg agtgcctggt atccgaggac aaaaaggaga tgttggcttc    10140
atgggtcccc ggggcctcaa gggtgaacgg ggagtgaagg gagcctgtgg ccttgatgga   10200
gagaagggag acaaggggaga agctggtccc ccaggccgcc ccgggctggc aggacacaaa   10260
ggagagatgg gggagcctgg tgtgccgggc cagtcggggg ccctggcaa ggagggcctg    10320
atcggtccca agggtgaccg aggcttgac gggcagccag gcccaaggg tgaccaggc    10380
gagaaggggg agcggggaac cccaggaatt gggggcttcc caggccccag tggaaatgat   10440
ggctctgctg gtccccagg gccacctggc agtgttggtc ccagaggccc cgaaggactt    10500
cagggccaga agggtgagcg agtccccccc ggagagagag tggtggggc tcctggggtc    10560
cctggagctc ctgcgagag aggggagcag gggcggccag ggcctgccgg tcctcgaggc    10620
gagaaggggag aagctgcact gacggaggat gacatccggg gctttgtgcg ccaagaatg    10680
agtcagcact gtgcctgcca gggccagttc atcgcatctg gatcacgacc cctccctagt    10740
tatgctgcag acactgccgg ctcccagctc catgctgtgc ctgtgctccg cgtctctcat    10800
gcagaggagg aagagcgggt accccctgag gatgatgagt actctgaata ctccgagtat   10860
tctgtggagg agtaccagga ccctgaagct cctgggata gtgatgaccc ctgttccctg    10920
ccactggatg agggctcctg cactgcctac acctgcgct ggtaccatcg ggctgtgaca   10980
ggcagcacag aggcctgtca cccttttgtc tatggtggct gtgaggggaa tgccaaccgt   11040
tttgggaccc gtgaggcctg cgagcgccgc tgcccacccc gggtggtcca gagccagggg   11100
acaggtactg cccaggactg a                                             11121
```

```
SEQ ID NO: 16       moltype = AA  length = 3706
FEATURE             Location/Qualifiers
REGION              1..3706
                    note = Synthetic Construct
source              1..3706
                    mol_type = protein
```

-continued

```
                          organism = synthetic construct
SEQUENCE: 16
MTSSGPGPRF LLLLPLLLPP AASASDRPRG RDPVNPEKLL VITVATAETE GYLRFLRSAE    60
FFNYTVRTLG LGEEWRGGDV ARTVGGGQKV RWLKKEMEKY ADREDMIIMF VDSYDVILAG   120
SPTELLKKFV QSGSRLLFSA ESFCWPEWGL AEQYPEVGTG KRFLNSGGFI GFATTIHQIV   180
RQWKYKDDDD DQLFYTRLYL DPGLREKLSL NLDHKSRIFQ NLNGALDEVV LKFDRNRVRI   240
RNVAYDTLPI VVHGNGPTKL QLNYLGNYVP NGWTPEGGCG FCNQDRRTLP GGQPPPRVFL   300
AVFVEQPTPF LPRFLQRLLL LDYPPDRVTL FLHNNEVFHE PHIADSWPQL QDHFSAVKLV   360
GPEEALSPGE ARDMAMDLCR QDPECEFYFS LDADAVLTNL QTLRILIEEN RKVIAPMLSR   420
HGKLWSNFWG ALSPDEYYAR SEDYVELVQR KRVGVWNVPY ISQAYVIRGD TLRMELPQRD   480
VFSGSDTDPD MAFCKSFRDK GIFLHLSNQH EFGRLLATSR YDTEHLHPDL WQIFDNPVDW   540
KEQYIHENYS RALEGEGIVE QPCPDVYWFP LLSEQMCDEL VAEMEHYGQW SGGRHEDSRL   600
AGGYENVPTV DIHMKQVGYE DQWLQLLRTY VGPMTESLFP GYHTKARAVM NFVVRYRPDE   660
QPSLRPHHDS STFTLNVALN HKGLDYEGGG CRFLRYDCVI SSPRKGWALL HPGRLTHYHE   720
GLPTTWGTRY IMVSFVDPRA KRGSGEGRGS LLTCGDVEEN PGPTLRLLVA ALCAGILAEA   780
PRVRAQHRER VTCTRLYAAD IVFLLDGSSS IGRSNFREVR SFLEGLVLPF SGAASAQGVR   840
FATVQYSDDP RTEFGLDALG SGGDVIRAIR ELSYKGGNTR TGAAILHVAD HVFLPQLARP   900
GVPKVCILIT DGKSQDLVDT AAQRLKGQGV KLFAVGIKNA DPEELKRVAS QPTSDFFFFV   960
NDFSILRTLL PLVSRRVCTT AGGVPVTRPP DDSTSAPRDL VLSEPSSQSL RVQWTAASGP  1020
VTGYKVQYTP LTGLGQPLPS ERQEVNVPAG ETSVRLRGLR PLTEYQVTVI ALYANSIGEA  1080
VSGTARTTAL EGPELTIQNT TAHSLLVAWR SVPGATGYRV TWRVLSGGPT QQQELGPGQG  1140
SVLLRDLEPG TDYEVTVSTL FGRSVGPATS LMARTDASVE QTLRPVILGP TSILLSWNLV  1200
PEARGYRLEW RRETGLEPPQ KVVLPSDVTR YQLDGLQPGT EYRLTLYTLL EGHEVATPAT  1260
VVPTGPELPV SPVTDLQATE LPGQRVRVSW SPVPGATQYR IIVRSTQGVE RTLVLPGSQT  1320
AFDLDDVQAG LSYTVRVSAR VGPREGSASV LTVRREPETP LAVPGLRVVV SDATRVRVAW  1380
GPVPGASGFR ISWSTGSGPE SSQTLPPDST ATDITGLQPG TTYQVAVSVL RGREEGPAAV  1440
IVARTDPLGP VRTVHVTQAS SSSVTITWTR VPGATGYRVS WHSAHGPEKS QLVSGEATVA  1500
ELDGLEPDTE YTVHVRAHVA GVDGPPASVV VRTAPEPVGR VSRLQILNAS SDVLRITWVG  1560
VTGATAYRLA WGRSEGGPMR HQILPGNTDS AEIRGLEGGV SYSVRVTALV GDREGTPVSI  1620
VVTTPPEAPP ALGTLHVVQR GEHSLRLRWE PVPRAQGFLL HWQPEGGQEQ SRVLGPELSS  1680
YHLDGLEPAT QYRVRLSVLG PAGEGPSAEV TARTESPRVP SIELRVVDTS IDSVTLAWTP  1740
VSRASSYILS WRPLRGPGQE VPGSPQTLPG ISSSQRVTGL EPGVSYIFSL TPVLDGVRGP  1800
EASVTQTPVC PRGLADVVFL PHATQDNAHR AEATRRVLER LVLALGPLGP QAVQVGLLSY  1860
SHRPSPLFPL NGSHDLGIIL QRIRDMPYMD PSGNNLGTAV VTAHRYMLAP DAPGRRQHVP  1920
GVMVLLVDEP LRGDIFSPIR EAQASGLNVV MLGMAGADPE QLRRLAPGMD SVQTFFAVDD  1980
GPSLDQAVSG LATALCQASF TTQPRPEPCP VYCPKGQKGE PGEMGLRGQV GPPGDPGLPG  2040
RTGAPGPQGP PGSATAKGER GFPGADGRPG SPGRAGNPGT PGAPGLKGSP GLPGPRGDPG  2100
ERGPRGPKGE PGAPGQVIGG EGPGLPGRKG DPGPSGPPGR RGPLGDPGPR GPPGLPGTAM  2160
KGDKGDRGER GPPGPGEGGI APGEPGLPGL PGSPGPQGPV GPPGKKGEKG DSEDGAPGLP  2220
GQPGSPGEQG PRGPPGAIGP KGDRGFPGPL GEAGEKGERG PPGPAGSRGL PGVAGRPGAK  2280
GPEGPPGPTG RQGEKGEPGR PGDPAVVGPA VAGPKGEKGD VGPAGPRGAT GVQGERGPPG  2340
LVLPGDPGPK GDPGDRGPIG LTGRAGPPGD SGPPGEKGDP GRPGPPGPVG PRGRDGEVGE  2400
KGDEGPPGDP GLPGKAGERG LRGAPGVRGP VGEKGDQGDP GEDGRNGSPG SSGPKGDRGE  2460
PGPPGPPGRL VDTGPGAREK GEPGDRGQEG PRGPKGDPGL PGAPGERGIE GFRGPPGPQG  2520
DPGVRGPAGE KGDRGPPGLD GRSGLDGKPG AAGPSGPNGA AGKAGDPGRD GLPGLRGEQG  2580
LPGPSGPPGL PGKPGEDGKP GLNGKNGEPG DPGEDGRKGE KGDSGASGRE GRDGPKGERG  2640
APGILGPQGP PGLPGPVGPP GQGFPGVPGG TGPKGDRGET GSKGEQGLPG ERGLRGEPGS  2700
VPNVDRLLET AGIKASALRE IVETWDESSG SFLPVPERRR GPKGDSGEQG PPGKEGPIGF  2760
PGERGLKGDR GDPGPQGPPG LALGERGPPG PSGLAGEPGK PGIPGLPGRA GGVGEAGRPG  2820
ERGERGEKGE RGEQGRDGPP GLPGTPGPPG PPGPKVSVDE PGPGLSGEQG PPGLKGAKGE  2880
PGSNGDGPGK GDRGVPGIKG DRGEPGPRGQ DGNPGLPGER GMAGPEGKPG LQGPRGPPGP  2940
VGGHGDPGPP GAPGLAGPAG PQGPSGLKGE PGETGPPGRG LTGPTGAVGL PGPPGPSGLV  3000
GPQGSPGLPG QVGETGKPGA PGRDGASGKD GDRGSPGVPG SPGLPGPVGP KGEPGPTGAP  3060
GQAVVGLPGA KGEKGAPGGL AGDLVGEPGA KGDRGLPGPR GEKGEAGRAG EPGDPGEDGQ  3120
KGAPGPKGFK GDPGVGVPGS PGPPGPPGVK GDLGLPGLPG APGVVGFPGQ TGPRGEMGQP  3180
GPSGERGLAG PPGREGIPGP LGPPGPPGSV GPPGASGLKG DKGDPGVGLP GPRGERGEPG  3240
IRGEDGRPGQ EGPRGLTGPP GSRGERGEKG DVGSAGLKGD KGDSAVILGP PGPRGAKGDM  3300
GERGPRGLDG DKGPRGDNGD PGDKGSKGEP GDKGSAGLPG LRGLLGPGQG PGAAGIPGDP  3360
GSPGKDGVPG IRGEKGDVGF MGPRGLKGER GVKGACGLDG EKGDKGEAGP PGRPGLAGHK  3420
GEMGEPGVPG QSGAPGKEGL IGPKGDRGFD GQPGPGKGDQ GEKGERGTPGI GGFPGPSGND  3480
GSAGPPGPPG SVGPRGPEGL QGGQKGERGPP GERVVGAPGV PGAPGERGEQ GRPGPAGPRG  3540
EKGEAALTED DIRGFVRQEM SQHCACQGQF IASGSRPLPS YAADTAGSQL HAVPVLRVSH  3600
AEEEERVPPE DDEYSEYSEY SVEEYQDPEA PWDSDDPCSL PLDEGSCTAY TLRWYHRAVT  3660
GSTEACHPFV YGGCGGNANR FGTREACERR CPPRVVQSQG TGTAQD             3706
```

```
SEQ ID NO: 17        moltype = DNA   length = 11112
FEATURE              Location/Qualifiers
misc_feature         1..11112
                     note = Synthetic Construct
source               1..11112
                     mol_type = other DNA
                     organism = synthetic construct
SEQUENCE: 17
atgacgctgc ggcttctggt ggccgcgctc tgcgccggga tcctggcaga ggcgccccga    60
gtgcgagccc agcacaggga gagagtgacc tgcacgcgcc tttacgccgc tgacattgtg   120
ttcttactgg atggctcctc atccattggc cgcagcaatt ccgcgaggt ccgcagcttt    180
ctcgaagggc tggtgctgcc tttctctgga gcagccagtg cacagggtgt gcgctttgcc   240
acagtgcagt acagcgatga cccacggaca gagttcggcc tggatgcact ggctctgggg   300
ggtgatgtga tccgcgccat ccgtgagctt agctacaagg ggggcaacac tcgcacaggg   360
```

-continued

```
gctgcaattc tccatgtggc tgaccatgtc ttcctgcccc agctggcccg acctggtgtc   420
cccaaggtct gcatcctgat cacagacggg aagtcccagg acctggtgga cacagctgcc   480
caaaggctga aggggcaggg ggtcaagcta tttgctgtgg ggatcaagaa tgctgaccct   540
gaggagctga agcgagttgc ctcacagccc accagtgact tcttcttctt cgtcaatgac   600
ttcagcatct tgaggacact actgcccctc gtttcccgga gagtgtgcac gactgctggt   660
ggcgtgcctg tgacccgacc tccggatgac tcgacctctg ctccacgaga cctggtgctg   720
tctgagccaa gcagccaatc cttgagagta cagtggacag cggccagtgg ccctgtgact   780
ggctacaagg tccagtacac tcctctgacg gggctgggac agccactgcc gagtgagcgg   840
caggaggtga acgtcccagc tggtgagacc agtgtgcggc tgcggggtct ccggccactg   900
accgagtacc aagtgactgt gattgccctc tacgccaaca gcatcgggga ggctgtgagc   960
gggacagctc ggaccactgc cctagaaggg ccggaactga ccatccagaa taccacagcc  1020
cacagcctcc tggtggcctg gcggagtgtg ccaggtgcca ctggctaccg tgtgacatgg  1080
cgggtcctca gtggtgggcc cacacagcag caggagctgg gccctgggca gggttcagtg  1140
ttgctgcgtg acttggagcc tggcacggac tatgaggtga ccgtgagcac cctatttggc  1200
cgcagtgtgg ggcccgccac ttccctgatg gctcgcactg acgcttctgt tgagcagacc  1260
ctgcgccccg tcatcctggg ccccacatcc atcctccttt cctggaactt ggtgcctgag  1320
gcccgtggct accggttgga atggcggcgt gagactggct tggagccacc gcagaaggtg  1380
gtactgccct ctgatgtgac ccgctaccag ttggatgggc tgcagccggg cactgagtac  1440
cgcctcacac tctacactct gctggagggc cacgaggtgg ccacccctgc aaccgtggtt  1500
cccactggac cagagctgcc tgtgagccct gtaacagacc tgcaagccac cgagctgccc  1560
gggcagcggg tgcgagtgtc ctggagccca gtccctggtg ccacccagta ccgcatcatt  1620
gtgcgcagca cccaggggg tgagcggacc ctggtgcttc ctgggagtca gacagcattc  1680
gacttggatg acgttcaggc tgggcttagc tacactgtgc gggtgtctgc tcgagtgggt  1740
ccccgtgagg gcagtgccag tgtcctcact gtccgccggg agccggaaac tccacttgct  1800
gttccagggc tgcgggttgt ggtgtcagat gcaacgcgag tgagggtggc ctggggaccc  1860
gtccctggag ccagtggatt tcggattagc tggagcacag gcagtggtcc ggagtccagc  1920
cagacactgc ccccagactc tactgccaca gacatcacag ggctgcagcc tggaaccacc  1980
taccaggtgg ctgtgtcggt actgcgaggc agagaggagg ccctgctgc agtcatcgtg  2040
gctcgaacgc acccactggg cccagtgagg acggtccatg tgactcaggc cagcagctca  2100
tctgtcacca ttacctggac cagggttcct ggcgccacag gatacaggg ttcctggcac  2160
tcagcccacg gcccagagaa atcccagttg gtttctgggg aggccacggt ggctgagctg  2220
gatggactgg agcagatac tgagtatacg gtgcatgtga gggcccatgt ggctggcgtg  2280
gatgggcccc ctgcctctgt ggttgtgagg actgcccctg agcctgtggg tcgtgtgtcg  2340
aggctgcaga tcctcaatgc ttccagcgac gttctacgga tcacctgggt aggggtcact  2400
ggagccacag cttacagact ggcctggggc cggagtgcag gcggcccat gaggcaccag  2460
atactcccag gaaacacaga ctctgcagag atccgggtc tcgaaggtgg agtcagctac  2520
tcagtgcgag tgactgcact tgtcggggac cgcgagggca cacctgtctc cattgttgtc  2580
actacgccgc ctgaggctcc gccagccctg gggacgcttc acgtggtgca gcgcggggag  2640
cactcgctga ggctgcgctg ggagccggtg cccagagcgc agggcttcct tctgcactgg  2700
caacctgagg gtggccagga acagtcccgg gtcctggggc ccgagctcag cagctatcac  2760
ctggacgggc tggagccagc gacacagtac cgcgtgaggc tgagtgtcct agggccagct  2820
ggagaagggc cctctgcaga ggtgactgcg cgcactgagt cacctcgtgt tccaagcatt  2880
gaactacgtg tggtggacac ctcgatcgac tcggtgactt tggcctggac tccagtgtcc  2940
agggcatcca gctacatcct atcctggcgg ccactcagg gccctggcca ggaagtgcct  3000
gggtcccgc agacacttcc agggatctca agctcccagc gggtgacagg gctagagcct  3060
ggcgtctctt acatcttctc cctgacgcct gtcctggatg gtgtgcgggg tcctgaggca  3120
tctgtcacac agacgccagt gtgcccccgt ggcctggcgg atgtggtgtt cctaccacat  3180
gccactcaag acaatgctca ccgtgcggag gctacgagga gggtcctgga gcgtctggtg  3240
ttggcacttg ggcctcttgg gccacaggca gttcaggttg gcctgctgtc ttacagtcat  3300
cggccctccc cactgttccc actgaatggc tcccatgacc ttggcattat cttgcaaagg  3360
atccgtgaca tgccctacat ggacccaagt gggaacaacc tgggcacagc cgtggtcaca  3420
gctcacagat acatgttggc accagatgct cctgggcgcc gccagcacgt accaggggtg  3480
atggttctgc tagtggatga accttgaga ggtgacatat tcagcccat ccgtgaggcc  3540
caggcttctg ggcttaatgt ggtgatggttg ggaatggctg gagcggaccc agagcagctg  3600
cgtccgttgg cgccgggtat ggactctgtc cagaccttct tcgccgtgga tgatgggcca  3660
agcctggacc aggcagtcag tggtctggcc acagccctgt gtcaggcatc cttcactact  3720
cagccccggc cagagccctg cccagtgtat tgtccaaagg gccagaaggg ggaacctgga  3780
gagatgggcc tgagaggaca agttgggcct cctggcgacc ctggcctccc gggcaggacc  3840
ggtgctcccg gcccccaggg gcccctgga agtgccactg ccaagggcga gagggggcttc  3900
cctggagcag atgggcgtcc aggcagccct ggccgcgccg ggaatcctgg gaccctgga  3960
gcccctggcc taaagggctc tccagggttg cctggccctc gtggggaccc gggagagcga  4020
ggacctcgag gcccaaaggg ggagccgggg gctcccggac aagtcatcgg aggtgaagga  4080
cctgggcttc ctgggcggaa aggggaccct ggaccatcgg gcccccctgg acctcgtgga  4140
ccactggggg accaggacc ccgtggcccc ccagggcttc ctggaacagc catgaagggt  4200
gacaaaggcg atcgtgggga gcggggtccc cctggaccag gtgaaggtgg cattgctcct  4260
ggggagcctg ggctgccggg tcttcccgga agcctggac cccaaggccc gttggcccc  4320
cctgaaaga aaggagaaaa aggtgactct gaggatggag ctccaggcct cccaggacaa  4380
cctgggtctc cgggtgagca gggcccacgg ggacctcctg gagctattgg ccccaaaggt  4440
gaccggggct ttccagggcc cctgggtgag gctggagaga agggcgaacg tggacccca  4500
ggcccagcgc gatcccgggg gctgccaggg gttgctggac gtcctggagc caagggtcct  4560
gaagggccac caggacccac tggccgcaa ggagagaagg gggagcctgg tcgccctggg  4620
gaccctgcag tggtgggacc tgctgttgct ggacccaaag agaaaagggg agatgtgggg  4680
cccgctgggc ccagaggagc taccggagtc aagggggaac ggggccccacc cggcttggtt  4740
cttcctggag accctggccc caagggagac cctggaccct ggggtcccat tggccttact  4800
ggcagagcag gaccccagg tgactcaggc cctcctggag agaaggggag ccctgggcgg  4860
cctgcccccc aggacctgt tggcccccga ggacgagatg tgtgaagttgg agagaaaggt  4920
gacgagggtc ctccgggtga cccggggtttg cctggaaaag caggcgagcg tggccttcgg  4980
ggggcacctg gagttcgggg gcctgtgggt gaaaaggag accagggaga tcctggagag  5040
gatggacgaa atggcagccc tggatcatct ggacccaagg gtgaccgtgg ggagccgggt  5100
```

-continued

```
cccccaggac ccccgggacg gctggtagac acaggacctg gagccagaga gaagggagag   5160
cctgggacc  gcggacaaga gggtcctcga gggcccaagg gtgatcctgg cctccctgga   5220
gccctgggg  aaaggggcat tgaagggttt cggggacccc caggcccaca gggggaccca   5280
ggtgtccgag gcccagcagg agaaaaggggt gaccgggggtc ccctgggct  ggatggccgg   5340
agcggactgg atgggaaacc aggagccgct gggccctctg ggccgaatgg tgctgcaggc   5400
aaagctgggg acccagggag agacgggctt ccaggcctcc gtggagaaca gggcctccct   5460
ggcccctctg gtcccctgg attaccggga aagccaggcg aggatggcaa acctggcctg   5520
aatggaaaaa acgagaacc  tggggaccct ggagaagacg ggaggaaggg agagaaagga   5580
gattcaggcg cctctgggag agaaggtcgt gatggcccca agggtgagcg tggagctcct   5640
ggtatccttg gaccccaggg gcctccaggc ctcccaggc  cagtgggccc tcctggccag   5700
ggttttcctg gtgtcccagg aggcacgggc cccaagggtg accgtgggga gactggatcc   5760
aaagggagc  agggcctccc tggagagcgt ggcctgcgag gagagcctgg aagtgtgccg   5820
aatgtggatc ggttgctgga aactgctggc atcaaggcat ctgccctgcg ggagatcgtg   5880
gagacctggg atgagagctc tggtagcttc ctgcctgtgc ccgaacggcg tcgaggcccc   5940
aaggggggact caggcgaaca gggccccca  ggcaaggagg gccccatcgg ctttcctgga   6000
gaacgcgggc tgaagggcga ccgtggagac cctggccctc aggggccacc tggtctggcc   6060
cttggggaga ggggcccccc cgggccttcc ggccttgccg gggagcctgg aaagcctggt   6120
attcccgggc tccaggcag  ggctgggggt gtgggagagg caggaaggcc aggagagagg   6180
ggagaacggg gagagaaagg agaacgtgga gaacagggca gagatggccc tcctggactc   6240
cctgaaccc  ctgggccccc cggaccccct ggccccaagg tgtctgtgga tgagccaggt   6300
cctggactct ctggagaaca gggaccccct ggactcaagg gtgctaaggg ggagccgggc   6360
agcaatggtg accaaggtcc caaaggagac aggggtgtgc caggcatcaa agagaccagg   6420
ggagagcctg gaccgagggg tcaggacggc aaacccgggtc taccaggaga gcgtggtatg   6480
gctgggcctg aagggaagcc gggtctgcag ggtccaagag gcccccctgg cccagtgggt   6540
ggtcatggag acctggacc  acctggtgcc ccgggtcttg ctggccctgc aggaccccaa   6600
ggaccttctg gcctgaaggg ggagcctgga gagacaggac tccaggacg  ggcctgact   6660
ggacctactg gagctgtggg acttcctgga cccccggcc  cttcaggcct tgtgggtcca   6720
cagggggtctc caggtttgcc tggacaagtg ggggagacag ggaagccggg agccccaggt   6780
cgagatggtg ccagtggaaa agatggagac agagggagcc ctggtgtgcc agggtcacca   6840
ggtctgcctg gccctgtcgg acctaaagga gaacctggcc ccacggggcc ccctggacag   6900
gctgtggtcg ggctccctgg agcaaaggga gagaaggggag cccctggagg ccttgctgga   6960
gacctggtgg gtgagccggg agccaaaggt gaccgaggac tgccagggcc gcgaggcgag   7020
aagggtgaag ctggccgtgc aggggagccc ggagaccctg gggaagatgg tcagaaaggg   7080
gctccaggac ccaaaggttt caagggtgac ccaggagtcg gggtcccggg ctccctgggg   7140
cctcctggcc ctccaggtgt gaaggggagat ctgggcctcc ctggcctgcc cggtgctcct   7200
ggtgttgttg ggttcccggg tcagacaggc cctcgaggag agatgggtca gccaggccct   7260
agtggagagc ggggtctggc aggcccccca gggagagaag gaatcccagg acccctgggg   7320
ccacctggac caccgggggtc agtgggacca cctgggggcct ctggactcaa aggagacaag   7380
ggagaccctg gagtagggct gcctgggccc cgaggcgagc gtggggagcc aggcatccgg   7440
ggtgaagatg gccgcccgg  ccaggaggga ccccgaggac tcacggggcc ccctggcagc   7500
aggggagagc gtggggagaa gggtgatgtt gggagtgcag gactaaaggg tgacaaggga   7560
gactcagctg tgatcctggg gcctccaggc ccacgggggtg ccaagggggga catgggtgaa   7620
cgagggcctc ggggcttgga tggtgacaaa ggacctcggc gagacaatgg ggaccctggt   7680
gacaagggca gcaagggaga gcctggtgac aaggggctcag ccgggttgcc aggactgcgt   7740
ggactcctgg gaccccaggg tcaacctggt gcagcaggga tccctggtga cccgggggatcc   7800
ccaggaaagg atggagtgcc tggtatccga ggagaaaaag gagatgttgg cttcatgggt   7860
ccccgggcc  tcaagggtga acggggggagtg aagggagcct gtggccttga tggagagaag   7920
ggagacaagg gagaagctgg tccccccagc cgccccgggc tggcaggaca caaaggagag   7980
atggggggagc ctggtgtgcc gggccagtcg ggggccctg  gcaaggaggg cctgatcggt   8040
cccaagggtg accgaggctt tgacgggcag ccaggcccca agggtgacca gggcgagaaa   8100
ggggacgggg gaaccccagg aattgggggc ttcccaggcc ccagtggaaa tgatggctct   8160
gctggtcccc cagggccacc tggcagtgtt ggtcccagag gccccgaagg acttcagggc   8220
cagaagggtg agcgaggtcc ccccggagag agagtggtgg gggctcctgg ggtccctgga   8280
gctcctggcg agagagggga gcaggggcgg ccagggcctg ccggtcctcg aggcgagaag   8340
ggagaagctg cactgacgga ggatgacatc cgggggctttg tgcgccaaga gatgagtcag   8400
cactgtgcct gccagggcca gttcatcgca tctggatcac gaccctccc  tagttatgct   8460
gcagacactg ccggctccca gctccatgct gtgcctgtgc tccgcgtctc tcatgcagag   8520
gaggaagagc gggtaccccc tgaggatgat gagtactctg aatactccga gtattctgtg   8580
gaggagtacc aggaccctga agctccttgg gatagtgatg acccctgttc cctgccactg   8640
gatgagggct cctgcactgc ctacacactg cgctggtacc atcgggctgt gacaggcagc   8700
acagaggcct gtcacccttt tgtctatggt ggctgtggag ggaatgccaa ccgtttttggg   8760
acccgtgagg cctgcgagcg ccgctgccca ccccggggtgg tccagagcca ggggacaggt   8820
actgcccagg acggaagcgg agctactaac ttcagcctgc tgaagcaggc tggagacgtg   8880
gaggagaacc ctggacctac ctcctcgggg cctggaccc  ggttcctgct gctgctgccg   8940
ctgctgctgc cccctgcggc ctcagcctcc gaccggcccc ggggcccgaga cccggtcaac   9000
ccagagaagc tgctggtgat cactgtggcc acagctgaaa ccgagggggta cctgcgtttc   9060
ctgcgctctg cggagttctt caactacact gtgcggaccc tgggcctggg agaggagtgg   9120
cgagggggggtg atgtggctcg aacagttggt ggaggacaga aggtccggtg gttaaagaag   9180
gaaatggaa  aatacgatcga gcgggaggat atgatcatca tgtttgtgga tagctacgac   9240
gtgattctgg ccggcagccc cacagagctg ctgaagaagt cgtccagag  tggcagccgc   9300
ctgctcttct ctgcagagag cttctgctgg cccgagtggg ggctggcgga gcagtaccct   9360
gaggtgggca cggggaagcg cttcctcaat tctggtggat catcggttt  tgccaccacc   9420
atccaccaaa tcgtgcgcca gtggaagtac aaggatgatg acgacgacca gctgttctac   9480
acacggctct acctggaccc aggactgagg gagaaactca gccttaatct ggatcataag   9540
tctcggatct ttcagaacct caacggggct ttagatgaag tggttttaaa gtttgatcgg   9600
aaccgtgtgc gtatccggaa cgtggcctac gacacgctcc ccattgtggt ccatggaaac   9660
ggtcccacta agctgcagct caactacctg ggaaactacg tccccaatgg ctggactcct   9720
gagggaggct gtggcttctg caaccaggac cggaggacac tccgggggggg gcagcctccc   9780
cccgggtgt  ttctggccgt gtttgtggaa cagcctactc cgtttctgcc ccgcttcctg   9840
```

```
cagcggctgc tactcctgga ctatcccccc gacagggtca cccttttcct gcacaacaac  9900
gaggtcttcc atgaacccca catcgctgac tcctggccgc agctccagga ccacttctca  9960
gctgtgaagc tcgtggggcc ggaggaggct ctgagcccag gcgaggccag ggacatggcc  10020
atggacctgt gtcggcagga ccccgagtgt gagttctact tcagcctgga cgccgacgct  10080
gtcctcacca acctgcagac cctgcgtatc ctcattgagg agaacaggaa ggtgatcgcc  10140
cccatgctgt cccgccacgg caagctgtgg tccaacttct ggggcgccct gagccccgat  10200
gagtactacg cccgctccga ggactacgtg gagctggtgc agcggaagcg agtgggtgtg  10260
tggaatgtac catacatctc ccaggcctat gtgatccggg gtgataccct gcggatggag  10320
ctgcccagga gggatgtgtt ctcgggcagt gacacagacc cggacatggc cttctgtaag  10380
agctttcgag acaagggcat cttcctccat ctgagcaatc agcatgaatt tggccggctc  10440
ctggccactt ccagatacga cacggagcac ctgcaccccg acctctggca gatcttcgac  10500
aaccccgtcg actggaagga gcagtacatc cacgagaact acagccgggc cctggaaggg  10560
gaaggaatcg tggagcagcc atgcccggac gtgtactggt ccccactgct gtcagaacaa  10620
atgtgtgatg agctggtggc agagatggag cactacggcc agtggtcagg cggccggcat  10680
gaggattcaa ggctggctgg aggctacgag aatgtgccca ccgtggacat ccacatgaag  10740
caggtggggt acgaggacca gtggctgcag ctgctgcgga cgtatgtggg ccccatgacc  10800
gagagcctgt ttcccggtta ccacaccaag gcgcgggcgg tgatgaactt tgtggttcgc  10860
taccggccag acgagcagcc gtctctgcgg ccacaccagg actcatccac cttcaccctc  10920
aacgttgccc tcaaccacaa gggcctggac tatgagggag gtggctgccg cttcctgcgc  10980
tacgactgtg tgatctcctc cccgaggaag ggctgggcac tcctgcaccc cggccgcctc  11040
acccactacc acgaggggct gccaacgacc tggggcacac gctacatcat ggtgtccttt  11100
gtcgacccct ga                                                         11112
```

```
SEQ ID NO: 18            moltype = AA  length = 3703
FEATURE                 Location/Qualifiers
REGION                  1..3703
                        note = Synthetic Construct
source                  1..3703
                        mol_type = protein
                        organism = synthetic construct
SEQUENCE: 18
MTLRLLVAAL CAGILAEAPR VRAQHRERVT CTRLYAADIV FLLDGSSSIG RSNFREVRSF   60
LEGLVLPFSG AASAQGVRFA TVQYSDDPRT EFGLDALGSG GDVIRAIREL SYKGGNTRTG  120
AAILHVADHV FLPQLARPGV PKVCILITDG KSQDLVDTAA QRLKGQGVKL FAVGIKNADP  180
EELKRVASQP TSDFFFFVND FSILRTLLPL VSRRVCTTAG GVPVTRPPDD STSAPRDLVL  240
SEPSSQSLRV QWTAASGPVT GYKVQYTPLT GLGQPLPSER QEVNVPAGET SVRLRGLRPL  300
TEYQVTVIAL YANSIGEAVS GTARTTALEG PELTIQNTTA HSLLVAWRSV PGATGYRVTW  360
RVLSGGPTQQ QELGPGQGSV LLRDLEPGTD YEVTVSTLFG RSVGPATSLM ARTDASVEQT  420
LRPVILGPTS ILLSWNLVPE ARGYRLEWRR ETGLEPPQKV VLPSDVTRYQ LDGLQPGTEY  480
RLTLYTLLEG HEVATPATVV PTGPELPVSP VTDLQATELP GQRVRVSWSP VPGATQYRII  540
VRSTQGVERT LVLPGSQTAF DLDDVQAGLS YTVRVSARVG PREGSASVLT VRREPETPLA  600
VPGLRVVVSD ATRVRVAWGP VPGASGFRIS WSTGSGPESS QTLPPDSTAT DITGLQPGTT  660
YQVAVSVLRG REEGPAAVIV ARTDPLGPVR TVHVTQASSS SVTITWTRVP GATGYRVSWH  720
SAHGPEKSQL VSGEATVAEL DGLEPDTEYT VHVRAHVAGV DGPPASVVVR TAPEPVGRVS  780
RLQILNASSD VLRITWVGVT GATAYRLAWG RSEGGPMRHQ ILPGNTDSAE IRGLEGGVSY  840
SVRVTALVGD REGTPVSIVV TTPPEAPPAL GTLHVVQRGE HSLRLRWEPV PRAQGFLLHW  900
QPEGGQEQSR VLGPELSSYH LDGLEPATQY RVRLSVLGAG GEGPSAEVTA RTESPRVPSI  960
ELRVVDTSID SVTLAWTPVS RASSYILSWR PLRGPGQEVP GSPQTLPGIS SSQRVTGLEP  1020
GVSYIFSLTP VLDGVRGPEA SVTQTPVCPR GLADVVFLPH ATQDNAHRAE ATRRVLERLV  1080
LALGPLGPQA VQVGLLSYSH RPSPLFPLNG SHDLGIILQR IRDMPYMDPS GNNLGTAVVT  1140
AHRYMLAPDA PGRRQHVPGV MVLLVDEPLR GDIFSPIREA QASGLNVVML GMAGADPEQL  1200
RRLAPGMDSV QTFFAVDDGP SLDQAVSGLA TALCQASFTT QPRPEPCPVY CPKGQKGEPG  1260
EMGLRGQVGP PGDPGLPGRT GAPGPQGPPG SATAKGERGF PGADGRPGSP GRAGNPGTPG  1320
APGLKGSPGL PGPRGDPGER GPRGPKGEPG APGQVIGGEG PGLPGRKGDP GPSGPPGPRG  1380
PLGDPGPRGP PGLPGTAMKG DKGDRGERGP PGPGEGGIAP GEPGLPGLPG SPGPQGPVGP  1440
PGKKGEKGDS EDGAPGLPGQ PGSPGEQGPR GPPGAIGPKG DRGFPGPLGE AGEKGERGPP  1500
GPAGSRGLPG VAGRPGAKGP EGPPGPTGRQ GEKGEPGRPG DPAVVGPAVA GPKGEKGDVG  1560
PAGPRGATGV QGERGPPGLV LPGDPGPKGD PGDRGPIGLT GRAGPPGDSG PPGEKGDPGR  1620
PGPPGPVGPR GRDGEVGEKG DEGPPGDPGL PGKAGERGLR GAPGVRGPVG EKGDQGDPGL  1680
DGRNGSPGSS GPKGDRGEPG PPGPPGRLVD TGPGAREKGE PGDRGQEGPR GPKGDPGLPG  1740
APGERGRIEGF RGPPGPQGDP GVRGPAGEKG DRGPPGLDGR SGLDGKPGAA GPSGPNGAAG  1800
KAGDPGRDGL PGLRGEQGLP GPSGPPGLPG KPGEDGKPGL NGKNGEPGDP GEDGRKGEKG  1860
DSGASGREGR DGPKGERGAP GILGPQGPPG LPGPVGPPGQ GPGPVPGGTG PKGDRGETGS  1920
KGEQGLPGER GLRGEPGSVP NVDRLLETAG IKASALREIV ETWDESSGSF LPVPERRRGP  1980
KGDSGEQGPP GKEGPIGFPG ERGLKGDRGD PGPQGPPGLA LGERGPPGPS GLAGEPGKPG  2040
IPGLPGRAGG VGEAGRPGER GERGEKGERG EQGRDGPPGL PGTPGPPGPP GPKVSVDEPG  2100
PGLSGEQGPP GLKGAKGEPG SNGDQGPKGD RGVPGIKGDR GEPGPRGQDG NPGLPGERGM  2160
AGPEGKPGLQ GPRGPPGPVG GHGDPGPPGA PGLAGPAGPQ GPSGLKGEPG ETGPPGRGLT  2220
GPTGAVGLPG PPGPSGLVGP QGSPGLPGQV GETGKPGAPG RDGASGKDGD RGSPGVPGSP  2280
GLPGPVGPKG EPGPTGAPGQ AVVGLPGAKG EKGAPGGLAG DLVGEPGAKG DRGLPGPRGE  2340
KGEAGRAGEP GDPGEDGQKG APGPKGFKGD PGVGVPGSPG PPGPPGVKGD LGLPGLPGAP  2400
GVVGFPGQTG PRGEMGQPGP SGERGLAGPP GREGIPGPLG PPGPPGSVGP PGASGLKGDK  2460
GDPGVGLPGP RGERGEPGIR GEDGRPGQEG PRGLTGPPGS RGERGEKGDV GSAGLKGDKG  2520
DSAVILGPPG PRGAKGDMGE RGPRGLDGDK GPRGDNGDPG DKGSKGEPGD KGSAGLPGLR  2580
GLLGPQGQPG AAGIPGDPGS PGKDGVPGIR GEKGDVGFMG PRGLKGERGV KGACGLDGEK  2640
GDKGEAGPPG RPGLAGHKGE MGEPGVPGQS GAPGKEGLIG PKGDRGFDGQ PGPKGDQGEK  2700
GERGTPGIGG FPGPSGNDGS AGPPGPPGSV GPRGPEGLQG QKGERGPPGE RVVGAPGVPG  2760
APGERGREQGR PGPAGPRGEK GEAALTEDDI RGFVRQEMSQ HCACQGQFIA SGSRPLPSYA  2820
ADTAGSQLHA VPVLRVSHAE EEERVPPEDD EYSEYSEYSV EEYQDPEAPW DSDDPCSLPL  2880
```

-continued

```
DEGSCTAYTL RWYHRAVTGS TEACHPFVYG GCGGNANRFG TREACERRCP PRVVQSQGTG  2940
TAQDGSGATN FSLLKQAGDV EENPGPTSSG PGPRFLLLLP LLLPPAASAS DRPRGRDPVN  3000
PEKLLVITVA TAETEGYLRF LRSAEFFNYT VRTLGLGEEW RGGDVARTVG GGQKVRWLKK  3060
EMEKYADRED MIIMFVDSYD VILAGSPTEL LKKFVQSGSR LLFSAESFCW PEWGLAEQYP  3120
EVGTGKRFLN SGGFIGFATT IHQIVRQWKY KDDDDDQLFY TRLYLDPGLR EKLSLNLDHK  3180
SRIFQNLNGA LDEVVLKFDR NRVRIRNVAY DTLPIVVHGN GPTKLQLNYL GNYVPNGWTP  3240
EGGCGFCNQD RRTLPGGQPP PRVFLAVFVE QPTPFLPRFL QRLLLLDYPP DRVTLFLHNN  3300
EVFHEPHIAD SWPQLQDHFS AVKLVGPEEA LSPGEARDMA MDLCRQDPEC EFYFSLDADA  3360
VLTNLQTLRI LIEENRKVIA PMLSRHGKLW SNFWGALSPD EYYARSEDYV ELVQRKRVGV  3420
WNVPYISQAY VIRGDTLRME LPQRDVFSGS DTDPDMAFCK SFRDKGIFLH LSNQHEFGRL  3480
LATSRYDTEH LHPDLWQIFD NPVDWKEQYI HENYSRALEG EGIVEQPCPD VYWFPLLSEQ  3540
MCDELVAEME HYGQWSGGRH EDSRLAGGYE NVPTVDIHMK QVGYEDQWLQ LLRTYVGPMT  3600
ESLFPGYHTK ARAVMNFVVR YRPDEQPSLR PHHDSSTFTL NVALNHKGLD YEGGGCRFLR  3660
YDCVISSPRK GWALLHPGRL THYHEGLPTT WGTRYIMVSF VDP                    3703

SEQ ID NO: 19          moltype = DNA   length = 11112
FEATURE                Location/Qualifiers
misc_feature           1..11112
                       note = Synthetic Construct
source                 1..11112
                       mol_type = other DNA
                       organism = synthetic construct
SEQUENCE: 19
atgacctcct cggggcctgg accccggttc ctgctgctgc tgccgctgct gctgcccct    60
gcggcctcag cctccgaccg gcccgggggc cgagacccgg tcaacccaga gaagctgctg   120
gtgatcactg tggccacagc tgaaaccgag gggtacctgc gtttcctgcg ctctcggag    180
ttcttcaact acactgtgcg gaccctgggc ctgggagagg agtggcgagg gggtgatgtg   240
gctcgaacag ttggtggagg acagaaggtc cggtggttaa agaaggaaat ggagaaatac   300
gctgaccggg aggatatgat catcatgttt gtggatagct acgacgtgat tctggccggc   360
agcccacag agctgctgaa gaagttcgtc cagagtgggca gccgcctgct cttctctgca   420
gagagcttct gctggcccga gtggggggctg gcggagcagt accctgaggt gggcacgggg   480
aagcgcttcc tcaattctgg tggattcatc ggttttgcca ccaccatcca ccaaatcgtg   540
cgccagtgga agtacaagga tgatgacgac gaccagctgt tctacacacg gctctacctg   600
gacccaggac tgagggagaa actcagcctt aatcttggatc ataagtctcg gatcttcag   660
aacctcaacg gggctttaga tgaagtggtt ttaaagtttg atcggaaccg tgtgcgtatc   720
cggaacgtgg cctacgacac gctccccatt gtggtccatg gaaacggtcc cactaagctg   780
cagctcaact acctgggaaa ctacgtcccc aatggctgga ctcctgaggg aggctgtggc   840
ttctgcaacc aggaccggag gacactcccg ggggggcagc ctccccccg ggtgtttctg    900
gccgtgtttg tggaacagcc tactccgttt ctgcccgct tcctgcagcg gctgctactc    960
ctggactatc cccccgacag ggtcaccctt ttcctgcaca acaacgaggt cttccatgaa  1020
ccccacatcg ctgactcctg gccgcagctc caggaccact tctcagctgt gaagctcgtg  1080
gggccggagg aggctctgag cccaggcgag gccagggaca tggccatgga cctgtgtcgg  1140
caggaccccg agtgtgagtt ctacttcagc ctggacgccg acgtgtcct caccaacctg  1200
cagaccctgc gtatcctcat tgaggagaac aggaaggtga tcgcccccat gctgtcccgc  1260
cacggcaagc tgtggtccaa cttctggggc gccctgagcc ccgatgagta ctacgcccgc  1320
tccgaggact acgtggagct ggtgcagcgg aagcgagtgg gtgtgtggaa tgtaccatac  1380
atctcccagg cctatgtgat ccggggtgat accctgcgga tggccttct gtaagagctt  1440
ggcatcttcc tccatctgag caatcagcat gaatttggcc ggctcctggc cacttccaga  1500
tacgacacgg agcacctgca ccccgacctc tggcagatct cgacaacccc cgtcgactgg  1620
aaggagcagt acatccacga gaactacagc cgggccctgg aaggggaagg aatcgtggag  1680
cagccatgcc cggacgtgta ctggttccca ctgctgtcag aacaaatgtg tgatgagctg  1740
gtggcagaga tggagcacta cggccagtgg tcaggcggcc ggcatgagga ttcaaggctg  1800
gctgaggct acgagaatgt gcccaccgtg gacatccaca tgaagcaggt ggggtacgag  1860
gaccagtggc tgcagctgct gcggacgtat gtggggcccc tgaccgagag cctgtttccc  1920
ggttaccaca ccaaggcgcg ggcggtgatg aactttgtgg ttcgctaccg gccagacgag  1980
cagccgtctc tgcggccaca ccacgactca tccaccttca ccctcaacgt tgccctcaac  2040
cacaaggggcc tggactatga gggaggtggc tgccgcttcc tgcgctacga ctgtgtgatc  2100
tcctccccga ggaagggctg ggcactcctg caccccggcc gcctcacccca ctaccacgag  2160
gggctgccaa cgacctgggg cacacgctac atcatggtgt cctttgtcga ccccggaagc  2220
ggagctacta acttcagcct gctgaagcag gctggaacg tggaggagaa ccctggacct  2280
acgctgcggc ttctggtggc cgcgctctgc gccgggatcc tggcagaggc gccccgagtg  2340
cgagcccagc acagggagag agtgacctgc acgcgccttt acgccgctga cattgtgttc  2400
ttactggatg gctcctcatc cattggccgc agcaatttcc gcgagtactc cagctttctc  2460
gaagggctgg tgctgccttt ctctggagca gccagtgcac agggtgtgcg ctttgccaca  2520
gtgcagtaca gcgatgaccc acggacagag ttcggcctgg atgcacttgg ctctgggggt  2580
gatgtgatcc gcgccatccg tgagcttagc tacaaggggg gcaacactcg cacagggggct  2640
gcaattctcc atgtggctga ccatgtcttc ctgcccccagc tggcccgacc tggtgtcccc  2700
aaggtctgca tcctgatcac agacgggaag tcccaggacc tggtggacac agctgcccaa  2760
aggctgaagg ggcagggggt caagctattt gctgtgggga tcaagaatgc tgaccctgag  2820
gagctgaagc gagttgcctc acagcccacc agtgacttct tcttcttcgt caatgacttc  2880
agcatcttga ggacactact gccctcgtt tccggagag tgtgcacgac tgctggtggc  2940
gtgcctgtga cccgacctcc ggatgactcg acctctgctc cacagacct ggtgctgtct  3000
gagccaggac gccaatcctt gagagtacag tggacacggg ccagtggacc tgtgactggc  3060
tacaaggtcc agtacactcc tctgacgggg ctgggacagc cactgccgag tgagcggcag  3120
gaggtgaacg tcccagctgg tgagaccagt gtgcggctgc ggggtctccg gccactgacc  3180
gagtaccaag tgactgtgat tgccctctac gccaacagca tcgggggagc tgtgagcggg  3240
acagctcgga ccactgccct agaagggccg gaactgacca tccagaatac cacagcccac  3300
agcctcctgg tggcctggcg gagtgtgcca ggtgccactg ctaccgtgt gacatggcgg  3360
```

-continued

```
gtcctcagtg gtgggcccac acagcagcag gagctgggcc ctgggcaggg ttcagtgttg   3420
ctgcgtgact tggagcctgg cacgggactat gaggtgaccg tgagcaccct atttggccgc   3480
agtgtggggc ccgccacttc cctgatggct cgcactgacg cttctgttga gcagaccctg   3540
cgcccggtca tcctgggccc cacatccatc ctcctttcct ggaacttggt gcctgaggcc   3600
cgtggctacc ggttggaatg gcggcgtgag actggcttgg agccaccgca gaaggtggta   3660
ctgccctctg atgtgacccg ctaccagttg gatgggctgc agccgggcac tgagtaccgc   3720
ctcacactct acactctgct ggagggccac gaggtggcca cccctgcaac cgtggttccc   3780
actgaccag agctgcctgt gagccctgta acagacctgc aagccaccga gctgcccggg   3840
cagcgggtgc gagtgtcctg gagcccagtc cctggtgcca cccagtaccg catcattgtg   3900
cgcagcaccc aggggttga gcggaccctg gtgcttcctg ggagtcagac agcattcgac   3960
ttggatgacg ttcaggctgg gcttagctac actgtgcggg tgtctgctcg agtgggtccc   4020
cgtgagggca gtgccagtgt cctcactgtc cgccgggagc cggaaactcc acttgctgtt   4080
ccagggctgc gggttgtggt gtcagatgca acgcgagtga gggtggcctg gggacccgtc   4140
cctggagcca gtggatttcg gattagctgg agcacaggca gtggtccgga gtccagccag   4200
acactgcccc cagactctac tgccacagac atcacagggc tgcagcctgg aaccacctac   4260
caggtggctg tgtcggtact gcgaggcaga gaggagggcc ctgctgcagt catcgtggct   4320
cgaacggacc cactgggccc agtgaggacg gtccatgtga ctcaggccag cagctcatct   4380
gtcaccatta cctggaccag ggttcctggc gccacaggat acaggggtttc ctggcactca   4440
gcccacggcc cagagaaatc ccagttggtt tctgggggagg ccacggtggc tgagctggat   4500
ggactggagc cagatactga gtatacggtg catgtgaggg cccatgtggc tggcgtggat   4560
gggccccctg cctctgtggt tgtgaggact gcccctgagc ctgtgggtcg tgtgtcgagg   4620
ctgcagatcc tcaatgcttc cagcgacgtt ctacggatca ctgggtagg ggtcactgga   4680
gccacagctt acagactggc ctggggccgg agtgaaggcg gccccatgag gcaccagata   4740
ctcccaggaa acacagactc tgcagagatc cggggtctcg aagtggagt cagctactca   4800
gtgcgagtga ctgcacttgt cggggaccgc gagggcacac ctgtctccat tgttgtcact   4860
acgcgcctg aggctccgcc agccctgggg acgcttcacg tggtgcagcg cggggagcac   4920
tcgctgaggc tgcgctggga gccggtgccc agagcgcagg gcttccttct gcactggcaa   4980
cctgagggtg gccaggaaca gtcccgggtc ctggggcccg agctcagcag ctatcacctg   5040
gacgggctgg agccagcgac acagtaccgc gtgaggctga gtgtcctagg gccagctgga   5100
gaagggccct ctgcagaggt gactgcgcgc actgagtcac ctcgtgttcc aagcattgaa   5160
ctacgtgtgg tggacacctc gatcgactcg gtgactttgg cctggactcc agtgtccagg   5220
gcatccagct acatcctatc ctggcggcca ctcagaggcc ctggccagga agtgcctggg   5280
tccccgcaga cacttccagg gatctcaagc tcccagcggg tgacagggct agagcctggc   5340
gtctcttaca tcttctccct gacgcctgtc ctggatggtg tgcggggtcc tgaggcatct   5400
gtcacacaga cgccagtgtg cccccgtggc ctggcggatg tggtgttcct accacatgcc   5460
actcaagaca atgctcaccg tgcggaggct acgaggaggg tcctggagcg tctggtgttg   5520
gcacttgggc ctcttgggcc acaggcagtt caggttggcc tgctgtctta cagtcatcgg   5580
ccctccccac tgttcccact gaatggctcc catgaccttg gcattatctt gcaaaggatc   5640
cgtgacatgc cctacatgga cccaagtggg aacaacctgg gcacagccgt ggtcacagct   5700
cacagataca tgttggcacc agatgctcct gggcgccgcc agcacgtacc aggggtgatg   5760
gttctgctag tggatgaacc cttgagaggt gacatattca gccccatccg tgaggcccag   5820
gcttctgggc ttaatgtggt gatgtgga atggctggag cggacccaga gcagctgcgt   5880
cgcttggcgc cgggtatgga ctctgtccag accttcttcg ccgtggatga tgggccaagc   5940
ctggaccagg cagtcagtgg tctgccaca gccctgtgtc aggcatcctt cactactcag   6000
ccccggccag agccctgccc agtgtattgt ccaaagggcc agaaggggga acctggagag   6060
atgggcctga gaggacaagt tgggcctcct ggcgaccctg gcctcccggg caggaccggt   6120
gctcccggcc cccaggggcc ccctggaagt gccactgcca aggcgagagg gggcttccct   6180
ggagcagatg ggcgtccagg cagccctggc cgcgccggga atcctgggac ccctggagcc   6240
cctggcctaa agggctctcc agggttgcct ggccctcgtg gggacccggg agagcgagga   6300
cctcgaggcc caaaggggga gccgggggct cccgacaag tcatcggagg tgaaggacct   6360
gggcttcctg ggcggaaagg ggaccctgga ccatcggacc ccctggacc tcgtggacca   6420
ctgggggacc caggacccg tggcccccca gggcttcctg gaacagccat gaagggtgac   6480
aaaggcgatc gtggggagcg gggtcccct ggaccaggtg aagtggcat tgctcctggg   6540
gagcctgggc tgccgggtct tcccggaagc cctggacccc aaggccccgt tggcccccct   6600
ggaaagaaag gagaaaaagg tgactctgag gatggagctc caggcctccc aggacaacct   6660
gggtctccgg gtgagcaggg cccacgggga cctcctggag ctattggccc caaaggtgac   6720
cggggctttc cagggcccct gggtgaggct ggagagaagg gcgaacgtgg acccccaggc   6780
ccagcgggat cccggggggct gccaggggtt gctggacgtc ctggagccaa gggtcctgaa   6840
gggccaccag gacccactgg ccgccaagga gagaagggg agctggtcg ccctggggac   6900
cctgcagtgg tgggacctgc tgttgctgga cccaaaggaa aaagggaga tgtggggccc   6960
gctgggccca gaggagctac cggagtccaa ggggaacggg gcccacccgg cttggttctt   7020
cctggagacc ctgccccaa gggagaccct ggagaccggg gtccattgg ccttactggc   7080
agagcaggac ccccaggtga ctcagggcct cctggagaga aggagaccc tgggcggcct   7140
ggcccccag gacctgttgg cccccgagga cgagatgact aagttggaga gaaaggtgac   7200
gagggtcctc cgggtgaccc gggttttgcct ggaaaagcag gcgagcgtgg ccttcggggg   7260
gcacctggag ttcggggggcc tgtgggtgaa aaggagacc agggagatcc tggagaggat   7320
ggacgaaatg gcagccctgg atcatctgga cccaagggtg accgtgggga gccgggtccc   7380
ccaggacccc cgggacggct ggtagacaca ggacctggag ccagagagaa gggagagctc   7440
ggggaccgcg gacaagaggg tcctcgaggg cccaaggttg atcctggcct ccctggagcc   7500
cctgggggaaa ggggcattga agggtttcgg ggacccccag gcccacaggg ggacccaggt   7560
gtccgaggcc cagcaggaga aaaggggtgac cggggtcccc ctgggctgga tggcggagc   7620
ggactggatg ggaaaccagg agccgctggg ccctctgggc cgaatggtgc tgcagcaaa   7680
gctgggacc caggagagaa cgggcttcca ggcctccgtg gagaacaggg cctccctggc   7740
ccctctggtc ccctggatt accgggaaag ccaggcgagg atggcaaac tggcctgaat   7800
ggaaaaaacg gagaacctgg ggaccctgga gaagacgagg ggaagggaga gaaaggagat   7860
tcaggcgcct ctgggagaga aggtcgtgat ggcccaagg gtgagcgtgg agctcctggt   7920
atccttggac cccaggggcc tccaggcctc ccagggccag tgggccctcc tggccaggt   7980
tttcctggtg tcccaggagg cacgggcccc aaggtgacc gtggggagac tggatccaaa   8040
ggggagcagg gcctccctgg agagcgtggc ctgcgaggag agcctggaag tgtgccgaat   8100
```

-continued

```
gtggatcggt tgctggaaac tgctggcatc aaggcatctg ccctgcggga gatcgtggag     8160
acctgggatg agagctctgg tagcttcctg cctgtgcccg aacggcgtcg aggccccaag     8220
ggggactcag gcgaacaggg cccccaggc aaggagggcc ccatcggctt tcctggagaa     8280
cgcgggctga agggcgaccg tggagaccct ggccctcagg ggccacctgg tctggccctt     8340
ggggagaggg gccccccggg gccttccggc cttgccgggg agcctggaaa gcctggtatt     8400
cccgggctcc caggcagggc tgggggtgtg ggagaggcag gaaggccagg agagagggga     8460
gaacggggag agaaaggaga acgtggagaa cagggcagag atggccctcc tggactccct     8520
ggaaccctg ggccccccgg accccctggc cccaaggtgt ctgtggatga gccaggtcct     8580
ggactctctg gagaacaggg accccctgga ctcaagggtg ctaaggggga gccgggcagc     8640
aatggtgacc aaggtcccaa aggagacagg ggtgtgccag gcatcaaagg agaccgggga     8700
gagcctggac cgaggggtca ggacggcaac ccgggtctac caggagagcg tggtatggct     8760
gggcctgaag ggaagccggg tctgcagggt ccaagaggcc ccctggccc agtgggtggt     8820
catggagacc ctggaccacc tggtgccccg ggtcttgctg ccctgcagg accccaagga     8880
ccttctggcc tgaaggggga gcctggagag acaggaccct caggacgggg cctgactgga     8940
cctactggag ctgtgggact tcctggaccc cccggccctt caggccttgt gggtccacag     9000
gggtctccag gtttgcctgg acaagtgggg gagacaggga agccgggagc cccaggtcga     9060
gatggtgcca gtggaaaaga tggagacaga gggagccctg gtgtgccagg gtcaccaggt     9120
ctgcctggcc ctgtcggacc taaaggagaa cctggcccca cggggccccc tggacaggct     9180
gtggtcgggc tccctggagc aaagggagag aagggagccc ctggaggcct tgctggagac     9240
ctggtcgggtg agccgggagc caaaggtgac cgaggactgc cagggccgcg aggcgagaag     9300
ggtgaagctg gccgtgcagg ggagcccgga gaccctgggg aagatggtca gaaaggggct     9360
ccaggaccca aagtttcaa gggtgaccca ggagtcgggg tcccgggctc ccctgggcct     9420
cctggccctc caggtgtgaa gggagatctg ggcctccctg gcctgccgg tgctcctggt     9480
gttgttgggt tcccgggtca gacaggccct cgaggagaga tgggtcagcc aggccctagt     9540
ggagagcggg gtctggcagg cccccaggg agagaaggaa tcccaggacc cctggggcca     9600
cctggaccac cggggtcagt gggaccacct ggggcctctg gactcaaagg agacaaggga     9660
gaccctggag tagggctgcc tgggccccga ggcgagcgtg gggagccagg catccggggt     9720
gaagatggcc gccccggcca ggagggaccc cgaggactca cggggccccc tggcagcagg     9780
ggagagcgtg gggagaaggg tgatgttggg agtgcaggac taaagggtga caagggagac     9840
tcagctgtga tcctggggcc tccaggccca cggggtgcca aggggacat gggtgaacga     9900
gggcctcggg gcttggatgg tgacaaagga cctcgggggag acaatgggga ccctggtgac     9960
aagggcagca agggagagcc tggtgacaag ggctcagccg ggttgccagg actgcgtgga     10020
ctcctgggac cccagggtca acctggtgca gcagggatcc ctggtgaccc gggatcccca     10080
ggaaaggatg gagtgcctgg tatccgagga gaaaaaggag atgttggctt catgggtccc     10140
cggggcctca agggtgaacg gggagtgaag ggagcctgtg gcttgatgg agagaaggga     10200
gacaagggag aagctggtcc cccaggccgc cccgggctgg caggacacaa aggagagatg     10260
ggggagcctg gtgtgccggg ccagtcgggg gcccctggca aggagggcct gatcggtccc     10320
aagggtgacc gaggctttga cgggcagcca ggccccaagg gtgaccaggg cgagaaaggg     10380
gagcgggaa ccccaggaat tgggggcttc ccaggcccca gtggaaatga tggctctgct     10440
ggtccccccag ggccacctgg cagtgttggt cccagaggcc ccgaaggact tcagggccag     10500
aagggtgagc gaggtccccc cggagagaga gtggtggggg ctcctggggt ccctggagct     10560
cctggcgaga gaggggagca ggggcggcca gggcctgccg gtcctcgagg cgagaaggga     10620
gaagctgcac tgacggagga tgacatccgg ggctttgtgc gccaagagat gagtcagcac     10680
tgtgcctgcc agggccagtt catcgcatct ggatcacgac ccctccctag ttatgctgca     10740
gacactgccg gctcccagct ccatgctgtg cctgtgctcc gcgtctctca tgcagaggag     10800
gaagagcggg taccccctga ggatgatgag tactctgaat actccgagta ttctgtggag     10860
gagtaccagg accctgaagc tccttgggat agtgatgacc ctgttccct gccactggat     10920
gagggctcct gcactgccta caccctcgcg tggtaccatc gggctgtgac aggcagcaca     10980
gaggcctgtc accttttgt ctatggtggc tgtggaggga atgccaaccg ttttgggacc     11040
cgtgaggcct gcgagcgccg ctgcccaccc cgggtggtcc agagccaggg gacaggtact     11100
gcccaggact ga                                                         11112
```

SEQ ID NO: 20            moltype = AA  length = 3703
FEATURE                  Location/Qualifiers
REGION                   1..3703
                         note = Synthetic Construct
source                   1..3703
                         mol_type = protein
                         organism = synthetic construct
SEQUENCE: 20
```
MTSSGPGPRF LLLLPLLLPP AASASDRPRG RDPVNPEKLL VITVATAETE GYLRFLRSAE     60
FFNYTVRTLG LGEEWRGGDV ARTVGGGQKV RWLKKEMEKY ADREDMIIMF VDSYDVILAG     120
SPTELLKKFV QSGSRLLFSA ESFCWPEWGL AEQYPEVGTG KRFLNSGGFI GFATTIHQIV     180
RQWKYKDDDD DQLFYTRLYL DPGLREKLSL NLDHKSRIFQ NLNGALDEVV LKFDRNRVRI     240
RNVAYDTLPI VVHGNGPTKL QLNYLGNYVP NGWTPEGGCG FCNQDRRTLP GGQPPPRVFL     300
AVFVEQPTPF LPRFLQRLLL LDYPPDRVTL FLHNNEVFHE PHIADSWPQL QDHFSAVKLV     360
GPEEALSPGE ARDMAMDLCR QDPECEFYFS LDADAVLTNL QTLRILIEEN RKVIAPMLSR     420
HGKLWSNFWG ALSPDEYYAR SEDYVELVQR KRVGVWNVPY ISQAYVIRGD TLRMELPQRD     480
VFSGSDTDPD MAFCKSFRDK GIFLHLSNQH EFGRLLATSR YDTEHLHPDL WQIFDNPVDW     540
KEQYIHENYS RALEGEGIVE QPCPDVYWFP LLSEQMCDEL VAEMEHYGQW SGGRHEDSRL     600
AGGYENVPTV DIHMKQVGYE DQWLQLLRTY VGPMTESLFP GYHTKARAVM NFVVRYRPDE     660
QPSLRPHHDS STFTLNVALN HKGLDYEGGG CRFLRYDCVI SSPRKGWALL HPGRLTHYHE     720
GLPTTWGTRY IMVSFVDPGS GATNFSLLKQ AGDVEENPGP TLRLLVAALC AGILAEAPRV     780
RAQHRERVTC TRLYAADIVF LLDGSSSIGR SNFREVRSFL EGLVLPFSGA ASAQGVRFAT     840
VQYSDDPRTE FGLDALGSGG DVIRAIRELS YKGGNTRTGA AILHVADHVF LPQLARPGVP     900
KVCILITDGK SQDLVDTAAQ RLKGQGVKLF AVGIKNADPE ELKRVASQPT SDFFFFVNDF     960
SILRTLLPLV SRRVCTTAGG VPVTRPPDDS TSAPRDLVLS EPSSQSLRVQ WTAASGPVTG     1020
YKVQYTPLTG LGQPLPSERQ EVNVPAGETS VRLRGLRPLT EYQVTVIALY ANSIGEAVSG     1080
TARTTALEGP ELTIQNTTAH SLLVAWRSVP GATGYRVTWR VLSGGPTQQQ ELGPGQGSVL     1140
```

```
LRDLEPGTDY EVTVSTLFGR SVGPATSLMA RTDASVEQTL RPVILGPTSI LLSWNLVPEA  1200
RGYRLEWRRE TGLEPPQKVV LPSDVTRYQL DGLQPGTEYR LTLYTLLEGH EVATPATVVP  1260
TGPELPVSPV TDLQATELPG QRVRVSWSPV PGATQYRIIV RSTQGVERTL VLPGSQTAFD  1320
LDDVQAGLSY TVRVSARVGP REGSASVLTV RREPETPLAV PGLRVVVSDA TRVRVAWGPV  1380
PGASGFRISW STGSGPESSQ TLPPDSTATD ITGLQPGTTY QVAVSVLRGR EEGPAAVIVA  1440
RTDPLGPVRT VHVTQASSSS VTITWTRVPG ATGYRVSWHS AHGPEKSQLV SGEATVAELD  1500
GLEPDTEYTV HVRAHVAGVD GPPASVVVRT APEPVGRVSR LQILNASSDV LRITWVGVTG  1560
ATAYRLAWGR SEGGPMRHQI LPGNTDSAEI RGLEGGVSYS VRVTALVGDR EGTPVSIVVT  1620
TPPEAPPALG TLHVVQRGEH SLRLRWEPVP RAQGFLLHWQ PEGGQEQSRV LGPELSSYHL  1680
DGLEPATQYR VRLSVLGPAG EGPSAEVTAR TESPRVPSIE LRVVDTSIDS VTLAWTPVSR  1740
ASSYILSWRP LRGPGQEVPG SPQTLPGISS SQRVTGLEPG VSYIFSLTPV LDGVRGPEAS  1800
VTQTPVCPRG LADVVFLPHA TQDNAHRAEA TRRVLERLVL ALGPLGPQAV QVGLLSYSHR  1860
PSPLFPLNGS HDLGIILQRI RDMPYMDPSG NNLGTAVVTA HRYMLAPDAP GRRQHVPGVM  1920
VLLVDEPLRG DIFSPIREAQ ASGLNVVMLG MAGADPEQLR RLAPGMDSVQ TFFAVDDGPS  1980
LDQAVSGLAT ALCQASFTTQ PRPEPCPVYC PKGQKGEPGE MGLRGQVGPP GDPGLPGRTG  2040
APGPQGPPGS ATAKGERGFP GADGRPGSPG RAGNPGTPGA PGLKGSPGLP GPRGDPGERG  2100
PRGPKGEPGA PGQVIGGEGP GLPGRKGDPG PSGPPGPRGP LGDPGPRGPP GLPGTAMKGD  2160
KGDRGERGPP GPGEGGIAPG EPGLPGLPGS PGPQGPVGPP GKKGEKGDSE DGAPGLPGQP  2220
GSPGEQGPRG PPGAIGPKGD RGFPGPLGEA GEKGERGPPG PAGSRGLPGV AGRPGAKGPE  2280
GPPGPTGRQG EKGEPGRPGD PAVVGPAVAG PKGEKGDVGP AGPRGATGVQ GERGPPGLVL  2340
PGDPGPKGDP GDRGPIGLTG RAGPPGDSGP PGEKGDPGRP GPPGPVGPRG RDGEVGEKGD  2400
EGPPGDPGLP GKAGERGLRG APGVRGPVGE KGDQGDPGGD GRNGSPGSSG PKGDRGEPGP  2460
PGPPGRLVDT GPGAREKGEP GDRGQEGPRG PKGDPGLPGA PGERGIEGFR GPPGPQGDPG  2520
VRGPAGEKGD RGPPGLDGRS GLDGKPGAAG PSGPNGAAGK AGDPGRDGLP GLRGEQGLPG  2580
PSGPPGLPGK PGEDGKPGLN GKNGEPGDPG EDGRKGEKGD SGASGREGRD GPKGERGAPG  2640
ILGPQGPPGL PGPVGPPGQG FPGVPGGTGP KGDRGETGSK GDQGLPGERG LRGEPGSVPN  2700
VDRLLETAGI KASALREIVE TWDESSGSFL PVPERRRGPK GDSGEQGPPG KEGPIGFPGE  2760
RGLKGDRGDP GPQGPPGLAL GERGPPGPSG LAGEPGKPGI PGLPGRAGGV GEAGRPGERG  2820
ERGEKGERGE QGRDGPPGLP GTPGPPGPPG PKVSVDEPGP GLSGEQGPPG LKGAKGEPGS  2880
NGDQGPKGDR GVPGIKGDRG EPGPRGQDGN PGLPGERGMA GPEGKPGLQG PRGPPGPVGG  2940
HGDPGPPGAP GLAGPAGPQG PSGLKGEPGE TGPPGRGLTG PTGAVGLPGP PGPSGLVGPQ  3000
GSPGLPGQVG ETGKPGAPGR DGASGKDGDR GSPGVPGSPG LPGPVGPKGE PGPTGAPGQA  3060
VVGLPGAKGE KGAPGGLAGD LVGEPGAKGD RGLPGPRGEK GEAGRAGEPG DPGEDGQKGA  3120
PGPKGPKGDP GVGVPGSPGP PGPPGVKGDL GLPGLPGAPG VVGFPGQTGP RGEMGQPGPS  3180
GERGLAGPPG REGIPGPLGP PGPPGSVGPP GASGLKGDKG DPGVGLPGPR GERGEPGIRG  3240
EDGRPGQEGP RGLTGPPGSR GERGEKGDVG SAGLKGDKGD SAVILGPPGP RGAKGDMGER  3300
GPRGLDGDKG PRGDNGDPGD KGSKGEPGDK GSAGLPGLRG LLGPQGQPGA AGIPGDPGSP  3360
GKDGVPGIRG EKGDVGFMGP RGLKGERGVK GACGLDGEKG DKGEAGPPGR PGLAGHKGEM  3420
GEPGVPGQSG APGKEGLIGP KGDRGFDGQP GPKGDQGEKG ERGTPGIGGF PGPSGNDGSA  3480
GPPGPPGSVG PRGPEGLQGQ KGERGPPGER VVGAPGVPGA PGERGEQGRP GPAGPRGEKG  3540
EAALTEDDIR GFVRQEMSQH CACQGQFIAS GSRPLPSYAA DTAGSQLHAV PVLRVSHAEE  3600
EERVPPEDDE YSEYSEYSVE EYQDPEAPWD SDDPCSLPLD EGSCTAYTLR WYHRAVTGST  3660
EACHPFVYGG CGGNANRFGT REACERRCPP RVVQSQGTGT AQD                    3703
```

```
SEQ ID NO: 21          moltype = DNA   length = 11115
FEATURE                Location/Qualifiers
misc_feature           1..11115
                       note = Synthetic Construct
source                 1..11115
                       mol_type = other DNA
                       organism = synthetic construct
SEQUENCE: 21
atgacgctgc ggcttctggt ggccgcgctc tgcgccggga tcctggcaga ggcgccccga   60
gtgcgagccc agcacaggga gagagtgacc tgcacgcgcc tttacgccgc tgacattgtg  120
ttcttactgg atggctcctc atccattggc cgcagcaatt tccgcgaggt ccgcagcttt  180
ctcgaagggc tggtgctgcc tttctctgga gcagccagtg cacagggtgt gcgctttgcc  240
acagtgcagt acagcgatga cccacgggaca gagttcggcc tggatgcact ggctctgggg  300
ggtgatgtga tccgcgccat ccgtgagctt agctacaagg ggggcaacac tcgcacaggg  360
gctcaattcc tccatgtggc tgaccatgtc ttcctgcccc agctggcccg acctggtgtc  420
cccaaggtct gcatcctgat cacagacggg aagtcccagg acctggtgga cacagctgcc  480
caaaggctga aggggcaggg ggtcaagcta tttgctgtgg ggatcaagaa tgctgaccct  540
gaggagctga agcgagttgc ctcacagccc accagtgact tcttcttctt cgtcaatgac  600
ttcagcatct tgaggacact actgcccctc gtttcccgga gagtgtgcac gactgctggt  660
ggcgtgcctg tgacccgacc tccggatgac tcgacctctg ctccacgaga cctggtgctg  720
tctgagccaa gcagccaatc cttgagagta cagtggacag cggccagtgg ccctgtgact  780
ggctacaagg tccagtacac tcctctgacg gggctgggac agccactgcc gagtgagcgg  840
caggaggtga acgtcccagc tggtgagacc agtgtgcggc tgcggggtct ccggccactg  900
accgagtacc aagtgactgt gattgccctc tacgccaaca gcatcgggga ggctgtgagc  960
gggacagctc ggaccactgc cctagaaggg ccggaactga ccatccagaa taccacagcc  1020
cacagcctcc tggtggcctg gcggagtgtg ccaggtgcca ctggctaccg tgtgacatgg  1080
cgggtcctca gtggtgggcc cacacagcag caggagctgg ccctgggca gggttcagtg  1140
ttgctgcgtg acttggagcc tggcacggac tatgaggtga ccgtgagcac cctatttggc  1200
cgcagtgtgg ggccgccac ttccctgatg gctcgcactg acgcttctgt tgagcagacc  1260
ctgcgcccag tcatcctggg ccccacatcc atcctccttt cctggaactt ggtgcctgag  1320
gcccgtggct accggttgga atggcggcgt gagactggct tggagccacc gcagaaggtg  1380
gtactgcccct ctgatgtgac ccgctaccag ttggatgggc tgcagccggg cactgagtac  1440
cgcctcacac tctacactct gctggagggc cacgaggtgg ccacccctgc aaccgtggtt  1500
cccactggac cagagctgcc tgtgagccct gtaacagacc tgcaagccac cgagctgccc  1560
gggcagcggg tgcgagtgtc ctggagccca gtccctggtg ccacccagta ccgcatcatt  1620
```

-continued

```
gtgcgcagca cccagggggt tgagcggacc ctggtgcttc ctgggagtca gacagcattc   1680
gacttggatg acgttcaggc tgggcttagc tacactgtgc gggtgtctgc tcgagtgggt   1740
ccccgtgagg gcagtgccag tgtcctcact gtccgccggg agccggaaac tccacttgct   1800
gttccagggc tgcgggttgt ggtgtcagat gcaacgcgag tgagggtggc ctggggaccc   1860
gtccctggag ccagtggatt tcggattagc tggagcacag gcagtggtcc ggagtccagc   1920
cagacactgc ccccagactc tactgccaca gacatcacag ggctgcagcc tggaaccacc   1980
taccaggtgg ctgtgtcggt actgcgaggc agagaggagg gccctgctgc agtcatcgtg   2040
gctcgaacgg acccactggg cccagtgagg acggtccatg tgactcaggc cagcagctca   2100
tctgtcacca ttacctggac caggggttcct ggcgccacag gatacagggt ttcctggcac   2160
tcagcccacg gcccagagaa atcccagttg gtttctgggg aggccacggt ggctgagctg   2220
gatggactgg agccagatac tgagtatacg gtgcatgtga gggcccatgt ggctggcgtg   2280
gatgggcccc ctgcctctgt ggttgtgagg actgccctg agcctgtggg tcgtgtgtcg   2340
aggctgcaga tcctcaatgc ttccagcgac gttctacgga tcacctgggt aggggtcact   2400
ggagccacag cttacagact ggcctggggc cggagtgaag gcggccccat gaggcaccag   2460
atactcccag gaaacacaga ctctgcagag atccggggtc tcgaaggtgg agtcagctac   2520
tcagtgcgag tgactgcact tgtctcgggggac cgcgagggca cacctgtctc cattgttgtc   2580
actacgccgc ctgaggctcc gccagccctg gggacgcttc acgtggtgca gcgcggggag   2640
cactcgctga ggctgcgctg ggagccggtg cccagacgc agggcttcct tctgcactgg   2700
caacctgagg gtggccagga acagtcccgg gtcctggggc ccgagctcag cagctatcac   2760
ctggacgggc tggagccagc gacacagtac cgcgtgaggc tgagtgtcct agggccagct   2820
ggagaagggc cctctgcaga ggtgactgcg cgcactgagt cacctcgtgt tccaagcatt   2880
gaactacgtg tggtggacac ctcgatcgac tcggtgactt tggcctggac tccagtgtcc   2940
agggcatcca gctacatcct atcctggcgg ccactcagag gccctggcca ggaagtgcct   3000
gggtccccgc agacacttcc agggatctca agctcccagc gggtgacagg gctagagcct   3060
ggcgtctctt acatcttctc cctgacgcct gtcctggatg gtgtgcgggg tcctgaggca   3120
tctgtcacac agacgccagt gtgcccccgt ggcctgggca atgtggtgtt cctaccacat   3180
gccactcaag acaatgctca ccgtgcggag gctacgagga gggtcctgga gcgtctggtg   3240
ttggcacttg ggcctcttgg gccacaggca gttcaggttg gcctgctgtc ttacagtcat   3300
cggccctccc cactgttccc actgaatggc tcccatgacc ttggcattat cttgcaaagg   3360
atccgtgaca tgccctacat ggacccaagt gggaacaacc tgggcacagc cgtggtcaca   3420
gctcacagat acatgttggc accagatgct cctgggcgcc gccagcacgt accagggggtg   3480
atggttctgc tagtggatga accttgaga ggtgacatat tcagccccat ccgtgaggcc   3540
caggcttctg ggcttaatgt ggtgatgttg ggaatggctg gagcggaccc agagcagctg   3600
cgtcgcttgg cgccgggtat ggactctgtc cagaccttct tcgccgtgga tgatgggcca   3660
agcctggacc aggcagtcag tggtctggcc acagccctgt gtcaggcatc cttcactact   3720
cagccccggc cagagccctg cccagtgtat tgtccaaagg gccagaaggg ggaacctgga   3780
gagatgggcc tgagaggaca agtgggcct cctggcgacc ctggcctccc gggcaggacc   3840
ggtgctcccg gcccccaggg gcccctgga agtgccactg ccaagggcga gaggggcttc   3900
cctggagcag atgggcgtcc aggcagccct ggccgccgcg ggaatcctgg gaccctgga   3960
gcccctggcc taaagggctc tccagggttg cctggcccctc gtggggaccc gggagagcga   4020
ggacctcgag gcccaaaggg gggagccgggg gctcccggac aagtcatcgg aggtgaagga   4080
cctgggcttc ctgggcggaa aggggaccct ggaccatcgg gccccctgg acctcgtgga   4140
ccactggggg acccaggacc ccgtggcccc ccagggcttc ctggaacagc catgaagggt   4200
gacaaaggcg atcgtgggga gcggggtccc cctggaccag gtgaaggtgg cattgctcct   4260
ggggagcctg ggctgccggg tcttcccgga agccctggac cccaaggccc cgttggcccc   4320
cctggaaaga aaggagaaaa aggtgactct gaggatggag ctccaggcct cccaggacaa   4380
cctggtctc cgggtgagca gggcccacgg ggacctcctg gagctattgg ccccaaaggt   4440
gaccggggct ttccagggcc cctgggtgag gctggagaga agggcgaacg tggaccccca   4500
ggcccagcgg gatcccgggg gctgccaggg gttgctggac gtcctggagc caagggtcct   4560
gaagggccac caggacccac tggccgccaa ggagagaagg gggagcctgg tcgccctggg   4620
gaccctgcag tggtgggacc tgctgttgct ggacccaaag gagaaaaggg agatgtggga   4680
cccgctgggc ccagaggagc taccggagtc caagggaac ggggcccacc cggcttggtt   4740
cttcctggag accctggccc caagggagac cctggagacc ggggtcccat tggccttact   4800
ggcagagcag gaccccagg tgactcaggg cctcctggag agaagggaga ccctgggcgg   4860
cctggcccc caggacctgt tggcccccga ggacgagatg gtgaagttgg agagaaaggt   4920
gacgagggtc ctccgggtga cccgggtttg cctggaaaag caggcgagcg tggccttcgg   4980
ggggcacctg gagttcgggg gcctgtgggg gaaaagggag accagggaga tcctggagag   5040
gatggacgaa atggcagccc tggatcatct ggacccaagg gtgaccgtgg ggagccgggt   5100
ccccaggac cccgggacg gctggtagac acaggacctg gagccagaga gaagggagag   5160
cctggggacc gcggacaaga gggtcctcga gggccccaagg gtgatcctgg cctccctgga   5220
gcccctgggg aaaggggcat tgaagggttt cggggacccc caggcccaca gggggaccca   5280
ggtgtccgag gcccagcagg agaaaagggt gaccggggtc ccctgggct ggatggccgg   5340
agcggactgg atgggaaacc aggagccgct gggcctctg ggccgaatgg tgctgcaggc   5400
aaagctgggg acccaggggag agacgggctt ccaggcctc gtggagaaca gggcctccct   5460
ggccctctg gtcccctgg attaccggga aagccaggcg aggatggcaa acctggcctg   5520
aatgaaaaaa acgagaacc tggggaccct ggagaagacg ggaggaaggg agagaaagga   5580
gattcaggcg cctctgggag agaaggtcgt gatggcccca agggtgagcg tggagctcct   5640
ggtatccttg gaccccaggg gcctccaggc ctcccagggc cagtgggccc tcctggccag   5700
ggttttcctg gtgtcccagg aggcacggc cccaagggtg accggggct gggactggtcc   5760
aaaggggagc agggcctccc tggagagcgt ggcctgcgag gagagcctgg aagtgtgccg   5820
aatgtggatc ggttgctgga aactgctggc atcaaggcat ctgccctgcg ggagatcgtg   5880
gagacctggg atgagagctc tggtagcttc ctgcctgtgc ccgaacgcg tcgaggcccc   5940
aagggggact caggcgaaca gggcccccca ggcaaggagg ccccatcgg ctttcctgga   6000
gaacgcgggg tgaaggcga ccgtgagac cctggccctc agggggccacc tggtctggcc   6060
cttggggaga gggcccccccc cgggccttcc ggccttgccg gggagcctgg aaagcctggt   6120
attcccgggc tcccaggcag ggctgggggt gtggagagg caggaaggcc aggagagagg   6180
ggagaacggg gagagaaagg agaacgtgga gaacagggca gagatggccc tcctggactc   6240
cctggaaccc ctgggccccc cggaccccct ggccccaagg tgtctgtgga tgagccaggt   6300
cctggactct ctggagaaca gggaccccct ggactcaagg gtgctaaggg gggagccgggc   6360
```

```
agcaatggtg accaaggtcc caaaggagac aggggtgtgc caggcatcaa aggagaccgg   6420
ggagagcctg gaccgagggg tcaggacggc aacccgggtc taccaggaga gcgtggtatg   6480
gctgggcctg aagggaagcc gggtctgcag ggtccaagag gcccccctgg cccagtgggt   6540
ggtcatggag accctggacc acctggtgcc ccgggtcttg ctggccctgc aggaccccaa   6600
ggaccttctg gcctgaaggg ggagcctgga gagacaggac ctccaggacg gggcctgact   6660
ggacctactg gagctgtggg acttcctgga ccccccggcc cttcaggcct tgtgggtcca   6720
caggggtctc caggtttgcc tggacaagtg ggggagacag ggaagccggg agccccaggt   6780
cgagatggtg ccagtggaaa agatggagac agagggagcc ctggtgtgcc agggtcacca   6840
ggtctgcctg gccctgtcgg acctaaagga gaacctggcc cacggggggc ccctggacag   6900
gctgtggtcg ggctccctgg agcaaaggga gagaagggag cccctggagg ccttgctgga   6960
gacctggtgg gtgagccggg agccaaaggt gaccgaggac tgccagggcc gcgaggcgag   7020
aagggtgaag ctggccgtgc aggggagccc ggagaccctg gggaagatgg tcagaaaggg   7080
gctccaggac ccaaaggttt caagggtgac ccaggagtcg gggtcccggg ctcccctggg   7140
cctcctggcc ctccaggtgt gaagggagat ctgggcctcc ctggcctgcc cggtgctcct   7200
ggtgttgttg ggttcccggg tcagacaggc cctcgaggag agatggggtca gccaggccct   7260
agtggagagc ggggtctggc aggcccccca gggagagaag gaatcccagg accctgggg   7320
ccacctggac caccgggggtc agtgggacca cctgggcct ctggactcaa aggagacaag   7380
ggagacctg gagtagggct gcctgggccc cgaggcgagc gtgggggagcc aggcatccgg   7440
ggtgaagatg gccgcccgg caggagggga ccccgaggac tcacggggcc ccctggcagc   7500
aggggagagc gtggggagaa gggtgatgtt gggagtgcag gactaaaggg tgacaaggga   7560
gactcagctg tgatcctggg gcctccaggc ccacgggggtg ccaaggggga catgggtgaa   7620
cgagggcctc ggggcttgga tggtgacaaa ggacctcggg gagacaatgg gaccctggt   7680
gacaagggca gcaagggaga gcctggtgac aagggctcag ccgggttgcc aggactgcgt   7740
ggactcctgg gaccccaggg tcaacctggt gcagcaggga tccctggtga cccgggatcc   7800
ccaggaaagg atgagtgcc tggtatccga ggagaaaaag gagatgttgg cttcatgggt   7860
ccccgggggcc tcaagggtga acggggagtg aagggagcct gtggccttga tggagagaag   7920
ggagacaagg gagaagctgg tccccccaggc cgcccccggc tggcaggaca caaaggagag   7980
atggggggagc ctggtgtgcc gggccagtcg ggggcccctg gcaaggaggg cctgatcggt   8040
cccaagggtg accgaggctt tgacgggcag ccaggcccca agggtgacca gggcgagaaa   8100
ggggagcggg gaaccccagg aattgggggc ttcccaggcc ccagtggaaa tgatggctct   8160
gctggtcccc cagggccacc tggcagtgtt ggtcccagag gccccgaagg acttcagggc   8220
cagaagggtg agcgaggtcc ccccggagag agagtggtgg gggctcctgg ggtccctgga   8280
gctcctggcg agagagggga gcaggggcgg ccagggcctg ccggtcctcg aggcgagaag   8340
ggagaagctg cactgacgga ggatgacatc cggggcttg tgcgccaaga gatgagtcag   8400
cactgtgcct gccagggcca gttcatcgca tctggatcac gaccctccc tagttatgct   8460
gcagacactg ccggctccca gctccatgct gtgcctgtgc tccgcgtctc tcatgcagag   8520
gaggaagagc gggtaccccc tgaggatgat gagtactctg aatactccga gtattctgtg   8580
gaggagtacc aggaccctga agctccttgg gatagtgatg acccctgttc cctgccactg   8640
gatgagggct cctgcactgc ctacacctgt gctggtacc atcgggctgt gacaggcagc   8700
acagaggcct gtcacccttt tgtctatggt ggctgtggag ggaatgccaa ccgtttttgg   8760
acccgtgagg cctgcgagcg ccgctgccca ccccgggtgg tccagagcca ggggacaggt   8820
actgcccagg acggaagcgg acagtgtact aattatgctc tcttgaaatt ggctggagat   8880
gttgagagca accctggacc tacctcctcg gggcctggac cccggttcct gctgctgctg   8940
ccgctgctgc tgcccectgc ggcctcagcc tccgaccggc cccgggggccg agacccggtc   9000
aacccagaga agctgctggt gatcactgtg gccacagctg aaaccgaggg gtacctgcgt   9060
ttcctgcgct ctgcggagtt cttcaactac actgtgcgga ccctgggcct gggagaggag   9120
tggcgaggag gtgatgtggc tcgaacagtt ggtggaggac agaaggtccg gtggttaaag   9180
aaggaaatgg agaaatacgc tgaccggag gatatgatca tcatgtttgt ggatagctac   9240
gacgtgattc tggccggcag ccccacagag ctgctgaaga gttcgtcca gagtggcagc   9300
cgcctgctct tctctgcaga gagcttctgc tggcccgagt gggggctggc ggagcagtac   9360
cctggaatgg gcacggggaa gcgcttcctc aattctggtg gattcatcgg ttttgccacc   9420
accatccacc aaatcgtgcg ccagtggaag tacaaggatg atgacgacga ccagctgttc   9480
tacacacggc tctacctgga cccaggactg agggagaaac tcagccttaa tctggatcat   9540
aagtctcgga tctttcagaa cctcaacggg gctttagatg aagtggtttt aaagtttgat   9600
cggaaccgtg tgcgtatccg gaacgtggcc tacgacacgc tccccattgt ggtccatgga   9660
aacggtccca ctaagctgca gctcaactac ctgggaaact acgtccccaa tggctggact   9720
cctgagggag gctgtggctt ctgcaaccag gaccggagga cactcccggg ggggcagcct   9780
cccccccggg tgtttctggc cgtgtttgtg gaacagccta ctccgtttct gccccgcttc   9840
ctgcagcggc tgctactcct ggactatccc ccgcacaggg tcaccctttt cctgcacaac   9900
aacgaggtct tccatgaacc ccacatcgct gactcctgcc cgcagctcca ggaccacttc   9960
tcagctgtga agctcgtggg gccggaggag gctctgagcc caggcgaggc cagggacatg  10020
gccatggacc tgtgtcggca ggaccccgag tgtgagttct acttcagcct ggacgccgac  10080
gctgtcctca ccaacctgca gaccctgcgt atcctcattg aggagaacag gaaggtgatc  10140
gcccccatgc tgtcccgcca cggcaagctg tggtccaact acgtccccaa tggctggact  10200
gatgagtact acgccgcgctc cgaggactac gtggagctgg tgcagcggaa gcgagtgggt  10260
gtgtggaatg taccatacat ctcccaggcc tatgtgatcc ggggtgatac cctgcgatg  10320
gagctgcccc agagggatgt gttctcgggc agtgacacag acccggacat ggccttctgt  10380
aagagctttc gagacaaggg catcttcctc catctgagca atcagcatga atttggccgg  10440
ctcctggcca cttccagata cgacacggag cacctgcacc ccgacctctg gcagatcttc  10500
gacaaccccg tcgactggaa ggagcagtac atccacagaga actacagccg ggccctggaa  10560
ggggaaggaa tcgtggagca gccatgcccg gacgtgtact ggttcccact gctgtcagaa  10620
caaatgtgtg atgagctggt ggcagagatg gagcactacg gccagtggtc aggcggccga  10680
catgaggatt caaggctggc tggaggctac gagaatgtgc ccaccgtgga catccacatg  10740
aagcaggtgg ggtacgagga ccagtggtg cagctgctgc aggggccatg gggcccccatg  10800
accgagagcc tgtttcccgg ttaccacacc aaggcgcggg cggtgatgaa ctttgtggtt  10860
cgctaccggc cagacgagca gccgtctctg cggccacacc acgactcatc cacctttcacc  10920
ctcaacgttg ccctcaacca caaggccctg gactatgagg gaggtggctg ccgcttcctg  10980
cgctacgact gtgtgatctc ctccccgagg aagggctggg cactcctgca ccccggccgc  11040
ctcaccccact accacgaggg gctgccaacg acctggggca cacgctacat catggtgtcc  11100
```

-continued

```
tttgtcgacc cctga                                                        11115

SEQ ID NO: 22          moltype = AA   length = 3704
FEATURE                Location/Qualifiers
REGION                 1..3704
                       note = Synthetic Construct
source                 1..3704
                       mol_type = protein
                       organism = synthetic construct
SEQUENCE: 22
MTLRLLVAAL CAGILAEAPR VRAQHRERVT CTRLYAADIV FLLDGSSSIG RSNFREVRSF   60
LEGLVLPFSG AASAQGVRFA TVQYSDDPRT EFGLDALGSG GDVIRAIREL SYKGGNTRTG   120
AAILHVADHV FLPQLARPGV PKVCILITDG KSQDLVDTAA QRLKGQGVKL FAVGIKNADP   180
EELKRVASQP TSDFFFFVND FSILRTLLPL VSRRVCTTAG GVPVTRPPDD STSAPRDLVL   240
SEPSSQSLRV QWTAASGPVT GYKVQYTPLT GLGQPLPSER QEVNVPAGET SVRLRGLRPL   300
TEYQVTVIAL YANSIGEAVS GTARTTALEG PELTIQNTTA HSLLVAWRSV PGATGYRVTW   360
RVLSGGPTQQ QELGPGQGSV LLRDLEPGTD YEVTVSTLFG RSVGPATSLM ARTDASVEQT   420
LRPVILGPTS ILLSWNLVPE ARGYRLEWRR ETGLEPPQKV VLPSDVTRYQ LDGLQPGTEY   480
RLTLYTLLEG HEVATPATVV PTGPELPVSP VTDLQATELP GQRVRVSWSP VPGATQYRII   540
VRSTQGVERT LVLPGSQTAF DLDDVQAGLS YTVRVSARVG PREGSASVLT VRREPETPLA   600
VPGLRVVVSD ATRVRVAWGP VPGASGFRIS WSTGSGPESS QTLPPDSTAT DITGLQPGTT   660
YQVAVSVLRG REEGPAAVIV ARTDPLGPVR TVHVTQASSS SVTITWTRVP GATGYRVSWH   720
SAHGPEKSQL VSGEATVAEL DGLEPDTEYT VHVRAHVAGV DGPPASVVVR TAPEPVGRVS   780
RLQILNASSD VLRITWVGVT GATAYRLAWG RSEGGPMRHQ ILPGNTDSAE IRGLEGGVSY   840
SVRVTALVGD REGTPVSIVV TTPPEAPPAL GTLHVVQRGE HSLRLRWEPV PRAQGFLLHW   900
QPEGGQEQSR VLGPELSSYH LDGLEPATQY RVRLSVLGPA GEGPSAEVTA RTESPRVPSI   960
ELRVVDTSID SVTLAWTPVS RASSYILSWR PLRGPGQEVP GSPQTLPGIS SSQRVTGLEP   1020
GVSYIFSLTP VLDGVRGPEA SVTQPVCPR  GLADVVFLPH ATQDNAHRAE ATRRVLERLV   1080
LALGPLGPQA VQVGLLSYSH RPSPLFPLNG SHDLGIILQR IRDMPYMDPS GNNLGTAVVT   1140
AHRYMLAPDA PGRRQHVPGV MVLLVDEPLR GDIFSPIREA QASGLNVVML GMAGADPEQL   1200
RRLAPGMDSV QTFFAVDDGP SLDQAVSGLA TALCQASFTT QPRPEPCPVY CPKGQKGEPG   1260
EMGLRGQVGP PGDPGLPGRT GAPGPQGPPG SATAKGERGF PGADGRPGSP GRAGNPGTPG   1320
APGLKGSPGL PGPRGDPGER GPRGPKGEPG APGQVIGGEG PGLPGRKGDP GPSGPPGPRG   1380
PLGDPGPRGP PGLPGTAMKG DKGDRGERGP PGPGEGGIAP GEPGLPGLPG SPGPQGPVGP   1440
PGKKGEKGDS EDGAPGLPGQ PGSPGEQGPR GPPGAIGPKG DRGFPGPLGE AGEKGERGPP   1500
GPAGSRGLPG VAGRPGAKGP EGPPGPTGRQ GEKGEPGRPG DPAVVGPAVA GPKGEKGDVG   1560
PAGPRGATGV QGERGPPGLV LPGDPGPKGD PGDRGPIGLT GRAGPPGDSG PPGEKGDPGR   1620
PGPPGPVGPR GRDGEVGEKG DEGPPGDPGL PGKAGERGLR GAPGVRGPVG EKGDQGDPGE   1680
DGRNGSPGSS GPKGDRGEPG PPGPPGRLVD TGPGAREKGE PGDRGQEGPR GPKGDPGLPG   1740
APGERGIEGF RGPPGPQGDP GVRGPAGEKG DRGPPGLDGR SGLDGKPGAA GPSGPNGAAG   1800
KAGDPGRDGL PGLRGEQGLP GPSGPPGLPG KPGEDGKPGL NGKNGEPGDP GEDGRKGEKG   1860
DSGASGREGR DGPKGERGAP GILGPQGPPG LPGPVGPPGQ PGPGVPGGTG PKGDRGETGS   1920
KGEQGLPGER GLRGEPGSVP NVDRLLETAG IKASALREIV ETWDESSGSF LPVPERRRGP   1980
KGDSGEQGPP GKEGPIGFPG ERGLKGDRGD PGPQGPPGLA LGERGPPGPS GLAGEPGKPG   2040
IPGLPGRAGG VGEAGRPGER GERGEKGERG EQGRDGPPGL PGTPGPPGPP GPKVSVDEPG   2100
PGLSGEQGPP GLKGAKGEPG SNGDQGPKGD RGVPGIKGDR GEPGPRGQDG NPGLPGERGM   2160
AGPEGKPGLQ GPRGPPGPVG GHGDPGPPGA PGLAGPAGPQ GPSGLKGEPG ETGPPGRGLT   2220
GPTGAVGLPG PPGPSGLVGP QGSPGLPGQV GETGKPGAPG RDGASGKDGD RGSPGVPGSP   2280
GLPGPVGPKG EPGPTGAPGQ AVVGLPGAKG EKGAPGGLAG DLVGEPGAKG DRGLPGPRGE   2340
KGEAGRAGEP GDPGEDGQKG APGPKGFKGD PGVGVPGSPG PPGPPGVKGD LGLPGLPGAP   2400
GVVGFPGQTG PRGEMGQPGP SGERGLAGPP GREGIPGDTG PGPPGSVGP  PGASGLKGDK   2460
GDPGVGLPGP RGERGEPGIR GEDGRPGQEG PRGLTGPPGS RGERGEKGDV GSAGLKGDKG   2520
DSAVILGPPG PRGAKGDMGE RGPRGLDGDK GPRGDNGDPG DKGSKGEPGD KGSAGLPGLR   2580
GLLGPQGQPG AAGIPGDPGS PGKDGVPGIR GEKGDVGFMG PRGLKGERGV KGACGLDGEK   2640
GDKGEAGPPG RPGLAGHKGE MGEPGVPGQS GAPGKEGLIG PKGDRGFDGQ PGPKGDQGEK   2700
GERGTPGIGG FPGPSGNDGS AGPPGPPGSV GPRGPEGLQG QKGERGPPGE RVVGAPGVPG   2760
APGERGEQGR PGPAGPRGEK GEAALTEDDI RGFVRQEMSQ HCACQGQFIA SGSRPLPSYA   2820
ADTAGSQLHA VPVLRVSHAE EEERVPPEDD EYSEYSEYSV EEYQDPEAPW DSDDPCSLPL   2880
DEGSCTAYTL RWYHRAVTGS TEACHPFVYG GCGGNANRFG TREACERRCP PRVVQSQGTG   2940
TAQDGSGQCT NYALLKLAGD VESNPGPTSS GPGPRFLLLL PLLLPPAASA SDRPRGRDPV   3000
NPEKLLVITV ATAETEGYLR FLRSAEFFNY TVRTLGLGEE WRGGDVARTV GGGQKVRWLK   3060
KEMEKYADRE DMIIMFVDSY DVILAGSPTE LLKKFVQSGS RLLFSAESFC WPEWGLAEQY   3120
PEVGTGKRFL NSGGFIGFAT TIHQIVRQWK YKDDDDDQLF YTRLYLDPGL REKLSLNLDH   3180
KSRIFQNLNG ALDEVVLKFD RNRVRIRNVA YDTLPIVVHG NGPTKLQLNY LGNYVPNGWT   3240
PEGGCGFCNQ DRRTLPGGQP PPRVFLAVFV EQPTPFLPRF LQRLLLLLDYP PDRVTLFLHN   3300
NEVFHEPHIA DSWPQLQDHF SAVKLVGPEE ALSPGEARDM AMDLCRQDPE CEFYFSLDAD   3360
AVLTNLQTLR ILIEENRKVI APMLSRHGKL WSNFWGALSP DEYYARSEDY VELVQRKRVG   3420
VWNVPYISQA YVIRGDTLRM ELPQRDVFSG SDTDPDMAFC KSFRDKGIFL HLSNQHEFGR   3480
LLATSRYDTE HLHPDLWQIF DNPVDWKEQY IHENYSRALE GEGIVEQPCP DVYWFPLLSE   3540
QMCDELVAEM EHYGQWSSGR HEDSRLAGGY ENVPTVDIHM KQVGYEDQWL QLLRTYVGPM   3600
TESLFPGYHT KARAVMNFVV RYRPDEQPSL RPHHDSSTFT LNVALNHKGL DYEGGGCRFL   3660
RYDCVISSPR KGWALLHPGR LTHYHEGLPT TWGTRYIMVS FVDP                   3704

SEQ ID NO: 23          moltype = DNA   length = 11115
FEATURE                Location/Qualifiers
misc_feature           1..11115
                       note = Synthetic Construct
source                 1..11115
                       mol_type = other DNA
```

```
                    organism = synthetic construct
SEQUENCE: 23
atgacctcct cggggcctgg accccggttc ctgctgctgc tgccgctgct gctgcccct   60
gcggcctcag cctccgaccg gccccggggc cgagacccgg tcaacccaga gaagctgctg   120
gtgatcactg tggccacagc tgaaaccgag gggtacctgc gtttcctgcg ctctgcggag   180
ttcttcaact acactgtgcg gaccctgggc ctgggagagg agtggcgagg gggtgatgtg   240
gctcgaacag ttggtggagg acagaaggtc cggtggttaa agaaggaaat ggagaaatac   300
gctgaccggg aggatatgat catcatgttt gtggatagct acgacgtgat tctggccggc   360
agcccacag agctgctgaa gaagttcgtc cagagtggca gccgcctgct cttctctgca   420
gagagcttct gctggcccga gtgggggctg gcggagcagt acctgaggt gggcacgggg   480
aagcgcttcc tcaattctgg tggattcatc ggtttttgcca ccaccatcca ccaaatcgtg   540
cgccagtgga agtacaagga tgatgacgac gaccagctgt tctacacacg gctctacctg   600
gacccaggac tgagggagaa actcagcctt aatctggatc ataagtctcg gatctttcag   660
aacctcaacg gggctttaga tgaagtggtt ttaaagtttg atcggaaccg tgtgcgtatc   720
cggaacgtgg cctacgacac gctccccatt gtggtccatg gaaacggtcc cactaagctg   780
cagctcaact acctgggaaa ctacgtcccc aatggctgga ctcctgaggg aggctgtggc   840
ttctgcaacc aggaccggag gacactcccg ggggggcagc ctccccccg ggtgtttctg   900
gccgtgtttg tggaacagcc tactccgttt ctgcccgct tcctgcagcg gctgctactc   960
ctggactatc cccccgacag ggtcaccctt ttcctgcaca acaacgaggt cttccatgaa   1020
ccccacatcg ctgactcctg gccgcagctc caggaccact tctcagctgt gaagctcgtg   1080
gggccggagg aggctctgag cccaggcgag gccagggaca tggccatgga cctgtgtcgg   1140
caggaccccg agtgtgagtt ctacttcagc ctggacgccg acgctgtcct caccaacctg   1200
cagaccctgc gtatcctcat tgaggagaac aggaaggtga tcgcccccat gctgtccccgc   1260
cacggcaagc tgtggtccaa cttctggggc gccctgagcc ccgatgagta ctacgcccgc   1320
tccgaggact acgtggagct ggtgcagcgg aagcgagtg gtgtgtggaa tgtaccatac   1380
atctcccagg cctatgtgat ccggggtgat accctgcgga ttggagctgcc ccagagggat   1440
gtgttctcgg gcagtgacac agacccggac atggccttct gtaagagctt tcgagacaag   1500
ggcatcttcc tccatctgag caatcagcat gaatttggcc ggctcctggc cacttccaga   1560
tacgacacgg agcacctgca ccccgacctc tggcagatct tcgacaaccc cgtcgactgg   1620
aaggagcagt acatccacga gaactacagc cgggccctgg aagggggaag aatcgtggag   1680
cagccatgcc cggacgtgta ctggttccca ctgctgtcag aacaaatgtg tgatgacgag   1740
gtggcagaga tggagcacta cggccagtgg tcaggcggcc ggcatgagga ttcaaggctg   1800
gctgaggct acgagaatgt gcccaccgtg gacatccaca tgaagcaggt ggggtacgag   1860
gaccagtggc tgcagctgct gcggacgtat gtgggcccca tgaccgagag cctgtttccc   1920
ggttaccaca ccaaggcgcg ggcggtgatg aactttgtgg ttcgctaccg gccagacgag   1980
cagccgtctc tgcggccaca ccacgactca tccacacttc ccctcaacgt tgccctcaac   2040
cacaagggcc tggactatga gggaggtggc tgccgcttcc tgcgctacga ctgtgtgatc   2100
tcctcccga ggaagggctg ggcactcctg cacccccggc gcctcacccc actaccacgag   2160
gggctgccaa cgacctgggg cacacgctac atcatggtgt cctttgtcga ccccggaagc   2220
ggacagtgta ctaattatgc tctcttgaaa ttggctggag atgttgagag caaccctgga   2280
cctacgctgc ggcttctggt ggccgcgctc tgcgccggga tcctggcaga ggcgccccga   2340
gtgcgagccc agcacaggga gagagtgacc tgcacgcgcc tttacgccgc tgacattgtg   2400
ttcttactgg atggctcctc atccattggc cgcagcaatt tccgcgaggc gactcgcagctt   2460
ctcgaagggc tggtgctgcc ttttctgga gcagccagtg cacagggtgt gcgctttgcc   2520
acagtgcagt acagcgatga cccacggaca gagttcggcc tggatgcact tggctctggg   2580
ggtgatgtga tccgcgccat ccgtgagctt agctacaagg ggggcaacac tcgcacaggg   2640
gctgcaattc tccatgtggc tgaccatgtc ttcctgcccc agtggcccc acctggtgtc   2700
cccaaggtct gcatcctgat cacagacggg aagtcccagg acctggtgga cacagctgcc   2760
caaaggctga aggggcaggg ggtcaagcta tttgctgtgg ggatcaagaa tgctgaccct   2820
gaggagctga agcgagttgc ctcacagccc accagtgact tcttcttctt cgtcaatgac   2880
ttcagcatct tgaggacact actgcccctc gtttcccgga gagtgtgcac gactgctggt   2940
ggcgtgcctg tgacccgacc tccggatgac tcgacctctg ctccacgaga cctggtgctg   3000
tctgagccaa gcagccaatc cttgagagta cagtggacag cggccagtgg ccctgtgact   3060
ggctacaagg tccagtacac tcctctgacg gggctgggac agccactgcc gagtgagcgg   3120
caggaggtga acgtcccagc tggtgagacc agtgtgcggc tgcgggggtct ccggccactg   3180
accgagtacc aagtgactgt gattgccctc tacgccaaca gcatcgggga ggctgtgagc   3240
gggacagctc ggaccactgc cctagaaggg ccggaactga ccatccagaa taccacagcc   3300
cacagcctcc tggtggcctg gcggagtgtg ccaggtgcca ctggctaccg tgtgacatgt   3360
cgggtcctca gtggtgggcc cacacagcag caggagcctgg gccctgggca gggttcagtg   3420
ttgctgcgtg acttggagc tggcacggac tatgaggtga ccgtgagcac cctatttggc   3480
cgcagtgtgg ggcccgccac ttccctgatg gctcgcactg acgcttctgt tgagcagacc   3540
ctgcgcccgt catcctgggg ccccacatcc atcctcctt cctggaactt ggtgcctgag   3600
gcccgtggct accggttgga atggcggcgt gagactggct tggagccacc gcagaaggtg   3660
gtactgccct ctgatgtgac ccgctaccag ttggatgtgg tgcagccgga cactgagtac   3720
cgcctcacac tctacactct gctgagggc cacgaggtga ccaccctgc aaccgtggtt   3780
cccactggac cagagctgcc tgtgagccct gtaacagacc tgcaagccac cgagctgccc   3840
gggcagcggg tgcgagtgtc ctggagccca gtccctggtg ccacccagta ccgcatcatt   3900
gtgcgcagca cccaggggt tgagcggacc ctggtgcttc tgggagtca gacagcattc   3960
gacttggatg acgttcaggc tgggcttagc tacactgtga cggtgtctgc tcagagtggt   4020
ccccgtgagg gcagtgccag tgtcctcact gtccgcgggg agccggaaac tccacttgct   4080
gttccagggc tgcgggttgt ggtgtcagat gcaacgcgag tgagggtggc ctggggaccc   4140
gtccctggag ccagtggatt tcggattagc tggagcacag gcagtggtcc ggagtccagc   4200
cagacactgc ccccagactc tactgccaca gacatcacag ggctgcagcc tggaaccacc   4260
taccaggtgg ctgtgtcggt actgcgagc agagaggagg gccgtgcctgc agtcatcgtg   4320
gctcgaacgg acccactggg cccagtgagg acgggccatg tgactcaggc cagcagctca   4380
tctgtcacca ttacctggac cagggttcct ggcgccacag gatacagggt ttcctggcac   4440
tcagcccacg gcccagagaa atcccagttg gtttctgggg aggccacggt ggctgagctg   4500
gatggactgg agccagatac tgagtatacg gtgcatgtga gggcccatgt ggctggcgtg   4560
gatgggcccc ctgcctctgt ggttgtgagg actgcccctg agcctgtggg tcgtgtgtcg   4620
```

-continued

```
aggctgcaga tcctcaatgc ttccagcgac gttctacgga tcacctgggt aggggtcact   4680
ggagccacag cttacagact ggcctggggc cggagtgaag gcggccccat gaggcaccag   4740
atactcccag gaaacacaga ctctgcagag atccggggtc tcgaaggtgg agtcagctac   4800
tcagtgcgag tgactgcact tgtcggggac cgcgagggca cacctgtctc cattgttgtc   4860
actacgccgc ctgaggctcc gccagccctg gggacgcttc acgtggtgca gcgcggggag   4920
cactcgctga ggctgcgctg ggagccggtg cccagagcgc agggcttcct tctgcactgg   4980
caacctgagg gtggccagga acagtcccgg gtcctggggc ccgagctcag cagctatcac   5040
ctggacgggc tggagccagc gacacagtac cgcgtgaggc tgagtgtcct agggccagct   5100
ggagaagggc cctctgcaga ggtgactgcg cgcactgagt cacctcgtgt tccaagcatt   5160
gaactacgtg tggtggacac ctcgatcgac tcggtgactt tggcctggac tccagtgtcc   5220
agggcatcca gctacatcct atcctggcgg ccactcagag gccctggcca ggaagtgcct   5280
gggtccccgc agacacttcc agggatctca agctcccagc gggtgacagg gctagagcct   5340
ggcgtctctt acatcttctc cctgacgcct gtcctggatg gtgtgcgggg tcctgaggca   5400
tctgtcacac agacgccagt gtgcccccgt ggcctggcag atgtggtgtt cctaccacat   5460
gccactcaag acaatgctca ccgtgcggag gctacgagga gggtcctgga gcgtctggtg   5520
ttggcacttg ggcctcttgg gccacaggca gttcaggttg gcctgctgtc ttacagtcat   5580
cggccctccc cactgttccc actgaatggc tcccatgacc ttggcattat cttgcaaagg   5640
atccgtgaca tgccctacat ggacccaagt gggaacaacc tgggcacagc cgtggtcaca   5700
gctcacagat acatgttggc accagatgct cctgggcgcc gccagcacgt accaggggtg   5760
atggttctgc tagtggatga accttgaga ggtgacatat tcagccccat ccgtgaggcc   5820
caggcttctg ggcttaatgt ggtgatgttg ggaatggctg gagcggaccc agagcagctg   5880
cgtcgcttgg cgccgggtat ggactctgtc cagaccttct tcgccgtgga tgatgggcca   5940
agcctggacc aggcagtcag tggtctggcc acagccctgt gtcaggcatc cttcactact   6000
cagccccggc cagagccctg cccagtgtat tgtccaaagg gccagaaggg ggaacctgga   6060
gagatgggcc tgagaggaca agttgggcct cctggcgacc ctggcctccc gggcaggacc   6120
ggtgctcccg gcccccaggg gcccctgga agtgccactg ccaagggcca gagggcttc   6180
cctggagcag atgggcgtcc aggcagccct ggccgcgccg ggaatcctgg gaccctggga   6240
gcccctggcc taaagggctc tccagggttg cctggccctc gtggggaccc gggagagcga   6300
ggacctcgag gcccaaaggg ggagccgggg gctcccggac aagtcatcgg aggtgaagga   6360
cctgggcttc ctgggcggaa aggggaccct ggaccatcgg gcccccctgg acctcgtgga   6420
ccactggggg acccaggacc ccgtggcccc ccagggcttc ctggaacagc catgaagggt   6480
gacaaaggcg atcgtgggga gcggggtccc cctggaccag gtgaaggtgg cattgctcct   6540
ggggagcctg ggctgccggg tcttcccgga agccctggac cccaaggccc cgttggcccc   6600
cctggaaaga aaggagaaaa aggtgactct gaggatggag ctccaggcct cccaggacaa   6660
cctgggtctc cgggtgagca gggcccacgg ggacctcctg gagctattgg ccccaaaggt   6720
gaccgggggct ttccagggcc cctgggtgag gctggagaga agggcgaacg tggacccca   6780
ggcccagcgg gatcccgggg gctgccaggg gttgctggac gtcctggagc caagggtcct   6840
gaagggccac caggacccac tggccgcaa ggagagaag gggagcctgg tcgccctggg   6900
gaccctgcag tggtgggacc tgctgttgct ggacccaaag gagaaaaggg agatgtggga   6960
cccgctgggc ccagaggagc taccggagtc caagggaac ggggcccacc cggcttggtt   7020
cttcctggag accctggccc caagggagac cctggagacc ggggtcccat tggccttact   7080
ggcagagcag gaccccagg tgactcaggg cctcctggag agaagggaga ccctgggcgg   7140
cctggccccc caggacctgt tggcccccga ggacgagatg gtgaagttgg agagaaaggt   7200
gacgagggtc ctccgggtga cccgggtttg cctggaaaaa caggcgagcg tggccttcgg   7260
ggggcacctg gagttcgggg gcctgtgggt gaaaagggag accagggaga tcctggagag   7320
gatggacgaa atggcagccc tggatcatct ggacccaagg gtgaccgtgg ggagccgggt   7380
ccccaggac ccccggacg gctggtagac acaggacctg gaaccagaga gaagggagag   7440
cctggggacc gcgacaaga gggtcctcga gggcccaagg gtgatcctgg cctccctgga   7500
gcccctggg aaaggggcat tgaagggttt cggggacccc caggcccaca gggggaccca   7560
ggtgtccgag gcccagcagg agaaaagggt gaccggggtc ccctgggct ggatggccgg   7620
agcggacgtg atgggaaacc aggagccgct gggcctctg ggccgaatgg tgctgcaggc   7680
aaagctgggg acccagggag agacgggctt ccaggcctcc gtggagaaca gggcctccct   7740
ggcccctctg gtccccctgg attaccggga aagccaggcg aggatggcaa acctggcctg   7800
aatggaaaaa acgagaacc tggggaccct ggagaagacg ggaggaaggg agagaaagga   7860
gattcaggcg cctctgggag agaaggtcgt gatggcccca agggtgagcg tggagctcct   7920
ggtatccttg gaccccaggg gcctccaggc ctcccagggc cagtgggcc tcctggccag   7980
ggtttttcctg gtgtcccagg aggcacgggc cccaagggtg accgtgggga gactggatcc   8040
aaaggggagc agggcctccc tggagagcgt ggcctgcgag gagagcctgg aagtgtgccg   8100
aatgtggatc ggttgctgga aactgctggc atcaaggcat ctgccctgcg ggagatcgga   8160
gagacctggg atgagagctc tggtagcttc ctgcctgtgc ccgaacgggg tcgaggcccc   8220
aaggggact caggcgaaca gggcccccca ggcaaggagg gccccatcgg ctttcctgga   8280
gaacgcgggc tgaagggcga ccgtggagac cctggccctc aggggccacc tggtctggcc   8340
cttgggggaga ggggcccccc cgggccttcc ggccttgccg gggagcctgg aaagcctggt   8400
attcccgggc tcccaggcag ggctgggggt gtgggagag caggaaggc aggagaagga   8460
ggagaacggg gagagaaagg agaacgtgga gaacagggca gagatggccc tcctggactc   8520
cctgaaccc ctgggcccc cggacccct ggccccaag tgtctgtgga tgagccaggt   8580
cctggactct ctggagaaca gggaccccct ggactcaagg gtgctaaggg ggagccgggc   8640
agcaatggtg accaaggtcc caaaggagac aggggtgtgc caggcatcaa aggagaccgg   8700
ggagacgctg gaccgagggg tcaggacggc aacccggtc taccaggaga gcgtggtatg   8760
gctgggcctg aagggaagcc gggtctgcag ggtccaagag gcccccctgg cccagtgggt   8820
ggtcatggag accctggacc acctggtgcc ccgggtcttg ctggccctgc aggaccccaa   8880
ggaccttctg gctgaagggg ggagcctgga gagacaggac ctccaggacg gggcctgact   8940
ggacctactg gagctgtggg acttcctgga ccccccggcc cttcaggcct tgtgggtcca   9000
cagggggtctc caggtttgcc tggacaagtg ggggacaacg gaagccaggt agccccaggt   9060
cgagatggtg ccagtggaaa agatggagac agagggagcc ctggtgtgcc agggtcacca   9120
ggtctgcctg gcctgtcgg acctaaagga gaacctggcc ccacggggc ccctggacag   9180
gctgtggtcg ggctccctgg agcaaaggga gagaaggag ccctggagg ccttgctgga   9240
gacctggtgg gtgagccggg agccaaaggt gaccgaggac tgccagggcc gcgaggcgag   9300
aagggtgaag ctggccgtgc aggggagccc ggagaccctg gggaagatgg tcagaaaggg   9360
```

```
gctccaggac ccaaaggttt caagggtgac ccaggagtcg gggtcccggg ctcccctggg   9420
cctcctggcc ctccaggtgt gaagggagat ctgggcctcc ctggcctgcc cggtgctcct   9480
ggtgttgttg ggttcccggg tcagacaggc cctcgaggag agatgggtca gccaggccct   9540
agtggagagc ggggtctggc aggcccccca gggagagaag gaatcccagg accctgggg    9600
ccacctggac caccggggtc agtgggacca cctgggccc ctggactcaa aggagacaag    9660
ggagaccctg gagtagggct gcctgggccc cgaggcgagc gtggggagcc aggcatccgg   9720
ggtgaagatg gccgccccgg ccaggaggga ccccgaggac tcacggggcc ccctggcagc   9780
aggggagagc gtggggagaa gggtgatgtt gggagtgcag gactaaaggg tgacaaggga   9840
gactcagctg tgatcctggg gcctccaggc ccacggggtg ccaaggggga catgggtgaa   9900
cgagggcctc ggggcttgga tggtgacaaa ggacctcggg gagacaatgg ggaccctggt   9960
gacaagggca gcaagggaga gcctggtgac aagggctcag ccgggttgcc aggactgcgt   10020
ggactcctgg gaccccaggg tcaacctggt gcagcaggga tccctggtga cccgggatcc   10080
ccaggaaagg atggagtgcc tggtatccga ggagaaaaag gagatgttgg cttcatgggt   10140
ccccgggccc tcaagggtga acggggagtg aagggagcct gtggccttga tggagagaag   10200
ggagacaagg gagaagctgg tcccccaggc cgcccgggc tggcaggaca caaaggagag    10260
atgggggagc ctggtgtgcc gggccagtcg gggcccctg gcaaggaggg cctgatcggt     10320
cccaagggtg accgaggctt tgacgggcag ccaggcccca agggtgacca gggcgagaaa   10380
ggggacgggg gaaccccagg aattggggc ttcccaggcc ccagtggaaa tgatggctct     10440
gctggtcccc cagggccacc tggcagtgtt ggtcccagag gccccgaagg acttcagggc   10500
cagaagggtg agcgaggtcc cccggagag agagtggtgg gggctcctgg ggtccctgga     10560
gctcctggcg agagagggga gcaggggcgg ccagggcctg ccggtcctcg aggcgagaag   10620
ggagaagctg cactgacgga ggatgacatc cggggctttg tgcgccaaga gatgagtcag   10680
cactgtgcct gccagggcca gttcatcgca tctggatcac gacccctcc tagttatgct    10740
gcagacactg ccggctccca gctccatgct gtgcctgtgc tccgcgtctc tcatgcagag   10800
gaggaagagc gggtaccccc tgaggatgat gagtactctg aatactccga gtattctgtg    10860
gaggagtacc aggaccctga agctccttgg gatagtgatg accctgttc cctgccactg     10920
gatgagggct cctgcactgc ctacaccctg cgctggtacc atcgggctgt gacaggcagc   10980
acagaggcct gtcaccctt tgtctatggt ggctgtggag ggaatgccaa ccgtttgg    11040
acccgtgagg cctgcgagcg ccgctgccca ccccggtgg tccagagcca ggggacaggt     11100
actgcccagg actga                                                      11115
```

SEQ ID NO: 24          moltype = AA  length = 3704
FEATURE                Location/Qualifiers
REGION                 1..3704
                       note = Synthetic Construct
source                 1..3704
                       mol_type = protein
                       organism = synthetic construct
SEQUENCE: 24

```
MTSSGPGPRF LLLLPLLLPP AASASDRPRG RDPVNPEKLL VITVATAETE GYLRFLRSAE   60
FFNYTVRTLG LGEEWRGGDV ARTVGGGQKV RWLKKEMEKY ADREDMIIMF VDSYDVILAG   120
SPTELLKKFV QSGSRLLFSA ESFCWPEWGL AEQYPEVGTG KRFLNSGGFI GFATTIHQIV   180
RQWKYKDDDD DQLFYTRLYL DPGLREKLSL NLDHKSRIFQ NLNGALDEVV LKFDRNRVRI   240
RNVAYDTLPI VVHGNGPTKL QLNYLGNYVP NGWTPEGGCG FCNQDRRTLP GGQPPPRVFL   300
AVFVEQPTPF LPRFLQRLLL LDYPPDRVTL FLHNNEVFHE PHIADSWPQL QDHFSAVKLV   360
GPEEALSPGE ARDMAMDLCR QDPECEFYFS LDADAVLTNL QTLRILIEEN RKVIAPMLSR   420
HGKLWSNFWG ALSPDEYYAR SEDYVELVQR KRVGVWNVPY ISQAYVIRGD TLRMELPQRD   480
VFSGSDTDPD MAFCKSFRDK GIFLHLSNQH EFGRLLATSR YDTEHLHPDL WQIFDNPVDW   540
KEQYIHENYS RALEGEGIVE QPCPDVYWFP LLSEQMCDEL VAEMEHYGQW SGGRHEDSRL   600
AGGYENVPTV DIHMKQVGYE DQWLQLLRTY VGPMTESLFP GYHTKARAVM NFVVRYRPDE   660
QPSLRPHHDS STFTLNVALN HKGLDYEGGG CRFLRYDCVI SSPRKGWALL HPGRLTHYHE   720
GLPTTWGTRY IMVSFVDPGS GQCTNYALLK LAGDVESNPG PTLRLLVAAL CAGILAEAPR   780
VRAQHRERVT CTRLYAADIV FLLDGSSSIG RSNFREVRSF LEGLVLPFSG AASAQGVRFA   840
TVQYSDDPRT EFGLDALGSG GDVIRAIREL SYKGGNTRTG AAILHVADHV FLPQLARPGV   900
PKVCILITDG KSQDLVDTAA QRLKGQGVKL FAVGIKNADP EELKRVASQP TSDFFFFVND   960
FSILRTLLPL VSRRVCTTAG GVPVTRPPDD STSAPRDLVL SEPSSQSLRV QWTAASGPVT   1020
GYKVQYTPLT GLGQPLPSER QEVNVPAGET SVRLRGLRPL TEYQVTVIAL YANSIGEAVS   1080
GTARTTALEG PELTIQNTTA HSLLVAWRSV PGATGYRVTW RVLSGGPTQQ QELGPGQGSV   1140
LLRDLEPGTD YEVTVSTLFG RSVGPATSLM ARTDASVEQT LRPVILGPTS ILLSWNLVPE   1200
ARGYRLEWRR ETGLEPPQKV VLPSDVTRYQ LDGLQPGTEY RLTLYTLLEG HEVATPATVV   1260
PTGPELPVSP VTDLQATELP GQRVRVSWSP VPGATQYRII VRSTQGVERT LVLPGSQTAF   1320
DLDDVQAGLS YTVRVSARVG PREGSASVLT VRREPETPLA VPGLRVVVSD ATRVRVAWGP   1380
VPGASGFRIS WSTGSGPESS QTLPPDSTAT DITGLQPGTT YQVAVSVLRG REEGPAAVIV   1440
ARTDPLGPVR TVHVTQASSS SVTITWTRVP GATGYRVSWH SAHGPEKSQL VSGEATVAEL   1500
DGLEPDTEYT VHVRAHVAGV DGPPASVVVR TAPEPVGRVS RLQILNASSD VLRITWVGVT   1560
GATAYRLAWG RSEGGPMRHQ ILPGNTDSAE IRGLEGGVSY SVRVTALVGD REGTPVSIVV   1620
TTPPEAPPAL GTLHVVQRGE HSLRLRWEPV PRAQGFLLHW QPEGGQEQSR VLGPELSSYH   1680
LDGLEPATQY RVRLSVLGPA GEGPSAEVTA RTESPRVPSI ELRVVDTSID SVTLAWTPVS   1740
RASSYILSWR PLRGPGQEVP GSPQTLPGIS SSQRVTGLEP GVSYIFSLTP VLDGVRGPEA   1800
SVTQTPVCPR GLADVVFLPH ATQDNAHRAE ATRRVLERLV LALGPLGPQA VQVGLLSYSH   1860
RPSPLFPLNG SHDLGIILQR IRDMPYMDPS GNNLGTAVVT AHRYMLAPDA PGRRQHVPGV   1920
MVLLVDEPLR GDIFSPIREA QASGLNVVML GMAGADPEQL RRLAPGMDSV QTFFAVDDGP   1980
SLDQAVSGLA TALCQASFTT QPRPEPCPVY CPKGQKGEPG EMGLRGQVGP PGDPGLPGRT   2040
GAPGPQGPPG SATAKGERGF PGADGRPGSP GRAGNPGTPG APGLKGSPGL PGPRGDPGER   2100
GPRGPKGEPG APGQVIGGEG PGLPGRKGDP GPSGPPGPRG PLGDPGPRGP GPLPGTAMKG   2160
DKGDRGERGP PGPGEGGIAP GEPGLPGLPG SPGPQGPVGP PGKKGEKGDS EDGAPGLPGQ   2220
PGSPGEQGPR GPPGAIGPKG DRGFPGPLGE AGEKGERGPP GPAGSRGLPG VAGRPGAKGP   2280
EGPPGPTGRQ GEKGEPGCRPG DPAVVGPAVA GPKGEKGDVG PAGPRGATGV QGERGPPGLV   2340
LPGDPGPKGD PGDRGPIGLT GRAGPPGDSG PPGEKGDPGR PGPPGPVGPR GRDGEVGEKG   2400
```

-continued

```
DEGPPGDPGL PGKAGERGLR GAPGVRGPVG EKGDQGDPGE DGRNGSPGSS GPKGDRGEPG  2460
PPGPPGRLVD TGPGAREKGE PGDRGQEGPR GPKGDPGLPG APGERGIEGF RGPPGPQGDP  2520
GVRGPAGEKG DRGPPGLDGR SGLDGKPGAA GPSGPNGAAG KAGDPGRDGL PGLRGEQGLP  2580
GPSGPPGLPG KPGEDGKPGL NGKNGEPGDP GEDGRKGEKG DSGASGREGR DGPKGERGAP  2640
GILGPQGPPG LPGPVGPPGQ GFPGVPGGTG PKGDRGETGS KEQGLPGER GLRGEPGSVP  2700
NVDRLLETAG IKASALREIV ETWDESSGSF LPVPERRRGP KGDSGEQGPP GKEGPIGFPG  2760
ERGLKGDRGD PGPQGPPGLA LGERGPPGPS GLAGEPGKPG IPGLPGRAGG VGEAGRPGER  2820
GERGEKGERG EQGRDGPPGL PGTPGPPGPP GPKVSVDEPG PGLSGEQGPP GLKGAKGEPG  2880
SNGDQGPKGD RGVPGIKGDR GEPGPRGQDG NPGLPGERGM AGPEGKPGLQ GPRGPPGPVG  2940
GHGDPGPPGA PGLAGPAGPQ GPSGLKGEPG ETGPPGRGLT GPTGAVGLPG PPGPSGLVGP  3000
QGSPGLPGQV GETGKPGAPG RDGASGKDGD RGSPGVPGSP GLPGPVGPKG EPGPTGAPGQ  3060
AVVGLPGAKG EKGAPGGLAG DLVGEPGAKG DRGLPGPRGE KGEAGRAGEP GDPGEDGQKG  3120
APGPKGFKGD PGVGVPGSPG PPGPPGVKGD LGLPGLPGAP GVVGFPGQTG PRGEMGQPGP  3180
SGERGLAGPP GREGIPGPLG PPGPPGSVGP PGASGLKGDK GDPGVGLPGP RGERGEPGIR  3240
GEDGRPGQEG PRGLTGPPGS RGERGEKGDV GSAGLKGDKG DSAVILGPPG PRGAKGDMGE  3300
RGPRGLDGDK GPRGDNGDPG DKGSKGEPGD KGSAGLPGLR GLLGPQGQPG AAGIPGDPGS  3360
PGKDGVPGIR GEKGDVGFMG PRGLKGERGV KGACGLDGEK GDKGEAGPPG RPGLAGHKGE  3420
MGEPGVPGQS GAPGKEGLIG PKGDRGFDGQ PGPKGDQGEK GERGTPGIGG FPGPSGNDGS  3480
AGPPGPPGSV GPRGPEGLQG QKGERGFPPGE RVVGAPGVPG APGERGEQGR PGPAGPRGEK  3540
GEAALTEDDI RGFVRQEMSQ HCACQGQFIA SGSRPLPSYA ADTAGSQLHA VPVLRVSHAE  3600
EEERVPPEDD EYSEYSEYSV EEYQDPEAPW DSDDPCSLPL DEGSCTAYTL RWYHRAVTGS  3660
TEACHPFVYG GCGGNANRFG TREACERRCP PRVVQSQGTG TAQD                   3704
```

```
SEQ ID NO: 25          moltype = DNA  length = 11121
FEATURE                Location/Qualifiers
misc_feature           1..11121
                       note = Synthetic Construct
source                 1..11121
                       mol_type = other DNA
                       organism = synthetic construct
SEQUENCE: 25
atgacgctgc ggcttctggt ggccgcgctc tgcgccggga tcctggcaga ggcgccccga   60
gtgcgagccc agcacaggga gagagtgacc tgcacgcgcc tttacgccgc tgacattgtg  120
ttcttactgg atggctcctc atccattggc cgcagcaatt tccgcgaggt ccgcagcttt  180
ctcgaagggc tggtgctgcc tttctctgga gcagccagtg cacagggtgt gcgctttgcc  240
acagtgcagt cacagcgatga cccacgggaca gagttcggcc tggatgcact tggctctggg  300
ggtgatgtga tccgcgccat ccgtgagctt agctacaagg ggggcaacac tcgcacaggg  360
gctgcaattc tccatgtggc tgaccatgtc ttcctgcccc agctggcccg acctggtgtc  420
cccaaggtct gcatcctgat cacagacggg aagtcccagg acctggtgtga cacagctgcc  480
caaaggctga aggggcaggg ggtcaagcta tttgctgtgg ggatcaagaa tgctgaccct  540
gaggagctga agcgagttgc ctcacagccc accagtgact tcttcttctt cgtcaatgac  600
ttcagcatct tgaggacact actgcccctc gtttccggga gagtgtgcac gactgctggt  660
ggcgtgcctg tgacccgacc tccggatgac tcgacctctg ctccacgaga cctggtgctg  720
tctgagccaa gcagccaatc cttgagagta cagtggacag cggccagtgg ccctgtgact  780
ggctacaagg tccagtacac tcctctgacg gggctgggac agccactgcc gagtgagcgg  840
caggaggtga acgtcccagc tggtgagacc agtgtgcggc tgcggggtct ccggccactg  900
accgagtacc aagtgactgt gattgccctc tacgccaaca gcatcgggga ggctgtgagc  960
gggacagctc ggaccactgc cctagaaggg ccggaactga ccatccagaa taccacagcc  1020
cacagcctcc tggtggcctg gcggagtgtg ccaggtgcca ctggctaccg tgtgacatgg  1080
cgggtcctca gtggtgggcc cacacagcag caggagctgg gccctgggca gggttcagtg  1140
ttgctgcgtg acttggagcc tggcacggac tatgaggtga ccgtgagcac cctatttggc  1200
cgcagtgtgg ggcccgccac ttccctgatg gctcgcactg acgcttctgt tgagcagacc  1260
ctgcgcccgg tcatcctggg ccccacatcc atcctcctt cctggaactt ggtgcctgag  1320
gcccgtggct accggttgga atggcggcgt gagactggct tggagccacc gcagaaggtg  1380
gtactgccct ctgatgtgac ccgctaccag ttggatgggc tgcagccggg cactgagtac  1440
cgcctcacac tctacactct gctggagggc cacgaggtgg ccaccccctgc aaccgtggtt  1500
cccactggac cagagctgcc tgtgagccct gtaacagacc tgcaagccac cgagctgccc  1560
gggcagcggg tgcgagtgtc ctggagccca gtccctggtg ccacccagta ccgcatcatt  1620
gtgcgcagca cccagggggt tgagcagacc ctggtgcttc ctgggagtca gacagcattc  1680
gacttggatg acgttcaggc tgggcttagc tacactgtgc gggtgtctgc tcgagtgggg  1740
ccccgtgagg gcagtgccag tgtcctcact gtccgccggg agccggaaac tccacttgct  1800
gttccagggc tgcgggttgt ggtgtcagat gcaacgcgag tgagggtggc ctggggaccc  1860
gtccctggag ccagtggatt tcggattagc tggagcacag gcagtggtcc ggagtccagc  1920
cagacactgc ccccagactc tactgccaca gacatccagg ggctgcagcc tggaaccacc  1980
taccaggtgg ctgtgtcggt actgcgaggc agagaggagg ccctgctgc agtcatcgtg  2040
gctcgaacgg acccactggg cccagtgagg acgtccatg tgactcaggc cagcagctca  2100
tctgtcacca ttacctggac cagggttcct ggcgccacag gatacagggt ttcctggcac  2160
tcagcccacg gcccagagaa atcccagttg gtttctgggg aggccacggt ggctgagctg  2220
gatggactgg agccagatac tgagtatacg gtgcatgtga gggccatgt ggctggcgtg  2280
gatgggcccc ctgcctctgt ggttgtgagg actgccctg agcctgtggg tcgtgtgtcg  2340
aggctgcaga tcctcaatgc ttccagcgac gttctacgga tcacctgggt aggggtcact  2400
ggagccacag cttacagact ggcctggggc cggagtgaag cggcccat gaggcaccag  2460
atactcccag gaaacacaga ctctgcagag atccgggggtc tcgaaggtgg agtcagctac  2520
tcagtgcgag tgactgcact tgtcggggac cgcgagggca cactgtctc cattgttgtc  2580
actacgccgc ctgaggctcc gccagccctg gggacgcttc acgtggtgca gcgcgggggag  2640
cactcgctga ggctgcgctg ggagccggtg cccagagcgc agggcttcct tctgcactgg  2700
caacctgagg gtgccaggac acagtcccgg gtcctggggc ccgagctcag cagctatcac  2760
ctggacgggc tggagccagc gacacagtac cgcgtgaggc tgagtgtcct agggccagct  2820
ggagaagggc cctctgcaga ggtgactgcg cgcactgagt cacctcgtgt tccaagcatt  2880
```

-continued

```
gaactacgtg tggtggacac ctcgatcgac tcggtgactt tggcctggac tccagtgtcc   2940
agggcatcca gctacatcct atcctggcgg ccactcagag gccctggcca ggaagtgcct   3000
gggtccccgc agacacttcc agggatctca agctcccagc gggtgacagg gctagagcct   3060
ggcgtctctt acatcttctc cctgacgcct gtcctggatg gtgtgcgggg tcctgaggca   3120
tctgtcacac agacgccagt gtgcccccgt ggctggcgg atgtggtgtt cctaccacat   3180
gccactcaag acaatgctca ccgtgcggag gctacgagga gggtcctgga gcgtctggtg   3240
ttggcacttg ggcctcttgg gccacaggca gttcaggttg gcctgctgtc ttacagtcat   3300
cggccctccc cactgttccc actgaatggc tcccatgacc ttggcattat cttgcaaagg   3360
atccgtgaca tgccctacat ggacccaagt gggaacaacc tgggcacagc cgtggtcaca   3420
gctcacagat acatgttggc accagatgct cctgggcgcc gccagcacgt accaggggtg   3480
atggttctgc tagtggatga acccttgaga ggtgacatat tcagccccat ccgtgaggcc   3540
caggcttctg ggcttaatgt ggtgatgttg ggaatggctg gagcggaccc agagcagctg   3600
cgtcgcttgg cgccgggtat ggactctgtc cagaccttct tcgccgtgga tgatgggcca   3660
agcctggacc aggcagtcag tggtctggcc acagccctgt gtcaggcatc cttcactact   3720
cagccccggc cagagccctg cccagtgtat tgtccaaagg gccagaaggg ggaacctgga   3780
gagatgggcc tgagaggaca agttgggcct cctggcgacc ctggcctccc gggcaggacc   3840
ggtgctcccg gcccccaggg gcccctggaa agtgccactg ccaagggcga gaggggcttc   3900
cctggagcag atgggcgtcc aggcagccct ggccgcgcg ggaatcctgg gaccctgga   3960
gcccctggcc taaagggctc tccagggttg cctggccctc gtggggaccc gggagagcga   4020
ggacctcgag gcccaaaggg gggagccggg gctcccggac aagtcatcgg aggtgaagga   4080
cctgggcttc ctgggcggaa aggggaccct ggaccatcgg gcccccctgg acctcgtgga   4140
ccactgggg acccaggacc ccgtggcccc ccagggcttc ctggaacagc catgaagggt   4200
gacaaaggcg atcgtgggga gcggggtccc cctggaccag gtgaaggtgg cattgctcct   4260
ggggagcctg ggctgccggg tcttcccgga agccctggac cccaaggccc cgttggcccc   4320
cctggaaaga aaggagaaaa aggtgactct gaggatggag ctccaggcct cccaggacaa   4380
cctgggtctc cgggtgagca gggcccacgg ggacctcctg gagctattgg ccccaaaggt   4440
gaccggggct ttccaggcc cctgggtgag gctggagaga agggcgaacg tggaccccca   4500
ggcccagcgg gatcccgggg gctgccaggg gttgctggac gtcctggagc caagggtcct   4560
gaagggccac caggacccac tggccgccaa ggagagaagg gggagcctgg tcgccctggg   4620
gaccctgcag tggtgggacc tgctgttgct ggacccaaag gagaaaaggg agatgtgggg   4680
cccgctgggc ccagaggagc taccggagtc caagggtaac ggggcccacc cggcttggtt   4740
cttcctggag accctggccc caagggagac cctggagacc ggggtcccat tggccttact   4800
ggcagagcag gaccccagg tgactcaggg cctcctggag agaagggaga ccctgggcgg   4860
cctggccccc caggacctgt tggcccccga ggacgagatg gtgaagttgg agagaaaggt   4920
gacgaggggtc ctccgggtga cccgggtttg cctggaaaag caggcgagcg tggccttcgg   4980
ggggcacctg gagttcgggg gcctgtgggt gaaaagggag accagggaga tcctggagag   5040
gatgacgaa atggcagccc tggatcatct ggacccaagg gtgaccgtgg ggagccgggt   5100
ccccccaggac ccccgggacg gctggtagac acaggacctg gagccagaga gaaggagag   5160
cctgggacc gcggacaaga gggtcctcga gggcccaagg gtgatcctgg cctccctgga   5220
gcccctgggg aaaggggcat tgaaggggttt cggggacccc caggcccaca gggggaccca   5280
ggtgtccgag gcccagcagg agaaaagggt gaccggggtc ccctgggct ggatggccgg   5340
agcggactgg atgggaaacc aggagccgct gggccctctg ggccgaatgg tgctgcaggc   5400
aaagctgggg acccagggag agacggcttt ccaggcctcc gtggagaaca gggcctccct   5460
ggcccctctg gtccccctgg attaccggga aagccaggcg aggatggcaa acctggcctg   5520
aatgaaaaaa acgagaacc tgggggaccct ggagaagacg ggaggaaggg agagaaagga   5580
gattcaggcg cctctgggag agaaggtcgt gatggcccca agggtgagcg tggagctcct   5640
ggtatccttg gaccccaggg gcctccaggc ctcccaggc cagtgggccc tcctggccag   5700
ggttttcctg gtgtcccagg aggcacgggc cccaagggtg accgtgggga gactggatcc   5760
aaaggggagc agggcctccc tggagagcgt ggcctgcgag gagagcctgg aagtgtgccg   5820
aatgtggatc ggttgctgga aactgctggc atcaaggcat ctgccctgcg ggagatcgtg   5880
gagacctggg atgagagctc tggtagcttc ctgcctgtgc cgcaacggcg tcgaggcccc   5940
aaggggact caggcgaaca gggccccca ggcaaggagg gccccatcgg ctttcctgga   6000
gaacgcgggc tgaagggcga ccgtggagac cctggccctc aggggccacc tggtctggcc   6060
cttggggaga ggggcccccc cgggccttcc ggccttgccg gggagcctgg aaagcctggt   6120
attcccgggc tcccaggcag ggctggggt gtgggagagg caggaaggcc aggagagagg   6180
ggagaacggg gagagaaagg agaacgtgga gaacagggca gagatgggcc tcctggactc   6240
cctggaaccc ctgggcccccc cggaccccct ggccccaagg tgtctgtgga tgagccaggt   6300
cctggactct ctggagaaca gggaccccct ggactcaagg gtgctaaggg ggagccgggc   6360
agcaatggtg accaaggtcc caaaggaac aggggtgtgc caggcatcaa aggagaccgg   6420
ggagagcctg gaccgagggg tcaggacggc aacccggtc taccaggaga gcgtggtatg   6480
gctgggcctg aagggaagcc gggtctgcag ggtccaagag gcccccctgg cccagtgggg   6540
ggtcatggag accctggacc acctggtgcc ccgggtcttg ctggccctgc aggacccaa   6600
ggaccttctg gcctgaaggg ggagcctgga gagacaggac ctccaggacg gggcctgact   6660
ggacctactg gagctgtggg acttctgga cccccccgcc cttcaggcct tgtgggtcca   6720
caggggtctc caggtttgcc tggacaagtg ggggagacag ggaagccggg agccccaggt   6780
cgagatggtc ccagtggaaa agatggagac agagggagcc ctggtgtgcc agggtcacca   6840
ggtctgcctg gccctgtcgg acctaaagga gaacctggcc ccacggggc ccctggacag   6900
gctgtggtcg ggctccctgg agcaaaggga gagaaggag ccctggagg ccttgctgga   6960
gacctggtcg gtgagccgga agccaaaggt gaccgaggac tgccagggcg gcgaggcgag   7020
aagggtgaag ctggccgtgc aggggagccc ggagaccctg gggaagatgg tcagaaaggg   7080
gctccaggac ccaaaggttt caaggggtgac ccaggagtcg gggtcccggg ctccctgggg   7140
cctcctggcc ctccaggtgt gaaggagat ctgggcctcc ctggcctgcc cggtgctcct   7200
ggtgttgttg ggttcccggg tcagacaggc cctcgggag agatgggtca gccaggccct   7260
agtggagge gggtctggc aggccccca gggagagaa gaatcccagg accctggggg   7320
ccacctggac caccggggtc agtgggacca cctgggccct ctggactcaa aggagacaag   7380
ggagaccctg gagtagggct gcctgggccc cgaggcgagc gtggggagcc aggcatccgg   7440
ggtgaagatg gccgcccgg ccaggaggga ccccgaggac tcacggggcc ccctggcagc   7500
aggggagagc gtgggggagaa gggtgatgtt gggagtgcag gactaaaggg tgacaaggga   7560
gactcagctg tgatcctggg gcctccaggc ccacgggtgtg ccaagggga catgggtgaa   7620
```

-continued

```
cgagggcctc ggggcttgga tggtgacaaa ggacctcggg gagacaatgg ggaccctggt    7680
gacaagggca gcaagggaga gcctggtgac aagggctcag ccgggttgcc aggactgcgt    7740
ggactcctgg gaccccaggg tcaacctggt gcagcaggga tccctggtga cccgggatcc    7800
ccaggaaagg atggagtgcc tggtatccga ggagaaaaag gagatgttgg cttcatgggt    7860
ccccggggcc tcaagggtga acggggagtg aagggagccc gtggccttga tggagagaag    7920
ggagacaagg gagaagctgg tccccccaggc cgccccgggc tggcaggaca caaaggagag    7980
atgggggagc ctggtgtgcc gggccagtcg ggggcccctg gcaaggaggg cctgatcggt    8040
cccaagggtg accgaggctt tgacgggcag ccaggcccca agggtgacca gggcgagaaa    8100
ggggagcggg gaaccccagg aattgggggc ttcccaggcc ccagtggaaa tgatggctct    8160
gctggtcccc cagggccacc tggcagtgtt ggtcccagag gccccgaagg acttcagggc    8220
cagaagggtg agcgaggtcc ccccggagag agagtggtgg gggctcctgg ggtccctgga    8280
gctcctggcg agagaggga gcaggggcgg ccagggcctg ccggtcctcg aggcgagaag    8340
ggagaagctg cactgacgga ggatgacatc cggggctttg tgcgccaaga gatgagtcag    8400
cactgtgcct gccagggcca gttcatcgca tctggatcac gacccctccc tagttatgct    8460
gcagacactg ccggctccca gctccatgct gtgcctgtgc tccgcgtctc tcatgcagag    8520
gaggaagagc gggtacccc tgaggatgat gagtactctg aatactccga gtattctgtg    8580
gaggagtacc aggaccctga agctccttgg gatagtgatg accctgttc cctgccactg    8640
gatgagggct cctgcactgc ctacaccctg cgctggtacc atcgggctgt gacaggcagc    8700
acagaggcct gtcaccctt tgtctatggt ggctgtggag ggaatgccaa ccgttttggg    8760
acccgtgagg cctgcgagcg ccgctgccca ccccgggtgg tccagagcca ggggacaggt    8820
actgcccagg acggaagcgg agtgaaacag actttgaatt ttgaccttct caagttggcg    8880
ggagacgtgg agtccaaccc tggacctacc tcctcgggc ctggacccg gttcctgctg    8940
ctgctgccgc tgctgctgcc ccctgcggcc tcagcctccg accggccccg gggccgagac    9000
ccggtcaacc cagagaagct gctggtgatc actgtggcca cagctgaaac cgaggggtac    9060
ctgcgtttcc tgcgctctgc ggagttcttc aactacactg tgcggaccct gggcctggga    9120
gaggagtggc gagggggtga tgtggctcga acagttggtg gagcacagaa ggtccggtgg    9180
ttaaagaagg aaatggagaa atacgctgac cgggaggata tgatcatcat gtttgtggat    9240
agctacgacg tgattctggc cggcagcccc acagagctgc tgaagaagtt cgtccagagt    9300
ggcagccgcc tgctcttctc tgcagagagc ttctgctggc ccgagtgggg gctggcggag    9360
cagtaccctg aggtgggcac ggggaagcgc ttcctcaatt ctggtggatt catcggtttt    9420
gccaccacca tccaccaaat cgtgcgccag tggaagtaca aggatgatga cgacgaccag    9480
ctgttctaca cacggctcta cctggaccca ggactgaggg agaaactcag ccttaatctg    9540
gatcataagt ctcggatctt tcagaacctc aacggggctt tagatgaagt ggttttaaag    9600
tttgatcgga accgtgtgcg tatccggaac gtggcctacg acacgctccc cattgtggtc    9660
catggaaacg gtcccactaa gctgcagctc aactacactg gaaactacgt ccccaatgcc    9720
tggactcctg agggaggctg tggcttctgc aaccaggacc ggaggacact cccggggggg    9780
cagcctcccc cccgggtgtt tctggccgtg tttgtggaac agcctactcc gtttctgccc    9840
cgcttcctgc agcggctgct actcctggac tatccccccg acagggtcac cctttttctg    9900
cacaacaacg aggtcttcca tgaaccccac atcgctgact cctggccgca gctccaggac    9960
cacttctcag ctgtgaagct cgtgggggcg gaggaggctc tgagcccagg cgaggccagg    10020
gacatggcca tggacctgtg tcggcaggac cccgagtgtg agttctactt cagcctggac    10080
gccgacgctg tcctcaccaa cctgcagacc ctgcgtatcc tcattgagga gaacaggaag    10140
gtgatcgccc ccatgctgtc ccgccacggc aagctgtgat ccaacttctg gggcgccctg    10200
agccccgatg agtactacgc ccgctccgag gactacgtgg agctggtgca gcggaagcga    10260
gtgggtgtgt ggaatgtacc atacatctcc caggcctatg tgatccgggg tgataccctg    10320
cggatgggagc tgcccagag ggatgtgttc tcgggcagtg acacagaccc ggacatggcc    10380
ttctgtaaga gctttcgaga caagggcatc ttcctccatc tggcaatca gcatgaattt    10440
ggccggctcc tggccacttc cagatacgac acggagcacc tgcaccccga cctctgcag    10500
atcttcgaca accccgtcga ctggaaggag cagtacatcc acgagaacta cagcggggcc    10560
ctggaagggg aaggaatcgt ggagcagcca tgcccggacg tgtactggtt cccactgctg    10620
tcagaacaaa tgtgtgatga gctggtggca gagatgaagc actacggcca gtggtcaggc    10680
ggccggcatg aggattcaag gctggctgga ggctacgaga atgtgcccac cgtggacatc    10740
cacatgaagc aggtgggggta cgaggaccag tggctgcagc tgctgcggac gtatgtgggc    10800
cccatgacca gagacctgtt tcccggttac cacaccaagg cgcgggcggt gatgaacttt    10860
gtggttcgct accggccaga cgagcagccg tctctgcggg cacaccacga ctcatccacc    10920
ttcacccttca acgttgccct caaccacacag ggcctggact atgagggagg tggctgccgc    10980
ttcctgcgct acgactgtgt gatctcctcc ccgaggaagg gctgggcact cctgcacccc    11040
ggccgcctcc cccactacca cgaggggctg ccaacgacct ggggcacacg ctacatcatg    11100
gtgtcctttg tcgaccccctg a                                             11121
```

```
SEQ ID NO: 26            moltype = AA  length = 3706
FEATURE                  Location/Qualifiers
REGION                   1..3706
                         note = Synthetic Construct
source                   1..3706
                         mol_type = protein
                         organism = synthetic construct
SEQUENCE: 26
MTLRLLVAAL CAGILAEAPR VRAQHRERVT CTRLYAADIV FLLDGSSSIG RSNFREVRSF    60
LEGLVLPFSG AASAQGVRFA TVQYSDDPRT EFGLDALGSG GDVIRAIREL SYKGGNTRTG    120
AAILHVADHV FLPQLARPGV PKVCILITDG KSQDLVDTAA QRLKGQGVKL FAVGIKNADP    180
EELKRVASQP TSDFFFFVND FSILRTLLPL VSRRVCTTAG GVPVTRPPDD STSAPRDLVL    240
SEPSSQSLRV QWTAASGPVT GYKVQYTPLT GLGQPLPSER QEVNVPAGET SVRLRGLRPL    300
TEYQVTVIAL YANSIGEAVS GTARTTALEG PELTIQNTTA HSLLVAWRSV PGATGYRVTW    360
RVLSGGPTQQ QELGPGQGSV LLRDLEPGTD YEVTVSTLFG RSVGPATSLM ARTDASVEQT    420
LRPVILGPTS ILLSWNLVPE ARGYRLEWRR ETGLEPPQKV VLPSDVTRYQ LDGLQPGTEY    480
RLTLYTLLEG HEVATPATVV PTGPELPVSP VTDLQATELP GQRVRVSWSP VPGATQYRII    540
VRSTQGVERT LVLPGSQTAF DLDDVQAGLS YTVRVSARVG PREGSASVLT VRREPETPLA    600
VPGLRVVVSD ATRVRVAWGP VPGASGFRIS WSTGSGPESS QTLPPDSTAT DITGLQPGTT    660
```

```
YQVAVSVLRG REEGPAAVIV ARTDPLGPVR TVHVTQASSS SVTITWTRVP GATGYRVSWH    720
SAHGPEKSQL VSGEATVAEL DGLEPDTEYT VHVRAHVAGV DGPPASVVVR TAPEPVGRVS    780
RLQILNASSD VLRITWVGVT GATAYRLAWG RSEGGPMRHQ ILPGNTDSAE IRGLEGGVSY    840
SVRVTALVGD REGTPVSIVV TTPPEAPPAL GTLHVVQRGE HSLRLRWEPV PRAQGFLLHW    900
QPEGGQEQSR VLGPELSSYH LDGLEPATQY RVRLSVLGPA GEGPSAEVTA RTESPRVPSI    960
ELRVVDTSID SVTLAWTPVS RASSYILSWR PLRGPGQEVP GSPQTLPGIS SSQRVTGLEP   1020
GVSYIFSLTP VLDGVRGPEA SVTQTPVCPR GLADVVFLPH ATQDNAHRAE ATRRVLERLV   1080
LALGPLGPQA VQVGLLSYSH RPSPLFPLNG SHDLGIILQR IRDMPYMDPS GNNLGTAVVT   1140
AHRYMLAPDA PGRRQHVPGV MVLLVDEPLR GDIFSPIREA QASGLNVVML GMAGADPEQL   1200
RRLAPGMDSV QTFFAVDDGP SLDQAVSGLA TALCQASFTT QPRPEPCPVY CPKGQKGEPG   1260
EMGLRGQVGP PGDPGLPGRT GAPGPQGPPG SATAKGERGF PGADGRPGSP GRAGNPGTPG   1320
APGLKGSPGL PGPRGDPGER GPRGPKGEPG APGQVIGGEG PGLPGRKGDP GPSGPPGPRG   1380
PLGDPGPRGP PGLPGTAMKG DKGDRGERGP PGPGEGGIAP GEGPGLPGLPG SPGPQGPVGP   1440
PGKKGEKGDS EDGAPGLPGQ PGSPGEGQPR GPPGAIGPKG DRGFPGPLGE AGEKGERGPP   1500
GPAGSRGLPG VAGRPGAKGP EGPPGPTGRQ GEKGEPGRPG DPAVVGPAVA GPKGEKGDVG   1560
PAGPRGATGV QGERGPPGLV LPGDPGPKGD PGDRGPIGLT GRAGPPGDSG PPGEKGDPGR   1620
PGPPGPVGPR GRDGEVGEKG DEGPPGDPGL PGKAGERGLR GAPGVRGPVG EKGDQGDPGE   1680
DGRNGSPGSS GPKGDRGEPG PPGPPGRLVD TGPGAREKGE PGDRGQEGPR GPKGDPGLPG   1740
APGERGIEGF RGPPGPQGDP GVRGPAGEKG DRGPPGLDGR SGLDGKPGAA GPSGPNGAAG   1800
KAGDPGRDGL PGLRGEQGLP GPSGPPGLPG KPGEDGKPGL NGKNGEPGDP GEDGRKGEKG   1860
DSGASGREGR DGPKGERGAP GILGPQGPPG LPGPVGPPGQ GFPGVPGGTG PKGDRGETGS   1920
KGEQGLPGER GLRGEPGSVP NVDRLLETAG IKASALREIV ETWDESSGSF LPVPERRRGP   1980
KGDSGEQGPP GKEGPIGFPG ERGLKGDRGD PGPQGPPGLA LGERGPPGPS GLAGEPGKPG   2040
IPGLPGRAGG VGEAGRPGER GERGEKGERG EQGRDGPPGL PGTPGPPGPP GPKVSVDEPG   2100
PGLSGEQGPP GLKGAKGEPG SNGDQGPKGD RGVPGIKGDR GEPGPRGQDG NPGLPGERGM   2160
AGPEGKPGLQ GPRGPPGPVG GHGDPGPPGA PGLAGPAGPQ GPSGLKGEPG ETGPPGRGLT   2220
GPTGAVGLPG PPGPSGLVGP QGSPGLPGQV GETGKPGAPG RDGASGKDGD RGSPGVPGSP   2280
GLPGPVGPKG EPGPTGAPGQ AVVGLPGAKG EKGAPGGLAG DLVGEPGAKG DRGLPGPRGE   2340
KGEAGRAGEP GDPGEDGQKG APGPKGFKGD PGVGVPGSPG PPGPPGVKGD LGLPGLPGAP   2400
GVVGFPGQTG PRGEMGQPGP SGERGLAGPP GREGIPGPLG HGNGPTKLQL NYLGNYVPNG   2460
GDPGVGLPGP RGERGEPGIR GEDGRPGQEG PRGLTGPPGS RGERGEKGDV GSAGLKGDKG   2520
DSAVILGPPG PRGAKGDMGE RGPRGLDGDK GPRGDNGDPG DKGSKGEPGD KGSAGLPGLR   2580
GLLGPQGQPG AAGIPGDPGS PGKDGVPGIR GEKGDVGFMG PRGLKGERGV KGACGLDGEK   2640
GDKGEAGPPG RPGLAGHKGE MGEPGVPGQS GAPGKEGLIG PKGDRGFDGQ PGPKGDQGEK   2700
GERGTPGIGG FPGPSGNDGS AGPPGPPGSV GPRGPEGLQG QKGERGPPGE RVVGAPGVPG   2760
APGERGEQGR PGPAGPRGEK GEAALTEDDI RGFVRQEMSQ HCACQGQFIA SGSRPLPSYA   2820
ADTAGSQLHA VPVLRVSHAE EEERVPPEDD EYSEYSEYSV EEYQDPEAPW DSDDPCSLPL   2880
DEGSCTAYTL RWYHRAVTGS TEACHPFVYG GCGGNANRFG TREACERRCP PRVVQSQGTG   2940
TAQDGSGVKQ TLNFDLLKLA GDVESNPGPT SSGPGPRFLL LLPLLLLPPAA SASDRPRGRD   3000
PVNPEKLLVI TVATAETEGY LRFLRSAEFF NYTVRTLGLG EEWRGGDVAR TVGGGQKVRW   3060
LKKEMEKYAD REDMIIMFVD SYDVILAGSP TELLKKFVQS GSRLLFSAES FCWPEWGLAE   3120
QYPEVGTGKR FLNSGGFIGF ATTIHQIVRQ WKYKDDDDDQ LFYTRLYLDP GLREKLSLNL   3180
DHKSRIFQNL NGALDEVVLK FDRNRVRIRN VAYDTLPIVV HGNGPTKLQL NYLGNYVPNG   3240
WTPEGGCGFC NQDRRTLPGG QPPPRVFLAV FVEQPTPFLP RFLQRLLLLD YPPDRVTLFL   3300
HNNEVFHEPH IADSWPQLQD HFSAVKLVGP EEALSPGEAR DMAMDLCRQD PECEFYFSLD   3360
ADAVLTNLQT LRILIEENRK VIAPMLSRHG KLWSNFWGAL SPDEYYARSE DYVELVQRKR   3420
VGVWNVPYIS QAYVIRGDTL RMELPQRDVF SGSDTDPDMA FCKSFRDKGI FLHLSNQHEF   3480
GRLLATSRYD TEHLHPDLWQ IFDNPVDWKE QYIHENYSRA LEGEGIVEQP CPDVYWFPLL   3540
SEQMCDELVA EMEHYGQWSG GRHEDSRLAG GYENVPTVDI HMKQVGYEDQ WLQLLRTYVG   3600
PMTESLFPGY HTKARAVMNF VVRYRPDEQP SLRPHHDSST FTLNVALNHK GLDYEGGGCR   3660
FLRYDCVISS PRKGWALLHP GRLTHYHEGL PTTWGTRYIM VSFVDP             3706
```

```
SEQ ID NO: 27            moltype = DNA   length = 11121
FEATURE                  Location/Qualifiers
misc_feature             1..11121
                         note = Synthetic Construct
source                   1..11121
                         mol_type = other DNA
                         organism = synthetic construct
SEQUENCE: 27
atgacctcct cggggcctgg accccggttc ctgctgctgc tgccgctgct gctgcccct     60
gcggcctcag cctccgaccg gccccggggc cgagacccgg tcaacccaga gaagctgctg    120
gtgatcactg tggccacagc tgaaaccgag gggtacctgc gtttcctgcg ctctgcggag    180
ttcttcaact acactgtgcg gaccctgggc ctgggagagg agtggcgagg gggtgatgtg    240
gctcgaacag ttggtggagg acagaaggtc cggtggttaa agaaggaaat ggagaaatac    300
gctgaccggg aggatatgat catcatgttt gtggatagct acgacgtgat tctgccggc     360
agccccacag agctgctgaa gaagttcgtc cagagtggca gccgcctgct cttctctgca    420
gagagcttct gctggcccga gtgggggctg cgggagcagt accctgaggt gggcacgggg    480
aagcgcttcc tcaattctgg tggattcatc ggttttggcg ccaccatcca ccaaatcgtg    540
cgccagtgga agtacaagga tgatgacgac gaccagctgt tctacacacg gctctacctg    600
gacccaggac tgagggagaa actcagcctt aatctggatc ataagtctcg gatctttcag    660
aacctcaacg gggctttaga tgaagtggtt ttaaagtttg atcggaaccg tgtgcgtatc    720
cggaacgtgg cctacgacac gctccccatt gtggtccatg gaaacggtcc cactaagctg    780
cagctcaact acctgggaaa ctacgtcccc aatggctgga ctcctgaggg aggctgtggc    840
ttctgcaacc aggaccggag gacactcccg gggggggcagc ctcccccccg ggtgtttctg    900
gccgtgtttg tggaacagcc tactccgttt ctgccccgct tcctgcagcg gctgctactc    960
ctggactatc cccccgacag ggtcaccctt ttcctgcaca acaacgaggt cttccatgaa   1020
ccccacatcg ctgactcctg gccgcagctc caggaccact tctcagctgt gaagctcgtg   1080
gggccggagg aggctctgag cccaggcgag gccaggggaca tggccatgga cctgtgtcgg   1140
```

```
caggacccg agtgtgagtt ctacttcagc ctggacgccg acgctgtcct caccaacctg    1200
cagaccctgc gtatcctcat tgaggagaac aggaaggtga tcgcccccat gctgtcccgc    1260
cacggcaagc tgtggtccaa cttctggggc gccctgagcc ccgatgagta ctacgcccgc    1320
tccgaggact acgtggagct ggtgcagcgg aagcgagtgg gtgtgtgaa tgtaccatac     1380
atctcccagg cctatgtgat ccggggtgat accctgcgga tggagctgcc ccagagggat    1440
gtgttctcgg gcagtgacac agacccggac atggccttct gtaagagctt tcgagacaag    1500
ggcatcttcc tccatctgag caatcagcat gaatttggcc ggctcctggc cacttccaga    1560
tacgacacgg agcacctgca ccccgacctc tggcagatct tcgacaaccc cgtcgactgg    1620
aaggagcagt acatccacga gaactacagc cgggccctgg aagggaagg aatcgtggag     1680
cagccatgcc cggacgtgta ctggttccca ctgctgtcag aacaaatgtg tgatgagctg    1740
gtggcagaga tggagcacta cggccagtgg tcaggcggcc ggcatgagga ttcaaggctg    1800
gctggaggct acgagaatgt gcccaccgtg gacatccaca tgaagcaggt ggggtacgag    1860
gaccagtggc tgcagctgct gcggacgtat gtgggcccca tgaccgagag cctgtttccc    1920
ggttaccaca ccaaggcgcg ggcggtgatg aactttgtgg ttcgctaccg gccagacgag    1980
cagccgtctc tgcggccaca ccacgactca tccaccttca ccctcaacgt tgccctcaac    2040
cacaagggcc tggactatga gggaggtggc tgccgcttcc tgcgctacga ctgtgtgatc    2100
tcctccccga ggaagggctg ggcactcctg caccccggcc gcctcaccca ctaccacgag    2160
gggctgccaa cgacctgggg cacacgctac atcatggtgt cctttgtcga ccccggaagc    2220
ggagtgaaac agactttgaa ttttgacctt ctcaagttgg cgggagacgt ggagtccaac    2280
cctgaccta cgctgcggct tctggtggcc gcgctctgcg ccgggatcct ggcagaggcg     2340
ccccgagtgc gagcccagca cagggagaga gtgacctgca cgcgcctta cgccgctgac     2400
attgtgttct tactggatgg ctcctcatcc atggcccgca gcaatttccg cgaggtccgc    2460
agctttctcg aagggctggt gctgcctttc tctggagcag ccagtgcaca gggtgtgcgc    2520
tttgccacag tgcagtacag cgatgaccca cggacagagt tcggcctgga tgcacttggc    2580
tctgggggtg atgtgatccg cgccatccgt gagcttagct acaaggggg caacactcgc     2640
acaggggctg caattctcca tgtggctgac catgtcttcc tgccccagct ggcccgacct    2700
ggtgtcccca aggtctgcat cctgatcaca gacgggaagt cccaggacct ggtggacaca    2760
gctgcccaaa ggctgaaggg gcagggggtc aagctatttg ctgtggggat caagaatgct    2820
gaccctgagg agctgaagcg agttgcctca cagcccacca gtgacttctt cttcttcgtc    2880
aatgacttca gcatcttgag gacactactg cccctcgttt cccggagagt gtgcacgact    2940
gctggtggcg tgcctgtgac ccgacctccg gatgactcga cctctgctcc acgagacctg    3000
gtgctgtctg agccaagcag ccaatccttg agagtacagt ggacagcggc cagtggccct    3060
gtgactggct acaaggtcca gtacactcct ctgacggggc tgggacagcc actgccgagt    3120
gagcggcagg aggtgaacgt cccagctggt gagaccagtg tgcggctgcg gggtctccgg    3180
ccactgacca agtaccaagt gactgtgatt gccctcacg ccaacagcat cagggaggct      3240
gtgagcggga cagctcggac cactgcccta gaagggccgg aactgaccat ccagaatacc    3300
acagcccaca gcctcctggt ggcctggcgg agtgtgccag gtgccactgg ctaccgtgtg    3360
acatggcggg tcctcagtgg tgggcccaca cagcagcagg agctgggccc tgggcagggt    3420
tcagtgttgc tgcgtgactt ggagcctggc acggactatg aggtgaccgt gagcaccta     3480
tttggccgca gtgtgggcc cgccacttcc ctgatggctc gcactgacgc ttctgttgag     3540
cagaccctgc gcccggtcat cctgggcccc acatccatcc tcctttcctg gaacttggtg    3600
cctgaggccc gtggctaccg gttggaatgg cggcgtgaga ctggcttgga gccaccgcag    3660
aaggtggtac tgccctctga tgtgacccgc taccagttgg atgggctgca gccgggcact    3720
gagtaccgcc tcacactcta cactctgctg gagggccacg aggtggccac ccctgcaacc    3780
gtggttccca ctgaccaga gctgcctgtg agccctgtaa cagacctgca agccaccgag     3840
ctgcccggc agcgggtgcg agtgtcctgg agcccagtcc ctggtgccac ccagtaccgc     3900
atcattgtgc gcagcacca gggggtggag cggaccctgg tgcttcctgg gagtcagaca     3960
gcattcgact tggatgacgt tcaggctggg cttagctaca ctgtgcgggt gtctgctcga     4020
gtgggtcccc gtgagggcag tgccagtgtc ctcactgtcc gccgggagcc ggaaactcca    4080
cttgctgttc cagggctgcg ggttgtggtg tcagatgcaa cgcgagtgag ggtggcctgg    4140
ggaccgtcc ctggagccag tggatttcgg attagctgga gcacaggcag tggtccggag      4200
tccagccaga cactgccccc agactctact gccacagaca tcacagggct gcagcctgga    4260
accacctacc aggtggctgt gtcggtactg cgaggcagag aggagggccc tgctgcagtc    4320
atcgtggctc gaacggaccc actgggccca gtgaggacgg tccatgtgac tcaggccagc    4380
agctcatctg tcaccattac ctggaccaag gttcctggcc ccacaggata cagggtttcc    4440
tggcactcag cccacggccc agagaaatcc cagttggttt ctggggaggc cacggtggct    4500
gagctggatg gactggagcc agatactgag tatacggtgc atgtgagggc ccatgtggct    4560
ggcgtggatg ggcccctgc ctctgtggtt gtgaggactg cccctgagcc tgtgggtcgt       4620
gtgtcgaggc tgcagatcct caatgcttcc agcgacgttc tacggatcac ctgggtaggg    4680
gtcactggag ccacagctta cagactggcc tggggccgga gtgaaggcgg ccccatgag      4740
caccagatac tcccaggaaa cacagactct gcagagatcc ggggtctcga aggtggagtc    4800
agctactcag tgcgagtgac tgcacttgtc ggggaccgcg agggcacacc tgtctccatt    4860
gttgtcacta cgcccgcctga ggctccgcca gccctgggga cgcttcacgt ggtgcagcgc    4920
ggggagcact cgctgaggct gcgctgggag ccggtgccca cgccaggag cttccttctg      4980
cactggcaac ctgaggctgg ccaggaacag tcccgggtcc tggggcccga gctcagcagc    5040
tatcacctgg acgggctgga ccagcgacac cagtaccgcg tgaggctgag tgtcctaggg    5100
ccagctggag aagggccctc tgcagaggtg actgcgcgca ctgagtcacc tcgtgttcca    5160
agcattgaac tacgtgtggt ggacacctcg atcgactcgg tgactttggc ctggactcca    5220
gtgtccaggg catccagcta catcctatcc tggcggccac tcagaggccc tcagcaggaa     5280
gtgcctgggt ccccgcagac acttccaggg atctcaagct cccagcgggt gacagggcta    5340
gagcctggcg tctcttacat cttctccctg acgcctgtcc tggatggtgt gcggggtcct     5400
gaggcatctg tcacacagac gccagtgtgc ccccgtggcc tggcggatgt ggtgttccta    5460
ccacatgcca ctcaagacaa tgctcaccgt gcggaggcta cgaggagggt cctggagcgt     5520
ctggtgttgg cacttgggcc tcttgggcca caggcagttc aggttggct gctgtcttac       5580
agtcatcggc cctccccact gttcccactg aatggctccc atgaccttgg cattatcttg    5640
caaaggatcc gtgacatgcc ctacatggac ccaagtggga acaacctggg cacagccgtg    5700
gtcacagctc acagatacat gttggcacca gatgctcctg ggcgccgcca gcacgtacca    5760
ggggtgatgg ttctgctagt ggatgaaccc ttgagaggtg acatattcag ccccatccgt    5820
gaggcccagg cttctgggct taatgtggtg atgttgggaa tggctggagc ggacccagag    5880
```

```
cagctgcgtc gcttggcgcc gggtatggac tctgtccaga ccttcttcgc cgtggatgat   5940
gggccaagcc tggaccaggc agtcagtggt ctggccacag ccctgtgtca ggcatccttc   6000
actactcagc cccggccaga gccctgccca gtgtattgtc caaagggcca gaagggggaa   6060
cctggagaga tgggcctgag aggacaagtt gggcctcctg gcgaccctgg cctcccgggc   6120
aggaccggtg ctcccggccc ccaggggccc cctggaagtg ccactgccaa gggcgagagg   6180
ggcttccctg gagcagatgg gcgtccaggc agccctggcc gcgccgggaa tcctgggacc   6240
cctggagccc ctggcctaaa gggctctcca gggttgcctg gccctcgtgg ggacccggga   6300
gagcgaggac ctcgaggccc aaaggggggag ccgggggctc ccggacaagt catcggaggt   6360
gaaggacctg ggcttcctgg gcggaaaggg gaccctggac catcgggccc ccctggacct   6420
cgtggaccac tggggaccc aggacccgt ggcccccag ggcttcctgg aacagccatg   6480
aagggtgaca aaggcgatcg tggggagcgg ggtccccctg gaccaggtga aggtggcatt   6540
gctcctgggg agcctgggct gccgggtctt cccggaagcc ctggacccca aggccccgtt   6600
ggcccccctg gaaagaaagg agaaaaaggt gactctgagg atggagctcc aggcctccca   6660
ggacaacctg ggtctccggg tgagcagggc ccacgggagc ctcctggagc tattggcccc   6720
aaaggtgacc ggggcttttcc agggccctg ggtgaggctg gagagaaggg cgaacgtgga   6780
cccccaggcc cagcgggatc ccgggggctg ccaggggttg ctggacgtcc tggagccaag   6840
ggtcctgaag ggccaccagg acccactggc cgccaaggag agaaggggga gcctggtcgc   6900
cctgggggacc ctgcagtggt ggacctgct gttgctgcac ccaaaggaca aaagggagat   6960
gtggggcccg ctgggcccag aggagctacc ggagtccaag gggaacgggg cccacccggc   7020
ttggttcttc ctggagaccc tggccccaag ggagaccctg gagaccgggg tcccattggc   7080
cttactggca gagcaggacc cccaggtgac tcagggcctc ctggagagaa gggagaccct   7140
gggcggagcg gcccccccagg acctgttggc ccccgaggac gagatggtga agttggagag   7200
aaaggtgacg agggtcctcc gggtgacccg ggtttgcctg gaaaagcagg cgagcgtggc   7260
cttcggggg cacctggagt tcgggggcct gtgggtgaaa agggagacca gggagatcct   7320
ggagaggatg gacgaaatgg cagccctgga tcatctggac ccaagggtga ccgtgggggag   7380
ccgggtcccc caggaccccc gggacggctg gtagacacag gacctggagc cagagagaag   7440
ggagagcctg gggaccgcgg acaagagggt cctcgagggc ccaagggtga tcctggcctc   7500
cctggagccc ctggggaaag gggcattgaa gggtttcggg gaccccccagg cccacagggg   7560
gacccaggtg tccgaggccc agcaggagaa aaggtgacc ggggtccccc tgggctggat   7620
ggccggagcg gactggatgg gaaaccagga gccgctgggc cctctgggcc gaatggtact   7680
gcaggcaaag ctgggggaccc agggagagac gggcttccag gcctccgtgg agaacagggc   7740
ctccctggcc cctctggtcc ccctggatta ccgggaaagc caggcgagga tggcaaacct   7800
ggcctgaatg gaaaaaacgg agaacctggg gaccctggag aagacgggag gaaggagag   7860
aaaggagatt caggcgcctc tgggagagaa ggtcgtgatg gcccccaaggg tgagcgtgga   7920
gctcctggta tccttggacc ccagggggcct ccaggcctcc cagggccagt gggccctcct   7980
ggccagggtt ttcctggtgt cccaggagg acgggcccca agggtgaccg tggggagact   8040
ggatccaaag gggagcaggg cctccctgga gagcgtggcc tgcgaggaga gcctggaagt   8100
gtgccgaatg tggatcggtt gctggaaact gctggcatca aggcatctgc cctgcgggag   8160
atcgtggaca cctgggatga gagctctggt agcttcctgc ctgtgcccga acggcgtcga   8220
ggcccccaagg gggactcagg cgaacagggc ccccaggca aggaggggccc catcggcttt   8280
cctggagaac gcgggctgaa gggcgaccgt ggagaccctg gccctcaggg gccacctggt   8340
ctggcccttg gggagagggg cccccccggg ccttccggcc ttgccgggga gctggaaag   8400
cctggtattc ccgggctccc aggcaggggct gggggtgtgg agaggccagg aaggccagga   8460
gagaggggag aacgggggaga gaaaggagaa cgtggagaac agggcagaga tggccctcct   8520
ggactccctg gaacccctgg gccccccgga ccccctggcc ccaaggtgtc tgtggatgag   8580
ccaggtcctg gactctctgg agaacaggga ccccctggac tcaagggtgc taaggggggag   8640
ccgggcagca atggtgacca aggtcccaaa ggagacaggg gtgtgccagg catcaaagga   8700
gaccggggag agcctggacc gagggggtcag gacggcaacc cgggtctacc aggagagcgt   8760
ggtatggctg ggcctgaagg gaagccgggt ctgcaggggtc caagaggccc ccctggccca   8820
gtgggtggtc atggagaccc tggaccacct ggtgccccgg gtcttgctgg ccctgcagga   8880
ccccaaggac cttctggcct gaaggggaga cctggagaga caggacctcc aggacgggggcg   8940
ctgactggac ctactggagc tgtgggactt cctggacccc ccggccccttc aggccttgtg   9000
ggtccacagg ggtctccagg tttgcctgga caagtggggg agacagggaa gccgggagcc   9060
ccaggtcgag atggtgccag tggaaaagat ggagacagag ggagccctgg tgtgccaggg   9120
tcaccaggtc tgcctggccc tgtcggacct aaaggagaac ctggccccac ggggggccctt   9180
ggacaggctg tggtcgggct cctggagca aagggaggaa agggagcccc tggaggcctt   9240
gctggagacc tggtgggtga gccgggaagcc aaaggtgacc gaggactgcc agggccgcga   9300
ggcgagaagg gtgaagctgg ccgtgcaggg gagcccggga accctgggga agatggtcag   9360
aaaggggctc caggacccaa aggttttcaag ggtgaccag gagtcgggt cccgggctcc   9420
cctgggcctc ctggccctcc aggtgtgaag ggagatctgg gcctccctgg cctgcccggt   9480
gctcctggtg ttgttgggtt cccgggtcag acaggccctc gaggagagat gggtcagcca   9540
ggccctagtg gagagcgggg tctggcaggc ccccaggga gagaaggaat cccaggaccc   9600
ctggggccac ctggaccacc ggggtcagtg ggaccacctg gggcctctgg actcaaagga   9660
gacaagggag accctggagt agggctgcct gggccccagg gcgagcgtgg ggagccgctg   9720
atccggggtg aagatggccg ccccggccag gagggacccc gaggactcac ggggcccct   9780
ggcagcaggg gagagcgtgg ggagaagggt gatgttggga gtgcaggact aaaggggtgac   9840
aagggagact cagctgtgat cctgggggcct ccaggcccac ggggtgccaa gggggacatg   9900
ggtgaacagg ggcctcgggg cttggatggt gacaaaggac ctcggggaga caatggggac   9960
cctggtgcaa agggcagcaa ggagagcct ggtgacaagg gctcagccgg gttgccagga   10020
ctgcgtggac tcctgggacc ccaggtcaa cctggtgcag cagggatccc tggtgacccg   10080
ggatccccag gaaaggatgg agtgcctggt atccggagga aaaaaggaga tgttggcttc   10140
atgggtccc ggggcctcaa gggtgaacgg ggagtgaagg gagcctgtgg ccttgatgga   10200
gagaagggag acaagggaga agctggtccc ccaggccgcc ccgggctggc aggacacaaa   10260
ggagagatgg ggacgctgg tgtgccaggga cagtcggggg ccctggcaa gggagggctg   10320
atcggtccca agggtgaccg aggctttgac gggcagccag gccccaaggg tgaccagggc   10380
gagaaagggg agcggggaac cccaggaatt gggggcttcc caggccccag tggaaatgat   10440
ggctctgctg gtcccccagg gccacctggc agtgttggtc ccagaggccc cgaaggactt   10500
cagggccaga agggtgagcg aggtcccccc ggagagagag tggtgggggc tcctgggggtc   10560
cctggagctc ctggcgagag aggggagcag gggcggccag ggcctgccgg tcctcgaggc   10620
```

-continued

```
gagaagggag aagctgcact gacggaggat gacatccggg gctttgtgcg ccaagagatg   10680
agtcagcact gtgcctgcca gggccagttc atcgcatctg gatcacgacc cctccctagt   10740
tatgctgcag acactgccgg ctcccagctc catgctgtgc ctgtgctccg cgtctctcat   10800
gcagaggagg aagagcgggt accccctgag gatgatgagt actctgaata ctccgagtat   10860
tctgtggagg agtaccagga ccctgaagct ccttgggata gtgatgaccc ctgttccctg   10920
ccactggatg agggctcctg cactgcctac accctgcgct ggtaccatcg ggctgtgaca   10980
ggcagcacag aggcctgtca ccctttttgtc tatggtggct gtggagggaa tgccaaccgt   11040
tttgggaccc gtgaggcctg cgagcgccgc tgcccacccc gggtggtcca gagccagggg   11100
acaggtactg cccaggactg a                                              11121
```

SEQ ID NO: 28          moltype = AA  length = 3706
FEATURE                Location/Qualifiers
REGION                 1..3706
                       note = Synthetic Construct
source                 1..3706
                       mol_type = protein
                       organism = synthetic construct
SEQUENCE: 28

```
MTSSGPGPRF LLLLPLLLPP AASASDRPRG RDPVNPEKLL VITVATAETE GYLRFLRSAE   60
FFNYTVRTLG LGEEWRGGDV ARTVGGGQKV RWLKKEMEKY ADREDMIIMF VDSYDVILAG   120
SPTELLKKFV QSGSRLLFSA ESFCWPEWGL AEQYPEVGTG KRFLNSGGFI GFATTIHQIV   180
RQWKYKDDDD DQLFYTRLYL DPGLREKLSL NLDHKSRIFQ NLNGALDEVV LKFDRNRVRI   240
RNVAYDTLPI VVHGNGPTKL QLNYLGNYVP NGWTPEGGCG FCNQDRRTLP GGQPPPRVFL   300
AVFVEQPTPF LPRFLQRLLL LDYPPDRVTL FLHNNEVFHE PHIADSWPQL QDHFSAVKLV   360
GPEEALSPGE ARDMAMDLCR QDPECEFYFS LDADAVLTNL QTLRILIEEN RKVIAPMLSR   420
HGKLWSNFWG ALSPDEYYAR SEDYVELVQR KRVGVWNVPY ISQAYVIRGD TLRMELPQRD   480
VFSGSDTDPD MAFCKSFRDK GIFLHLSNQH EFGRLLATSR YDTEHLHPDL WQIFDNPVDW   540
KEQYIHENYS RALEGEGIVE QPCPDVYWFP LLSEQMCDEL VAEMEHYGQW SGGRHEDSRL   600
AGGYENVPTV DIHMKQVGYE DQWLQLLRTY VGPMTESLFP GYHTKARAVM NFVVRYRPDE   660
QPSLRPHHDS STFTLNVALN HKGLDYEGGG CRFLRYDCVI SSPRKGWALL HPGRLTHYHE   720
GLPTTWGTRY IMVSFVDPGS GVKQTLNFDL LKLAGDVESN PGPTLRLLVA ALCAGILAEA   780
PRVRAQHRER VTCTRLYAAD IVFLLDGSSS IGRSNFREVR SFLEGLVLPF SGAASAQGVR   840
FATVQYSDDP RTEFGLDALG SGGDVIRAIR ELSYKGGNTR TGAAILHVAD HVFLPQLARP   900
GVPKVCILIT DGKSQDLVDT AAQRLKGQGV KLFAVGIKNS DPEELKRVAS QPTSDFFFFV   960
NDFSILRTLL PLVSRRVCTT AGGVPVTRPP DDSTSAPRDL VLSEPSSQSL RVQWTAASGP   1020
VTGYKVQYTP LTGLGQPLPS ERQEVNVPAG ETSVRLRGLR PLTEYQVTVI ALYANSIGEA   1080
VSGTARTTAL EGPELTIQNT TAHSLLVAWR SVPGATGYRV TWRVLSGGPT QQQELGPGQG   1140
SVLLRDLEPG TDYEVTVSTL FGRSVGPATS LMARTDASVE QTLRPVILGP TSILLSWNLV   1200
PEARGYRLEW RRETGLEPPQ KVVLPSDVTR YQLDGLQPGT EYRLTLYTLL EGHEVATPAT   1260
VVPTGPELPV SPVTDLQATE LPGQRVRVSW SPVPGATQYR IIVRSTQGVE RTLVLPGSQT   1320
AFDLDDVQAG LSYTVRVSAR VGPREGSASV LTVRREPETP LAVPGLRVVV SDATRVRVAW   1380
GPVPGASGFR ISWSTGSGPE SSQTLPPDST ATDITGLQPG TTYQVAVSVL RGREEGPAAV   1440
IVARTDPLGP VRTVHVTQAS SSSVTITWTR VPGATGYRVS WHSAHGPEKS QLVSGEATVA   1500
ELDGLEPDTE YTVHVRAHVA GVDGPPASVV VRTAPEPVGR VSRLQILNAS SDVLRITWVG   1560
VTGATAYRLA WGRSEGGPMR HQILPGNTDS AEIRGLEGGV SYSVRVTALV GDREGTPVSI   1620
VVTTPPEAPP ALGTLHVVQR GEHSLRLRWE PVPRAQGFLL HWQPEGGQEQ SRVLGPELSS   1680
YHLDGLEPAT QYRVRLSVLG PAGEGPSAEV TARTESPRVP SIELRVVDTS IDSVTLAWTP   1740
VSRASSYILS WRPLRGPGQE VPGSPQTLPG ISSSQRVTGL EPGVSYIFSL TPVLDGVRGP   1800
EASVTQTPVC PRGLADVVFL PHATQDNAHR AEATRRVLER LVLALGPLGP QAVQVGLLSY   1860
SHRPSPLFPL NGSHDLGIIL QRIRDMPYMD PSGNNLGTAV VTAHRYMLAP DAPGRRQHVP   1920
GVMVLLVDEP LRGDIFSPIR EAQASGLNVV MLGMAGADPE QLRRLAPGMD SVQTFFAVDD   1980
GPSLDQAVSG LATALCQASF TTQPRPEPCP VYCPKGQKGE PGEMGLRGQV GPPGDPGLPG   2040
RTGAPGPQGP PGSATAKGER GFPGADGRPG SPGRAGNPGT PGAPGLKGSP GLPGPRGDPG   2100
ERGPRGPKGE PGAPGQVIGG EGPGLPGRKG DPGPSGPPGP RGPLGDPGPR GPPGLPGTAM   2160
KGDKGDRGER GPPGPGEGGI APGEPGLPGL PGSPGPQGPV GPPGKKGEKG DSEDGAPGLP   2220
GQPGSPGEQG PRGPPGAIGP KGDRGFPGPL GEAGEKGERG PPGPAGSRGL PGVAGRPGAK   2280
GPEGPPGPTG RQGEKGEPGR PGDPAVVGPA VAGPKGEKGD VGPAGPRGAT GVQGERGPPG   2340
LVLPGDPGPK GDPGDRGPIG LTGRAGPPGD SGPPGEKGDP GRPGPPGPVG PRGRDGEVGE   2400
KGDEGPPGDP GLPGKAGERG LRGAPGVRGP VGEKGDQGDP GEDGRNGSPG SSGPKGDRGE   2460
PGPPGPPGRL VDTGPGAREK GEPGDRGQEG PRGPKGDPGL PGAPGERGIE GFRGPPGPQG   2520
DPGVRGPAGE KGDRGPPGLD GRSGLDGKPG AAGPSGPNGA AGKAGDPGRD GLPGLRGEQG   2580
LPGPSGPPGL PGKPGEDGKP GLNGKNGEPG DPGEDGRKGE KGDSGASGRE GRDGPKGERG   2640
APGILGPQGP PGLPGPVGPP GQGFPGVPGG TGPKGDRGET GSKGEQGLPG ERGLRGEPGS   2700
VPNVDRLLET AGIKASALRE IVETWDESSG SFLPVPERRR GPKGDSGEQG PPGKEGPIGF   2760
PGERGLKGDR GDPGPQGPPG LALGERGPPG PSGLAGEPGK PGIPGLPGRA GGVGEAGRPG   2820
ERGERGEKGE RGEQGRDGPP GLPGTPGPPG PPGPKVSVDE PGPGLSGEQG PPGLKGAKGE   2880
PGSNGDQGPK GDRGVPGIKG DRGEPGPRGQ DGNPGLPGER GMAGPEGKPG LQGPRGPPGP   2940
VGGHGDPGPP GAPGLAGPAG PQGPSGLKGE PGETGPPGRG LTGPTGAVGL PGPPGPSGLV   3000
GPQGSPGLPG QVGETGKPGA PGRDGASGKD GDRGSPGVPG SPGLPGPVGP KGEPGPTGAP   3060
GQAVVGLPGA KGEKGAPGGL AGDLVGEPGA KGDRGLPGPR GEKGEAGRAG EPGDPGEDGQ   3120
KGAPGPKGFK GDPGVGVPGS PGPPGPPGVK GDLGLPGLPG APGVVGFPGQ TGPRGEMGQP   3180
GPSGERGLAG PPGREGIPGP LGPPGPPGSV GPPGASGLKG DKGDPGVGLP GPRGERGEPG   3240
IRGEDGRPGQ EGPRGLTGPP GSRGERGEKG DVGSAGLKGD KGDSAVILGP PGPRGAKGDM   3300
GERGPRGLDG DKGPRGDNGD PGDKGSKGEP GDKGSAGLPG LRGLLGPGQG PGAAGIPGDP   3360
GSPGKDGVPG IRGEKGDVGF MGPRGLKGER GVKGACGLDG EKGDKGEAGP PGRPGLAGHK   3420
GEMGEPGVPG QSGAPGKEGL IGPKGDRGFD GQPGPKGDQG EKGERGTPGI GGFPGPSGND   3480
GSAGPPGPPS SVGPRGPEGL QGGKGERGPP GERVVGAPGV PGAPGERGEQ GRPGPAGPRG   3540
EKGEAALTED DIRGFVRQEM SQHCACQGQF IASGSRPLPS YAADTAGSQL HAVPVLRVSH   3600
AEEEERVPPE DDEYSEYSEY SVEEYQDPEA PWDSDDPCSL PLDEGSCTAY TLRWYHRAVT   3660
```

```
GSTEACHPFV YGGCGGNANR FGTREACERR CPPRVVQSQG TGTAQD                    3706

SEQ ID NO: 29          moltype = DNA   length = 1299
FEATURE                Location/Qualifiers
source                 1..1299
                       mol_type = unassigned DNA
                       organism = Homo sapiens
SEQUENCE: 29
atgaccacct ccatccgcca gttcacctcc tccagctcca tcaagggctc ctccggcctg   60
gggggcggct cgtcccgcac ctcctgccgg ctgtctggcg gcctgggtgc cggctcctgc   120
aggctgggat ctgctggcgg cctgggcagc accctcgggg gtagcagcta ctccagctgc   180
tacagctttg gctctggtgg tggctatggc agcagctttg ggggtgttga tgggctgctg   240
gctggaggtg agaaggccac catgcagaac ctcaatgacc gcctggcctc ctacctggac   300
aaggtgcgtg ccctggagga ggccaacact gagctggagg tgaagatccg tgactggtac   360
cagaggcagg ccccggggcc cgcccgtgac tacagccagt actacaggac aattgaggag   420
ctgcagaaca agatcctcac agccaccgtg gacaatgcca acatcctgct acagattgac   480
aatgcccgtc tggctgctga tgacttccgc accaagtttg agacagagca ggccctgcgc   540
ctgagtgtgg aggccgacat caatggcctg cgcagggtgc tggatgagct gaccctggcc   600
agagccgacc tggagatgca gattgagaac ctcaaggagg agctggccta cctgaagaag   660
aaccacgagg aggagatgaa cgccctgcga ggccaggtgg gtggtgagat caatgtggag   720
atggacgctg ccccaggcgt ggacctgagc cgcatcctca acgagatgcg tgaccagtat   780
gagaagatgg cagagaagaa ccgcaaggat gccgaggatt ggttcttcag caagacagag   840
gaactgaacc gcgaggtggc caccaacagt gagctggtgc agagtggcaa gagtgagatc   900
tcggagctcc ggcgcaccat gcaggccttg gagatagagc tgcagtccca gctcagcatg   960
aaagcatccc tggagggcaa cctggcggag acagagaacc gctactgcgt gcagctgtcc   1020
cagatccagg ggctgattgg cagcgtggag gagcagctgg cccagcttcg ctgcgagatg   1080
gagcagcaga accaggaata caaaatcctg ctggatgtga agacgcggct ggagcaggag   1140
attgccacct accgccgcct gctggaggga gaggatgccc acctgactca gtacaagaaa   1200
gaaccggtga ccacccgtca ggtgcgtacc attgtggaag aggtccagga tggcaaggtc   1260
atctcctccc gcgagcaggt ccaccagacc acccgctga                          1299

SEQ ID NO: 30          moltype = AA   length = 432
FEATURE                Location/Qualifiers
source                 1..432
                       mol_type = protein
                       organism = Homo sapiens
SEQUENCE: 30
MTTSIRQFTS SSSIKGSSGL GGGSSRTSCR LSGGLGAGSC RLGSAGGLGS TLGGSSYSSC   60
YSFGSGGGYG SSFGGVDGLL AGGEKATMQN LNDRLASYLD KVRALEEANT ELEVKIRDWY   120
QRQAPGPARD YSQYYRTIEE LQNKILTATV DNANILLQID NARLAADDFR TKFETEQALR   180
LSVEADINGL RRVLDELTLA RADLEMQIEN LKEELAYLKK NHEEEMNALR GQVGGEINVE   240
MDAAPGVDLS RILNEMRDQY EKMAEKNRKD AEDWFFSKTE ELNREVATNS ELVQSGKSEI   300
SELRRTMQAL EIELQSQLSM KASLEGNLAE TENRYCVQLS QIQGLIGSVE EQLAQLRCEM   360
EQQNQEYKIL LDVKTRLEQE IATYRRLLEG EDAHLTQYKK EPVTTRQVRT IVEEVQDGKV   420
ISSREQVHQT TR                                                       432
```

COMPOSITIONS AND METHODS FOR THE TREATMENT OF WOUNDS, DISORDERS, AND DISEASES OF THE SKIN

CROSS REFERENCE TO RELATED APPLICATIONS

The present application is a continuation of U.S. patent application Ser. No. 18/060,515, filed Nov. 30, 2022, which is a continuation of U.S. patent application Ser. No. 17/529, 161, filed Nov. 17, 2021, now abandoned, which is a continuation of U.S. patent application Ser. No. 16/598,982, filed Oct. 10, 2019, now issued as U.S. Pat. No. 11,185,564, which is a continuation of U.S. patent application Ser. No. 16/177,153, filed Oct. 31, 2018, now issued as U.S. Pat. No. 10,441,614, which is a continuation of U.S. patent application Ser. No. 15/851,488, filed Dec. 21, 2017, now issued as U.S. Pat. No. 10,155,016, which is a continuation of U.S. patent application Ser. No. 15/393,151, filed Dec. 28, 2016, now issued as U.S. Pat. No. 9,877,990, which claims the benefit of U.S. Provisional Patent Application Ser. No. 62/320,316, filed Apr. 8, 2016, and all of the aforementioned applications are incorporated herein by reference in their entireties for all purposes.

REFERENCE TO AN ELECTRONIC SEQUENCE LISTING

The contents of the electronic sequence listing (761342000106SEQLIST.xml; Size: 171,492 bytes; and Date of Creation: Jun. 27, 2023) is herein incorporated by reference in its entirety.

FIELD OF THE INVENTION

The present disclosure relates, in part, to pharmaceutical compositions and methods of use for providing prophylactic, palliative, or therapeutic relief of a wound, disorder, or disease of the skin in a subject, including a subject having, or at risk of developing, one or more symptoms of epidermolysis bullosa.

BACKGROUND

A number of serious disease-related skin conditions are associated with one or more genetic disorders in patients suffering from these diseases. One such disease, epidermolysis bullosa (EB), is a group of genetic disorders that cause the skin and mucous membranes of an affected individual to blister and erode in response to minor injury or friction, such as scraping, rubbing, or scratching. Dystrophic epidermolysis bullosa (DEB) is one of the major forms of EB. The signs and symptoms of this condition vary widely among affected individuals, ranging from mild (blistering may only affect the hands, feet, knees, and elbows) to severe (widespread blistering and scarring, possibly leading to vision loss, disfigurement, and other serious, and sometimes fatal, medical conditions).

Dystrophic epidermolysis bullosa is classified into three major types. Autosomal dominant dystrophic epidermolysis bullosa (referred to as dominant dystrophic epidermolysis bullosa or DDEB) is typically the mildest form, with blistering often restricted to the hands, feet knees and elbows. The other two types of dystrophic epidermolysis bullosa, Hallopeau-Siemens type recessive dystrophic epidermolysis bullosa, and non-Hallopeau-Siemens type recessive epidermolysis bullosa (collectively referred to as recessive dystrophic epidermolysis bullosa or RDEB) are more severe. RDEB is most often characterized by extensive blistering and scarring of the skin and mucosal membranes. Blisters are routinely present over the whole body, including on mucous membranes (such as the lining of the mouth and digestive tract), and healing of these blisters results in extensive scarring. Damage to the mouth and esophagus can make it difficult to chew and swallow food, leading to chronic malnutrition and slow growth. Complications from extensive scarring can include fusion of the fingers and toes, joint deformities, and eye inflammation leading to vision loss. Additionally, patients suffering from RDEB have a high risk of developing squamous cell carcinoma, which can be unusually aggressive in this patient population, often becoming life-threatening. Although the three types of dystrophic epidermolysis bullosa differ in severity, they have many shared features, and are caused by the same genetic mutations.

Dystrophic epidermolysis bullosa is caused by mutations to the Col7a1 gene, which encodes the Collagen alpha-1 (VII) chain protein (Collagen 7). More than 240 distinct mutations to this gene have been identified in DEB patients. Additionally, a significant decrease in expression of the PLOD3 gene, which encodes the collagen modifying Lysyl hydroxylase 3 enzyme (LH3), has also been observed in dystrophic epidermolysis patients. Collagen alpha-1 (VII) chain protein functions to strengthen and stabilize the skin, while Lysyl hydroxylase 3 plays a critical role in the synthesis and secretion of functional Collagen alpha-1 (VII) chain protein. Briefly, Col7a1 transcripts are translated, and the resulting peptides are post-translationally modified by hydroxylating their proline residues (by prolyl hydroxylases) and their lysine residues (by lysyl hydroxylases, such as LH3). Hydroxylysine residues can then be glycosylated, and subsequently, three glycosylated peptides form a triple helix known as pro-collagen, and are secreted from the cell. The secreted pro-collagen can then associate in to higher-order structures, forming anchoring fibrils. The anchoring fibrils are then available to help organize, stabilize, and aid in adherence of the epithelial basement membrane. The epithelial basement membrane is responsible for anchoring the epithelium to the underlying loose connective tissue, and is essential for dermal-epidermal stability (dermoepidermal junction integrity). Mutations in the Col7a1 gene, and diminished levels of PLOD3 expression, impair the ability of Collagen alpha-1 (VII) chain protein to properly connect the epidermis to the dermis in dystrophic epidermolysis bullosa patients, leading to fragile skin.

Treatment options for epidermolysis bullosa patients are limited, and current care focuses on managing the symptoms of the disease, including providing medication to control pain and itching, administering oral antibiotics to stave off infections resulting from open wounds on the skin and mucosa, and surgical strategies to address scarring and deformities. Investigational methods for treating the underlying causes of epidermolysis bullosa include administering purified Collagen 7, fibroblasts containing Collagen 7, or viral vectors encoding Collagen 7, by intradermal injection. Because many DEB patients have multiple wounds spanning large areas of trauma-prone sites (such as the sacrum, hips, feet, lower back, and hands), any treatment involving intradermal injection would be extremely invasive, as these large wound areas would all need to be injected, likely repeatedly, although injection time intervals are unclear.

Thus there exists a clear need for less invasive/minimally invasive/non-invasive treatment options for epidermolysis bullosa patients that can address the deficiencies in the Collagen alpha-1 (VII) chain protein, as well as deficiencies in the Lysyl hydroxylase 3 protein, observed in this patient population.

All references cited herein, including patent applications, patent publications, non-patent literature, and UniProtKB/Swiss-Prot Accession numbers are herein incorporated by reference in their entirety, as if each individual reference were specifically and individually indicated to be incorporated by reference.

BRIEF SUMMARY

In order to meet these needs, the present disclosure relates, in part, to pharmaceutical compositions and methods of use for providing prophylactic, palliative, or therapeutic relief of a wound, disorder, or disease of the skin in a subject, especially in a subject having, or at risk of developing, one or more symptoms of epidermolysis bullosa. In particular, the present disclosure relates, in part, to a method of treating an individual by administering (e.g., topically or transdermally administering) a pharmaceutical composition comprising one or more polynucleotides encoding a Collagen alpha-1 (VII) chain polypeptide, a Lysyl hydroxylase 3 polypeptide, a Keratin type I cytoskeletal 17 polypeptide and/or a chimeric polypeptide thereof.

Accordingly, certain aspects of the present disclosure relate to a pharmaceutical composition comprising a virus comprising a vector, wherein the vector comprises one or more transgenes encoding a Collagen alpha-1 (VII) chain polypeptide, a Lysyl hydroxylase 3 polypeptide, or a chimeric polypeptide thereof, and a pharmaceutically acceptable carrier. In some embodiments, the virus is an adenovirus, adeno-associated virus, retrovirus, lentivirus, sendai virus, herpes simplex virus, vaccinia virus, or any hybrid virus thereof. In some embodiments, the virus is replication-defective. In some embodiments, the virus is a herpes simplex virus (HSV). In some embodiments, the herpes simplex virus is a herpes simplex type 1 virus, a herpes simplex type 2 virus, or any derivatives thereof. In some embodiments, the herpes simplex virus comprises a modified envelope. In some embodiments, the modified envelope alters the herpes simplex virus tissue tropism relative to a wild-type herpes simplex virus. In some embodiments, the modified envelope comprises a mutant herpes simplex virus glycoprotein. In some embodiments, the vector is an HSV-1 amplicon or an HSV-1 hybrid amplicon. In some embodiments, the HSV-1 hybrid amplicon is an HSV/AAV hybrid amplicon, an HSV/EBV hybrid amplicon, and HSV/EBV/RV hybrid amplicon, or an HSV/Sleeping Beauty hybrid amplicon. In some embodiments, the vector is a recombinant herpes simplex virus genome. In some embodiments, the recombinant herpes simplex virus genome is a recombinant HSV-1 genome, a recombinant HSV-2 genome, or any derivatives thereof. In some embodiments, the recombinant herpes simplex virus genome comprises an inactivating mutation in an immediate early herpes simplex virus gene. In some embodiments, the herpes simplex virus gene is ICP0, ICP4, ICP22, ICP27, ICP47, tk, UL41, or UL55. In some embodiments, the recombinant herpes simplex virus genome comprises an inactivating mutation in the ICP4, ICP27, and UL55 genes. In some embodiments, the recombinant herpes simplex virus genome comprises an inactivating mutation in the ICP4, ICP22, ICP27, ICP47, and UL55 genes. In some embodiments, the inactivating mutation in the ICP4, ICP27, and UL55 genes is a deletion of the coding sequence of the ICP4, ICP27, and UL55 genes. In some embodiments, the inactivating mutation in the ICP22 and ICP47 genes is a deletion in the promoter region of the ICP22 and ICP47 genes. In some embodiments, the recombinant herpes simplex virus genome comprises an inactivating mutation in the ICP4 and ICP22 genes. In some embodiment, the recombinant herpes simplex virus genome comprises an inactivating mutation in the ICP0 and ICP4 genes. In some embodiments, the recombinant herpes simplex virus genome comprises an inactivating mutation in the ICP0, ICP4, and ICP22 genes. In some embodiments, the recombinant herpes simplex virus genome comprises an inactivating mutation in the ICP0, ICP4, ICP22, and ICP27 genes. In some embodiments, the recombinant herpes simplex virus genome comprises an inactivating mutation in the ICP0, ICP4, ICP22, ICP27, and UL55 genes. In some embodiments, the inactivating mutation is a deletion of the coding sequence of the genes. In some embodiments, the recombinant herpes simplex virus genome further comprises an inactivating mutation in the ICP47 gene, an inactivating mutation in the UL41 gene, or an inactivation mutation in the ICP47 and UL41 genes. In some embodiments, the recombinant herpes simplex virus genome comprises the one or more transgenes within one or more viral gene loci. In some embodiments, the recombinant herpes simplex virus genome comprises the one or more transgenes within one or more of the ICP4 viral gene loci. In some embodiments, the recombinant herpes simplex virus genome comprises the one or more transgenes within the UL41 viral gene locus. In some embodiments, the vector is capable of replicating within a target cell when delivered into said target cell. In some embodiments, the pharmaceutically acceptable carrier is suitable for topical or transdermal administration. In some embodiments, the one or more transgenes comprises an miRNA binding site. In some embodiments, the one or more transgenes are operably linked to one or more heterologous promoters. In some embodiments, the one or more heterologous promoters are one or more of the human cytomegalovirus (HCMV) immediate early promoter, the elongation factor-1 (EF1) promoter, and/or any combinations thereof. In some embodiment, the vector comprises a transgene encoding a Collagen alpha-1 (VII) chain polypeptide. In some embodiments, the vector comprises two transgenes, wherein each transgene encodes a Collagen alpha-1 (VII) chain polypeptide. In some embodiments, the Collagen alpha-1 (VII) chain polypeptide has at least 80% sequence identity to the sequence of SEQ ID NO: 2. In some embodiments, the collagen alpha-1 (VII) chain polypeptide is a fragment, wherein the fragment has at least 100 consecutive amino acids of SEQ ID NO: 2. In some embodiments, the Collagen alpha-1 (VII) chain polypeptide enhances, increases, augments, and/or supplements anchoring fibril formation of a subject when the polypeptide is expressed in one or more target cells of the subject. In some embodiments, the Collagen alpha-1 (VII) chain polypeptide enhances, increases, augments, and/or supplements epithelial basement membrane organization and/or epithelial basement adherence of a subject when the polypeptide is expressed in one or more target cells of the subject. In some embodiments, the Lysyl hydroxylase 3 polypeptide has at least 80% sequence identity to the sequence of SEQ ID NO: 4. In some embodiments, the Lysyl hydroxylase 3 polypeptide is a fragment, wherein the fragment has at least 100 consecutive amino acids of SEQ ID NO: 4. In some embodiments, the Lysyl hydroxylase 3 polypeptide enhances, increases, augments, and/or supplements the formation of hydroxylysine residues on one or more collagen polypeptides of a subject when the Lysyl hydroxylase 3 polypeptide is expressed in one or more target cells of the subject. In some embodiments, the Lysyl hydroxylase 3 polypeptide enhances, increases, augments, and/or supplements anchoring fibril formation, epithelial basement membrane organization, and/or epithelial basement adherence of a subject when the polypeptide is expressed in one or more target cells of the subject. In some embodiments, the vector comprises at least a first transgene and a second transgene. In some embodiments, the first transgene encodes a Collagen alpha-1 (VII) chain polypeptide and the second transgene encodes a Lysyl hydroxylase 3 polypeptide. In some embodiments, the vector comprises a transgene that is polycistronic. In some embodiments, the polycistronic transgene encodes a Collagen alpha-1 (VII) chain polypeptide on a first open reading frame (ORF) and a Lysyl hydroxylase 3 polypeptide on a second open reading frame (ORF). In some embodiments, the first and second ORFs are separated by an internal ribosomal entry site (IRES). In some embodiments, the Collagen alpha-1 (VII) chain polypeptide and the Lysyl hydroxylase 3 polypeptide are at about an equimolar ratio when the polypeptides are expressed in one or more target cells of a subject. In some embodiments, the Collagen alpha-1 (VII) chain polypeptide and the Lysyl hydroxylase 3 polypeptide enhance, increase, augment, and/or supplement anchoring fibril formation, epithelial basement membrane organization, and/or epithelial basement adherence of a subject when the polypeptides are expressed in one or more target cells of the subject. In some embodiments, the chimeric polypeptide comprises a linker polypeptide between the Collagen alpha-1 (VII) chain polypeptide and the Lysyl hydroxylase 3 polypeptide. In some embodiments, the linker polypeptide is a T2A, P2A, E2A, or F2A linker polypeptide. In some embodiments, the linker polypeptide has at least 80% sequence identity to the sequence of SEQ ID NO: 6, SEQ ID NO: 8, SEQ ID NO: 10 or SEQ ID NO: 12. In some embodiments, the chimeric polypeptide has at least 80% sequence identity to the sequence of SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28. In some embodiments, the chimeric polypeptide enhances, increases, augments, and/or supplements anchoring fibril formation, epithelial basement membrane organization, and/or epithelial basement adherence of a subject when the polypeptide is expressed in one or more target cells of the subject.

Other aspects of the present disclosure relate to a method of providing prophylactic, palliative, or therapeutic relief of a wound, disorder, or disease of the skin in a subject, the method comprising topically or transdermally administering a pharmaceutical composition capable of enhancing, increasing, augmenting, and/or supplementing the levels of a Collagen alpha-1 (VII) chain polypeptide and/or a Lysyl hydroxylase 3 polypeptide in one or more cells of the subject. In some embodiments, the pharmaceutical composition comprises a virus comprising a vector, wherein the vector comprises one or more transgenes encoding a Collagen alpha-1 (VII) chain polypeptide, a Lysyl hydroxylase 3 polypeptide, or a chimeric polypeptide thereof, and a pharmaceutically acceptable carrier. In some embodiments, the virus is an adenovirus, adeno-associated virus, retrovirus, lentivirus, sendai virus, herpes simplex virus, vaccinia virus, or any hybrid virus thereof. In some embodiments, the virus is replication-defective. In some embodiments, the virus is a herpes simplex virus (HSV). In some embodiments, the herpes simplex virus is a herpes simplex type 1 virus, a herpes simplex type 2 virus, or any derivatives thereof. In some embodiments, the herpes simplex virus comprises a modified envelope. In some embodiments, the modified envelope alters the herpes simplex virus tissue tropism relative to a wild-type herpes simplex virus. In some embodiments, the modified envelope comprises a mutant herpes simplex virus glycoprotein. In some embodiments, the vector is an HSV-1 amplicon or an HSV-1 hybrid amplicon. In some embodiments, the HSV-1 hybrid amplicon is an HSV/AAV hybrid amplicon, an HSV/EBV hybrid amplicon, and HSV/EBV/RV hybrid amplicon, or an HSV/Sleeping Beauty hybrid amplicon. In some embodiments, the vector is a recombinant herpes simplex virus genome. In some embodiments, the recombinant herpes simplex virus genome is a recombinant HSV-1 genome, a recombinant HSV-2 genome, or any derivatives thereof. In some embodiments, the recombinant herpes simplex virus genome comprises an inactivating mutation in an immediate early herpes simplex virus gene. In some embodiments, the herpes simplex virus gene is ICP0, ICP4, ICP22, ICP27, ICP47, tk, UL41, or UL55. In some embodiments, the recombinant herpes simplex virus genome comprises an inactivating mutation in the ICP4, ICP27, and UL55 genes. In some embodiments, the recombinant herpes simplex virus genome comprises an inactivating mutation in the ICP4, ICP22, ICP27, ICP47, and UL55 genes. In some embodiments, the inactivating mutation in the ICP4, ICP27, and UL55 genes is a deletion of the coding sequence of the ICP4, ICP27, and UL55 genes. In some embodiments, the inactivating mutation in the ICP22 and ICP47 genes is a deletion in the promoter region of the ICP22 and ICP47 genes. In some embodiments, the recombinant herpes simplex virus genome comprises an inactivating mutation in the ICP4 and ICP22 genes. In some embodiment, the recombinant herpes simplex virus genome comprises an inactivating mutation in the ICP0 and ICP4 genes. In some embodiments, the recombinant herpes simplex virus genome comprises an inactivating mutation in the ICP0, ICP4, and ICP22 genes. In some embodiments, the recombinant herpes simplex virus genome comprises an inactivating mutation in the ICP0, ICP4, ICP22, and ICP27 genes. In some embodiments, the recombinant herpes simplex virus genome comprises an inactivating mutation in the ICP0, ICP4, ICP22, ICP27, and UL55 genes. In some embodiments, the inactivating mutation is a deletion of the coding sequence of the genes. In some embodiments, the recombinant herpes simplex virus genome further comprises an inactivating mutation in the ICP47 gene, an inactivating mutation in the UL41 gene, or an inactivation mutation in the ICP47 and UL41 genes. In some embodiments, the recombinant herpes simplex virus genome comprises the one or more transgenes within one or more viral gene loci. In some embodiments, the recombinant herpes simplex virus genome comprises the one or more transgenes within one or more of the ICP4 viral gene loci. In some embodiments, the recombinant herpes simplex virus genome comprises the one or more transgenes within the UL41 viral gene locus. In some embodiments, the vector is capable of replicating within a target cell when delivered into said target cell. In some embodiments, the pharmaceutically acceptable carrier is suitable for topical or transdermal administration. In some embodiments, the one or more transgenes comprises an miRNA binding site. In some embodiments, the one or more transgenes are operably linked to one or more heterologous promoters. In some embodiments, the one or more heterologous promoters are one or more of the human cytomegalovirus (HCMV) immediate early promoter, the elongation factor-1 (EF1) promoter, and/or any combinations thereof. In some embodiments, the vector comprises a transgene encoding a Collagen alpha-1 (VII) chain polypeptide. In some embodiments, the vector comprises two transgenes, wherein each transgene encodes a Collagen alpha-1 (VII) chain polypeptide. In some embodiments, the Collagen alpha-1 (VII) chain polypeptide has at least 80% sequence identity to the sequence of SEQ ID NO: 2. In some embodiments, the collagen alpha-1 (VII) chain polypeptide is a fragment, wherein the fragment has at least 100 consecutive amino acids of SEQ ID NO: 2. In some embodiments, the Collagen alpha-1 (VII) chain polypeptide enhances, increases, augments, and/or supplements anchoring fibril formation of a subject when the polypeptide is expressed in one or more target cells of the subject. In some embodiments, the Collagen alpha-1 (VII) chain polypeptide enhances, increases, augments, and/or supplements epithelial basement membrane organization and/or epithelial basement adherence of a subject when the polypeptide is expressed in one or more target cells of the subject. In some embodiments, the Lysyl hydroxylase 3 polypeptide has at least 80% sequence identity to the sequence of SEQ ID NO: 4. In some embodiments, the Lysyl hydroxylase 3 polypeptide is a fragment, wherein the fragment has at least 100 consecutive amino acids of SEQ ID NO: 4. In some embodiments, the Lysyl hydroxylase 3 polypeptide enhances, increases, augments, and/or supplements the formation of hydroxylysine residues on one or more collagen polypeptides of a subject when the Lysyl hydroxylase 3 polypeptide is expressed in one or more target cells of the subject. In some embodiments, the Lysyl hydroxylase 3 polypeptide enhances, increases, augments, and/or supplements anchoring fibril formation, epithelial basement membrane organization, and/or epithelial basement adherence of a subject when the polypeptide is expressed in one or more target cells of the subject. In some embodiments, the vector comprises at least a first transgene and a second transgene. In some embodiments, the first transgene encodes a Collagen alpha-1 (VII) chain polypeptide and the second transgene encodes a Lysyl hydroxylase 3 polypeptide. In some embodiments, the vector comprises a transgene that is polycistronic. In some embodiments, the polycistronic transgene encodes a Collagen alpha-1 (VII) chain polypeptide on a first open reading frame (ORF) and a Lysyl hydroxylase 3 polypeptide on a second open reading frame (ORF). In some embodiments, the first and second ORFs are separated by an internal ribosomal entry site (IRES). In some embodiments, the Collagen alpha-1 (VII) chain polypeptide and the Lysyl hydroxylase 3 polypeptide are at about an equimolar ratio when the polypeptides are expressed in one or more target cells of a subject. In some embodiments, the Collagen alpha-1 (VII) chain polypeptide and the Lysyl hydroxylase 3 polypeptide enhance, increase, augment, and/or supplement anchoring fibril formation, epithelial basement membrane organization, and/or epithelial basement adherence of a subject when the polypeptides are expressed in one or more target cells of the subject. In some embodiments, the chimeric polypeptide comprises a linker polypeptide between the Collagen alpha-1 (VII) chain polypeptide and the Lysyl hydroxylase 3 polypeptide. In some embodiments, the linker polypeptide is a T2A, P2A, E2A, or F2A linker polypeptide. In some embodiments, the linker polypeptide has at least 80% sequence identity to the sequence of SEQ ID NO: 6, SEQ ID NO: 8, SEQ ID NO: 10 or SEQ ID NO: 12. In some embodiments, the chimeric polypeptide has at least 80% sequence identity to the sequence of SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28. In some embodiments, the chimeric polypeptide enhances, increases, augments, and/or supplements anchoring fibril formation, epithelial basement membrane organization, and/or epithelial basement adherence of a subject when the polypeptide is expressed in one or more target cells of the subject. In some embodiments, the pharmaceutical composition is administered one, two three, four, five or more times per day. In some embodiments, the pharmaceutical composition is administered to one or more affected and/or unaffected areas of the subject. In some embodiments, the disease or disorder of the skin is one or more of epidermolysis bullosa, skin cancer, psoriasis, lichen planus, lupus, rosacea, eczema, cutaneous candidiasis, cellulitis, impetigo, decubitus ulcers, erysipelas, ichthyosis vulgaris, dermatomyositis, acrodermatitis, stasis dermatitis, nethertons syndrome, epidermolysis bullosa simplex (LAMB3 gene), autosomal recessive congenital ichthyosis, xeroderma pigmentosa, and pemphigoid.

Other aspects of the present disclosure relate to an isolated chimeric polypeptide, wherein the isolated chimeric polypeptide comprises a Collagen alpha-1 (VII) chain polypeptide, a Lysyl hydroxylase 3 polypeptide, and a linker polypeptide, wherein the Collagen alpha-1 (VII) chain polypeptide and the Lysyl hydroxylase 3 polypeptide are separated by the linker polypeptide, to polynucleotides encoding the same, to vectors comprising the polynucleotides, and to host cells comprising the vectors. In some embodiments, the vector is an HSV-1 amplicon or an HSV-1 hybrid amplicon. In some embodiments, the HSV-1 hybrid amplicon is an HSV/AAV hybrid amplicon, an HSV/EBV hybrid amplicon, and HSV/EBV/RV hybrid amplicon, or an HSV/Sleeping Beauty hybrid amplicon. In some embodiments, the vector is a recombinant herpes simplex virus genome. In some embodiments, the recombinant herpes simplex virus genome is a recombinant HSV-1 genome, a recombinant HSV-2 genome, or any derivatives thereof. In some embodiments, the recombinant herpes simplex virus genome comprises an inactivating mutation in an immediate early herpes simplex virus gene. In some embodiments, the herpes simplex virus gene is ICP0, ICP4, ICP22, ICP27, ICP47, tk, UL41, or UL55. In some embodiments, the recombinant herpes simplex virus genome comprises an inactivating mutation in the ICP4, ICP27, and UL55 genes. In some embodiments, the recombinant herpes simplex virus genome comprises an inactivating mutation in the ICP4, ICP22, ICP27, ICP47, and UL55 genes. In some embodiments, the inactivating mutation in the ICP4, ICP27, and UL55 genes is a deletion of the coding sequence of the ICP4, ICP27, and UL55 genes. In some embodiments, the inactivating mutation in the ICP22 and ICP47 genes is a deletion in the promoter region of the ICP22 and ICP47 genes. In some embodiments, the recombinant herpes simplex virus genome comprises an inactivating mutation in the ICP4 and ICP22 genes. In some embodiment, the recombinant herpes simplex virus genome comprises an inactivating mutation in the ICP0 and ICP4 genes. In some embodiments, the recombinant herpes simplex virus genome comprises an inactivating mutation in the ICP0, ICP4, and ICP22 genes. In some embodiments, the recombinant herpes simplex virus genome comprises an inactivating mutation in the ICP0, ICP4, ICP22, and ICP27 genes. In some embodiments, the recombinant herpes simplex virus genome comprises an inactivating mutation in the ICP0, ICP4, ICP22, ICP27, and UL55 genes. In some embodiments, the inactivating mutation is a deletion of the coding sequence of the genes. In some embodiments, the recombinant herpes simplex virus genome further comprises an inactivating mutation in the ICP47 gene, an inactivating mutation in the UL41 gene, or an inactivation mutation in the ICP47 and UL41 genes. In some embodiments, the recombinant herpes simplex virus genome comprises the polynucleotide within one or more viral gene loci. In some embodiments, the recombinant herpes simplex virus genome comprises the polynucleotide within one or more of the ICP4 viral gene loci. In some embodiments, the recombinant herpes simplex virus genome comprises the polynucleotide within the UL41 viral gene locus.

Other aspects of the present disclosure relate to a vector comprising one or more polynucleotides encoding a Collagen alpha-1 (VII) chain polypeptide, a Lysyl hydroxylase 3 polypeptide, a Keratin type I cytoskeletal 17 polypeptide, or any combinations thereof, wherein the vector is a recombinant herpes simplex virus genome, and to host cells comprising the vector. In some embodiments, the recombinant herpes simplex virus genome is a recombinant HSV-1 genome, a recombinant HSV-2 genome, or any derivatives thereof. In some embodiments, the recombinant herpes simplex virus genome comprises an inactivating mutation in an immediate early herpes simplex virus gene. In some embodiments, the herpes simplex virus gene is ICP0, ICP4, ICP22, ICP27, ICP47, tk, UL41, or UL55. In some embodiments, the recombinant herpes simplex virus genome comprises an inactivating mutation in the ICP4, ICP27, and UL55 genes. In some embodiments, the recombinant herpes simplex virus genome comprises an inactivating mutation in the ICP4, ICP22, ICP27, ICP47, and UL55 genes. In some embodiments, the inactivating mutation in the ICP4, ICP27, and UL55 genes is a deletion of the coding sequence of the ICP4, ICP27, and UL55 genes. In some embodiments, the inactivating mutation in the ICP22 and ICP47 genes is a deletion in the promoter region of the ICP22 and ICP47 genes. In some embodiments, the recombinant herpes simplex virus genome comprises an inactivating mutation in the ICP4 and ICP22 genes. In some embodiment, the recombinant herpes simplex virus genome comprises an inactivating mutation in the ICP0 and ICP4 genes. In some embodiments, the recombinant herpes simplex virus genome comprises an inactivating mutation in the ICP0, ICP4, and ICP22 genes. In some embodiments, the recombinant herpes simplex virus genome comprises an inactivating mutation in the ICP0, ICP4, ICP22, and ICP27 genes. In some embodiments, the recombinant herpes simplex virus genome comprises an inactivating mutation in the ICP0, ICP4, ICP22, ICP27, and UL55 genes. In some embodiments, the inactivating mutation is a deletion of the coding sequence of the genes. In some embodiments, the recombinant herpes simplex virus genome further comprises an inactivating mutation in the ICP47 gene, an inactivating mutation in the UL41 gene, or an inactivation mutation in the ICP47 and UL41 genes. In some embodiments, the recombinant herpes simplex virus genome comprises the one or more polynucleotides within one or more viral gene loci. In some embodiments, the recombinant herpes simplex virus genome comprises the one or more polynucleotides within one or more of the ICP4 viral gene loci. In some embodiments, the recombinant herpes simplex virus genome comprises the one or more polynucleotides within the UL41 viral gene locus. In some embodiments, the vector comprises one polynucleotide encoding a Collagen alpha-1 (VII) chain polypeptide. In some embodiments, the vector comprises two polynucleotides encoding a Collagen alpha-1 (VII) chain polypeptide.

Other aspects of the present disclosure relate to methods of collecting a herpes simplex virus, wherein a vector of interest is packaged within said herpes simplex virus. In some embodiments the method comprises the steps of contacting a host cell with a vector encoding a helper virus, contacting said host cell with a HSV-1 amplicon or HSV-1 hybrid amplicon comprising one or more polynucleotides described herein, and collecting the *Herpes simplex* virus generated by said host cell. In some embodiments, the method comprises the steps of contacting a complementing host cell with a recombinant herpes simplex virus genome vector comprising one or more polynucleotides described herein, and collecting the herpes simplex virus generated by said complementing host cell. In some embodiments, the collected herpes simplex virus is a herpes simplex type 1 virus, a herpes simplex type 2 virus, or any derivatives thereof.

Other aspects of the present disclosure relate to a kit comprising a pharmaceutical composition described herein and instructions for administering the pharmaceutical composition.

Other aspects of the present disclosure relate to relate to a pharmaceutical composition comprising a virus comprising a vector, wherein the vector comprises one or more transgenes encoding a Collagen alpha-1 (VII) chain polypeptide, a Lysyl hydroxylase 3 polypeptide, a Keratin type I cytoskeletal 17 polypeptide, or a chimeric polypeptide thereof, and a pharmaceutically acceptable carrier. In some embodiments, the virus is an adenovirus, adeno-associated virus, retrovirus, lentivirus, sendai virus, herpes simplex virus, vaccinia virus, or any hybrid virus thereof. In some embodiments, the virus is replication-defective. In some embodiments, the virus is a herpes simplex virus (HSV). In some embodiments, the herpes simplex virus is a herpes simplex type 1 virus, a herpes simplex type 2 virus, or any derivatives thereof. In some embodiments, the vector is an HSV-1 amplicon or an HSV-1 hybrid amplicon. In some embodiments, the HSV-1 hybrid amplicon is an HSV/AAV hybrid amplicon, an HSV/EBV hybrid amplicon, and HSV/EBV/RV hybrid amplicon, or an HSV/Sleeping Beauty hybrid amplicon. In some embodiments, the vector is a recombinant herpes simplex virus genome. In some embodiments, the recombinant herpes simplex virus genome is a recombinant HSV-1 genome, a recombinant HSV-2 genome, or any derivatives thereof. In some embodiments, the recombinant herpes simplex virus genome comprises an inactivating mutation in an immediate early herpes simplex virus gene. In some embodiments, the herpes simplex virus gene is ICP0, ICP4, ICP22, ICP27, ICP47, tk, UL41, or UL55. In some embodiments, the recombinant herpes simplex virus genome comprises an inactivating mutation in the ICP4, ICP27, and UL55 genes. In some embodiments, the recombinant herpes simplex virus genome comprises an inactivating mutation in the ICP4, ICP22, ICP27, ICP47, and UL55 genes. In some embodiments, the inactivating mutation in the ICP4, ICP27, and UL55 genes is a deletion of the coding sequence of the ICP4, ICP27, and UL55 genes. In some embodiments, the inactivating mutation in the ICP22 and ICP47 genes is a deletion in the promoter region of the ICP22 and ICP47 genes. In some embodiments, the recombinant herpes simplex virus genome comprises an inactivating mutation in the ICP4 and ICP22 genes. In some embodiment, the recombinant herpes simplex virus genome comprises an inactivating mutation in the ICP0 and ICP4 genes. In some embodiments, the recombinant herpes simplex virus genome comprises an inactivating mutation in the ICP0, ICP4, and ICP22 genes. In some embodiments, the recombinant herpes simplex virus genome comprises an inactivating mutation in the ICP0, ICP4, ICP22, and ICP27 genes. In some embodiments, the recombinant herpes simplex virus genome comprises an inactivating mutation in the ICP0, ICP4, ICP22, ICP27, and UL55 genes. In some embodiments, the inactivating mutation is a deletion of the coding sequence of the genes. In some embodiments, the recombinant herpes simplex virus genome further comprises an inactivating mutation in the ICP47 gene, an inactivating mutation in the UL41 gene, or an inactivation mutation in the ICP47 and UL41 genes. In some embodiments, the recombinant herpes simplex virus genome comprises the one or more transgenes within one or more viral gene loci. In some embodiments, the recombinant herpes simplex virus genome comprises the one or more transgenes within one or more of the ICP4 viral gene loci. In some embodiments, the recombinant herpes simplex virus genome comprises the one or more transgenes within the UL41 viral gene locus. In some embodiments, the vector is capable of replicating within a target cell when delivered into said target cell. In some embodiments, the pharmaceutically acceptable carrier is suitable for topical or transdermal administration. In some embodiments, the pharmaceutically acceptable carrier is suitable for subcutaneous or intradermal administration. In some embodiments, the one or more transgenes comprises an miRNA binding site. In some embodiment, the vector comprises a transgene encoding a Collagen alpha-1 (VII) chain polypeptide. In some embodiment, the vector comprises a transgene encoding a Lysyl hydroxylase 3 polypeptide. In some embodiment, the vector comprises a transgene encoding a Keratin type I cytoskeletal 17 polypeptide. In some embodiments, the vector comprises two transgenes, wherein each transgene encodes a Collagen alpha-1 (VII) chain polypeptide. In some embodiments, the Collagen alpha-1 (VII) chain polypeptide has at least 80% sequence identity to the sequence of SEQ ID NO: 2. In some embodiments, the collagen alpha-1 (VII) chain polypeptide is a fragment, wherein the fragment has at least 100 consecutive amino acids of SEQ ID NO: 2. In some embodiments, the Collagen alpha-1 (VII) chain polypeptide enhances, increases, augments, and/or supplements anchoring fibril formation of a subject when the polypeptide is expressed in one or more target cells of the subject. In some embodiments, the Collagen alpha-1 (VII) chain polypeptide enhances, increases, augments, and/or supplements epithelial basement membrane organization and/or epithelial basement adherence of a subject when the polypeptide is expressed in one or more target cells of the subject. In some embodiments, the Lysyl hydroxylase 3 polypeptide has at least 80% sequence identity to the sequence of SEQ ID NO: 4. In some embodiments, the Lysyl hydroxylase 3 polypeptide is a fragment, wherein the fragment has at least 100 consecutive amino acids of SEQ ID NO: 4. In some embodiments, the Lysyl hydroxylase 3 polypeptide enhances, increases, augments, and/or supplements the formation of hydroxylysine residues on one or more collagen polypeptides of a subject when the Lysyl hydroxylase 3 polypeptide is expressed in one or more target cells of the subject. In some embodiments, the Lysyl hydroxylase 3 polypeptide enhances, increases, augments, and/or supplements anchoring fibril formation, epithelial basement membrane organization, and/or epithelial basement adherence of a subject when the polypeptide is expressed in one or more target cells of the subject. In some embodiments, the Keratin type I cytoskeletal 17 polypeptide has at least 80% sequence identity to the sequence of SEQ ID NO: 30. In some embodiments, the Keratin type I cytoskeletal 17 polypeptide is a fragment, wherein the fragment has at least 100 consecutive amino acids of SEQ ID NO: 30. In some embodiments, the Keratin type I cytoskeletal 17 polypeptide enhances, increases, augments, and/or supplements wound healing in a subject. In some embodiments, the vector comprises at least a first transgene and a second transgene.

In some embodiments, the first transgene and the second transgene each encode a Collagen alpha-1 (VII) chain polypeptide. In some embodiments, the first transgene encodes a Collagen alpha-1 (VII) chain polypeptide and the second transgene encodes a Lysyl hydroxylase 3 polypeptide. In some embodiments, the first transgene encodes a Collagen alpha-1 (VII) chain polypeptide and the second transgene encodes a Keratin type I cytoskeletal 17 polypeptide. In some embodiments, the first transgene encodes a Lysyl hydroxylase 3 polypeptide and the second transgene encodes a Keratin type I cytoskeletal 17 polypeptide. In some embodiments, the vector comprises at least a first transgene, a second transgene, and a third transgene. In some embodiments, the first transgene encodes a Collagen alpha-1 (VII) chain polypeptide, the second transgene encodes a Lysyl hydroxylase 3 polypeptide, and the third transgene encodes a Keratin type I cytoskeletal 17 polypeptide.

Other aspects of the present disclosure relate to a method of providing prophylactic, palliative, or therapeutic relief of a wound, disorder, or disease of the skin in a subject, the method comprising administering to the subject a pharmaceutical composition comprising a vector, wherein the vector is a recombinant herpes simplex virus genome, and wherein the pharmaceutical composition is capable of enhancing, increasing, augmenting, and/or supplementing the levels of a Collagen alpha-1 (VII) chain polypeptide and/or a Lysyl hydroxylase 3 polypeptide and/or a Keratin type I cytoskeletal 17 polypeptide in one or more cells of the subject. In some embodiments, the pharmaceutical composition comprises a virus comprising the vector, wherein the vector comprises one or more transgenes encoding a Collagen alpha-1 (VII) chain polypeptide, a Lysyl hydroxylase 3 polypeptide, a Keratin type I cytoskeletal 17 polypeptide, or a chimeric polypeptide thereof, and a pharmaceutically acceptable carrier. In some embodiments, the virus is an adenovirus, adeno-associated virus, retrovirus, lentivirus, sendai virus, herpes simplex virus, vaccinia virus, or any hybrid virus thereof. In some embodiments, the virus is replication-defective. In some embodiments, the virus is a herpes simplex virus (HSV). In some embodiments, the herpes simplex virus is a herpes simplex type 1 virus, a herpes simplex type 2 virus, or any derivatives thereof. In some embodiments, the recombinant herpes simplex virus genome is a recombinant HSV-1 genome, a recombinant HSV-2 genome, or any derivatives thereof. In some embodiments, the recombinant herpes simplex virus genome comprises an inactivating mutation in an immediate early herpes simplex virus gene. In some embodiments, the herpes simplex virus gene is ICP0, ICP4, ICP22, ICP27, ICP47, tk, UL41, or UL55. In some embodiments, the recombinant herpes simplex virus genome comprises an inactivating mutation in the ICP4, ICP27, and UL55 genes. In some embodiments, the recombinant herpes simplex virus genome comprises an inactivating mutation in the ICP4, ICP22, ICP27, ICP47, and UL55 genes. In some embodiments, the inactivating mutation in the ICP4, ICP27, and UL55 genes is a deletion of the coding sequence of the ICP4, ICP27, and UL55 genes. In some embodiments, the inactivating mutation in the ICP22 and ICP47 genes is a deletion in the promoter region of the ICP22 and ICP47 genes. In some embodiments, the recombinant herpes simplex virus genome comprises an inactivating mutation in the ICP4 and ICP22 genes. In some embodiment, the recombinant herpes simplex virus genome comprises an inactivating mutation in the ICP0 and ICP4 genes. In some embodiments, the recombinant herpes simplex virus genome comprises an inactivating mutation in the ICP0, ICP4, and ICP22 genes. In some embodiments, the recombinant herpes simplex virus genome comprises an inactivating mutation in the ICP0, ICP4, ICP22, and ICP27 genes. In some embodiments, the recombinant herpes simplex virus genome comprises an inactivating mutation in the ICP0, ICP4, ICP22, ICP27, and UL55 genes. In some embodiments, the inactivating mutation is a deletion of the coding sequence of the genes. In some embodiments, the recombinant herpes simplex virus genome further comprises an inactivating mutation in the ICP47 gene, an inactivating mutation in the UL41 gene, or an inactivation mutation in the ICP47 and UL41 genes. In some embodiments, the recombinant herpes simplex virus genome comprises the one or more transgenes within one or more viral gene loci. In some embodiments, the recombinant herpes simplex virus genome comprises the one or more transgenes within one or more of the ICP4 viral gene loci. In some embodiments, the recombinant herpes simplex virus genome comprises the one or more transgenes within the UL41 viral gene locus. In some embodiments, the vector is capable of replicating within a target cell when delivered into said target cell. In some embodiments, the pharmaceutically acceptable carrier is suitable for topical or transdermal administration. In some embodiments, the pharmaceutically acceptable carrier is suitable for subcutaneous or intradermal administration. In some embodiments, the one or more transgenes comprises an miRNA binding site. In some embodiments, the vector comprises a transgene encoding a Collagen alpha-1 (VII) chain polypeptide. In some embodiments, the vector comprises a transgene encoding a Lysyl hydroxylase 3 polypeptide. In some embodiments, the vector comprises a transgene encoding a Keratin type I cytoskeletal 17 polypeptide. In some embodiments, the Collagen alpha-1 (VII) chain polypeptide has at least 80% sequence identity to the sequence of SEQ ID NO: 2. In some embodiments, the collagen alpha-1 (VII) chain polypeptide is a fragment, wherein the fragment has at least 100 consecutive amino acids of SEQ ID NO: 2. In some embodiments, the Collagen alpha-1 (VII) chain polypeptide enhances, increases, augments, and/or supplements anchoring fibril formation of a subject when the polypeptide is expressed in one or more target cells of the subject. In some embodiments, the Collagen alpha-1 (VII) chain polypeptide enhances, increases, augments, and/or supplements epithelial basement membrane organization and/or epithelial basement adherence of a subject when the polypeptide is expressed in one or more target cells of the subject. In some embodiments, the Lysyl hydroxylase 3 polypeptide has at least 80% sequence identity to the sequence of SEQ ID NO: 4. In some embodiments, the Lysyl hydroxylase 3 polypeptide is a fragment, wherein the fragment has at least 100 consecutive amino acids of SEQ ID NO: 4. In some embodiments, the Lysyl hydroxylase 3 polypeptide enhances, increases, augments, and/or supplements the formation of hydroxylysine residues on one or more collagen polypeptides of a subject when the Lysyl hydroxylase 3 polypeptide is expressed in one or more target cells of the subject. In some embodiments, the Lysyl hydroxylase 3 polypeptide enhances, increases, augments, and/or supplements anchoring fibril formation, epithelial basement membrane organization, and/or epithelial basement adherence of a subject when the polypeptide is expressed in one or more target cells of the subject. In some embodiments, the Keratin type I cytoskeletal 17 polypeptide has at least 80% sequence identity to the sequence of SEQ ID NO: 30. In some embodiments, the Keratin type I cytoskeletal 17 polypeptide is a fragment, wherein the fragment has at least 100 consecutive amino acids of SEQ ID NO: 30. In some embodiments, the Keratin type I cytoskeletal 17 polypeptide enhances, increases, augments, and/or supplements wound healing in a subject. In some embodiments, the vector comprises at least a first transgene and a second transgene. In some embodiments, the first transgene and the second transgene each encode a Collagen alpha-1 (VII) chain polypeptide. In some embodiments, the first transgene encodes a Collagen alpha-1 (VII) chain polypeptide and the second transgene encodes a Lysyl hydroxylase 3 polypeptide. In some embodiments, the first transgene encodes a Collagen alpha-1 (VII) chain polypeptide and the second transgene encodes a Keratin type I cytoskeletal 17 polypeptide. In some embodiments, the first transgene encodes a Lysyl hydroxylase 3 polypeptide and the second transgene encodes a Keratin type I cytoskeletal 17 polypeptide. In some embodiments, the vector comprises at least a first transgene, a second transgene, and a third transgene. In some embodiments, the first transgene encodes a Collagen alpha-1 (VII) chain polypeptide, the second transgene encodes a Lysyl hydroxylase 3 polypeptide, and the third transgene encodes a Keratin type I cytoskeletal 17 polypeptide. In some embodiments, the pharmaceutical composition is administered topically or transdermally to the subject. In some embodiments, the pharmaceutical composition is administered subcutaneously or intradermally to the subject. In some embodiments, the pharmaceutical composition is administered one, two three, four, five or more times per day. In some embodiments, the pharmaceutical composition is administered to one or more affected and/or unaffected areas of the subject. In some embodiments, the disease or disorder of the skin is one or more of epidermolysis bullosa, skin cancer, psoriasis, lichen planus, lupus, rosacea, eczema, cutaneous candidiasis, cellulitis, impetigo, decubitus ulcers, erysipelas, ichthyosis vulgaris, dermatomyositis, acrodermatitis, stasis dermatitis, nethertons syndrome, epidermolysis bullosa simplex (LAMB3 gene), autosomal recessive congenital ichthyosis, xeroderma pigmentosa, and pemphigoid.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 1A-F show schematics of wild-type and modified herpes simplex virus genomes. FIG. 1A shows a wild-type herpes simplex virus genome. FIG. 1B shows a modified herpes simplex virus genome comprising a transgene encoding a Collagen alpha-1 (VII) chain polypeptide. FIG. 1C shows a modified herpes simplex virus genome comprising two transgenes, one encoding a Collagen alpha-1 (VII) chain polypeptide and the other encoding a Lysyl hydroxylase 3 polypeptide, with the transgenes encoded on the same strand of DNA. FIG. 1D shows a modified herpes simplex virus genome comprising two transgenes, one encoding a Collagen alpha-1 (VII) chain polypeptide and the other encoding a Lysyl hydroxylase 3 polypeptide, with the transgenes encoded on opposite strands of DNA in an antisense orientation.

FIG. 1E shows a modified herpes simplex virus genome comprising a transgene that is polycistronic, encoding a Collagen alpha-1 (VII) chain polypeptide and a Lysyl hydroxylase 3 polypeptide separated by an internal ribosomal entry site (IRES). FIG. 1F shows a modified herpes simplex virus genome comprising a transgene encoding a chimeric polypeptide comprising a Collagen alpha-1 (VII) chain polypeptide, a linker polypeptide, and a Lysyl hydroxylase 3 polypeptide.

FIGS. 2A-G show additional schematics of wild-type and modified herpes simplex virus genomes. FIG. 2A shows a wild-type herpes simplex virus genome. FIG. 2B shows a modified herpes simplex virus genome comprising deletions of the coding sequences of ICP4 (both copies), ICP27, and UL55 and deletions of the promoter sequences of ICP22 and ICP47, with two transgenes encoding Collagen alpha-1 (VII) chain polypeptides integrated at the ICP4 loci. FIG. 2C shows a modified herpes simplex virus genome comprising deletions of the coding sequences of ICP4 (both copies) and ICP22, with two transgenes encoding Collagen alpha-1 (VII) chain polypeptides integrated at the ICP4 loci. FIG. 2D shows a modified herpes simplex virus genome comprising deletions of the coding sequences of ICP0 and ICP4 (both copies), with two transgenes encoding Collagen alpha-1 (VII) chain polypeptides integrated at the ICP4 loci. FIG. 2E shows a modified herpes simplex virus genome comprising deletions of the coding sequences of ICP0, ICP4 (both copies), and ICP22, with two transgenes encoding Collagen alpha-1 (VII) chain polypeptides integrated at the ICP4 loci. FIG. 2F shows a modified herpes simplex virus genome comprising deletions of the coding sequences of ICP0, ICP4 (both copies), ICP22, and ICP27, with two transgenes encoding Collagen alpha-1 (VII) chain polypeptides integrated at the ICP4 loci. FIG. 2G shows a modified herpes simplex virus genome comprising deletions of the coding sequences of ICP0, ICP4 (both copies), ICP22, ICP27, and UL55, with two transgenes encoding Collagen alpha-1 (VII) chain polypeptides integrated at the ICP4 loci.

FIG. 3 shows a schematic of "KB103", a replication-defective herpes simplex type-1 virus (HSV-1) carrying a human collagen 7 (COL7A1) expression cassette.

FIG. 5A shows human Col7 protein expression in uninfected normal and RDEB fibroblasts, as well as fibroblasts infected with KB103 at the indicated multiplicity of infection (MOI). FIG. 5B shows human Col7 protein expression in uninfected normal and RDEB keratinocytes, as well as keratinocytes infected with KB103 at the indicated multiplicity of infection (MOI). Human GAPDH protein expression is shown as a loading control.

FIG. 6 shows human COL7A1 protein expression in uninfected (control) or KB103 infected (C7, MOI 3) RDEB human dermal fibroblasts (EB HDF), normal human dermal keratinocytes (Normal HDK), and RDEB human dermal keratinocytes (RDEB HDK), as assessed by immunofluorescence.

FIG. 7 shows human Col7 and LH3 protein expression in uninfected normal and RDEB human dermal keratinocytes, as well as keratinocytes infected with KB103 at the indicated MOI. Human GAPDH protein expression is shown as a loading control.

FIG. 11 shows the quantification of viral genome copy number and human Col7 transcript levels in tissue isolated from KB103-infected mice.

FIG. 12 shows human Col7 protein expression in dermal tissue from KB103-infected mice by immunofluorescence, including the initiation of human Col7 deposition at the basement membrane zone (BMZ).

DETAILED DESCRIPTION

Figure 2C:
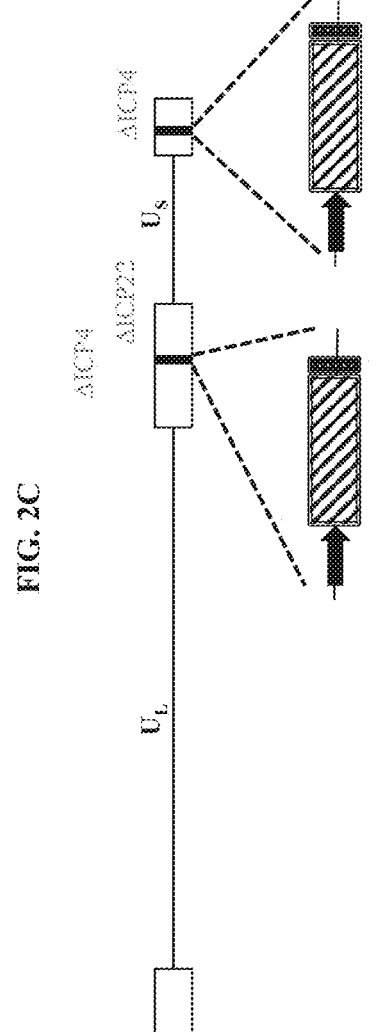
Figure 2D:
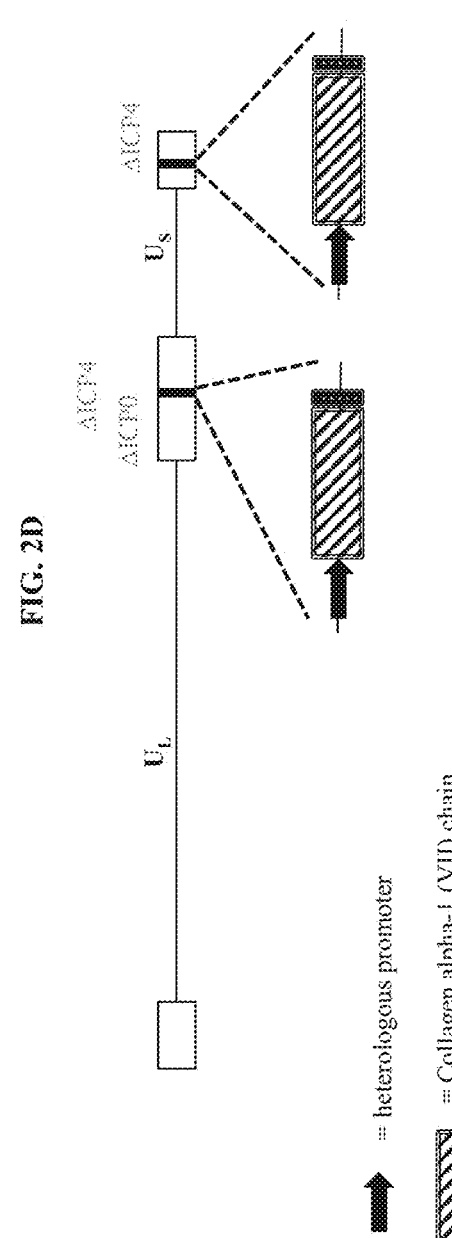

The present disclosure relates, in part, to pharmaceutical compositions comprising one or more polynucleotides encoding a Collagen alpha-1 (VII) chain polypeptide, a Lysyl hydroxylase 3 polypeptide, a Keratin type I cytoskeletal 17 polypeptide, and/or a chimeric polypeptide thereof. In some embodiments, the pharmaceutical composition comprises a vector, wherein the vector comprises one or more transgenes encoding a Collagen alpha-1 (VII) chain polypeptide, a Lysyl hydroxylase 3 polypeptide, a Keratin type I cytoskeletal 17 polypeptide, and/or a chimeric polypeptide thereof. In some embodiments, the vector comprises one or more transgenes suitable for enhancing, increasing, augmenting, and/or supplementing the levels of Collagen alpha-1 (VII) chain polypeptide and/or Lysyl hydroxylase 3 polypeptide and/or Keratin type I cytoskeletal 17 polypeptide in one or more cells of a subject. The present disclosure also relates, in part, to methods of providing prophylactic, palliative, or therapeutic relief of a wound, disorder, or disease of the skin (e.g. dystrophic epidermolysis bullosa) in a subject by administering (e.g., topically or transdermally administering) a pharmaceutical composition described herein.

The following description sets forth exemplary methods, parameters, and the like. It should be recognized, however, that such description is not intended as a limitation on the scope of the present disclosure but is instead provided as a description of exemplary embodiments.
General Techniques The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Gene Transfer Vectors for Mammalian Cells* (J. M. Miller and M. P. Calos, eds., 1987); *PCR: The Polymerase Chain*

*Reaction*, (Mullis et al., eds., 1994); *Short Protocols in Molecular Biology* (Wiley and Sons, 1999).

Definitions

Before describing the invention in detail, it is to be understood that this invention is not limited to particular compositions or biological systems, which can, of course, vary. It is also to be understood that the terminology used herein is for the purpose of describing particular embodiments only, and is not intended to be limiting.

As used herein, the singular forms "a", "an" and "the" include plural referents unless the content clearly dictates otherwise. Thus, for example, reference to "a molecule" optionally includes a combination of two or more such molecules, and the like.

As used herein, the term "about" refers to the usual error range for the respective value readily known to the skilled person in this technical field. Reference to "about" a value or parameter herein includes (and describes) embodiments that are directed to that value or parameter per se.

As used herein, the terms "polynucleotide", "nucleic acid sequence", "nucleic acid", and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing non-nucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog, and inter-nucleotide modifications.

As used herein, a nucleic acid is "operatively linked" or "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous.

As used herein, the term "vector" refers to discrete elements that are used to introduce heterologous nucleic acids into cells for either expression or replication thereof. An expression vector includes vectors capable of expressing nucleic acids that are operatively linked with regulatory sequences, such as promoter regions, that are capable of effecting expression of such nucleic acids. Thus, an expression vector may refer to a DNA or RNA construct, such as a plasmid, a phage, recombinant virus or other vector that, upon introduction into an appropriate host cell, results in expression of the nucleic acids. Appropriate expression vectors are well known to those of skill in the art and include those that are replicable in eukaryotic cells and those that remain episomal or those which integrate into the host cell genome.

As used herein, an "open reading frame" or "ORF" refers to a continuous stretch of nucleic acids, either DNA or RNA, that encode a protein or polypeptide. Typically, the nucleic acids comprise a translation start signal or initiation codon, such as ATG or AUG, and a termination codon.

As used herein, an "internal ribosome entry site" or "IRES" refers to a nucleotide sequence that allows for translation initiation in the middle, e.g. after the first start codon, of an mRNA sequence.

As used herein, an "untranslated region" or "UTR" refers to unstranslated nucleic acids at the 5' and/or 3' ends of an open reading frame. The inclusion of one or more UTRs in a polynucleotide may affect post-transcriptional regulation, mRNA stability, and/or translation of the polynucleotide.

As used herein, the term "transgene" refers to a polynucleotide that is capable of being transcribed into RNA and translated and/or expressed under appropriate conditions, after being introduced into a cell. In some aspects, it confers a desired property to a cell into which it was introduced, or otherwise leads to a desired therapeutic or diagnostic outcome.

As used herein, the terms "polypeptide," "protein," and "peptide" are used interchangeably and may refer to a polymer of two or more amino acids.

As used herein, a "subject", "host", or an "individual" refers to any animal classified as a mammal, including humans, domestic and farm animals, and zoo, sports, or pet animals, such as dogs, horses, cats, cows, as well as animals used in research, such as mice and rats, etc. In some embodiments, the mammal is human.

As used herein, "topical administration" or "topically administering" refers to the delivery of a composition to a subject by contacting, directly or otherwise, a formulation comprising the composition to all or a portion of the skin of a subject. The term encompasses several routes of administration including, but not limited to, topical and transdermal. Topical administration is used as a means to deliver a composition to the epidermis or dermis of a subject, or to specific strata thereof.

As used herein, an "effective amount" is at least the minimum amount required to effect a measurable improvement or prevention of one or more symptoms of a particular disorder. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, delaying the progression of the disease, and/or prolonging survival. An effective amount can be administered in one or more administrations.

Pharmaceutical Compositions

Polynucleotides

In one aspect, provided herein is a pharmaceutical composition comprising one or more polynucleotides encoding a Collagen alpha-1 (VII) chain (Col7) polypeptide, a Lysyl hydroxylase 3 (LH3) polypeptide, a Keratin type I cytoskeletal 17 (KRT17) polypeptide, and/or a chimeric polypeptide thereof. In some embodiments, the pharmaceutical composition comprises one or more polynucleotides encoding a Collagen alpha-1 (VII) chain polypeptide. In some embodiments, the pharmaceutical composition comprises one or more polynucleotides encoding a Lysyl hydroxylase 3 polypeptide. In some embodiments, the pharmaceutical composition comprises one or more polynucleotides encoding a Keratin type I cytoskeletal 17 polypeptide. In some embodiments, the pharmaceutical composition comprises one or more polynucleotides encoding a chimeric polypeptide. In some embodiments, the pharmaceutical composition comprises one or more polynucleotides encoding a Collagen alpha-1 (VII) chain polypeptide and a Lysyl hydroxylase 3 polypeptide. In some embodiments, the pharmaceutical composition comprises one or more polynucleotides encoding a Collagen alpha-1 (VII) chain polypeptide and a Keratin type I cytoskeletal 17 polypeptide. In some embodiments, the pharmaceutical composition comprises one or more polynucleotides encoding a Lysyl hydroxylase 3 polypeptide and a Keratin type I cytoskeletal 17 polypeptide. In some embodiments, the pharmaceutical composition comprises one or more polynucleotides encoding a Collagen alpha-1 (VII) chain polypeptide, a Lysyl hydroxylase 3 polypeptide, and a Keratin type I cytoskeletal 17 polypeptide.

In some embodiments, the pharmaceutical composition comprises a vector, wherein the vector encodes one or more transgenes comprising a polynucleotide described herein. In some embodiments, the pharmaceutical composition comprises a vector, wherein the vector comprises one or more transgenes encoding a Collagen alpha-1 (VII) chain polypeptide, a Lysyl hydroxylase 3 polypeptide, a Keratin type I cytoskeletal 17 polypeptide, and/or a chimeric polypeptide thereof. In some embodiments, the vector comprises one or more transgenes encoding a Collagen alpha-1 (VII) chain polypeptide. In some embodiments, the vector comprises one or more transgenes encoding a Lysyl hydroxylase 3 polypeptide. In some embodiments, one or more transgenes encoding a Keratin type I cytoskeletal 17 polypeptide. In some embodiments, the vector comprises one or more transgenes encoding a chimeric polypeptide. In some embodiments, the vector comprises one or more transgenes encoding a Collagen alpha-1 (VII) chain polypeptide and one or more transgenes encoding a Lysyl hydroxylase 3 polypeptide. In some embodiments, the vector comprises one or more transgenes encoding a Collagen alpha-1 (VII) chain polypeptide and one or more transgenes encoding a Keratin type I cytoskeletal 17 polypeptide. In some embodiments, the vector comprises one or more transgenes encoding a Lysyl hydroxylase 3 polypeptide and one or more transgenes encoding a Keratin type I cytoskeletal 17 polypeptide. In some embodiments, the vector comprises one or more transgenes encoding a Collagen alpha-1 (VII) chain polypeptide, one or more transgenes encoding a Lysyl hydroxylase 3 polypeptide, and one or more transgenes encoding a Keratin type I cytoskeletal 17 polypeptide.

In some embodiments, the pharmaceutical composition comprises a synthetic RNA, wherein the synthetic RNA encodes one or more transgenes comprising a polynucleotide described herein. In some embodiments, the pharmaceutical composition comprises a synthetic RNA, wherein the synthetic RNA comprises one or more transgenes encoding a Collagen alpha-1 (VII) chain polypeptide, a Lysyl hydroxylase 3 polypeptide, a Keratin type I cytoskeletal 17 polypeptide, and/or a chimeric polypeptide thereof. In some embodiments, the synthetic RNA comprises one or more transgenes encoding a Collagen alpha-1 (VII) chain polypeptide. In some embodiments, the synthetic RNA comprises one or more transgenes encoding a Lysyl hydroxylase 3 polypeptide. In some embodiments, the synthetic RNA comprises one or more transgenes encoding a Keratin type I cytoskeletal 17 polypeptide. In some embodiments, the synthetic RNA comprises one or more transgenes encoding a chimeric polypeptide. In some embodiments, the synthetic RNA comprises one or more transgenes encoding a Collagen alpha-1 (VII) chain polypeptide and one or more transgenes encoding a Lysyl hydroxylase 3 polypeptide. In some embodiments, the synthetic RNA comprises one or more transgenes encoding a Collagen alpha-1 (VII) chain polypeptide and one or more transgenes encoding a Keratin type I cytoskeletal 17 polypeptide. In some embodiments, the synthetic RNA comprises one or more transgenes encoding a Lysyl hydroxylase 3 polypeptide and one or more transgenes encoding a Keratin type I cytoskeletal 17 polypeptide. In some embodiments, the synthetic RNA comprises one or more transgenes encoding a Collagen alpha-1 (VII) chain polypeptide, one or more transgenes encoding a Lysyl hydroxylase 3 polypeptide, and one or more transgenes encoding a Keratin type I cytoskeletal 17 polypeptide.

Collagen Alpha-1 (VII) Chain

In some aspects, a polynucleotide of the present disclosure encodes a Collagen alpha-1 (VII) chain polypeptide. An example of a polynucleotide that encodes a Collagen alpha-1 (VII) chain polypeptide is SEQ ID NO: 1. Polynucleotides of the present disclosure also include polynucleotides having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 1.

In some embodiments, a polynucleotide encoding a Collagen alpha-1 (VII) chain polypeptide is a polynucleotide that encodes an N-terminal truncation, a C-terminal truncation, or a fragment of a Collagen alpha-1 (VII) chain polypeptide. Polynucleotides encoding an N-terminal truncation, a C-terminal truncation, or a fragment of a Collagen alpha-1 (VII) chain polypeptide include polynucleotides that have at least 25, at least 50, at least 75, at least 100, at least 125, at least 150, at least 175, at least 200, at least 250, at least 300, or at least 350, at least 500, at least 1000, at least 2500, at least 5000, at least 7500, but fewer than 8835, consecutive nucleotides of SEQ ID NO: 1.

In some embodiments, a polynucleotide encoding a Collagen alpha-1 (VII) chain polypeptide is a polynucleotide that encodes a polypeptide having an amino acid sequence of SEQ ID NO: 2. In some embodiments, a polynucleotide encoding a Collagen alpha-1 (VII) chain polypeptide is a polynucleotide that encodes a polypeptide having an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 2. In some embodiments, the present disclosure relates to polynucleotides that encode polypeptides that are homologs of the *H. sapiens* Collagen alpha-1 (VII) chain polypeptide. Methods of identifying polypeptides that are homologs of a polypeptide of interest are well known to one of skill in the art.

In some embodiments, a polynucleotide encoding a Collagen alpha-1 (VII) chain polypeptide is a polynucleotide that encodes N-terminal truncations, C-terminal truncations, or fragments of the amino acid sequence of SEQ ID NO: 2. N-terminal truncations, C-terminal truncations, or fragments may comprise at least 10, at least 12, at least 14, at least 16, at least 18, at least 20, at least 30, at least 40, at least 50, at least 75, at least 100, at least 250, at least 500, at least 750, at least 1000, at least 1500, at least 2000, or at least 2500, but fewer than 2944, consecutive amino acids of SEQ ID NO: 2.

In some embodiments, the polynucleotide encoding a Collagen alpha-1 (VII) chain polypeptide expresses the Collagen alpha-1 (VII) chain polypeptide when the polynucleotide is delivered into one or more target cells of a subject. In some embodiments, expression of the Collagen alpha-1 (VII) chain polypeptide enhances, increases, augments, and/or supplements the levels of a Collagen alpha-1 chain polypeptide in one or more target cells. In some embodiments, expression of the Collagen alpha-1 (VII) chain polypeptide enhances, increases, augments, and/or supplements the function of a Collagen alpha-1 chain polypeptide in one or more target cells. In some embodiments, expression of the Collagen alpha-1 (VII) chain polypeptide enhances, increases, augments, and/or supplements the activity of a Collagen alpha-1 chain polypeptide in one or more target cells. In some embodiments, expression of the Collagen alpha-1 (VII) chain polypeptide enhances, increases, augments, and/or supplements anchoring fibril formation of the subject. In some embodiments, expression of the Collagen alpha-1 (VII) chain polypeptide enhances, increases, augments, and/or supplements epithelial basement membrane organization and/or epithelial basement adherence of the subject. In some embodiments, expression of the Collagen alpha-1 (VII) chain polypeptide enhances, increases, augments, and/or supplements dermoepidermal junction integrity of the subject.

Lysyl Hydroxylase 3

In some aspects, a polynucleotide of the present disclosure encodes a Lysyl hydroxylase 3 polypeptide. An example of a polynucleotide that encodes a Lysyl hydroxylase 3 polypeptide is SEQ ID NO: 3. Polynucleotides of the present disclosure also include polynucleotides having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 3.

In some embodiments, a polynucleotide encoding a Lysyl hydroxylase 3 polypeptide is a polynucleotide that encodes an N-terminal truncation, a C-terminal truncation, or a fragment of a Lysyl hydroxylase 3 polypeptide. Polynucleotides encoding an N-terminal truncation, a C-terminal truncation, or a fragment of a Lysyl hydroxylase 3 polypeptide include polynucleotides that have at least 25, at least 50, at least 75, at least 100, at least 125, at least 150, at least 175, at least 200, at least 250, at least 300, at least 350, at least 500, at least 750, at least 1000, at least 1500, or at least 2000, but fewer than 2217, consecutive nucleotides of SEQ ID NO: 3.

In some embodiments, a polynucleotide encoding a Lysyl hydroxylase 3 polypeptide is a polynucleotide that encodes a polypeptide having an amino acid sequence of SEQ ID NO: 4. In some embodiments, a polynucleotide encoding a Lysyl hydroxylase 3 polypeptide is a polynucleotide that encodes a polypeptide having an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 4. In some embodiments, the present disclosure relates to polynucleotides encoding polypeptides that are homologs of the *H. sapiens* Lysyl hydroxylase 3 polypeptide. Methods of identifying polypeptides that are homologs of a polypeptide of interest are well known to one of skill in the art.

In some embodiments, a polynucleotide encoding a Lysyl hydroxylase 3 polypeptide is a polynucleotide that encodes N-terminal truncations, C-terminal truncations, or fragments of the amino acid sequence of SEQ ID NO: 4. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, or at least 700, but fewer than 738, consecutive amino acids of SEQ ID NO: 4.

In some embodiments, the polynucleotide encoding a Lysyl hydroxylase 3 polypeptide expresses the Lysyl hydroxylase 3 polypeptide when the polynucleotide is delivered into one or more target cells of a subject. In some embodiments, expression of the Lysyl hydroxylase 3 polypeptide enhances, increases, augments, and/or supplements the levels of a Lysyl hydroxylase 3 polypeptide in one or more target cells. In some embodiments, expression of the Lysyl hydroxylase 3 polypeptide enhances, increases, augments, and/or supplements the function of a Lysyl hydroxylase 3 polypeptide in one or more target cells. In some embodiments, expression of the Lysyl hydroxylase 3 polypeptide enhances, increases, augments, and/or supplements the activity of a Lysyl hydroxylase 3 polypeptide in one or more target cells. In some embodiments, expression of the Lysyl hydroxylase 3 polypeptide enhances, increases, augments, and/or supplements the formation of hydroxylysine residues on one or more collagen polypeptides of the subject. In some embodiments, expression of the Lysyl hydroxylase 3 polypeptide enhances, increases, augments, and/or supplements anchoring fibril formation of the subject. In some embodiments, expression of the Lysyl hydroxylase 3 polypeptide enhances, increases, augments, and/or supplements epithelial basement membrane organization and/or epithelial basement adherence of the subject. In some embodiments, expression of the Lysyl hydroxylase 3 polypeptide enhances, increases, augments, and/or supplements dermoepidermal junction integrity of the subject.

In some embodiments, the polynucleotide encoding a Collagen alpha-1 (VII) chain polypeptide and the polynucleotide encoding a Lysyl hydroxylase 3 polypeptide are delivered to the same cell of a subject. In some embodiments, the polynucleotide encoding a Collagen alpha-1 chain (VII) polypeptide and the polynucleotide encoding a Lysyl hydroxylase 3 polypeptide express the Collagen alpha-1 (VII) chain polypeptide and the Lysyl hydroxylase 3 polypeptide when the polynucleotides are delivered into the same cell of a subject. In some embodiments, the polynucleotide encoding a Collagen alpha-1 (VII) chain polypeptide and the polynucleotide encoding a Lysyl hydroxylase 3 polypeptide express the Collagen alpha-1 (VII) chain polypeptide and Lysyl hydroxylase 3 polypeptide at equimolar ratios.

Keratin Type I Cytoskeletal 17

In some aspects, a polynucleotide of the present disclosure encodes a Keratin type I cytoskeletal 17 polypeptide. An example of a polynucleotide that encodes a Keratin type I cytoskeletal 17 polypeptide is SEQ ID NO: 29. Polynucleotides of the present disclosure also include polynucleotides having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 29.

In some embodiments, a polynucleotide encoding a Keratin type I cytoskeletal 17 polypeptide is a polynucleotide that encodes an N-terminal truncation, a C-terminal truncation, or a fragment of a Keratin type I cytoskeletal 17 polypeptide. Polynucleotides encoding an N-terminal truncation, a C-terminal truncation, or a fragment of a Collagen alpha-1 (VII) chain polypeptide include polynucleotides that have at least 25, at least 50, at least 75, at least 100, at least 125, at least 150, at least 175, at least 200, at least 250, at least 300, or at least 350, at least 500, at least 1000, at least 1250, but fewer than 1299, consecutive nucleotides of SEQ ID NO: 29.

In some embodiments, a polynucleotide encoding a Keratin type I cytoskeletal 17 polypeptide is a polynucleotide that encodes a polypeptide having an amino acid sequence of SEQ ID NO: 30. In some embodiments, a polynucleotide encoding a Keratin type I cytoskeletal 17 polypeptide is a polynucleotide that encodes a polypeptide having an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 30. In some embodiments, the present disclosure relates to polynucleotides that encode polypeptides that are homologs of the *H. sapiens* Keratin type I cytoskeletal 17 polypeptide. Methods of identifying polypeptides that are homologs of a polypeptide of interest are well known to one of skill in the art.

In some embodiments, a polynucleotide encoding a Keratin type I cytoskeletal 17 polypeptide is a polynucleotide that encodes N-terminal truncations, C-terminal truncations, or fragments of the amino acid sequence of SEQ ID NO: 30. N-terminal truncations, C-terminal truncations, or fragments may comprise at least 10, at least 12, at least 14, at least 16, at least 18, at least 20, at least 30, at least 40, at least 50, at least 75, at least 100, at least 150, at least 200, at least 250, at least 300, at least 350, at least 400, at least 425, but fewer than 432, consecutive amino acids of SEQ ID NO: 30.

In some embodiments, the polynucleotide encoding a Keratin type I cytoskeletal 17 polypeptide expresses the Keratin type I cytoskeletal 17 polypeptide when the polynucleotide is delivered into one or more target cells of a subject. In some embodiments, expression of the Keratin type I cytoskeletal 17 polypeptide enhances, increases, augments, and/or supplements the levels of a Keratin type I cytoskeletal 17 polypeptide in one or more target cells. In some embodiments, expression of the Keratin type I cytoskeletal 17 polypeptide enhances, increases, augments, and/or supplements the function of a Keratin type I cytoskeletal 17 polypeptide in one or more target cells. In some embodiments, expression of the Keratin type I cytoskeletal 17 polypeptide enhances, increases, augments, and/or supplements the activity of a Keratin type I cytoskeletal 17 polypeptide in one or more target cells. In some embodiments, expression of the Keratin type I cytoskeletal 17 polypeptide enhances, increases, augments, and/or supplements wound healing in the subject.

Chimeric Polypeptide Comprising Linker

In some embodiments, a polynucleotide of the present disclosure encodes a chimeric polypeptide comprising a Collagen alpha-1 (VII) chain polypeptide and a Lysyl hydroxylase 3 polypeptide. In some embodiments, the polynucleotide encoding a chimeric polypeptide further comprises a polynucleotide encoding a linker polypeptide. In some embodiments, the polynucleotide encoding a linker polypeptide is a polynucleotide encoding a cleavable linker polypeptide. Examples of polynucleotides encoding cleavable linker polypeptides may include, but are not limited to, polynucleotides encoding a T2A, P2A, E2A, or F2A linker polypeptide. In some embodiments, the polynucleotide encoding a linker polypeptide is a polynucleotide encoding a T2A linker polypeptide. In some embodiments, the polynucleotide encoding a linker polypeptide is a polynucleotide encoding a P2A linker polypeptide. In some embodiments, the polynucleotide encoding a linker polypeptide is a polynucleotide encoding an E2A linker polypeptide. In some embodiments, the polynucleotide encoding a linker polypeptide is a polynucleotide encoding an F2A linker polypeptide.

In some aspects, a polynucleotide of the present disclosure encodes a linker polypeptide. Examples of polynucleotides that encode linker polypeptides are SEQ ID NO: 5, SEQ ID NO: 7, SEQ ID NO: 9, and SEQ ID NO: 11. Polynucleotides of the present disclosure also include polynucleotides having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 5, SEQ ID NO: 7, SEQ ID NO: 9, or SEQ ID NO: 11.

In some embodiments, a polynucleotide encoding a linker polypeptide is a polynucleotide that encodes an N-terminal truncation, a C-terminal truncation, or a fragment of a linker polypeptide. Polynucleotides encoding an N-terminal truncation, a C-terminal truncation, or a fragment of a linker polypeptide include polynucleotides that have at least 5, at least 10, at least 15, at least 20, at least 25, at least 30, at least 35, at least 40, at least 45, at least 50, at least 55, or at least 60, but fewer than 66, consecutive nucleotides of SEQ ID NO: 5, SEQ ID NO: 7, SEQ ID NO: 9, or SEQ ID NO: 11.

In some embodiments, a polynucleotide encoding a linker polypeptide is a polynucleotide that encodes a polypeptide having an amino acid sequence of SEQ ID NO: 6, SEQ ID NO: 8, SEQ ID NO: 10 or SEQ ID NO: 12. In some embodiments, a polynucleotide encoding a linker polypeptide is a polynucleotide that encodes a polypeptide having an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 6, SEQ ID NO: 8, SEQ ID NO: 10, or SEQ ID NO: 12.

In some embodiments, a polynucleotide encoding a linker polypeptide is a polynucleotide that encodes N-terminal truncations, C-terminal truncations, or fragments of the amino acid sequence of SEQ ID NO: 6, SEQ ID NO: 8, SEQ ID NO: 10, or SEQ ID NO: 12. N-terminal truncations, C-terminal truncations, or fragments may comprise at least 4, at least 6, at least 8, at least 10, at least 12, at least 14, at least 16, at least 18, or at least 20, but fewer than 22, consecutive amino acids of SEQ ID NO: 6, SEQ ID NO: 8, SEQ ID NO: 10, or SEQ ID NO: 12.

In some embodiments, the polynucleotide encoding a linker polypeptide further comprises a polynucleotide encoding one or more furin cleavage sites. In some embodiments, the polynucleotide encoding one or more furin cleavage sites encode an amino acid sequence that is the same or substantially similar to the sequence of the canonical furin cleavage site (Arg-X-(Arg/Lys)-Arg). In some embodiments, the one or more furin cleavage sites are encoded upstream of the linker polypeptide. In some embodiments, the one or more furin cleavage sites are encoded downstream of the linker polypeptide. In some embodiments, the one or more furin cleavage sites are encoded upstream of a T2A linker polypeptide. In some embodiments, the one or more furin cleavage sites are encoded downstream of a T2A linker polypeptide. In some embodiments, the one or more furin cleavage sites are encoded upstream of a P2A linker polypeptide. In some embodiments, the one or more furin cleavage sites are encoded downstream of a P2A linker polypeptide. In some embodiments, the one or more furin cleavage sites are encoded upstream of an E2A linker polypeptide. In some embodiments, the one or more furin cleavage sites are encoded downstream of an E2A linker polypeptide. In some embodiments, the one or more furin cleavage sites are encoded upstream of an F2A linker polypeptide. In some embodiments, the one or more furin cleavage sites are encoded downstream of an F2A linker polypeptide.

In some embodiments, the polynucleotide encoding a chimeric polypeptide encodes a chimeric polypeptide comprising a Collagen alpha-1 (VII) chain polypeptide, a linker polypeptide, and a Lysyl hydroxylase 3 polypeptide. In some embodiments, the polynucleotide encoding a chimeric polypeptide comprises, from 5' to 3', a polynucleotide encoding a Collagen alpha-1 (VII) chain polypeptide, a polynucleotide encoding a linker polypeptide, and a polynucleotide encoding a Lysyl hydroxylase 3 polypeptide. In some embodiments, the polynucleotide encoding a chimeric polypeptide comprises, from 5' to 3', a polynucleotide encoding a Lysyl hydroxylase 3 polypeptide, a polynucleotide encoding a linker polypeptide, and a polynucleotide encoding a Collagen alpha-1 (VII) chain polypeptide.

Examples of polynucleotides encoding chimeric polypeptides comprising a Collagen alpha-1 (VII) chain polypeptide, a linker polypeptide, and a Lysyl hydroxylase 3 polypeptide are SEQ ID NO: 13, SEQ ID NO: 15, SEQ ID NO: 17, SEQ ID NO: 19, SEQ ID NO: 21, SEQ ID NO: 23, SEQ ID NO: 25, and SEQ ID NO: 27. Polynucleotides of the present disclosure also include polynucleotides having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 13, SEQ ID NO: 15, SEQ ID NO: 17, SEQ ID NO: 19, SEQ ID NO: 21, SEQ ID NO: 23, SEQ ID NO: 25, or SEQ ID NO: 27.

In some embodiments, a polynucleotide encoding a chimeric polypeptide is a polynucleotide that encodes an N-terminal truncation, a C-terminal truncation, or a fragment of a chimeric polypeptide. Polynucleotides encoding an N-terminal truncation, a C-terminal truncation, or a fragment of a chimeric polypeptide include polynucleotides that have at least 25, at least 50, at least 75, at least 100, at least 125, at least 150, at least 175, at least 200, at least 250, at least 300, at least 350, at least 400, at least 450, at least 500, at least 550, at least 600, at least 650, at least 700, at least 750, at least 800, at least 850, at least 900, at least 950, at least 1000, at least 2000, at least 3000, at least 4000, at least 5000, at least 6000, at least 7000, at least 8000, at least 9000, or at least 10000, but fewer than 11121, consecutive nucleotides of SEQ ID NO: 13, SEQ ID NO: 15, SEQ ID NO: 17, SEQ ID NO: 19, SEQ ID NO: 21, SEQ ID NO: 23, SEQ ID NO: 25, or SEQ ID NO: 27.

In some embodiments, a polynucleotide encoding a chimeric polypeptide comprising a Collagen alpha-1 (VII) chain polypeptide, a linker polypeptide, and a Lysyl hydroxylase 3 polypeptide is a polynucleotide that encodes a polypeptide having an amino acid sequence of SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28. In some embodiments, a polynucleotide encoding a chimeric polypeptide comprising a Collagen alpha-1 (VII) chain polypeptide, a linker polypeptide, and a Lysyl hydroxylase 3 polypeptide is a polynucleotide that encodes a polypeptide having an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28.

In some embodiments, a polynucleotide encoding a chimeric polypeptide comprising a Collagen alpha-1 (VII) chain polypeptide, a linker polypeptide, and a Lysyl hydroxylase 3 polypeptide is a polynucleotide that encodes N-terminal truncations, C-terminal truncations, or fragments of the amino acid sequence of SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28. N-terminal truncations, C-terminal truncations, or fragments may comprise at least 25, at least 50, at least 75, at least 100, at least 125, at least 150, at least 175, at least 200, at least 250, at least 300, at least 350, at least 400, at least 450, at least 500, at least 550, at least 600, at least 650, at least 700, at least 750, at least 800, at least 850, at least 900, at least 950, at least 1000, at least 1250, at least 1500, at least 1750, at least 2000, at least 2250, at least 2500, at least 2750, at least 3000, at least 3250, or at least 3500, but fewer than 3706, consecutive amino acids of SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28.

In some embodiments, the polynucleotide encoding a chimeric polypeptide expresses the chimeric polypeptide when the polynucleotide is delivered into one or more target cells of a subject. In some embodiments, the chimeric polypeptide is cleaved after being expressed in one or more target cells. In some embodiments, the chimeric polypeptide is cleaved within the linker polypeptide when expressed in one or more target cells. In some embodiments, the chimeric polypeptide is cleaved into two polypeptides, one comprising the Collagen alpha-1 (VII) chain polypeptide and the other comprising the Lysyl hydroxylase 3 polypeptide. In some embodiments, expression of the chimeric polypeptide enhances, increases, augments, and/or supplements the levels of a Collagen alpha-1 chain polypeptide and/or a Lysyl hydroxylase 3 polypeptide in one or more target cells. In some embodiments, expression of the chimeric polypeptide enhances, increases, augments, and/or supplements the function of a Collagen alpha-1 chain polypeptide and/or a Lysyl hydroxylase 3 polypeptide in one or more target cells. In some embodiments, expression of the chimeric polypeptide enhances, increases, augments, and/or supplements the activity of a Collagen alpha-1 chain polypeptide and/or a Lysyl hydroxylase 3 polypeptide in one or more target cells. In some embodiments, expression of the chimeric polypeptide enhances, increases, augments, and/or supplements the formation of hydroxylysine residues on one or more collagen polypeptides of the subject. In some embodiments, expression of the chimeric polypeptide enhances, increases, augments, and/or supplements anchoring fibril formation of the subject. In some embodiments, expression of the chimeric polypeptide enhances, increases, augments, and/or supplements epithelial basement membrane organization and/or epithelial basement adherence of the subject. In some embodiments, expression of the chimeric polypeptide enhances, increases, augments, and/or supplements dermoepidermal junction integrity of the subject.

Polynucleotides of the present disclosure may be codon-optimized. In some embodiments, polynucleotides of the present disclosure are codon-optimized for human cells. In some embodiments, polynucleotides of the present disclosure are codon-optimized for mouse cells. In some embodiments, polynucleotides of the present disclosure are codon-optimized for rat cells. In some embodiments, polynucleotides of the present disclosure are codon-optimized for hamster cells. In some embodiments, polynucleotides of the present disclosure are codon-optimized for canine cells. In some embodiments, polynucleotides of the present disclosure are codon-optimized for yeast cells. In some embodiments, polynucleotides of the present disclosure are codon-optimized for bacterial cells. Polynucleotides of the present disclosure may be DNA polynucleotides, RNA polynucleotides, or a combination of one or more DNA polynucleotides and one or more RNA polynucleotides.

Vectors

In some aspects, the present disclosure relates to vectors, preferably expression vectors, containing one or more polynucleotides described herein. In some embodiments, the vectors are DNA vectors. Generally, vectors suitable to maintain, propagate, or express polynucleotides to produce one or more polypeptides in a subject may be used. Examples of suitable vectors include, but are not limited to, plasmids, cosmids, episomes, transposons, and viral vectors (e.g., adenoviral, vaccinia viral, Sindbis-viral, measles, herpes viral, lentiviral, retroviral, adeno-associated viral vectors, etc.). In some embodiments, the vector is capable of autonomous replication in a host cell. In some embodiments, the vector is incapable of autonomous replication in a host cell. In some embodiments, the vector is capable of integrating into a host DNA. Methods for making vectors containing one or more polynucleotides of interest are well known to one of skill in the art.

In some embodiments, the vector is a herpes simplex virus vector. In some embodiments, the herpes simplex virus vector is a herpes virus amplicon vector. Herpes virus amplicon vectors, including structural features and methods of making the vectors, are generally known in the art (de Silva S. and Bowers W. "Herpes Virus Amplicon Vectors". Viruses 2009, 1, 594-629). In some embodiments, the vector is an HSV-1 amplicon. In some embodiments, the vector is an HSV-1 hybrid amplicon. Examples of HSV-1 hybrid amplicons may include, but are not limited to, HSV/AAV hybrid amplicons, HSV/EBV hybrid amplicons, HSV/EBV/RV hybrid amplicons, and HSV/Sleeping Beauty hybrid amplicons. In some embodiments, the vector is an HSV/AAV hybrid amplicon. In some embodiments, the vector is an HSV/EBV hybrid amplicon. In some embodiments, the vector is an HSV/EBV/RV hybrid amplicon. In some embodiments, the vector is an HSV/Sleeping Beauty hybrid amplicons.

In some embodiments, the herpes simplex virus vector is a recombinant herpes simplex virus genome. In some embodiments, the recombinant herpes simplex virus genome has been engineered to decrease or eliminate expression of one or more toxic herpes simplex virus genes. Methods of engineering recombinant herpes simplex virus genomes are generally described in WO2015/009952. In some embodiments, the recombinant herpes simplex virus genome comprises an inactivating mutation. Examples of inactivating mutations may include, but are not limited to, deletions, insertions, point mutations, and rearrangements. In some embodiments, the recombinant herpes simplex virus genome comprises an inactivating mutation in at least one, at least two, at least three, at least four, at least five, at least six, at least seven, or all eight of the ICP0, ICP4, ICP22, ICP27, ICP47, tk, UL41 and UL55 herpes simplex virus genes. In some embodiments, the recombinant herpes simplex virus genome comprises an inactivating mutation in the ICP0 gene. In some embodiments, the recombinant herpes simplex virus genome comprises an inactivating mutation in the ICP4 (one or both copies) gene. In some embodiments, the recombinant herpes simplex virus genome comprises an inactivating mutation in the ICP22 gene. In some embodiments, the recombinant herpes simplex virus genome comprises an inactivating mutation in the ICP27 gene. In some embodiments, the recombinant herpes simplex virus genome comprises an inactivating mutation in the ICP47 gene. In some embodiments, the recombinant herpes simplex virus genome comprises an inactivating mutation in the UL41 gene. In some embodiments, the recombinant herpes simplex virus genome comprises an inactivating mutation in the UL55 gene. In some embodiments, the recombinant herpes simplex virus genome is a recombinant HSV-1 genome, a recombinant HSV-2 genome, or any derivatives thereof. In some embodiments, the recombinant herpes simplex virus genome is a recombinant HSV-1 genome. In some embodiments, the recombinant herpes simplex virus genome is a recombinant HSV-2 genome.

In some embodiments, the recombinant herpes simplex virus genome comprises an inactivating mutation in the ICP4 (one or both copies), ICP27, and UL55 genes. In some embodiments, the recombinant herpes simplex virus genome comprises an inactivating mutation in the ICP4 (one or both copies), ICP22, ICP27, ICP47, and UL55 genes. In some embodiments, the inactivating mutation in the ICP4 (one or both copies), ICP27, and/or UL55 genes is a deletion of the coding sequence of the ICP4 (one or both copies), ICP27, and/or UL55 genes. In some embodiments, the inactivating mutation in the ICP22 and ICP47 genes is a deletion in the promoter region of the ICP22 and ICP47 genes (e.g., the ICP22 and ICP47 coding sequences are intact but are not transcriptionally active). In some embodiments, the recombinant herpes simplex virus genome comprises a deletion in the coding sequence of the ICP4 (one or both copies), ICP27, and UL55 genes and a deletion in the promoter region of the ICP22 and ICP47 genes. In some embodiments, the recombinant herpes simplex virus genome further comprises an inactivating mutation in the UL41 gene. In some embodiments, the recombinant herpes simplex virus genome is a recombinant HSV-1 genome, a recombinant HSV-2 genome, or any derivatives thereof. In some embodiments, the recombinant herpes simplex virus genome is a recombinant HSV-1 genome. In some embodiments, the recombinant herpes simplex virus genome is a recombinant HSV-2 genome.

In some embodiments, the recombinant herpes simplex virus genome comprises an inactivating mutation in the ICP4 (one or both copies) and ICP22 genes. In some embodiments, the recombinant herpes simplex virus genome comprises an inactivating mutation in the ICP0 and ICP4 (one or both copies) genes. In some embodiments, the recombinant herpes simplex virus genome comprises an inactivating mutation in the ICP0, ICP4 (one or both copies), and ICP22 genes. In some embodiments, the recombinant herpes simplex virus genome comprises an inactivating mutation in the ICP0, ICP4 (one or both copies), ICP22, and ICP27 genes. In some embodiments, the recombinant herpes simplex virus genome comprises an inactivating mutation in the ICP0, ICP4 (one or both copies), ICP22, ICP27 and UL55 genes. In some embodiments, the inactivating mutation in the ICP0, ICP4 (one or both copies), ICP22, ICP27 and/or UL55 genes comprises a deletion of the coding sequence of the ICP0, ICP4 (one or both copies), ICP22, ICP27 and/or UL55 genes. In some embodiments, the recombinant herpes simplex virus genome comprises a deletion in the coding sequence of the ICP0, ICP4 (one or both copies), ICP22, ICP27, and UL55 genes. In some embodiments, the recombinant herpes simplex virus genome further comprises an inactivating mutation in the ICP47 gene. In some embodiments, the recombinant herpes simplex virus genome further comprises an inactivating mutation in the UL41 gene. In some embodiments, the recombinant herpes simplex virus genome further comprises an inactivating mutation in the ICP47 gene and the UL41 gene. In some embodiments, the recombinant herpes simplex virus genome is a recombinant HSV-1 genome, a recombinant HSV-2 genome, or any derivatives thereof. In some embodiments, the recombinant herpes simplex virus genome is a recombinant HSV-1 genome. In some embodiments, the recombinant herpes simplex virus genome is a recombinant HSV-2 genome.

In some embodiments, the recombinant herpes simplex virus genome comprises an inactivating mutation in the ICP4 (one or both copies), ICP22, and ICP27 genes. In some embodiments, the recombinant herpes simplex virus genome comprises an inactivating mutation in the ICP4 (one or both copies), ICP22, ICP27, ICP47, and UL55 genes. In some embodiments, the recombinant herpes simplex virus genome comprises an inactivating mutation in the ICP0, ICP4 (one or both copies), ICP22, and ICP27 genes. In some embodiments, the recombinant herpes simplex virus genome is a recombinant HSV-1 genome, a recombinant HSV-2 genome, or any derivatives thereof. In some embodiments, the recombinant herpes simplex virus genome is a recombinant HSV-1 genome. In some embodiments, the recombinant herpes simplex virus genome is a recombinant HSV-2 genome.

In some embodiments, a recombinant herpes simplex virus genome comprises one or more polynucleotides of the present disclosure within one, two, three, four, five, six, seven or more viral gene loci. Examples of suitable viral loci may include, without limitation, the ICP0, ICP4, ICP22, ICP27, ICP47, tk, UL41 and UL55 herpes simplex viral gene loci. In some embodiments, a recombinant herpes simplex virus genome comprises one or more polynucleotide of the present disclosure within one or more of the viral ICP4 gene loci (e.g., a recombinant virus carrying a polynucleotide encoding Col7 in one or both of the ICP4 loci, a recombinant virus carrying a polynucleotide encoding LH3 in one or both of the ICP4 loci, a recombinant virus carrying a polynucleotide encoding KRT17 in one or both of the ICP4 loci, a recombinant virus carrying a polynucleotide encoding Col7 in one of the ICP4 loci and a polynucleotide encoding KRT17 in the other ICP4 loci, a recombinant virus carrying a polynucleotide encoding Col7 in one of the ICP4 loci and a polynucleotide encoding LH3 in the other ICP4 loci, a recombinant virus carrying a polynucleotide encoding LH3 in one of the ICP4 loci and a polynucleotide encoding KRT17 in the other ICP4 loci, etc.). In some embodiments, a recombinant herpes simplex virus genome comprises one or more polynucleotide of the present disclosure within the viral UL41 gene locus. In some embodiments, a recombinant herpes simplex virus genome comprises one or more polynucleotide of the present disclosure within the viral ICP47 gene locus. In some embodiments, a recombinant herpes simplex virus genome comprises one or more polynucleotides of the present disclosure within one or more of the viral ICP4 gene loci, and one or more polynucleotide of the present disclosure within the viral UL41 gene locus (e.g., a recombinant virus carrying a polynucleotide encoding Col7 in one or both of the ICP4 loci and a polynucleotide encoding LH3 in the UL41 locus, a recombinant virus carrying a polynucleotide encoding Col7 in one or both of the ICP4 loci and a polynucleotide encoding Col7 in the UL41 locus, a recombinant virus carrying a polynucleotide encoding Col7 in one or both of the ICP4 loci and a polynucleotide encoding KRT17 in the UL41 locus, a recombinant virus carrying a polynucleotide encoding LH3 in one or both of the ICP4 loci and a polynucleotide encoding LH3 in the UL41 locus, a recombinant virus carrying a polynucleotide encoding LH3 in one or both of the ICP4 loci and a polynucleotide encoding Col7 in the UL41 locus, a recombinant virus carrying a polynucleotide encoding LH3 in one or both of the ICP4 loci and a polynucleotide encoding KRT17 in the UL41 locus, a recombinant virus carrying a polynucleotide encoding KRT17 in one or both of the ICP4 loci and a polynucleotide encoding LH3 in the UL41 locus, a recombinant virus carrying a polynucleotide encoding KRT17 in one or both of the ICP4 loci and a polynucleotide encoding Col7 in the UL41 locus, a recombinant virus carrying a polynucleotide encoding KRT17 in one or both of the ICP4 loci and a polynucleotide encoding KRT17 in the UL41 locus, etc.).

A vector may include a polynucleotide of the present disclosure in a form suitable for expression of the polynucleotide in a host cell. Expression vectors may include one or more regulatory sequences operatively linked to the polynucleotide to be expressed. The term "regulatory sequence" includes promoters, enhancers and other expression control elements (e.g., polyadenylation signals). Examples of suitable enhancers may include, but are not limited to, enhancer sequences from mammalian genes (such as globin, elastase, albumin, α-fetoprotein, insulin and the like), and enhancer sequences from a eukaryotic cell virus (such as SV40 enhancer on the late side of the replication origin (bp 100-270), the cytomegalovirus early promoter enhancer, the polyoma enhancer on the late side of the replication origin, adenovirus enhancers, and the like). Examples of promoters suitable for transcription in mammalian host cells may include, but are not limited to, promoters obtained from the genomes of viruses (such as polyoma virus, fowlpox virus, adenovirus (such as Adenovirus 2), bovine papilloma virus, avian sarcoma virus, cytomegalovirus, a retrovirus, hepatitis-B virus, Simian Virus 40 (SV40), and the like), or from heterologous mammalian promoters (such as the actin promoter, an immunoglobulin promoter, from heat-shock promoters, and the like), provided such promoters are compatible with the host cells. In some embodiments, polynucleotides of the present disclosure are operably linked to one or more heterologous promoters. In some embodiments, the one or more heterologous promoters are one or more of the human cytomegalovirus (HCMV) immediate early promoter, the elongation factor-1 (EF1) promoter, and/or any combinations thereof. In some embodiments, the one or more heterologous promoters are one or more of constitutive promoters, tissue-specific promoters, temporal promoters, spatial promoters, inducible promoters and repressible promoters. Regulatory sequences may include those which direct constitutive expression of a nucleotide sequence, as well as tissue-specific regulatory and/or inducible sequences. The design of the expression vector can depend on such factors as the host cell to be contacted with a polynucleotide of the present disclosure, the level of expression of protein desired, and the like. The expression vectors of the present disclosure can be introduced into host cells to thereby produce proteins or polypeptides (e.g., Collagen alpha-1 (VII) chain polypeptides, Lysyl hydroxylase 3 polypeptides, Keratin type I cytoskeletal 17 polypeptides, chimeric polypeptides, and the like) encoded by polynucleotides as described herein.

In some embodiments, a vector of the present disclosure comprises one or more transgenes comprising one or more polynucleotide described herein. The one or more transgenes may be inserted in any orientation in the vector. If the vector comprises two or more transgenes (e.g., two or more, three or more, etc.), the transgenes may be inserted in the same orientation or opposite orientations to one another. Without wishing to be bound be theory, incorporating two transgenes into a vector in an antisense orientation may help to avoid read-through and ensure proper expression of each transgene. In some embodiments, the vector comprises one or more transgenes encoding a polypeptide selected from the group consisting of a Collagen alpha-1 (VII) chain polypeptide, a Lysyl hydroxylase 3 polypeptide, a Keratin type I cytoskeletal 17 polypeptide, and/or chimeric polypeptides thereof. In some embodiments, the vector comprises a single transgene encoding a Collagen alpa-1 (VII) chain polypeptide. In some embodiments, the vector comprises two transgenes each encoding a Collagen alpa-1 (VII) chain polypeptide. In some embodiments, the vector comprises three transgenes each encoding a Collagen alpa-1 (VII) chain polypeptide. In some embodiments, the vector comprises a single transgene encoding a Lysyl hydroxylase 3 polypeptide. In some embodiments, the vector comprises two transgenes each encoding a Lysyl hydroxylase 3 polypeptide. In some embodiments, the vector comprises three transgenes each encoding a Lysyl hydroxylase 3 polypeptide. In some embodiments, the vector comprises a single transgene encoding a Keratin type I cytoskeletal 17 polypeptide. In some embodiments, the vector comprises two transgenes each encoding a Keratin type I cytoskeletal 17 polypeptide. In some embodiments, the vector comprises three transgenes each encoding a Keratin type I cytoskeletal 17 polypeptide. In some embodiments, the vector comprises a single transgene encoding a chimeric polypeptide comprising a Collagen alpha-1 (VII) chain polypeptide, a Lysyl hydroxylase 3 polypeptide, and/or a Keratin type I cytoskeletal 17 polypeptide.

In some embodiments, the vector comprises at least two transgenes (e.g. two, three, four, five, six, seven or more transgenes). In some embodiments, the at least first transgene encodes a Collagen alpha-1 (VII) chain polypeptide and the at least second transgene encodes a Lysyl hydroxylase 3 polypeptide. In some embodiments, the at least first transgene encodes a Lysyl hydroxylase 3 polypeptide and the at least second transgene encodes a Collagen alpha-1 (VII) chain polypeptide. In some embodiments, the at least first transgene encodes a Collagen alpha-1 (VII) chain polypeptide and the at least second transgene encodes a Keratin type I cytoskeletal 17 polypeptide. In some embodiments, the at least first transgene encodes a Keratin type I cytoskeletal 17 polypeptide and the at least second transgene encodes a Collagen alpha-1 (VII) chain polypeptide. In some embodiments, the at least first transgene encodes a Lysyl hydroxylase 3 polypeptide and the at least second transgene encodes a Keratin type I cytoskeletal 17 polypeptide. In some embodiments, the at least first transgene encodes a Keratin type I cytoskeletal 17 polypeptide and the at least second transgene encodes a Lysyl hydroxylase 3 polypeptide. In some embodiments, the at least first transgene encodes a Collagen alpha-1 (VII) chain polypeptide and the at least second transgene encodes a chimeric polypeptide comprising a Collagen alpha-1 (VII) chain polypeptide, a Lysyl hydroxylase 3 polypeptide, and/or a Keratin type I cytoskeletal 17 polypeptide. In some embodiments, the at least first transgene encodes a Lysyl hydroxylase 3 polypeptide and the at least second transgene encodes a chimeric polypeptide comprising a Collagen alpha-1 (VII) chain polypeptide, a Lysyl hydroxylase 3 polypeptide, and/or a Keratin type I cytoskeletal 17 polypeptide. In some embodiments, the at least first transgene encodes a Keratin type I cytoskeletal 17 polypeptide and the at least second transgene encodes a chimeric polypeptide comprising a Collagen alpha-1 (VII) chain polypeptide, a Lysyl hydroxylase 3 polypeptide, and/or a Keratin type I cytoskeletal 17 polypeptide.

In some embodiments, the vector comprises at least three transgenes (e.g. three, four, five, six, seven or more transgenes). In some embodiments, the at least first transgene encodes a Collagen alpha-1 (VII) chain polypeptide, the at least second transgene encodes a Lysyl hydroxylase 3 polypeptide, and the at least third transgene encodes a Keratin type I cytoskeletal 17 polypeptide.

In some embodiments, the vector comprises a transgene that is polycistronic. In some embodiments, the polycistronic transgene encodes a Collagen alpha-1 (VII) chain polypeptide on a first open reading frame (ORF) and a Lysyl hydroxylase 3 polypeptide on a second open reading frame (ORF). In some embodiments, the polycistronic transgene encodes a Lysyl hydroxylase 3 polypeptide on a first open reading frame (ORF) and a Collagen alpha-1 (VII) chain polypeptide on a second open reading frame (ORF). In some embodiments, the polycistronic transgene encodes a Collagen alpha-1 (VII) chain polypeptide on a first open reading frame (ORF) and a keratin type I cytoskeletal 17 polypeptide on a second open reading frame (ORF). In some embodiments, the polycistronic transgene encodes a Keratin type I cytoskeletal polypeptide on a first open reading frame (ORF) and a Collagen alpha-1 (VII) chain polypeptide on a second open reading frame (ORF). In some embodiments, the polycistronic transgene encodes a Lysyl hydroxylase 3 polypeptide on a first open reading frame (ORF) and a keratin type I cytoskeletal 17 polypeptide on a second open reading frame (ORF). In some embodiments, the polycistronic transgene encodes a Keratin type I cytoskeletal polypeptide on a first open reading frame (ORF) and a Lysyl hydroxylase 3 polypeptide on a second open reading frame (ORF).

In some embodiments, the polycistronic transgene encodes a Collagen alpha-1 (VII) chain polypeptide on a first open reading frame (ORF) and a chimeric polypeptide comprising a Collagen alpha-1 (VII) chain polypeptide, a Lysyl hydroxylase 3 polypeptide, and/or a Keratin type I cytoskeletal 17 polypeptide on a second open reading frame (ORF). In some embodiments, the polycistronic transgene encodes a Lysyl hydroxylase 3 polypeptide on a first open reading frame (ORF) and a chimeric polypeptide comprising a Collagen alpha-1 (VII) chain polypeptide, a Lysyl hydroxylase 3 polypeptide, and/or a Keratin type I cytoskeletal 17 polypeptide on a second open reading frame (ORF). In some embodiments, the polycistronic transgene encodes a Keratin type I cytoskeletal 17 polypeptide on a first open reading frame (ORF) and a chimeric polypeptide comprising a Collagen alpha-1 (VII) chain polypeptide, a Lysyl hydroxylase 3 polypeptide, and/or a Keratin type I cytoskeletal 17 polypeptide on a second open reading frame (ORF). In some embodiments, the first and second ORFs are separated by an internal ribosomal entry site (IRES).

In some embodiments, the polycistronic transgene encodes a Collagen alpha-1 (VII) chain polypeptide on a first open reading frame (ORF), a Keratin type I cytoskeletal 17 polypeptide on a second open reading frame (ORF), and a Lysyl hydroxylase 3 polypeptide on a third open reading frame (ORF). In some embodiments, the polycistronic transgene encodes a Collagen alpha-1 (VII) chain polypeptide on a first open reading frame (ORF), a Lysyl hydroxylase 3 polypeptide on a second open reading frame (ORF), and a Keratin type I cytoskeletal 17 polypeptide on a third open reading frame (ORF). In some embodiments, the polycistronic transgene encodes a Lysyl hydroxylase 3 polypeptide on a first open reading frame (ORF), a Collagen alpha-1 (VII) chain polypeptide on a second open reading frame (ORF), and a Keratin type I cytoskeletal 17 polypeptide on a third open reading frame (ORF). In some embodiments, the polycistronic transgene encodes a Lysyl hydroxylase 3 polypeptide on a first open reading frame (ORF), a Keratin type I cytoskeletal 17 polypeptide on a second open reading frame (ORF), and a Collagen alpha-1 (VII) chain polypeptide on a third open reading frame (ORF). In some embodiments, the polycistronic transgene encodes a Keratin type I cytoskeletal 17 polypeptide on a first open reading frame (ORF), a Lysyl hydroxylase 3 polypeptide on a second open reading frame (ORF), and a Collagen alpha-1 (VII) chain polypeptide on a third open reading frame (ORF). In some embodiments, the polycistronic transgene encodes a Keratin type I cytoskeletal 17 polypeptide on a first open reading frame (ORF), a Collagen alpha-1 (VII) chain polypeptide on a second open reading frame (ORF), and a Lysyl hydroxylase 3 polypeptide on a third open reading frame (ORF). In some embodiments, the first, second, and third ORFs are separated by an internal ribosomal entry site (IRES).

Examples of suitable IRES's may include, but are not limited to, a virally-derived IRES (e.g. an IRES derived from a poliovirus, rhinovirus, encephalomyocarditis virus, foot-and-mouth disease virus, hepatitis C virus, classic swine fever virus, rous sarcoma virus, human immunodeficiency virus, cricket paralysis virus, Kaposi's sarcoma-associated herpesvirus, etc.) and a cellular mRNA-derived IRES (e.g. an IRES derived from growth factor mRNAs, such as fibroblast growth factor 2, platelet-derived growth factor B, and vascular endothelial growth factor, an IRES derived from transcription factor mRNAs, such as antennapedia, ultrapithoraxm, and NF-κB repressing factor, an IRES derived from oncogene mRNAs, such as c-myc, pim-1, and protein kinase p58$^{PITSLRE}$ etc.).

Vectors of the present disclosure may further encode additional coding and non-coding sequences. Examples of additional coding and non-coding sequences may include, but are not limited to, sequences encoding additional polypeptide tags, introns, 5' and 3' UTRs, and the like. Examples of suitable polypeptide tags may include, but are not limited, to any combination of purification tags, such as his-tags, flag-tags, maltose binding protein and glutathione-S-transferase tags, detection tags, such as tags that may be detected photometrically (e.g., red fluorescent protein, etc.) and tags that have a detectable enzymatic activity (e.g., alkaline phosphatase, etc.), tags containing secretory sequences, leader sequences, and/or stabilizing sequences, protease cleavage sites (e.g., furin cleavage sites, TEV cleavage sites, Thrombin cleavage sites), and the like. In some embodiments, the 5' and/or 3'UTRs increase the stability, localization, and/or translational efficiency of the polynucleotides. In some embodiments, the 5' and/or 3'UTRs are modified to increase the stability, localization, and/or translational efficiency of the one or more polynucleotides. In some embodiments, the 5' and/or 3'UTRs improve the level and/or duration of protein expression. In some embodiments, the 5' and/or 3'UTRs include elements (e.g., one or more miRNA binding sites, etc.) that may block or reduce off-target transgene expression (e.g., inhibiting expression in specific cell types (e.g., neuronal cells), at specific times in the cell cycle, at specific developmental stages, etc.). In some embodiments, the 5' and/or 3'UTRs include elements (e.g., one or more miRNA binding sites, etc.) that may enhance transgene expression in specific cell types.

Synthetic RNA Polynucleotides

In some aspects, the present disclosure relates to synthetic RNAs, in particular synthetic mRNAs, containing one or more polynucleotides described herein. In some embodiments, the synthetic mRNA polynucleotides comprise a 5'-cap structure. Examples of 5'-cap structures may include, but are not limited to, cap-0, cap-1, cap-2, and cap-3 structures, and derivatives thereof. In some embodiments, the synthetic mRNA polynucleotides comprise a 3'-poly(A) tail. In some embodiments, the synthetic mRNA polynucleotides comprise one or more 5' and/or 3' UTRs flanking the one or more coding sequences contained within the synthetic mRNA polynucleotides. In some embodiments, the 5' and/or 3' UTRs increase the stability, localization, and/or translational efficiency of the synthetic mRNA polynucleotides. In some embodiments, the 5' and/or 3' UTRs are modified to increase the stability, localization, and/or translational efficiency of the synthetic mRNA polynucleotides. In some embodiments, the 5' and/or 3' UTRs improve the level and/or duration of protein expression. In some embodiments, the 5' and/or 3' UTRs are modified to improve the level and/or duration of protein expression. In some embodiments, the 5' and/or 3'UTRs include elements (e.g., miRNA binding sites, etc.) that may limit off-target expression (e.g., inhibiting expression in specific cell types (e.g., neuronal cells), at specific times in the cell cycle, at specific developmental stages, etc.). In some embodiments, the 5' UTRs comprise a Kozak sequence. In some embodiments, the Kozak sequence is the same or substantially similar to the Kozak consensus sequence. Methods for making synthetic mRNA polynucleotides containing one or more polynucleotides of interest are well known to one of skill in the art.

In some aspects, the synthetic mRNA polynucleotides of the present disclosure comprise one or more modified ribonucleotides. Examples of modified ribonucleotides may include, but are not limited to, 2-thiouridine, 5-azauridine, pseudouridine, 4-thiouridine, 5-methyluridine, 5-aminouridine, 5-hydroxyuridine, 5-methyl-5-azauridine, 5-amino-5-azauridine, 5-hydroxy-5-azauridine, 5-methylpseudouridine, 5-aminopseudouridine, 5-hydroxypseudouridine, 4-thio-5-azauridine, 4-thiopseudouridine, 4-thio-5-methyluridine, 4-thio-5-aminouridine, 4-thio-5-hydroxyuridine, 4-thio-5-methyl-5-azauridine, 4-thio-5-amino-5-azauridine, 4-thio-5-hydroxy-5-azauridine, 4-thio-5-methylpseudouridine, 4-thio-5-aminopseudouridine, 4-thio-5-hydroxypseudouridine, 2-thiocytidine, 5-azacytidine, pseudoisocytidine, N4-methylcytidine, N4-aminocytidine, N4-hydroxycytidine, 5-methylcytidine, 5-aminocytidine, 5-hydroxycytidine, 5-methyl-5-azacytidine, 5-amino-5-azacytidine, 5-hydroxy-5-azacytidine, 5-methylpseudoisocytidine, 5-aminopseudoisocytidine, 5-hydroxypseudoisocytidine, N4-methyl-5-azacytidine, N4-methylpseudoisocytidine, 2-thio-5-azacytidine, 2-thiopseudoisocytidine, 2-thio-N4-methylcytidine, 2-thio-N4-aminocytidine, 2-thio-N4-hydroxycytidine, 2-thio-5-methylcytidine, 2-thio-5-aminocytidine, 2-thio-5-hydroxycytidine, 2-thio-5-methyl-5-azacytidine, 2-thio-5-amino-5-azacytidine, 2-thio-5-hydroxy-5-azacytidine, 2-thio-5-methylpseudoisocytidine, 2-thio-5-aminopseudoisocytidine, 2-thio-5-hydroxypseudoisocytidine, 2-thio-N4-methyl-5-azacytidine, 2-thio-N4-methylpseudoisocytidine, N4-methyl-5-methylcytidine, N4-methyl-5-aminocytidine, N4-methyl-5-hydroxycytidine, N4-methyl-5-methyl-5-azacytidine, N4-methyl-5-amino-5-azacytidine, N4-methyl-5- hydroxy-5-azacytidine, N4-methyl-5-methylpseudoisocytidine, N4-methyl-5-aminopseudoisocytidine, N4-methyl-5-hydroxypseudoisocytidine, N4-amino-5-azacytidine, N4-aminopseudoisocytidine, N4-amino-5-methylcytidine, N4-amino-5-aminocytidine, N4-amino-5-hydroxycytidine, N4-amino-5-methyl-5-azacytidine, N4-amino-5-amino-5-azacytidine, N4-amino-5-hydroxy-5-azacytidine, N4-amino-5-methylpseudoisocytidine, N4-amino-5-aminopseudoisocytidine, N4-amino-5-hydroxypseudoisocytidine, N4-hydroxy-5-azacytidine, N4-hydroxypseudoisocytidine, N4-hydroxy-5-methylcytidine, N4-hydroxy-5-aminocytidine, N4-hydroxy-5-hydroxycytidine, N4-hydroxy-5-methyl-5-azacytidine, N4-hydroxy-5-amino-5-azacytidine, N4-hydroxy-5-hydroxy-5-azacytidine, N4-hydroxy-5-methylpseudoisocytidine, N4-hydroxy-5-aminopseudoisocytidine, N4-hydroxy-5-hydroxypseudoisocytidine, 2-thio-N4-methyl-5-methylcytidine, 2-thio-N4-methyl-5-aminocytidine, 2-thio-N4-methyl-5-hydroxycytidine, 2-thio-N4-methyl-5-methyl-5-azacytidine, 2-thio-N4-methyl-5-amino-5-azacytidine, 2-thio-N4-methyl-5-hydroxy-5-azacytidine, 2-thio-N4-methyl-5-methylpseudoisocytidine, 2-thio-N4-methyl-5-aminopseudoisocytidine, 2-thio-N4-methyl-5-hydroxypseudoisocytidine, 2-thio-N4-amino-5-azacytidine, 2-thio-N4-aminopseudoisocytidine, 2-thio-N4-amino-5-methylcytidine, 2-thio-N4-amino-5-aminocytidine, 2-thio-N4-amino-5-hydroxycytidine, 2-thio-N4-amino-5-methyl-5-azacytidine, 2-thio-N4-amino-5-amino-5-azacytidine, 2-thio-N4-amino-5-hydroxy-5-azacytidine, 2-thio-N4-amino-5-methylpseudoisocytidine, 2-thio-N4-amino-5-aminopseudoisocytidine, 2-thio-N4-amino-5-hydroxypseudoisocytidine, 2-thio-N4-hydroxy-5-azacytidine, 2-thio-N4-hydroxypseudoisocytidine, 2-thio-N4-hydroxy-5-methylcytidine, N4-hydroxy-5-aminocytidine, 2-thio-N4-hydroxy-5-hydroxycytidine, 2-thio-N4-hydroxy-5-methyl-5-azacytidine, 2-thio-N4-hydroxy-5-amino-5-azacytidine, 2-thio-N4-hydroxy-5-hydroxy-5-azacytidine, 2-thio-N4-hydroxy-5-methylpseudoisocytidine, 2-thio-N4-hydroxy-5-aminopseudoisocytidine, 2-thio-N4-hydroxy-5-hydroxypseudoisocytidine, N6-methyladenosine, N6-aminoadenosine, N6-hydroxyadenosine, 7-deazaadenosine, 8-azaadenosine, N6-methyl-7-deazaadenosine, N6-methyl-8-azaadenosine, 7-deaza-8-azaadenosine, N6-methyl-7-deaza-8-azaadenosine, N6-amino-7-deazaadenosine, N6-amino-8-azaadenosine, N6-amino-7-deaza-8-azaadenosine, N6-hydroxyadenosine, N6-hydroxy-7-deazaadenosine, N6-hydroxy-8-azaadenosine, N6-hydroxy-7-deaza-8-azaadenosine, 6-thioguanosine, 7-deazaguanosine, 8-azaguanosine, 6-thio-7-deazaguanosine, 6-thio-8-azaguanosine, 7-deaza-8-azaguanosine, and 6-thio-7-deaza-8-azaguanosine.

In some embodiments, a polynucleotide encoding a Collagen alpha-1 (VII) chain polypeptide and a polynucleotide encoding a Lysyl hydroxylase 3 polypeptide are contained within two separate synthetic mRNA polynucleotides. In some embodiments, a polynucleotide encoding a Collagen alpha-1 (VII) chain polypeptide and a polynucleotide encoding a Keratin type I cytoskeletal 17 polypeptide are contained within two separate synthetic mRNA polynucleotides. In some embodiments, a polynucleotide encoding a Lysyl hydroxylase 3 polypeptide and a polynucleotide encoding a Keratin type I cytoskeletal 17 polypeptide are contained within two separate synthetic mRNA polynucleotides. In some embodiments, a polynucleotide encoding a Collagen alpha-1 (VII) chain polypeptide, a polynucleotide encoding a Lysyl hydroxylase 3 polypeptide, and a polynucleotide encoding a Keratin type I cytoskeletal 17 polypeptide are contained within three separate synthetic mRNA polynucleotides.

In some embodiments, a polynucleotide encoding a Collagen alpha-1 (VII) chain polypeptide, a polynucleotide encoding a Lysyl hydroxylase 3 polypeptide, and/or a polynucleotide encoding a Keratin type I cytoskeletal 17 polypeptide is a single contiguous polynucleotide contained within a single synthetic mRNA polynucleotide. In some embodiments, the single contiguous polynucleotide encodes a Collagen alpha-1 (VII) chain polypeptide on a first open reading frame (ORF) and a Lysyl hydroxylase 3 polypeptide on a second open reading frame (ORF) in a single synthetic mRNA. In some embodiments, the single contiguous polynucleotide encodes a Lysyl hydroxylase 3 polypeptide on a first open reading frame (ORF) and a Collagen alpha-1 (VII) chain polypeptide on a second open reading frame (ORF) in a single synthetic mRNA. In some embodiments, the single contiguous polynucleotide encodes a Collagen alpha-1 (VII) chain polypeptide on a first open reading frame (ORF) and a keratin type I cytoskeletal 17 polypeptide on a second open reading frame (ORF) in a single synthetic mRNA. In some embodiments, the single contiguous polynucleotide encodes a Keratin type I cytoskeletal polypeptide on a first open reading frame (ORF) and a Collagen alpha-1 (VII) chain polypeptide on a second open reading frame (ORF) in a single synthetic mRNA. In some embodiments, the single contiguous polynucleotide encodes a Lysyl hydroxylase 3 polypeptide on a first open reading frame (ORF) and a keratin type I cytoskeletal 17 polypeptide on a second open reading frame (ORF) in a single synthetic mRNA. In some embodiments, the single contiguous polynucleotide encodes a Keratin type I cytoskeletal polypeptide on a first open reading frame (ORF) and a Lysyl hydroxylase 3 polypeptide on a second open reading frame (ORF) in a single synthetic mRNA. In some embodiments, the single contiguous polynucleotide encodes a Collagen alpha-1 (VII) chain polypeptide on a first open reading frame (ORF) and a chimeric polypeptide comprising a Collagen alpha-1 (VII) chain polypeptide, a Lysyl hydroxylase 3 polypeptide, and/or a Keratin type I cytoskeletal 17 polypeptide on a second open reading frame (ORF) in a single synthetic mRNA. In some embodiments, the single contiguous polynucleotide encodes a Lysyl hydroxylase 3 polypeptide on a first open reading frame (ORF) and a chimeric polypeptide comprising a Collagen alpha-1 (VII) chain polypeptide, a Lysyl hydroxylase 3 polypeptide, and/or a Keratin type I cytoskeletal 17 polypeptide on a second open reading frame (ORF) in a single synthetic mRNA. In some embodiments, the single contiguous polynucleotide encodes a Keratin type I cytoskeletal 17 polypeptide on a first open reading frame (ORF) and a chimeric polypeptide comprising a Collagen alpha-1 (VII) chain polypeptide, a Lysyl hydroxylase 3 polypeptide, and/or a Keratin type I cytoskeletal 17 polypeptide on a second open reading frame (ORF) in a single synthetic mRNA. In some embodiments, the two ORFs are separated by an IRES.

In some embodiments, the single contiguous polynucleotide encodes a Collagen alpha-1 (VII) chain polypeptide on a first open reading frame (ORF), a Keratin type I cytoskeletal 17 polypeptide on a second open reading frame (ORF), and a Lysyl hydroxylase 3 polypeptide on a third open reading frame (ORF) in a single synthetic mRNA. In some embodiments, the single contiguous polynucleotide encodes a Collagen alpha-1 (VII) chain polypeptide on a first open reading frame (ORF), a Lysyl hydroxylase 3 polypeptide on a second open reading frame (ORF), and a Keratin type I cytoskeletal 17 polypeptide on a third open reading frame (ORF) in a single synthetic mRNA. In some embodiments, the single contiguous polynucleotide encodes a Lysyl hydroxylase 3 polypeptide on a first open reading frame (ORF), a Collagen alpha-1 (VII) chain polypeptide on a second open reading frame (ORF), and a Keratin type I cytoskeletal 17 polypeptide on a third open reading frame (ORF) in a single synthetic mRNA. In some embodiments, the single contiguous polynucleotide encodes a Lysyl hydroxylase 3 polypeptide on a first open reading frame (ORF), a Keratin type I cytoskeletal 17 polypeptide on a second open reading frame (ORF), and a Collagen alpha-1 (VII) chain polypeptide on a third open reading frame (ORF) in a single synthetic mRNA. In some embodiments, the single contiguous polynucleotide encodes a Keratin type I cytoskeletal 17 polypeptide on a first open reading frame (ORF), a Lysyl hydroxylase 3 polypeptide on a second open reading frame (ORF), and a Collagen alpha-1 (VII) chain polypeptide on a third open reading frame (ORF) in a single synthetic mRNA. In some embodiments, the single contiguous polynucleotide encodes a Keratin type I cytoskeletal 17 polypeptide on a first open reading frame (ORF), a Collagen alpha-1 (VII) chain polypeptide on a second open reading frame (ORF), and a Lysyl hydroxylase 3 polypeptide on a third open reading frame (ORF) in a single synthetic mRNA. In some embodiments, the first, second, and third ORFs are separated by an internal ribosomal entry site (IRES).

Examples of suitable IRES's may include, but are not limited to, a virally-derived IRES (e.g. an IRES derived from a poliovirus, rhinovirus, encephalomyocarditis virus, foot-and-mouth disease virus, hepatitis C virus, classic swine fever virus, rous sarcoma virus, human immunodeficiency virus, cricket paralysis virus, Kaposi's sarcoma-associated herpesvirus, etc.) and a cellular mRNA-derived IRES (e.g. an IRES derived from growth factor mRNAs, such as fibroblast growth factor 2, platelet-derived growth factor B, and vascular endothelial growth factor, an IRES derived from transcription factor mRNAs, such as antennapedia, ultrapithoraxm, and NF-κB repressing factor, an IRES derived from oncogene mRNAs, such as c-myc, pim-1, and protein kinase p58$^{PITSLRE}$ etc.).

In some embodiments, a polynucleotide encoding any of the chimeric polypeptides comprising a Collagen alpha-1 (VII) chain polypeptide, a Lysyl hydroxylase 3 polypeptide, and/or a Keratin type I cytoskeletal 17 polypeptide described herein is encoded on a single ORF within a synthetic mRNA polynucleotide.

Synthetic mRNA polynucleotides of the present disclosure may further encode additional coding sequences. Examples of additional coding sequences may include, but are not limited to, sequences encoding additional polypeptide tags. Examples of suitable polypeptide tags may include, but are not limited to, any combination of purification tags, such as his-tags, flag-tags, maltose binding protein and glutathione-S-transferase tags, detection tags, such as tags that may be detected photometrically (e.g., red fluorescent protein, etc.) and tags that have a detectable enzymatic activity (e.g., alkaline phosphatase, etc.), tags containing secretory sequences, leader sequences, and/or stabilizing sequences, protease cleavage sites (such as furin cleavage sites), and the like.

Delivery Vehicle

Certain aspects of the present disclosure relate to a pharmaceutical composition comprising a delivery vehicle comprising one or more polynucleotides described herein. In some embodiments, the delivery vehicle is suitable for delivering one or more polynucleotides into one or more target cells.

In some embodiments, the delivery vehicle is a virus. Examples of viral delivery vehicles may include, but are not limited to, adenovirus, adeno-associated virus, retrovirus, lentivirus, sendai virus, herpes simplex virus, vaccinia virus, or any hybrid virus thereof. In some embodiments, the virus is replication-defective. In some embodiments, the virus is replication-competent. In some embodiments, the virus has been modified to alter its tissue tropism relative to the tissue tropism of an unmodified, wild-type virus. Methods for producing a virus comprising one or more polynucleotides are well known to one of skill in the art.

In some embodiments, the viral delivery vehicle is a herpes simplex virus. *Herpes simplex* virus delivery vehicles may be produced by a process disclosed, for example, in WO2015/009952. In some embodiments, the herpes simplex virus comprises a modified envelope. In some embodiments, the modified envelope comprises one or more (e.g., one, two, three, four or more) mutant herpes simplex virus glycoproteins. Examples of herpes simplex virus glycoproteins may include, but are not limited to, the glycoproteins gB, gD, gH, and gL. In some embodiments, the modified envelope alters the herpes simplex virus tissue tropism relative to a wild-type herpes simplex virus. In some embodiments, the herpes simplex virus is a herpes simplex type 1 virus, a herpes simplex type 2 virus, of any derivatives thereof. In some embodiments, the virus is a herpes simplex type 1 virus. In some embodiments, the virus is a herpes simplex type 2 virus.

In some embodiments, the delivery vehicle is a non-viral delivery vehicle. In some embodiments, the non-viral delivery vehicle is a chemical-based delivery vehicle (a chemical-based delivery reagent). Examples of chemical-based delivery vehicles may include, but are not limited to, calcium phosphate, dendrimers, liposomes (cationic liposomes, non-cationic liposome, and mixtures), exosomes, charged lipids, and cationic polymers (such as DEAE-dextran, polyethylenimine, and the like). In some embodiments, the non-viral delivery vehicle is a non-chemical delivery vehicle. Examples of non-chemical delivery vehicles may include, but are not limited to, electroporation, nucleofection, sonoporation, optical transfection, and particle-based vehicles (such as a gene gun, magnet-assisted transfection, impalefection, particle bombardment, and the like). In some embodiments, the non-viral delivery vehicle is a dendrimer, liposome, exosome, charged lipid or cationic polymer. In some embodiments, the non-viral delivery vehicle is a dendrimer. In some embodiments, the non-viral delivery vehicle is a liposome. In some embodiments, the non-viral delivery vehicle is an exosome. In some embodiments, the non-viral delivery vehicle is a charged lipid. In some embodiments, the non-viral delivery vehicle is a cationic polymer. Methods for producing one or more polynucleotides of interest in a complex with a non-viral delivery vehicle are well known to one of skill in the art.

Pharmaceutically Acceptable Carrier

Certain aspects of the present disclosure relates to a pharmaceutical composition comprising a pharmaceutically acceptable carrier. In some embodiments, the pharmaceutically acceptable carrier is a carrier sufficient for topical and/or transdermal administration/application. In some embodiments, the pharmaceutically acceptable carrier is a carrier sufficient for subcutaneous and/or intradermal administration/application. In some embodiments, the pharmaceutically acceptable carrier is minimally invasive or non-invasive. Pharmaceutically acceptable carriers are generally nontoxic to recipients at the dosages and concentrations employed, and may include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; polyols such as glycerol (e.g., formulations including 10% glycerol); salt-forming counter-ions such as sodium; metal complexes (e.g. Zn-protein complexes); and/or non-ionic surfactants such as polyethylene glycol (PEG). A thorough discussion of pharmaceutically acceptable carriers is available in REMINGTON'S PHARMACEUTICAL SCIENCES (Mack Pub. Co., N.J. 1991).

In some embodiments, the pharmaceutically acceptable carrier is suitable for topical or transdermal applications/administrations. Examples of carriers suitable for use in a topical or transdermal application/administration may include, but are not limited to, ointments, pastes, creams, suspensions, emulsions, fatty ointments, gels, powders, lotions, solutions, sprays, patches, microneedle arrays, and inhalants. In some embodiments, the pharmaceutically acceptable carrier comprises one or more of an ointment, paste, cream, suspension, emulsion, fatty ointment, gel, powder, lotion, solution, spray, and an inhalant. In some embodiments, the pharmaceutically acceptable carrier comprises an ointment. In some embodiments, the pharmaceutically acceptable carrier comprises a paste. In some embodiments, the pharmaceutically acceptable carrier comprises a cream. In some embodiments, the pharmaceutically acceptable carrier comprises a suspension. In some embodiments, the pharmaceutically acceptable carrier comprises an emulsion. In some embodiments, the pharmaceutically acceptable carrier comprises a gel. In some embodiments, the pharmaceutically acceptable carrier comprises a powder. In some embodiments, the pharmaceutically acceptable carrier comprises a lotion. In some embodiments, the pharmaceutically acceptable carrier comprises a solution. In some embodiments, the pharmaceutically acceptable carrier comprises a spray. In some embodiments, the pharmaceutically acceptable carrier comprises an inhalant. In some embodiments, the pharmaceutical carrier comprises a patch (e.g. a patch that adheres to the skin). In some embodiments, the pharmaceutically acceptable carrier comprises a microneedle array. Methods for making and using microneedle arrays suitable for pharmaceutical composition delivery are generally known in the art (Kim Y. et al. "Microneedles for drug and vaccine delivery". *Advanced Drug Delivery Reviews* 2012, 64 (14): 1547-68).

In some embodiments, the pharmaceutically acceptable carrier comprises a combination of two, three, four, five or more different pharmaceutically acceptable carriers suitable for topical or transdermal applications/administrations.

In some embodiments, the pharmaceutically acceptable carrier further comprises one or more additional components. Examples of additional components may include, but are not limited to, binding agents (e.g., pregelatinised maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); wetting agents (e.g., sodium lauryl sulphate, etc.); salt solutions; alcohols; polyethylene glycols; gelatin; lactose; amylase; magnesium stearate; talc; silicic acid; viscous paraffin; hydroxymethylcellulose; polyvinylpyrrolidone; sweetenings; flavorings; perfuming agents; colorants; moisturizers; sunscreens; antibacterial agents; agents able to stabilize polynucleotides or prevent their degradation, and the like.

Pharmaceutical compositions and formulations as described herein may be prepared by mixing the delivery vehicle comprising one or more polynucleotides described herein with one or more pharmaceutically acceptable carriers. The formulations to be used for in vivo administration are generally sterile. Sterility may be readily accomplished, e.g., by filtration through sterile filtration membranes.

Methods of Treatment

The present disclosure relates, in part, to pharmaceutical compositions and methods of use for providing prophylactic, palliative, or therapeutic relief of a wound, disorder, or disease of the skin in a subject. Examples of diseases or disorders of the skin may include, but are not limited to, epidermolysis bullosa, skin cancer, psoriasis, lichen planus, lupus, rosacea, eczema, cutaneous candidiasis, cellulitis, impetigo, decubitus ulcers, erysipelas, ichthyosis vulgaris, dermatomyositis, acrodermatitis, stasis dermatitis, nethertons syndrome, epidermolysis bullosa simplex (LAMB3 gene), autosomal recessive congenital ichthyosis, xeroderma pigmentosa, and pemphigoid. In some embodiments, the disease or disorder of the skin is epidermolysis bullosa. In some embodiments, a subject has, or at risk of developing, one or more symptoms of epidermolysis bullosa.

The polynucleotides and pharmaceutical compositions described herein are useful for providing prophylactic, palliative, or therapeutic relief of a wound, disorder, or disease of the skin in a subject, including the treatment of one or more symptoms of epidermolysis bullosa (e.g., recessive dystrophic epidermolysis bullosa, dominant dystrophic epidermolysis bullosa, etc.). Pharmaceutical compositions of the present disclosure may be administered by any suitable method known in the art, including, without limitation, by oral administration, sublinguall administration, buccal administration, topical administration, rectal administration, via inhalation, transdermal administration, subcutaneous injection, intradermal injection, intravenous (IV) injection, intra-arterial injection, intramuscular injection, intracardiac injection, intraosseous injection, intraperitoneal injection, transmucosal administration, vaginal administration, intravitreal administration, intra-articular administration, periarticular administration, local administration, epicutaneous administration, or any combinations thereof. The pharmaceutical compositions may be delivered to an individual via a variety of routes, including, but not limited to, subcutaneous, intradermal, topical, transdermal, and transmucosal administrations. The present disclosure thus also encompasses methods of delivering any of the polynucleotides or pharmaceutical compositions described herein to an individual (such as an individual having, or at risk of developing, epidermolysis bullosa).

In some embodiments, there is provided prophylactic, palliative, or therapeutic relief of a wound, disorder, or disease of the skin in a subject comprising administering an effective amount of a pharmaceutical composition capable of enhancing, increasing, augmenting, and/or supplementing the levels of a Collagen alpha-1 chain polypeptide and/or a Lysyl hydroxylase 3 polypeptide and/or Keratin type I cytoskeletal 17 polypeptide in one or more cells of the subject. In some embodiments, the pharmaceutical composition is administered intradermally and/or subcutaneously. In some embodiments, the pharmaceutical composition is administered topically and/or trandermally. In some embodiments, there is provided prophylactic, palliative, or therapeutic relief of a wound, disorder, or disease of the skin in a subject comprising topically administering an effective amount of a pharmaceutical composition capable of enhancing, increasing, augmenting, and/or supplementing the levels of a Collagen alpha-1 chain polypeptide and/or a Lysyl hydroxylase 3 polypeptide and/or a Keratin type I cytoskeletal 17 polypeptide in one or more cells of the subject. The pharmaceutical composition may be any pharmaceutical composition described herein. In some embodiments, the individual is suffering from epidermolysis bullosa. In some embodiments, the individual is suffering from dystrophic epidermolysis bullosa. In some embodiments, the individual is suffering from dominant dystrophic epidermolysis bullosa. In some embodiments, the individual is suffering from recessive dystrophic epidermolysis bullosa. In some embodiments, the pharmaceutical composition is administered one, two, three, four, five or more times per day. In some embodiments, the pharmaceutical composition is administered to one or more affected areas of an individual. In some embodiments, the pharmaceutical composition is administered to one or more unaffected areas of the individual.

In some embodiments, a pharmaceutical composition described herein may be used to treat or alleviate one or more symptoms of epidermolysis bullosa. Symptoms of epidermolysis bullosa (e.g., recessive dystrophic epidermolysis bullosa, dominant dystrophic epidermolysis bullosa, etc.) may include, but are not limited to blisters on the skin (especially blisters on the hands, feet, knees, and elbows), blisters on the mucosa, scarring of the skin, scarring of the mucosa, skin erosion, deformity of fingernails and/or toenails, loss of fingernails and/or toenails, internal blistering (including on the vocal chords, esophagus, and upper airway), thickening of the skin (especially thickening of the skin on the palms and the soles of the feet), blistering of the scalp, scarring of the scalp, hair loss (scarring alopecia), thin-appearing skin, atrophic scarring, milia, dental conditions (such as tooth decay and poorly formed enamel), joint deformities, fusion of the fingers and toes, and dysphagia.

In some embodiments, there is provided a method of therapeutically treating an individual suffering from epidermolysis bullosa comprising administering an effective amount of a pharmaceutical composition capable of enhancing, increasing, augmenting, and/or supplementing the levels of a Collagen alpha-1 chain polypeptide and/or a Lysyl hydroxylase 3 polypeptide and/or a Keratin type I cytoskeletal 17 polypeptide in one or more cells of the individual. In some embodiments, the pharmaceutical composition is administered intradermally and/or subcutaneously. In some embodiments, the pharmaceutical composition is administered topically and/or trandermally. In some embodiments, there is provided a method of therapeutically treating an individual suffering from epidermolysis bullosa comprising topically administering an effective amount of a pharmaceutical composition capable of enhancing, increasing, augmenting, and/or supplementing the levels of a Collagen alpha-1 chain polypeptide and/or a Lysyl hydroxylase 3 polypeptide and/or Keratin type I cytoskeletal 17 polypeptide in one or more cells of the individual. The pharmaceutical composition may be any pharmaceutical composition described herein. In some embodiments, the individual is suffering from dystrophic epidermolysis bullosa. In some embodiments, the individual is suffering from dominant dystrophic epidermolysis bullosa. In some embodiments, the individual is suffering from recessive dystrophic epidermolysis bullosa. In some embodiments, the pharmaceutical composition is administered one, two, three, four, five or more times per day. In some embodiments, the pharmaceutical composition is administered to one or more affected areas of an individual. In some embodiments, the pharmaceutical composition is administered to one or more unaffected areas of the individual.

In some embodiments, there is provided a method of prophylactically treating an individual suffering from epidermolysis bullosa comprising administering an effective amount of a pharmaceutical composition capable of enhancing, increasing, augmenting, and/or supplementing the levels of a Collagen alpha-1 chain polypeptide and/or a Lysyl hydroxylase 3 polypeptide and/or Keratin type I cytoskeletal 17 polypeptide in one or more cells of the individual. In some embodiments, the pharmaceutical composition is administered intradermally and/or subcutaneously. In some embodiments, the pharmaceutical composition is administered topically and/or trandermally. In some embodiments, there is provided a method of prophylactically treating an individual suffering from epidermolysis bullosa comprising topically administering an effective amount of a pharmaceutical composition capable of enhancing, increasing, augmenting, and/or supplementing the levels of a Collagen alpha-1 chain polypeptide and/or a Lysyl hydroxylase 3 polypeptide and/or Keratin type I cytoskeletal 17 polypeptide in one or more cells of the individual. The pharmaceutical composition may be any pharmaceutical composition described herein. In some embodiments, the individual is suffering from dystrophic epidermolysis bullosa. In some embodiments, the individual is suffering from dominant dystrophic epidermolysis bullosa. In some embodiments, the individual is suffering from recessive dystrophic epidermolysis bullosa. In some embodiments, the pharmaceutical composition is administered one, two, three, four, five or more times per day. In some embodiments, the pharmaceutical composition is administered to one or more affected areas of an individual. In some embodiments, the pharmaceutical composition is administered to one or more unaffected areas of the individual.

In some embodiments, there is provided a method of prophylactically treating an individual at risk of developing epidermolysis bullosa comprising administering an effective amount of a pharmaceutical composition capable of enhancing, increasing, augmenting, and/or supplementing the levels of a Collagen alpha-1 chain polypeptide and/or a Lysyl hydroxylase 3 polypeptide and/or Keratin type I cytoskeletal 17 polypeptide in one or more cells of the individual. In some embodiments, the pharmaceutical composition is administered intradermally and/or subcutaneously. In some embodiments, the pharmaceutical composition is administered topically and/or trandermally. In some embodiments, there is provided a method of prophylactically treating an individual at risk of developing epidermolysis bullosa comprising topically administering an effective amount of a pharmaceutical composition capable of enhancing, increasing, augmenting, and/or supplementing the levels of a Collagen alpha-1 chain polypeptide and/or a Lysyl hydroxylase 3 polypeptide and/or Keratin type I cytoskeletal 17 polypeptide in one or more cells of the individual. The pharmaceutical composition may be any pharmaceutical composition described herein. In some embodiments, the individual is at risk of developing dystrophic epidermolysis bullosa. In some embodiments, the individual is at risk of developing dominant dystrophic epidermolysis bullosa. In some embodiments, the individual is at risk of developing recessive dystrophic epidermolysis bullosa. In some embodiments, the pharmaceutical composition is administered one, two, three, four, five or more times per day. In some embodiments, the pharmaceutical composition is administered to one or more affected areas of an individual. In some embodiments, the pharmaceutical composition is administered to one or more unaffected areas of the individual.

In some embodiments, administering to an individual an effective amount of any of the pharmaceutical compositions described herein enhances, increases, augments, and/or supplements the levels of a Collagen alpha-1 chain polypeptide and/or a Lysyl hydroxylase 3 polypeptide and/or Keratin type I cytoskeletal 17 polypeptide in one or more cells of the individual. In some embodiments, administering to an individual an effective amount of any of the pharmaceutical compositions described herein enhances, increases, augments, and/or supplements the function of a Collagen alpha-1 chain polypeptide and/or a Lysyl hydroxylase 3 polypeptide and/or a Keratin type I cytoskeletal 17 polypeptide in one or more cells of the individual. In some embodiments, administering to an individual an effective amount of any of the pharmaceutical compositions described herein enhances, increases, augments, and/or supplements the activity of a Collagen alpha-1 chain polypeptide and/or a Lysyl hydroxylase 3 polypeptide and/or Keratin type I cytoskeletal 17 polypeptide in one or more cells of the individual.

In some embodiments, administering to an individual an effective amount of any of the pharmaceutical compositions described herein enhances, increases, augments, and/or supplements anchoring fibril formation of the individual. In some embodiments, administering to an individual an effective amount of any of the pharmaceutical compositions described herein enhances, increases, augments, and/or supplements epithelial basement membrane organization of the individual. In some embodiments, administering to an individual an effective amount of any of the pharmaceutical compositions described herein enhances, increases, augments, and/or supplements epithelial basement adherence of the individual. In some embodiments, administering to an individual an effective amount of any of the pharmaceutical compositions described herein enhances, increases, augments, and/or supplements dermoepidermal junction integrity of the individual. In some embodiments, administering to an individual an effective amount of any of the pharmaceutical compositions described herein enhances, increases, augments, and/or supplements wound healing in the individual. Without wishing to be bound by theory, it is believed that increasing, augmenting, and/or supplementing the levels of a Collagen alpha-1 (VII) chain polypeptide in one or more cells of an individual, by administering one or more of the pharmaceutical compositions described herein, will allow for increased production and secretion of functional Collagen alpha-1 (VII) chain protein in the individual. Without wishing to be bound by theory, it is believed that increasing, augmenting, and/or supplementing the levels of a Lysyl hydroxylase 3 polypeptide in one or more cells of an individual, by administering one or more of the pharmaceutical compositions described herein, will increase the post-translation modification of Collagen alpha-1 (VII) chain polypeptides, enhancing production and/or secretion of functional Collagen alpha-1 (VII) chain protein in the individual. Without wishing to be bound by theory, it is further believed that increasing, augmenting, and/or supplementing the levels of a Collagen alpha-1 (VII) chain polypeptide and a Lysyl hydroxylase 3 polypeptide in the same cell of an individual, by administering one or more of the pharmaceutical compositions described herein (be it by contacting a cell with two separate polynucleotides expressing the polypeptides, by contacting a cell with a single contiguous polynucleotide separately expressing the two polypeptides, or by contacting a cell with a single contiguous polynucleotide expressing a chimeric polypeptide), will have an additive effect on enhancing the production and secretion of functional Collagen alpha-1 (VII) chain protein. Without wishing to be bound by theory, it is believed that increased production and secretion of functional Collagen alpha-1 (VII) chain protein will allow for improved anchoring fibril formation, helping organize, stabilize, and aid in the adherence of the epithelial basement membrane in the individual. Without wishing to be bound by theory, it is believed that ultimately, this will lead to increased dermal-epidermal stability for those suffering from epidermolysis bullosa, treating existing wounds, and preventing or delaying reformation of wounds in the treated areas.

Isolated Polynucleotides and Polypeptides

Certain aspects of the present disclosure relate to isolated polynucleotides comprising a polynucleotide encoding a Collagen alpha-1 (VII) chain polypeptide. Other aspects of the present disclosure relate to isolated polynucleotides comprising a polynucleotide encoding a Lysyl hydroxylase 3 polypeptide. Other aspects of the present disclosure relate to isolated polynucleotides comprising a polynucleotide encoding a Keratin type I cytoskeletal 17 polypeptide.

Other aspects of the present disclosure relate to isolated polynucleotides comprising a polynucleotide encoding a Collagen alpha-1 (VII) chain polypeptide and a polynucleotide encoding a Lysyl hydroxylase 3 polypeptide separated by a polynucleotide encoding a linker polypeptide. In some embodiments, the isolated polynucleotide encodes a chimeric polypeptide comprising a Collagen alpha-1 (VII) chain polypeptide, a linker polypeptide, and a Lysyl hydroxylase 3 polypeptide.

In some embodiments, the polynucleotide encoding a linker polypeptide further comprises a polynucleotide encoding one or more furin cleavage sites. In some embodiments, the one or more furin cleavage sites are encoded upstream of the linker polypeptide. In some embodiments, the one or more furin cleavage sites are encoded downstream of the linker polypeptide. In some embodiments, the one or more furin cleavage sites are encoded upstream of a T2A linker polypeptide. In some embodiments, the one or more furin cleavage sites are encoded downstream of a T2A linker polypeptide. In some embodiments, the one or more furin cleavage sites are encoded upstream of a P2A linker polypeptide. In some embodiments, the one or more furin cleavage sites are encoded downstream of a P2A linker polypeptide. In some embodiments, the one or more furin cleavage sites are encoded upstream of an E2A linker polypeptide. In some embodiments, the one or more furin cleavage sites are encoded downstream of an E2A linker polypeptide. In some embodiments, the one or more furin cleavage sites are encoded upstream of an F2A linker polypeptide. In some embodiments, the one or more furin cleavage sites are encoded downstream of an F2A linker polypeptide.

An example of a polynucleotide encoding a Collagen alpha-1 (VII) chain polypeptide is SEQ ID NO: 1. Polynucleotides encoding a Collagen alpha-1 (VII) chain polypeptide also include polynucleotides having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 1.

An example of a polynucleotide encoding a Lysyl hydroxylase 3 polypeptide is SEQ ID NO: 3. Polynucleotides encoding a Lysyl hydroxylase 3 polypeptide also include polynucleotides having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 3.

An example of a polynucleotide encoding a Keratin type I cytoskeletal 17 polypeptide is SEQ ID NO: 29. Polynucleotides encoding a Keratin type I cytoskeletal 17 polypeptide also include polynucleotides having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 29.

Examples of polynucleotides encoding linker polypeptides are SEQ ID NO: 5, SEQ ID NO: 7, SEQ ID NO: 9, and SEQ ID NO: 11. Polynucleotides encoding linker polypeptides also include polynucleotides having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 5, SEQ ID NO: 7, SEQ ID NO: 9, or SEQ ID NO: 11.

Examples of polynucleotides that encode chimeric polypeptides comprising a Collagen alpha-1 (VII) chain polypeptide, a linker polypeptide, and a Lysyl hydroxylase 3 polypeptide are SEQ ID NO: 13, SEQ ID NO: 15, SEQ ID NO: 17, SEQ ID NO: 19, SEQ ID NO: 21, SEQ ID NO: 23, SEQ ID NO: 25, and SEQ ID NO: 27. Polynucleotides that encode chimeric polypeptides also include polynucleotides having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 13, SEQ ID NO: 15, SEQ ID NO: 17, SEQ ID NO: 19, SEQ ID NO: 21, SEQ ID NO: 23, SEQ ID NO: 25, or SEQ ID NO: 27.

Further aspects of the present disclosure relate to one or more (e.g., one or more, two or more, three or more, etc.) isolated polynucleotides described herein contained within a vector. In some embodiments, the vector is an adenoviral vector, an adeno-associated viral vector, a retroviral vector, a lentiviral vector, a herpes simplex viral vector, a vaccinia viral vector, or any hybrid viral vector thereof. In some embodiments, the vector is a herpes simplex viral vector. In some embodiments, the vector comprises one or more (e.g., one or more, two or more, three or more, four or more, five or more, etc.) transgenes.

In some embodiments, the herpes simplex virus vector is a herpes virus amplicon vector. In some embodiments, the vector is an HSV-1 amplicon. In some embodiments, the vector is an HSV-1 hybrid amplicon. Examples of HSV-1 hybrid amplicons may include, but are not limited to, HSV/AAV hybrid amplicons, HSV/EBV hybrid amplicons, HSV/EBV/RV hybrid amplicons, and HSV/Sleeping Beauty hybrid amplicons. In some embodiments, the vector is an HSV/AAV hybrid amplicon. In some embodiments, the vector is an HSV/EBV hybrid amplicon. In some embodiments, the vector is an HSV/EBV/RV hybrid amplicon. In some embodiments, the vector is an HSV/Sleeping Beauty hybrid amplicons. Further aspects of the present disclosure relate to a method of producing a viral delivery vehicle containing one or more polynucleotides described herein. In some embodiments, the method comprises contacting a host cell with one or more viral vectors containing one or more isolated polynucleotides described herein, and collecting the viral delivery vehicle generated by the host cell. Methods of culturing cells and contacting cells with one or more viral vectors of interest (e.g. by transduction or transfection) are well known to one of skill in the art.

In some embodiments, the herpes simplex virus vector is a recombinant herpes simplex virus genome. In some embodiments, the recombinant herpes simplex virus genome has been engineered to decrease or eliminate expression of one or more toxic herpes simplex virus genes. In some embodiments, the recombinant herpes simplex virus genome comprises an inactivating mutation. Examples of inactivating mutations may include, but are not limited to, deletions (e.g., deletion of the coding sequence of a gene or deletion of one or more of the gene's transcriptional regulatory elements), insertions, point mutations, and rearrangements. In some embodiments, the recombinant herpes simplex virus genome comprises an inactivating mutation in one or more immediate early genes. In some embodiments, the recombinant herpes simplex virus genome comprises an inactivating mutation in at least one, at least two, at least three, at least four, at least five, at least six, at least seven, or all eight of the ICP0, ICP4, ICP22, ICP27, ICP47, tk, UL41 and UL55 herpes simplex virus genes. In some embodiments, the recombinant herpes simplex virus genome comprises an inactivating mutation is in the ICP0 gene. In some embodiments, the recombinant herpes simplex virus genome comprises an inactivating mutation is in the ICP4 gene. In some embodiments, the recombinant herpes simplex virus genome comprises an inactivating mutation is in the ICP22 gene. In some embodiments, the recombinant herpes simplex virus genome comprises an inactivating mutation is in the ICP27 gene. In some embodiments, the recombinant herpes simplex virus genome comprises an inactivating mutation is in the ICP4, ICP22, and ICP27 genes. In some embodiments, the recombinant herpes simplex virus genome comprises an inactivating mutation in the ICP4, ICP27, and UL55 genes. In some embodiments, the recombinant herpes simplex virus genome comprises an inactivating mutation in the ICP4, ICP22, ICP27, ICP47, and UL55 genes. In some embodiments, the recombinant herpes simplex virus genome comprises an inactivating mutation is in the ICP0, ICP4, ICP22, and ICP27 genes. In some embodiments, the recombinant herpes simplex virus genome is a recombinant HSV-1 genome, a recombinant HSV-2 genome, or any derivatives thereof. In some embodiments, the recombinant herpes simplex virus genome is a recombinant HSV-1 genome. In some embodiments, the recombinant herpes simplex virus genome is a recombinant HSV-2 genome.

In some embodiments, an isolated recombinant herpes simplex virus genome comprises one or more (e.g., one or more, two or more, three or more, four or more, five or more, etc.) polynucleotides (e.g., transgenes) of the present disclosure within one, two, three, four, five, six, seven or more viral gene loci. Examples of suitable viral loci may include, without limitation, the ICP0, ICP4, ICP22, ICP27, ICP47, tk, UL41 and UL55 herpes simplex viral gene loci. In some embodiments, an isolated recombinant herpes simplex virus genome comprises one or more polynucleotide of the present disclosure within one or more of the viral ICP4 gene loci (e.g., a recombinant virus carrying a polynucleotide encoding Col7 in one or both of the ICP4 loci, a recombinant virus carrying a polynucleotide encoding LH3 in one or both of the ICP4 loci, a recombinant virus carrying a polynucleotide encoding KRT17 in one or both of the ICP4 loci, a recombinant virus carrying a polynucleotide encoding Col7 in one of the ICP4 loci and a polynucleotide encoding KRT17 in the other ICP4 loci, a recombinant virus carrying a polynucleotide encoding Col7 in one of the ICP4 loci and a polynucleotide encoding LH3 in the other ICP4 loci, a recombinant virus carrying a polynucleotide encoding LH3 in one of the ICP4 loci and a polynucleotide encoding KRT17 in the other ICP4 loci, etc.). In some embodiments, an isolated recombinant herpes simplex virus genome comprises one or more polynucleotide of the present disclosure within the viral UL41 gene locus. In some embodiments, an isolated recombinant herpes simplex virus genome comprises one or more polynucleotide of the present disclosure within the viral ICP47 gene locus. In some embodiments, an isolated recombinant herpes simplex virus genome comprises one or more polynucleotides of the present disclosure within one or more of the viral ICP4 gene loci, and one or more polynucleotide of the present disclosure within the viral UL41 gene locus (e.g., a recombinant virus carrying a polynucleotide encoding Col7 in one or both of the ICP4 loci and a polynucleotide encoding LH3 in the UL41 locus, a recombinant virus carrying a polynucleotide encoding Col7 in one or both of the ICP4 loci and a polynucleotide encoding Col7 in the UL41 locus, a recombinant virus carrying a polynucleotide encoding Col7 in one or both of the ICP4 loci and a polynucleotide encoding KRT17 in the UL41 locus, a recombinant virus carrying a polynucleotide encoding LH3 in one or both of the ICP4 loci and a polynucleotide encoding LH3 in the UL41 locus, a recombinant virus carrying a polynucleotide encoding LH3 in one or both of the ICP4 loci and a polynucleotide encoding Col7 in the UL41 locus, a recombinant virus carrying a polynucleotide encoding LH3 in one or both of the ICP4 loci and a polynucleotide encoding KRT17 in the UL41 locus, a recombinant virus carrying a polynucleotide encoding KRT17 in one or both of the ICP4 loci and a polynucleotide encoding LH3 in the UL41 locus, a recombinant virus carrying a polynucleotide encoding KRT17 in one or both of the ICP4 loci and a polynucleotide encoding Col7 in the UL41 locus, a recombinant virus carrying a polynucleotide encoding KRT17 in one or both of the ICP4 loci and a polynucleotide encoding KRT17 in the UL41 locus, etc.).

In some aspects, the isolated polynucleotides described herein are contained within a synthetic mRNA. In some embodiments, the synthetic mRNA comprises one or more modified ribonucleotides.

Certain aspects of the present disclosure relate to isolated polypeptides comprising a Collagen alpha-1 (VII) chain polypeptide. Other aspects of the present disclosure relate to isolated polypeptides comprising a Lysyl hydroxylase 3 polypeptide. Other aspects of the present disclosure relate to isolated polypeptides comprising a Keratin type I cytoskeletal 17 polypeptide.

Other aspects of the present disclosure relate to isolated chimeric polypeptides comprising a Collagen alpha-1 (VII) chain polypeptide and a Lysyl hydroxylase 3 polypeptide separated by a linker polypeptide.

In some embodiments, the linker polypeptide further comprises one or more furin cleavage sites. In some embodiments, the amino acid sequence of the furin cleavage site is the same or substantially similar to the sequence of the canonical furin cleavage site (Arg-X-(Arg/Lys)-Arg). In some embodiments, the one or more furin cleavage sites are at the N-terminus of the linker polypeptide. In some embodiments, the one or more furin cleavage sites are at the C-terminus of the linker polypeptide. In some embodiments, the linker polypeptide comprises, from N-terminus to C-terminus, one or more furin cleavage sites and a T2A linker polypeptide. In some embodiments, the linker polypeptide comprises, from N-terminus to C-terminus, a T2A linker polypeptide and one or more furin cleavage sites. In some embodiments, the linker polypeptide comprises, from N-terminus to C-terminus, one or more furin cleavage sites and a P2A linker polypeptide. In some embodiments, the linker polypeptide comprises, from N-terminus to C-terminus, a P2A linker polypeptide and one or more furin cleavage sites. In some embodiments, the linker polypeptide comprises, from N-terminus to C-terminus, one or more furin cleavage sites and an E2A linker polypeptide. In some embodiments, the linker polypeptide comprises, from N-terminus to C-terminus, an E2A linker polypeptide and one or more furin cleavage sites. In some embodiments, the linker polypeptide comprises, from N-terminus to C-terminus, one or more furin cleavage sites and an F2A linker polypeptide. In some embodiments, the linker polypeptide comprises, from N-terminus to C-terminus, an F2A linker polypeptide and one or more furin cleavage sites.

In some aspects, the isolated polypeptide comprising a Collagen alpha-1 (VII) chain polypeptide comprises the amino acid sequence of SEQ ID NO: 2. Isolated polypeptides may also comprise a Collagen alpha-1 (VII) chain polypeptide containing an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 2.

In some aspects, the isolated polypeptide comprising a Lysyl hydroxylase 3 polypeptide comprises the amino acid sequence of SEQ ID NO: 4. Isolated polypeptides may also comprise a Lysyl hydroxylase 3 polypeptide containing an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 4.

In some aspects, the isolated polypeptide comprising a Keratin type I cytoskeletal 17 polypeptide comprises the amino acid sequence of SEQ ID NO: 30. Isolated polypeptides may also comprise a Keratin type I cytoskeletal 17 polypeptide containing an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 30.

In some aspects, the chimeric polypeptide comprises a Collagen alpha-1 (VII) chain polypeptide containing the amino acid sequence of SEQ ID NO: 2. Chimeric polypeptides may also comprise a Collagen alpha-1 (VII) chain polypeptide containing an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 2.

In some aspects, the chimeric polypeptide comprises a Lysyl hydroxylase 3 polypeptide containing the amino acid sequence of SEQ ID NO: 4. Chimeric polypeptides may also comprise a Lysyl hydroxylase 3 polypeptide containing an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 4.

In some aspects, the chimeric polypeptide comprises a linker polypeptide containing the amino acid sequence of SEQ ID NO: 6, SEQ ID NO: 8, SEQ ID NO: 10 or SEQ ID NO: 12. Chimeric polypeptides may also comprise a linker polypeptide containing an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 6, SEQ ID NO: 8, SEQ ID NO: 10 or SEQ ID NO: 12.

In some aspects, the chimeric polypeptide is the amino acid sequence of SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28. Chimeric polypeptides may also be an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to the sequence of SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28.

Host Cells

Certain aspects of the present disclosure relate to one or more host cells comprising a vector comprising a polynucleotide described herein. In some embodiments, the vector is any of the isolated recombinant herpes simplex virus vectors described herein. In some embodiments, the host cells are bacterial cells (e.g., E. coli cells, etc.). In some embodiments, the host cells are fungal cells (e.g., S. cerevisiae cells, etc.). In some embodiments, the host cells are insect cells (e.g., S2 cells, etc.). In some embodiments, the host cells are mammalian cells. In some embodiments, the host cells are cells from a cell line. Examples of suitable host cells or cell lines may include, but are not limited to, 293, HeLa, SH-Sy5y, Hep G2, CACO-2, A549, L929, 3T3, K562, CHO-K1, MDCK, HUVEC, Vero, N20, COS-7, PSN1, VCaP, CHO cells, and the like. In some embodiments, the vector is an adenoviral vector, an adeno-associated viral vector, a retroviral vector, a lentiviral vector, a herpes simplex viral vector, a vaccinia viral vector, or any hybrid viral vectors thereof. In some embodiments, the vector is a herpes simplex viral vector. In some embodiments, the vector is an HSV-1 amplicon or HSV-1 hybrid amplicon. In some embodiments, the host cells comprise a helper virus. In some embodiments, the host cells comprising a helper virus are contacted with a vector described herein. In some embodiments, contacting a host cell comprising a helper virus with an HSV-1 amplicon or HSV-1 hybrid amplicon described herein results in the production of a virus comprising one or more vectors described herein. In some embodiments, the virus is collected from the supernatant of the contacted host cell. Methods of generating virus by contacting host cells comprising a helper virus with an HSV-1 amplicon or HSV-1/hybrid amplicon are known in the art. In some embodiments, the host cell is a complementing host cell. In some embodiments, the complementing host cell expresses one or more genes that are inactivated in any of the viral vectors described herein. In some embodiments, the complementing host cell is contacted with a recombinant herpes simplex virus genome described herein. In some embodiments, contacting a complementing host cell with a recombinant herpes simplex virus genome described herein results in the production of a virus comprising one or more vectors described herein. In some embodiments, the virus is collected from the supernatant of the contacted host cell. Methods of generating virus by contacting complementing host cells with a recombinant herpes simplex virus are generally described in U.S. Pat. No. 10,174,341 B2, which is incorporated herein by reference in its entirety for all purposes.

Articles of Manufacture or Kits

Certain aspects of the present disclosure relate to an article of manufacture or a kit comprising a pharmaceutical composition described herein. In some embodiments, the article of manufacture or kit comprises a package insert comprising instructions for administering the pharmaceutical composition to provide prophylactic, palliative, or therapeutic relief of a wound, disorder, or disease of the skin in a subject.

In some embodiments, the delivery vehicle comprising one or more polynucleotides described herein and pharmaceutically acceptable carrier are in the same container or separate containers. Suitable containers include, for example, bottles, vials, bags and syringes. The container may be formed from a variety of materials such as glass, plastic (such as polyvinyl chloride or polyolefin), or metal alloy (such as stainless steel or hastelloy). In some embodiments, the container comprises a label on, or associated with the container, wherein the label indicates directions for use. The article of manufacture or kit may further include other materials desirable from a commercial and user standpoint, including other buffers, diluents, filters, and the like.

Enumerated Embodiments

Embodiment 1: A pharmaceutical composition comprising:
  a) a virus comprising a vector, wherein the vector comprises one or more transgenes encoding a polypeptide selected from the group consisting of a Collagen alpha-1 (VII) chain polypeptide, a Lysyl hydroxylase 3 polypeptide, and a chimeric polypeptide thereof, and
  b) a pharmaceutically acceptable carrier.

Embodiment 2: The pharmaceutical composition of embodiment 1, wherein the virus is an adenovirus, adeno-associated virus, retrovirus, lentivirus, sendai virus, herpes simplex virus, vaccinia virus, or any hybrid virus thereof.

Embodiment 3: The pharmaceutical composition of embodiment 1, wherein the virus is a herpes simplex virus (HSV).

Embodiment 4: The pharmaceutical composition of any of embodiments 1 to 3, wherein the virus is replication-defective.

Embodiment 5: The pharmaceutical composition of embodiment 3, wherein the herpes simplex virus is a herpes simplex type 1 virus, a herpes simplex type 2 virus, or any derivatives thereof.

Embodiment 6: The pharmaceutical composition of embodiment 3, wherein the herpes simplex virus comprises a modified envelope.

Embodiment 7: The pharmaceutical composition of embodiment 6, wherein the modified envelope alters the herpes simplex virus tissue tropism relative to a wild-type herpes simplex virus.

Embodiment 8: The pharmaceutical composition of embodiment 6, wherein the modified envelope comprises a mutant herpes simplex virus glycoprotein.

Embodiment 9: The pharmaceutical composition of embodiment 1, wherein the vector is an HSV-1 amplicon or an HSV-1 hybrid amplicon.

Embodiment 10: The pharmaceutical composition of embodiment 9, wherein the HSV-1 hybrid amplicon is an HSV/AAV hybrid amplicon, an HSV/EBV hybrid amplicon, and HSV/EBV/RV hybrid amplicon, or an HSV/Sleeping Beauty hybrid amplicon.

Embodiment 11: The pharmaceutical composition of embodiment 1, wherein the vector is a recombinant herpes simplex virus genome.

Embodiment 12: The pharmaceutical composition of embodiment 11, wherein the recombinant herpes simplex virus genome is a recombinant HSV-1 genome, a recombinant HSV-2 genome, or any derivatives thereof.

Embodiment 13: The pharmaceutical composition of embodiment 11 or 12, wherein the recombinant herpes simplex virus genome comprises an inactivating mutation in an immediate early herpes simplex virus gene.

Embodiment 14: The pharmaceutical composition of embodiment 13, wherein the herpes simplex virus gene is selected from the group consisting of ICP0, ICP4, ICP22, ICP27, ICP47, tk, UL41, and UL55.

Embodiment 15: The pharmaceutical composition of any of embodiments 11 to 14, wherein the recombinant herpes simplex virus genome comprises an inactivating mutation in the ICP4 and ICP22 genes.

Embodiment 16: The pharmaceutical composition of any of embodiments 11 to 14, wherein the recombinant herpes simplex virus genome comprises an inactivating mutation in the ICP0 and ICP4 genes.

Embodiment 17: The pharmaceutical composition of embodiment 15 or embodiment 16, wherein the recombinant herpes simplex virus genome comprises an inactivating mutation in the ICP0, ICP4, and ICP22 genes.

Embodiment 18: The pharmaceutical composition of any of embodiments 15 to 17, wherein the recombinant herpes simplex virus genome comprises an inactivating mutation in the ICP0, ICP4, ICP22, and ICP27 genes.

Embodiment 19: The pharmaceutical composition of any of embodiments 15 to 18, wherein the recombinant herpes simplex virus genome comprises an inactivating mutation in the ICP0, ICP4, ICP22, ICP27, and UL55 genes.

Embodiment 20: The pharmaceutical composition of any of embodiments 15 to 18, wherein the inactivating mutation is a deletion of the coding sequence of the genes.

Embodiment 21: The pharmaceutical composition of any of embodiments 15 to 20, further comprising an inactivating mutation in the ICP47 gene.

Embodiment 22: The pharmaceutical composition of any of embodiments 11 to 21, further comprising an inactivating mutation in the UL41 gene.

Embodiment 23: The pharmaceutical composition of any of embodiments 11 to 22, wherein the recombinant herpes simplex virus genome comprises the one or more transgenes within one or more viral gene loci.

Embodiment 24: The pharmaceutical composition of any of embodiments 11 to 23, wherein the recombinant herpes simplex virus genome comprises the one or more transgenes within one or more of the ICP4 viral gene loci.

Embodiment 25: The pharmaceutical composition of any of embodiments 11 to 24, wherein the recombinant herpes simplex virus genome comprises the one or more transgenes within the UL41 viral gene locus.

Embodiment 26: The pharmaceutical composition of embodiment 1, wherein the vector is capable of replicating within a target cell when delivered into said target cell.

Embodiment 27: The pharmaceutical composition of embodiment 1, wherein the pharmaceutically acceptable carrier is suitable for topical or transdermal administration.

Embodiment 28: The pharmaceutical composition of embodiment 1, wherein the one or more transgenes comprises an miRNA binding site.

Embodiment 29: The pharmaceutical composition of embodiment 1, wherein the one or more transgenes are operably linked to one or more heterologous promoters.

Embodiment 30: The pharmaceutical composition of embodiment 29, wherein the one or more heterologous promoters are selected from the group consisting of the human cytomegalovirus (HCMV) immediate early promoter, the elongation factor-1 (EF1) promoter, and any combinations thereof.

Embodiment 31: The pharmaceutical composition of embodiment 1, wherein the vector comprises a transgene encoding a Collagen alpha-1 (VII) chain polypeptide.

Embodiment 32: The pharmaceutical composition of embodiment 1, wherein the vector comprises two transgenes, wherein each transgene encodes a Collagen alpha-1 (VII) chain polypeptide.

Embodiment 33: The pharmaceutical composition of embodiment 1, wherein the Collagen alpha-1 (VII) chain polypeptide has at least 80% sequence identity to the sequence of SEQ ID NO: 2.

Embodiment 34: The pharmaceutical composition of embodiment 1, wherein the collagen alpha-1 (VII) chain polypeptide is a fragment, wherein the fragment has at least 100 consecutive amino acids of SEQ ID NO: 2.

Embodiment 35: The pharmaceutical composition of embodiment 1, wherein the Collagen alpha-1 (VII) chain polypeptide enhances, increases, augments, and/or supplements anchoring fibril formation of a subject when the polypeptide is expressed in one or more target cells of the subject.

Embodiment 36: The pharmaceutical composition of embodiment 1, wherein the Collagen alpha-1 (VII) chain polypeptide enhances, increases, augments, and/or supplements epithelial basement membrane organization and/or epithelial basement adherence of a subject when the polypeptide is expressed in one or more target cells of the subject.

Embodiment 37: The pharmaceutical composition of embodiment 1, wherein the Lysyl hydroxylase 3 polypeptide has at least 80% sequence identity to the sequence of SEQ ID NO: 4.

Embodiment 38: The pharmaceutical composition of embodiment 1, wherein the Lysyl hydroxylase 3 polypeptide is a fragment, wherein the fragment has at least 100 consecutive amino acids of SEQ ID NO: 4.

Embodiment 39: The pharmaceutical composition of embodiment 1, wherein the Lysyl hydroxylase 3 polypeptide enhances, increases, augments, and/or supplements the formation of hydroxylysine residues on one or more collagen polypeptides of a subject when the Lysyl hydroxylase 3 polypeptide is expressed in one or more target cells of the subject.

Embodiment 40: The pharmaceutical composition of embodiment 1, wherein the Lysyl hydroxylase 3 polypeptide enhances, increases, augments, and/or supplements anchoring fibril formation, epithelial basement membrane organization, and/or epithelial basement adherence of a subject when the polypeptide is expressed in one or more target cells of the subject.

Embodiment 41: The pharmaceutical composition of embodiment 1, wherein the vector comprises at least a first transgene and a second transgene.

Embodiment 42: The pharmaceutical composition of embodiment 41, wherein the first transgene encodes a Collagen alpha-1 (VII) chain polypeptide and the second transgene encodes a Lysyl hydroxylase 3 polypeptide.

Embodiment 43: The pharmaceutical composition of embodiment 1, wherein the vector comprises a transgene that is polycistronic.

Embodiment 44: The pharmaceutical composition of embodiment 43, wherein the polycistronic transgene encodes a Collagen alpha-1 (VII) chain polypeptide on a first open reading frame (ORF) and a Lysyl hydroxylase 3 polypeptide on a second open reading frame (ORF).

Embodiment 45: The pharmaceutical composition of embodiment 44, wherein the first and second ORFs are separated by an internal ribosomal entry site (IRES).

Embodiment 46: The pharmaceutical composition of any of embodiments 42 to 45, wherein the Collagen alpha-1 (VII) chain polypeptide and the Lysyl hydroxylase 3 polypeptide are at about an equimolar ratio when the polypeptides are expressed in one or more target cells of a subject.

Embodiment 47: The pharmaceutical composition of any of embodiments 42 to 45, wherein the Collagen alpha-1 (VII) chain polypeptide and the Lysyl hydroxylase 3 polypeptide enhance, increase, augment, and/or supplement anchoring fibril formation, epithelial basement membrane organization, and/or epithelial basement adherence of a subject when the polypeptides are expressed in one or more target cells of the subject.

Embodiment 48: The pharmaceutical composition of embodiment 1, wherein the chimeric polypeptide comprises a linker polypeptide between the Collagen alpha-1 (VII) chain polypeptide and the Lysyl hydroxylase 3 polypeptide.

Embodiment 49: The pharmaceutical composition of embodiment 48, wherein the linker polypeptide is a T2A, P2A, E2A, or F2A linker polypeptide.

Embodiment 50: The pharmaceutical composition of embodiment 48 or 49, wherein the linker polypeptide has at least 80% sequence identity to the sequence of SEQ ID NO: 6, SEQ ID NO: 8, SEQ ID NO: 10 or SEQ ID NO: 12.

Embodiment 51: The pharmaceutical composition of any of embodiments 48 to 50, wherein the chimeric polypeptide has at least 80% sequence identity to the sequence of SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28.

Embodiment 52: The pharmaceutical composition of any of embodiments 48 to 51, wherein the chimeric polypeptide enhances, increases, augments, and/or supplements anchoring fibril formation, epithelial basement membrane organization, and/or epithelial basement adherence of a subject when the polypeptide is expressed in one or more target cells of the subject.

Embodiment 53: A method of providing prophylactic, palliative, or therapeutic relief of a wound, disorder, or disease of the skin in a subject, the method comprising topically or transdermally administering a pharmaceutical composition capable of enhancing, increasing, augmenting, and/or supplementing the levels of a Collagen alpha-1 (VII) chain polypeptide and/or a Lysyl hydroxylase 3 polypeptide in one or more cells of the subject.

Embodiment 54: The method of embodiment 53, wherein the pharmaceutical composition comprises:

a) a virus comprising a vector, wherein the vector comprises one or more transgenes encoding a polypeptide selected from the group consisting of a Collagen alpha-1 (VII) chain polypeptide, a Lysyl hydroxylase 3 polypeptide, and a chimeric polypeptide thereof, and b) a pharmaceutically acceptable carrier.

Embodiment 55: The method of embodiment 54, wherein the virus is an adenovirus, adeno-associated virus, retrovirus, lentivirus, sendai virus, herpes simplex virus, vaccinia virus, or any hybrid virus thereof.

Embodiment 56: The method of embodiment 54, wherein the virus is a herpes simplex virus (HSV).

Embodiment 57: The method of any of embodiments 54 to 56, wherein the virus is replication-defective.

Embodiment 58: The method of embodiment 56, wherein the herpes simplex virus is a herpes simplex type 1 virus, a herpes simplex type 2 virus, or any derivatives thereof.

Embodiment 59: The method of embodiment 56, wherein the herpes simplex virus comprises a modified envelope.

Embodiment 60: The method of embodiment 59, wherein the modified envelope alters the herpes simplex virus tissue tropism relative to a wild-type herpes simplex virus.

Embodiment 61: The method of embodiment 59, wherein the modified envelope comprises a mutant herpes simplex virus glycoprotein.

Embodiment 62: The method of embodiment 54, wherein the vector is an HSV-1 amplicon or an HSV-1 hybrid amplicon.

Embodiment 63: The method of embodiment 62, wherein the HSV-1 hybrid amplicon is an HSV/AAV hybrid amplicon, an HSV/EBV hybrid amplicon, and HSV/EBV/RV hybrid amplicon, or an HSV/Sleeping Beauty hybrid amplicon.

Embodiment 64: The method of embodiment 54, wherein the vector is a recombinant herpes simplex virus genome.

Embodiment 65: The method of embodiment 64, wherein the recombinant herpes simplex virus genome is a recombinant HSV-1 genome, a recombinant HSV-2 genome, or any derivatives thereof.

Embodiment 66: The method of embodiment 64 or 65, wherein the recombinant herpes simplex virus genome comprises an inactivating mutation in an immediate early herpes simplex virus gene.

Embodiment 67: The method of embodiment 66, wherein the herpes simplex virus gene is selected from the group consisting of ICP0, ICP4, ICP22, ICP27, ICP47, tk, UL41, and UL55.

Embodiment 68: The method of any of embodiments 64 to 67, wherein the recombinant herpes simplex virus genome comprises an inactivating mutation in the ICP4 and ICP22 genes.

Embodiment 69: The method of any of embodiments 64 to 67, wherein the recombinant herpes simplex virus genome comprises an inactivating mutation in the ICP0 and ICP4 genes.

Embodiment 70: The method of embodiment 68 or 69, wherein the recombinant herpes simplex virus genome comprises an inactivating mutation in the ICP0, ICP4, and ICP22 genes.

Embodiment 71: The method of any of embodiments 68 to 70, wherein the recombinant herpes simplex virus genome comprises an inactivating mutation in the ICP0, ICP4, ICP22, and ICP27 genes.

Embodiment 72: The method of any of embodiments 68 to 71, wherein the recombinant herpes simplex virus genome comprises an inactivating mutation in the ICP0, ICP4, ICP22, ICP27, and UL55 genes.

Embodiment 73: The method of any of embodiments 68 to 72, wherein the inactivating mutation is a deletion of the coding sequence of the genes.

Embodiment 74: The method of any of embodiments 68 to 73, further comprising an inactivating mutation in the ICP47 gene.

Embodiment 75: The method of any of embodiments 64 to 74, further comprising an inactivating mutation in the UL41 gene.

Embodiment 76: The method of any of embodiments 64 to 75, wherein the recombinant herpes simplex virus genome comprises the one or more transgenes within one or more viral gene loci.

Embodiment 77: The method of any of embodiments 64 to 76, wherein the recombinant herpes simplex virus genome comprises the one or more transgenes within one or more of the ICP4 viral gene loci.

Embodiment 78: The method of any of embodiments 64 to 77, wherein the recombinant herpes simplex virus genome comprises the one or more transgenes within the UL41 viral gene locus.

Embodiment 79: The method of embodiment 54, wherein the vector is capable of replicating within a target cell when delivered into said target cell.

Embodiment 80: The method of embodiment 54, wherein the pharmaceutically acceptable carrier is suitable for topical or transdermal administration.

Embodiment 81: The method of embodiment 54, wherein the one or more transgenes comprises an miRNA binding site.

Embodiment 82: The method of embodiment 54, wherein the one or more transgenes are operably linked to one or more heterologous promoters.

Embodiment 83: The method of embodiment 82, wherein the one or more heterologous promoters are selected from the group consisting of the human cytomegalovirus (HCMV) immediate early promoter, the elongation factor-1 (EF1) promoter, and any combinations thereof.

Embodiment 84: The method of embodiment 54, wherein the vector comprises a transgene encoding a Collagen alpha-1 (VII) chain polypeptide.

Embodiment 85: The method of embodiment 54, wherein the vector comprises two transgenes, wherein each transgene encodes a Collagen alpha-1 (VII) chain polypeptide.

Embodiment 86: The method of embodiment 54, wherein the Collagen alpha-1 (VII) chain polypeptide has at least 80% sequence identity to the sequence of SEQ ID NO: 2.

Embodiment 87: The method of embodiment 54, wherein the Collagen alpha-1 (VII) chain polypeptide is a fragment, wherein the fragment has at least 100 consecutive amino acids of SEQ ID NO: 2.

Embodiment 88: The method of embodiment 54, wherein the Collagen alpha-1 (VII) chain polypeptide enhances, increases, augments, and/or supplements anchoring fibril formation of a subject when the polypeptide is expressed in one or more target cells of the subject.

Embodiment 89: The method of embodiment 54, wherein the Collagen alpha-1 (VII) chain polypeptide enhances, increases, augments, and/or supplements epithelial basement membrane organization and/or epithelial basement adherence of a subject when the polypeptide is expressed in one or more target cells of the subject.

Embodiment 90: The method of embodiment 54, wherein the Lysyl hydroxylase 3 polypeptide has at least 80% sequence identity to the sequence of SEQ ID NO: 4.

Embodiment 91: The method of embodiment 54, wherein the Lysyl hydroxylase 3 polypeptide is a fragment, wherein the fragment has at least 100 consecutive amino acids of SEQ ID NO: 4.

Embodiment 92: The method of embodiment 54, wherein the Lysyl hydroxylase 3 polypeptide enhances, increases, augments, and/or supplements the formation of hydroxylysine residues on one or more collagen polypeptides of a subject when the Lysyl hydroxylase 3 polypeptide is expressed in one or more target cells of the subject.

Embodiment 93: The method of embodiment 54, wherein the Lysyl hydroxylase 3 polypeptide enhances, increases, augments, and/or supplements anchoring fibril formation, epithelial basement membrane organization, and/or epithelial basement adherence of a subject when the polypeptide is expressed in one or more target cells of the subject.

Embodiment 94: The method of embodiment 54, wherein the vector comprises at least a first transgene and a second transgene.

Embodiment 95: The method of embodiment 94, wherein the first transgene encodes a Collagen alpha-1 (VII) chain polypeptide and the second transgene encodes a Lysyl hydroxylase 3 polypeptide.

Embodiment 96: The method of embodiment 54, wherein the vector comprises a transgene that is polycistronic.

Embodiment 97: The method of embodiment 96, wherein the polycistronic transgene encodes a Collagen alpha-1 (VII) chain polypeptide on a first open reading frame (ORF) and a Lysyl hydroxylase 3 polypeptide on a second open reading frame (ORF).

Embodiment 98: The method of embodiment 97, wherein the first and second ORFs are separated by an internal ribosomal entry site (IRES).

Embodiment 99: The method of any of embodiments 95 to 98, wherein the Collagen alpha-1 (VII) chain polypeptide and the Lysyl hydroxylase 3 polypeptide are at about an equimolar ratio when the polypeptides are expressed in one or more target cells of a subject.

Embodiment 100: The method of any of embodiments 95 to 98, wherein the Collagen alpha-1 (VII) chain polypeptide and the Lysyl hydroxylase 3 polypeptide enhance, increase, augment, and/or supplement anchoring fibril formation, epithelial basement membrane organization, and/or epithelial basement adherence of a subject when the polypeptides are expressed in one or more target cells of the subject.

Embodiment 101: The method of embodiment 54, wherein the chimeric polypeptide comprises a linker polypeptide between the Collagen alpha-1 (VII) chain polypeptide and the Lysyl hydroxylase 3 polypeptide.

Embodiment 102: The method of embodiment 101, wherein the linker polypeptide is a T2A, P2A, E2A, or F2A linker polypeptide.

Embodiment 103: The method of embodiment 101 or 102, wherein the linker polypeptide has at least 80% sequence identity to the sequence of SEQ ID NO: 6, SEQ ID NO: 8, SEQ ID NO: 10 or SEQ ID NO: 12.

Embodiment 104: The method of any of embodiments 101 to 103, wherein the chimeric polypeptide has at least 80% sequence identity to the sequence of SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28.

Embodiment 105: The method of any of embodiments 101 to 104, wherein the chimeric polypeptide enhances, increases, augments, and/or supplements anchoring fibril formation, epithelial basement membrane organization, and/or epithelial basement adherence of a subject when the polypeptide is expressed in one or more target cells of the subject.

Embodiment 106: The method of embodiment 53, wherein the pharmaceutical composition is administered one, two three, four, five or more times per day.

Embodiment 107: The method of embodiment 53, wherein the pharmaceutical composition is administered to one or more affected and/or unaffected areas of the subject.

Embodiment 108: The method of embodiment 53, wherein the disease or disorder of the skin is one or more of epidermolysis bullosa, skin cancer, psoriasis, lichen planus, lupus, rosacea, eczema, cutaneous candidiasis, cellulitis, impetigo, decubitus ulcers, erysipelas, ichthyosis vulgaris, dermatomyositis, acrodermatitis, stasis dermatitis, nethertons syndrome, epidermolysis bullosa simplex (LAMB3 gene), autosomal recessive congenital ichthyosis, xeroderma pigmentosa, and pemphigoid.

Embodiment 109: An isolated chimeric polypeptide, wherein the isolated chimeric polypeptide comprises;

a) a Collagen alpha-1 (VII) chain polypeptide;

b) a Lysyl hydroxylase 3 polypeptide; and c) a linker polypeptide;

wherein the Collagen alpha-1 (VII) chain polypeptide and the Lysyl hydroxylase 3 polypeptide are separated by the linker polypeptide.

Embodiment 110: The isolated chimeric polypeptide of embodiment 109, wherein the Collagen alpha-1 (VII) chain polypeptide has at least 80% sequence identity to the sequence of SEQ ID NO: 2.

Embodiment 111: The isolated chimeric polypeptide of embodiment 109, wherein the Lysyl hydroxylase 3 polypeptide has at least 80% sequence identity to the sequence of SEQ ID NO: 4.

Embodiment 112: The isolated chimeric polypeptide of embodiment 109, wherein the linker polypeptide has at least 80% sequence identity to the sequence of SEQ ID NO: 6, SEQ ID NO: 8, SEQ ID NO: 10 or SEQ ID NO: 12.

Embodiment 113: The isolated chimeric polypeptide of any of embodiments 109 to 112, wherein the isolated chimeric polypeptide has at least 80% sequence identity to the sequence of SEQ ID NO: 14, SEQ ID NO: 16, SEQ ID NO: 18, SEQ ID NO: 20, SEQ ID NO: 22, SEQ ID NO: 24, SEQ ID NO: 26 or SEQ ID NO: 28.

Embodiment 114: A polynucleotide encoding the chimeric polypeptide of any of embodiments 109 to 113.

Embodiment 115: A vector comprising the polynucleotide of embodiment 114.

Embodiment 116: The vector of embodiment 115, wherein the vector is an HSV-1 amplicon or an HSV-1 hybrid amplicon.

Embodiment 117: The vector of embodiment 116 wherein the HSV-1 hybrid amplicon is an HSV/AAV hybrid ampli-con, an HSV/EBV hybrid amplicon, and HSV/EBV/RV hybrid amplicon, or an HSV/Sleeping Beauty hybrid ampli-con.

Embodiment 118: The vector of embodiment 115, wherein the vector is a recombinant herpes simplex virus genome.

Embodiment 119: The vector of embodiment 118, wherein the recombinant herpes simplex virus genome is a recombinant HSV-1 genome, a recombinant HSV-2 genome, or any derivatives thereof.

Embodiment 120: The vector of embodiment 118 or 119, wherein the recombinant herpes simplex virus genome comprises an inactivating mutation in an immediate early herpes simplex virus gene.

Embodiment 121: The vector of embodiment 120, wherein the herpes simplex virus gene is selected from the group consisting of ICP0, ICP4, ICP22, ICP27, ICP47, tk, UL41, and UL55.

Embodiment 122: The vector of any of embodiments 118 to 121, wherein the recombinant herpes simplex virus genome comprises an inactivating mutation in the ICP4 and ICP22 genes.

Embodiment 123: The vector of any of embodiments 118 to 121, wherein the recombinant herpes simplex virus genome comprises an inactivating mutation in the ICP0 and ICP4 genes.

Embodiment 124: The vector of embodiment 122 or 123, wherein the recombinant herpes simplex virus genome comprises an inactivating mutation in the ICP0, ICP4, and ICP22 genes.

Embodiment 125: The vector of any of embodiments 122 to 124, wherein the recombinant herpes simplex virus genome comprises an inactivating mutation in the ICP0, ICP4, ICP22, and ICP27 genes.

Embodiment 126: The vector of any of embodiments 122 to 125, wherein the recombinant herpes simplex virus genome comprises an inactivating mutation in the ICP0, ICP4, ICP22, ICP27, and UL55 genes.

Embodiment 127: The vector of any of embodiments 122 to 126, wherein the inactivating mutation is a deletion of the coding sequence of the genes.

Embodiment 128: The vector of any of embodiments 122 to 127, further comprising an inactivating mutation in the ICP47 gene.

Embodiment 129: The vector of any of embodiments 118 to 128, further comprising an inactivating mutation in the UL41 gene.

Embodiment 130: The vector of any of embodiments 118 to 129, wherein the recombinant herpes simplex virus genome comprises the polynucleotide within one or more viral gene loci.

Embodiment 131: The vector of any of embodiments 118 to 130, wherein the recombinant herpes simplex virus genome comprises the polynucleotide within one or more of the ICP4 viral gene loci.

Embodiment 132: The vector of any of embodiments 118 to 131, wherein the recombinant herpes simplex virus genome comprises the polynucleotide within the UL41 viral gene locus.

Embodiment 133: A vector comprising one or more polynucleotides encoding a Collagen alpha-1 (VII) chain polypeptide, a Lysyl hydroxylase 3 polypeptide, a Keratin type I cytoskeletal 17 polypeptide, or any combinations thereof, wherein the vector is a recombinant herpes simplex virus genome.

Embodiment 134: The vector of embodiment 133, wherein the recombinant herpes simplex virus genome is a recombinant HSV-1 genome, a recombinant HSV-2 genome, or any derivatives thereof.

Embodiment 135: The vector of embodiment 133 or 134, wherein the recombinant herpes simplex virus genome comprises an inactivating mutation in an immediate early herpes simplex virus gene.

Embodiment 136: The vector of embodiment 135, wherein the herpes simplex virus gene is selected from the group consisting of ICP0, ICP4, ICP22, ICP27, ICP47, tk, UL41, and UL55.

Embodiment 137: The vector of any of embodiments 133 to 136, wherein the recombinant herpes simplex virus genome comprises an inactivating mutation in the ICP4 and ICP22 genes.

Embodiment 138: The vector of any of embodiments 133 to 136, wherein the recombinant herpes simplex virus genome comprises an inactivating mutation in the ICP0 and ICP4 genes.

Embodiment 139: The vector of embodiment 137 or 138, wherein the recombinant herpes simplex virus genome comprises an inactivating mutation in the ICP0, ICP4, and ICP22 genes.

Embodiment 140: The vector of any of embodiments 137 to 139, wherein the recombinant herpes simplex virus genome comprises an inactivating mutation in the ICP0, ICP4, ICP22, and ICP27 genes.

Embodiment 141: The vector of any of embodiments 137 to 140, wherein the recombinant herpes simplex virus genome comprises an inactivating mutation in the ICP0, ICP4, ICP22, ICP27, and UL55 genes.

Embodiment 142: The vector of any of embodiments 137 to 141, wherein the inactivating mutation is a deletion of the coding sequence of the genes.

Embodiment 143: The vector of any of embodiments 137 to 142, further comprising an inactivating mutation in the ICP47 gene.

Embodiment 144: The vector of any of embodiments 133 to 143, further comprising an inactivating mutation in the UL41 gene.

Embodiment 145: The vector of any of embodiments 133 to 144, wherein the recombinant herpes simplex virus genome comprises the one or more polynucleotides within one or more viral gene loci.

Embodiment 146: The vector of any of embodiments 133 to 145, wherein the recombinant herpes simplex virus genome comprises the one or more polynucleotides within one or more of the ICP4 viral gene loci.

Embodiment 147: The vector of any of embodiments 133 to 146, wherein the recombinant herpes simplex virus genome comprises the one or more polynucleotides within the UL41 viral gene locus.

Embodiment 148: The vector of any of embodiments 133 to 147, wherein the vector comprises one polynucleotide encoding a Collagen alpha-1 (VII) chain polypeptide.

Embodiment 149: The vector of any of embodiments 133 to 147, wherein the vector comprises two polynucleotides encoding a Collagen alpha-1 (VII) chain polypeptide.

Embodiment 150: A host cell comprising the vector of any of embodiments 115 to 149.

Embodiment 151: A method of collecting a herpes simplex virus, wherein a vector of interest is packaged within said herpes simplex virus, the method comprising;
  a) contacting a host cell with a vector encoding a helper virus;

b) contacting said host cell with a vector of any of embodiments 115 to 117; and
  c) collecting the *Herpes simplex* virus generated by said host cell.

Embodiment 152: A method of collecting a herpes simplex virus, wherein a vector of interest is packaged within said herpes simplex virus, the method comprising;
  a) contacting a complementing host cell with a vector of any of embodiments 118 to 149; and
  b) collecting the herpes simplex virus generated by said complementing host cell.

Embodiment 153: The method of embodiment 151 or 152, wherein the herpes simplex virus is a herpes simplex type 1 virus, a herpes simplex type 2 virus, or any derivatives thereof.

Embodiment 154: A kit comprising:
  a) the pharmaceutical composition of any of embodiments 1 to 52; and
  b) instructions for administering the pharmaceutical composition.

Embodiment 155: A pharmaceutical composition comprising:
  a) a virus comprising a vector, wherein the vector comprises one or more transgenes encoding a polypeptide selected from the group consisting of a Collagen alpha-1 (VII) chain polypeptide, a Lysyl hydroxylase 3 polypeptide, a Keratin type I cytoskeletal 17 polypeptide, and a chimeric polypeptide thereof, and
  b) a pharmaceutically acceptable carrier.

Embodiment 156: The pharmaceutical composition of embodiment 155, wherein the virus is an adenovirus, adeno-associated virus, retrovirus, lentivirus, sendai virus, herpes simplex virus, vaccinia virus, or any hybrid virus thereof.

Embodiment 157: The pharmaceutical composition of embodiment 155, wherein the virus is a herpes simplex virus (HSV).

Embodiment 158: The pharmaceutical composition of any of embodiments 155 to 157, wherein the virus is replication-defective.

Embodiment 159: The pharmaceutical composition of any of embodiments 155 to 158, wherein the herpes simplex virus is a herpes simplex type 1 virus, a herpes simplex type 2 virus, or any derivatives thereof.

Embodiment 160: The pharmaceutical composition of any of embodiments 155 to 159, wherein the vector is an HSV-1 amplicon or an HSV-1 hybrid amplicon.

Embodiment 161: The pharmaceutical composition of embodiment 160, wherein the HSV-1 hybrid amplicon is an HSV/AAV hybrid amplicon, an HSV/EBV hybrid amplicon, and HSV/EBV/RV hybrid amplicon, or an HSV/Sleeping Beauty hybrid amplicon.

Embodiment 162: The pharmaceutical composition of any of embodiments 155 to 159, wherein the vector is a recombinant herpes simplex virus genome.

Embodiment 163: The pharmaceutical composition of embodiment 162, wherein the recombinant herpes simplex virus genome is a recombinant HSV-1 genome, a recombinant HSV-2 genome, or any derivatives thereof.

Embodiment 164: The pharmaceutical composition of embodiment 162 or 163, wherein the recombinant herpes simplex virus genome comprises an inactivating mutation in an immediate early herpes simplex virus gene.

Embodiment 165: The pharmaceutical composition of embodiment 164, wherein the herpes simplex virus gene is selected from the group consisting of ICP0, ICP4, ICP22, ICP27, ICP47, tk, UL41, and UL55.

Embodiment 166: The pharmaceutical composition of any of embodiments 162 to 165, wherein the recombinant herpes simplex virus genome comprises an inactivating mutation in the ICP4 and ICP22 genes.

Embodiment 167: The pharmaceutical composition of any of embodiments 162 to 165, wherein the recombinant herpes simplex virus genome comprises an inactivating mutation in the ICP0 and ICP4 genes.

Embodiment 168: The pharmaceutical composition of embodiment 166 or 167, wherein the recombinant herpes simplex virus genome comprises an inactivating mutation in the ICP0, ICP4, and ICP22 genes.

Embodiment 169: The pharmaceutical composition of any of embodiments 166 to 168, wherein the recombinant herpes simplex virus genome comprises an inactivating mutation in the ICP0, ICP4, ICP22, and ICP27 genes.

Embodiment 170: The pharmaceutical composition of any of embodiments 166 to 169, wherein the recombinant herpes simplex virus genome comprises an inactivating mutation in the ICP0, ICP4, ICP22, ICP27, and UL55 genes.

Embodiment 171: The pharmaceutical composition of any of embodiments 166 to 170, wherein the inactivating mutation is a deletion of the coding sequence of the genes.

Embodiment 172: The pharmaceutical composition of any of embodiments 166 to 171, further comprising an inactivating mutation in the ICP47 gene.

Embodiment 173: The pharmaceutical composition of any of embodiments 162 to 172, further comprising an inactivating mutation in the UL41 gene.

Embodiment 174: The pharmaceutical composition of any of embodiments 162 to 173, wherein the recombinant herpes simplex virus genome comprises the one or more transgenes within one or more viral gene loci.

Embodiment 175: The pharmaceutical composition of any of embodiments 162 to 174, wherein the recombinant herpes simplex virus genome comprises the one or more transgenes within one or more of the ICP4 viral gene loci.

Embodiment 176: The pharmaceutical composition of any of embodiments 162 to 175, wherein the recombinant herpes simplex virus genome comprises the one or more transgenes within the UL41 viral gene locus.

Embodiment 177: The pharmaceutical composition of embodiment 155, wherein the vector is capable of replicating within a target cell when delivered into said target cell.

Embodiment 178: The pharmaceutical composition of embodiment 155, wherein the pharmaceutically acceptable carrier is suitable for topical or transdermal administration.

Embodiment 179: The pharmaceutical composition of embodiment 155, wherein the pharmaceutically acceptable carrier is suitable for subcutaneous or intradermal administration.

Embodiment 180: The pharmaceutical composition of embodiment 155, wherein the one or more transgenes comprises an miRNA binding site.

Embodiment 181: The pharmaceutical composition of any of embodiments 155 to 180, wherein the vector comprises a transgene encoding a Collagen alpha-1 (VII) chain polypeptide.

Embodiment 182: The pharmaceutical composition of any of embodiments 155 to 180, wherein the vector comprises a transgene encoding a Lysyl hydroxylase 3 polypeptide.

Embodiment 183: The pharmaceutical composition of any of embodiments 155 to 180, wherein the vector comprises a transgene encoding a Keratin type I cytoskeletal 17 polypeptide.

Embodiment 184: The pharmaceutical composition of any of embodiments 155 to 180, wherein the Collagen alpha-1 (VII) chain polypeptide has at least 80% sequence identity to the sequence of SEQ ID NO: 2.

Embodiment 185: The pharmaceutical composition of any of embodiments 155 to 180, wherein the Collagen alpha-1 (VII) chain polypeptide is a fragment, wherein the fragment has at least 100 consecutive amino acids of SEQ ID NO: 2.

Embodiment 186: The pharmaceutical composition of any of embodiments 155 to 180, wherein the Collagen alpha-1 (VII) chain polypeptide enhances, increases, augments, and/or supplements anchoring fibril formation of a subject when the polypeptide is expressed in one or more target cells of the subject.

Embodiment 187: The pharmaceutical composition of any of embodiments 155 to 180, wherein the Collagen alpha-1 (VII) chain polypeptide enhances, increases, augments, and/or supplements epithelial basement membrane organization and/or epithelial basement adherence of a subject when the polypeptide is expressed in one or more target cells of the subject.

Embodiment 188: The pharmaceutical composition of any of embodiments 155 to 180, wherein the Lysyl hydroxylase 3 polypeptide has at least 80% sequence identity to the sequence of SEQ ID NO: 4.

Embodiment 189: The pharmaceutical composition of any of embodiments 155 to 180, wherein the Lysyl hydroxylase 3 polypeptide is a fragment, wherein the fragment has at least 100 consecutive amino acids of SEQ ID NO: 4.

Embodiment 190: The pharmaceutical composition of any of embodiments 155 to 180, wherein the Lysyl hydroxylase 3 polypeptide enhances, increases, augments, and/or supplements the formation of hydroxylysine residues on one or more collagen polypeptides of a subject when the Lysyl hydroxylase 3 polypeptide is expressed in one or more target cells of the subject.

Embodiment 191: The pharmaceutical composition of any of embodiments 155 to 180, wherein the Lysyl hydroxylase 3 polypeptide enhances, increases, augments, and/or supplements anchoring fibril formation, epithelial basement membrane organization, and/or epithelial basement adherence of a subject when the polypeptide is expressed in one or more target cells of the subject.

Embodiment 192: The pharmaceutical composition of any of embodiments 155 to 180, wherein the Keratin type I cytoskeletal 17 polypeptide has at least 80% sequence identity to the sequence of SEQ ID NO: 30.

Embodiment 193: The pharmaceutical composition of any of embodiments 155 to 180, wherein the Keratin type I cytoskeletal 17 polypeptide is a fragment, wherein the fragment has at least 100 consecutive amino acids of SEQ ID NO: 30.

Embodiment 194: The pharmaceutical composition of any of embodiments 155 to 180, wherein the Keratin type I cytoskeletal 17 polypeptide enhances, increases, augments, and/or supplements wound healing in a subject.

Embodiment 195: The pharmaceutical composition of any of embodiments 155 to 194, wherein the vector comprises at least a first transgene and a second transgene.

Embodiment 196: The pharmaceutical composition of embodiment 195, wherein the first transgene and the second transgene each encode a Collagen alpha-1 (VII) chain polypeptide.

Embodiment 197: The pharmaceutical composition of embodiment 195, wherein the first transgene encodes a Collagen alpha-1 (VII) chain polypeptide and the second transgene encodes a Lysyl hydroxylase 3 polypeptide.

Embodiment 198: The pharmaceutical composition of embodiment 195, wherein the first transgene encodes a Collagen alpha-1 (VII) chain polypeptide and the second transgene encodes a Keratin type I cytoskeletal 17 polypeptide.

Embodiment 199: The pharmaceutical composition of embodiment 195, wherein the first transgene encodes a Lysyl hydroxylase 3 polypeptide and the second transgene encodes a Keratin type I cytoskeletal 17 polypeptide.

Embodiment 200: The pharmaceutical composition of embodiment 155, wherein the vector comprises at least a first transgene, a second transgene, and a third transgene.

Embodiment 201: The pharmaceutical composition of embodiment 200, wherein the first transgene encodes a Collagen alpha-1 (VII) chain polypeptide, the second transgene encodes a Lysyl hydroxylase 3 polypeptide, and the third transgene encodes a Keratin type I cytoskeletal 17 polypeptide.

Embodiment 202: A method of providing prophylactic, palliative, or therapeutic relief of a wound, disorder, or disease of the skin in a subject, the method comprising administering to the subject a pharmaceutical composition comprising a vector, wherein the vector is a recombinant herpes simplex virus genome, and wherein the pharmaceutical composition is capable of enhancing, increasing, augmenting, and/or supplementing the levels of a Collagen alpha-1 (VII) chain polypeptide and/or a Lysyl hydroxylase 3 polypeptide and/or a Keratin type I cytoskeletal 17 polypeptide in one or more cells of the subject.

Embodiment 203: The method of embodiment 202, wherein the pharmaceutical composition comprises:

a) a virus comprising the vector, wherein the vector comprises one or more transgenes encoding a polypeptide selected from the group consisting of a Collagen alpha-1 (VII) chain polypeptide, a Lysyl hydroxylase 3 polypeptide, a Keratin type I cytoskeletal 17 polypeptide, and a chimeric polypeptide thereof, and b) a pharmaceutically acceptable carrier.

Embodiment 204: The method of embodiment 203, wherein the virus is an adenovirus, adeno-associated virus, retrovirus, lentivirus, sendai virus, herpes simplex virus, vaccinia virus, or any hybrid virus thereof.

Embodiment 205: The method of embodiment 203, wherein the virus is a herpes simplex virus (HSV).

Embodiment 206: The method of any of embodiments 203 to 205, wherein the virus is replication-defective.

Embodiment 207: The method of any of embodiment 203 to 206, wherein the herpes simplex virus is a herpes simplex type 1 virus, a herpes simplex type 2 virus, or any derivatives thereof.

Embodiment 208: The method of any of embodiments 202 to 207, wherein the recombinant herpes simplex virus genome is a recombinant HSV-1 genome, a recombinant HSV-2 genome, or any derivatives thereof.

Embodiment 209: The method of embodiment 202 to 208, wherein the recombinant herpes simplex virus genome comprises an inactivating mutation in an immediate early herpes simplex virus gene.

Embodiment 210: The method of embodiment 209, wherein the herpes simplex virus gene is selected from the group consisting of ICP0, ICP4, ICP22, ICP27, ICP47, tk, UL41, and UL55.

Embodiment 211: The method of any of embodiments 202 to 210, wherein the recombinant herpes simplex virus genome comprises an inactivating mutation in the ICP4 and ICP22 genes.

Embodiment 212: The method of any of embodiments 202 to 210, wherein the recombinant herpes simplex virus genome comprises an inactivating mutation in the ICP0 and ICP4 genes.

Embodiment 213: The method of embodiment 211 or 212, wherein the recombinant herpes simplex virus genome comprises an inactivating mutation in the ICP0, ICP4, and ICP22 genes.

Embodiment 214: The method of any of embodiments 211 to 213, wherein the recombinant herpes simplex virus genome comprises an inactivating mutation in the ICP0, ICP4, ICP22, and ICP27 genes.

Embodiment 215: The method of any of embodiments 211 to 214, wherein the recombinant herpes simplex virus genome comprises an inactivating mutation in the ICP0, ICP4, ICP22, ICP27, and UL55 genes.

Embodiment 216: The method of any of embodiments 211 to 215, wherein the inactivating mutation is a deletion of the coding sequence of the genes.

Embodiment 217: The method of any of embodiments 211 to 216, further comprising an inactivating mutation in the ICP47 gene.

Embodiment 218: The method of any of embodiments 202 to 217, further comprising an inactivating mutation in the UL41 gene.

Embodiment 219: The method of any of embodiments 202 to 218, wherein the recombinant herpes simplex virus genome comprises the one or more transgenes within one or more viral gene loci.

Embodiment 220: The method of any of embodiments 202 to 219, wherein the recombinant herpes simplex virus genome comprises the one or more transgenes within one or more of the ICP4 viral gene loci.

Embodiment 221: The method of any of embodiments 202 to 220, wherein the recombinant herpes simplex virus genome comprises the one or more transgenes within the UL41 viral gene locus.

Embodiment 222: The method of embodiment 202, wherein the vector is capable of replicating within a target cell when delivered into said target cell.

Embodiment 223: The method of embodiment 203, wherein the pharmaceutically acceptable carrier is suitable for topical or transdermal administration.

Embodiment 224: The method of embodiment 203, wherein the pharmaceutically acceptable carrier is suitable for subcutaneous or intradermal administration.

Embodiment 225: The method of embodiment 203, wherein the one or more transgenes comprises an miRNA binding site.

Embodiment 226: The method of any of embodiments 202 to 225, wherein the vector comprises a transgene encoding a Collagen alpha-1 (VII) chain polypeptide.

Embodiment 227: The method of any of embodiments 202 to 225, wherein the vector comprises a transgene encoding a Lysyl hydroxylase 3 polypeptide.

Embodiment 228: The method of any of embodiments 202 to 225, wherein the vector comprises a transgene encoding a Keratin type I cytoskeletal 17 polypeptide.

Embodiment 229: The method of any of embodiments 202 to 225, wherein the Collagen alpha-1 (VII) chain polypeptide has at least 80% sequence identity to the sequence of SEQ ID NO: 2.

Embodiment 230: The method of any of embodiments 202 to 225, wherein the Collagen alpha-1 (VII) chain polypeptide is a fragment, wherein the fragment has at least 100 consecutive amino acids of SEQ ID NO: 2.

Embodiment 231: The method of any of embodiments 202 to 225, wherein the Collagen alpha-1 (VII) chain polypeptide enhances, increases, augments, and/or supplements anchoring fibril formation of a subject when the polypeptide is expressed in one or more target cells of the subject.

Embodiment 232: The method of any of embodiments 202 to 225, wherein the Collagen alpha-1 (VII) chain polypeptide enhances, increases, augments, and/or supplements epithelial basement membrane organization and/or epithelial basement adherence of a subject when the polypeptide is expressed in one or more target cells of the subject.

Embodiment 233: The method of any of embodiments 202 to 225, wherein the Lysyl hydroxylase 3 polypeptide has at least 80% sequence identity to the sequence of SEQ ID NO: 4.

Embodiment 234: The method of any of embodiments 202 to 225, wherein the Lysyl hydroxylase 3 polypeptide is a fragment, wherein the fragment has at least 100 consecutive amino acids of SEQ ID NO: 4.

Embodiment 235: The method of any of embodiments 202 to 225, wherein the Lysyl hydroxylase 3 polypeptide enhances, increases, augments, and/or supplements the formation of hydroxylysine residues on one or more collagen polypeptides of a subject when the Lysyl hydroxylase 3 polypeptide is expressed in one or more target cells of the subject.

Embodiment 236: The method of any of embodiments 202 to 225, wherein the Lysyl hydroxylase 3 polypeptide enhances, increases, augments, and/or supplements anchoring fibril formation, epithelial basement membrane organization, and/or epithelial basement adherence of a subject when the polypeptide is expressed in one or more target cells of the subject.

Embodiment 237: The method of any of embodiments 202 to 225, wherein the Keratin type I cytoskeletal 17 polypeptide has at least 80% sequence identity to the sequence of SEQ ID NO: 30.

Embodiment 238: The method of any of embodiments 202 to 225, wherein the Keratin type I cytoskeletal 17 polypeptide is a fragment, wherein the fragment has at least 100 consecutive amino acids of SEQ ID NO: 30.

Embodiment 239: The method of any of embodiments 202 to 225, wherein the Keratin type I cytoskeletal 17 polypeptide enhances, increases, augments, and/or supplements wound healing in a subject.

Embodiment 240: The method of any of embodiments 202 to 239, wherein the vector comprises at least a first transgene and a second transgene.

Embodiment 241: The method of embodiment 240, wherein the first transgene and the second transgene each encode a Collagen alpha-1 (VII) chain polypeptide.

Embodiment 242: The method of embodiment 240, wherein the first transgene encodes a Collagen alpha-1 (VII) chain polypeptide and the second transgene encodes a Lysyl hydroxylase 3 polypeptide.

Embodiment 243: The method of embodiment 240, wherein the first transgene encodes a Collagen alpha-1 (VII) chain polypeptide and the second transgene encodes a Keratin type I cytoskeletal 17 polypeptide.

Embodiment 244: The method of embodiment 240, wherein the first transgene encodes a Lysyl hydroxylase 3 polypeptide and the second transgene encodes a Keratin type I cytoskeletal 17 polypeptide.

Embodiment 245: The method of any of embodiments 202 to 239, wherein the vector comprises at least a first transgene, a second transgene, and a third transgene.

Embodiment 246: The method of embodiment 245, wherein the first transgene encodes a Collagen alpha-1 (VII) chain polypeptide, the second transgene encodes a Lysyl hydroxylase 3 polypeptide, and the third transgene encodes a Keratin type I cytoskeletal 17 polypeptide.

Embodiment 247: The method of any of embodiments 202 to 246, wherein the pharmaceutical composition is administered topically or transdermally to the subject.

Embodiment 248: The method of any of embodiments 202 to 246, wherein the pharmaceutical composition is administered subcutaneously or intradermally to the subject.

Embodiment 249: The method of any of embodiments 202 to 248, wherein the pharmaceutical composition is administered one, two three, four, five or more times per day.

Embodiment 250: The method of any of embodiments 202 to 249, wherein the pharmaceutical composition is administered to one or more affected and/or unaffected areas of the subject.

Embodiment 251: The method of any of embodiments 202 to 250, wherein the disease or disorder of the skin is one or more of epidermolysis bullosa, skin cancer, psoriasis, lichen planus, lupus, rosacea, eczema, cutaneous candidiasis, cellulitis, impetigo, decubitus ulcers, erysipelas, ichthyosis vulgaris, dermatomyositis, acrodermatitis, stasis dermatitis, nethertons syndrome, epidermolysis bullosa simplex (LAMB3 gene), autosomal recessive congenital ichthyosis, xeroderma pigmentosa, and pemphigoid.

The specification is considered to be sufficient to enable one skilled in the art to practice the invention. Various modifications of the invention in addition to those shown and described herein will become apparent to those skilled in the art from the foregoing description and fall within the scope of the appended claims.

EXAMPLES

The present disclosure will be more fully understood by reference to the following example. It should not, however, be construed as limiting the scope of the present disclosure. It is understood that the examples and embodiments described herein are for illustrative purposes only and that various modifications or changes in light thereof will be suggested to persons skilled in the art and are to be included within the spirit and purview of this application and scope of the appended claims.

Figures 1A, 1B:
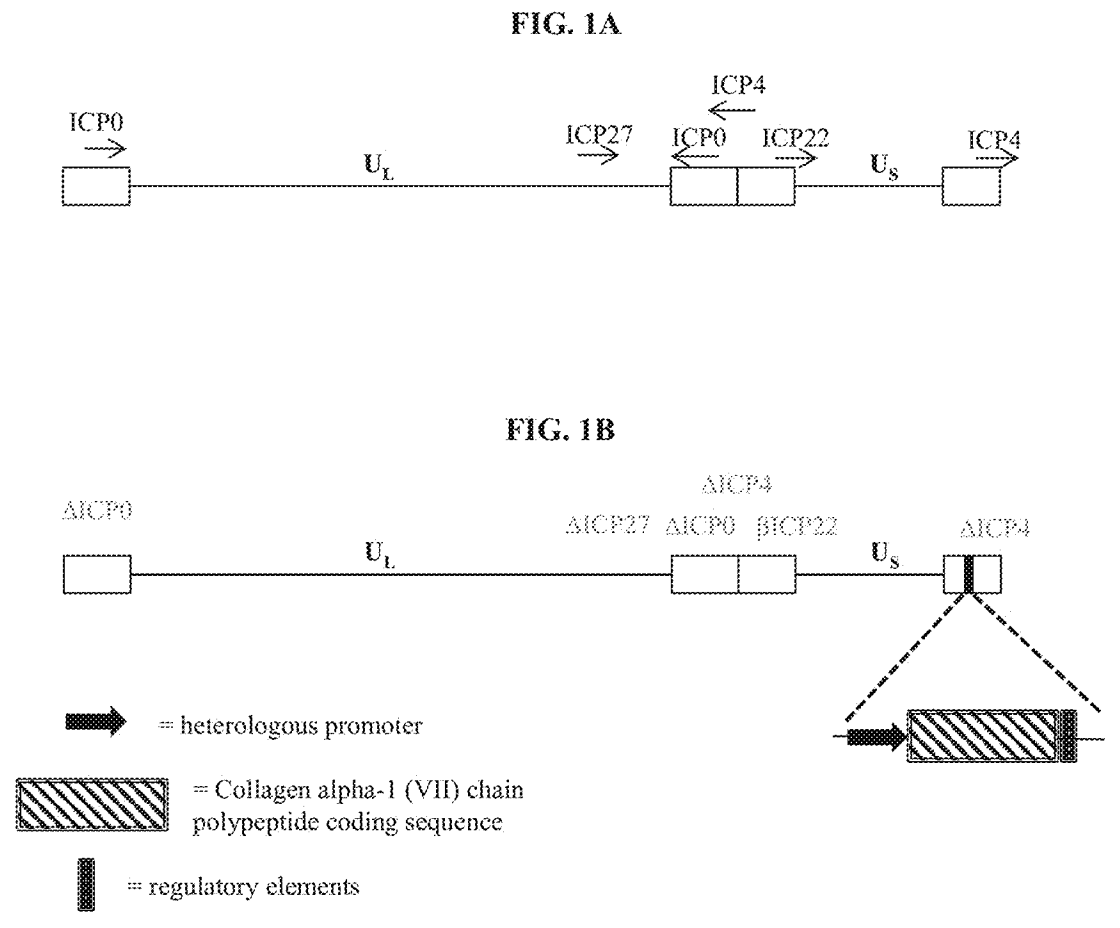

Example 1: Generating Modified *Herpes Simplex* Virus Vectors, and Producing/Isolating Virus Containing the Vectors To make modified herpes simplex virus genome vectors capable of expressing one or more transgenes in a target mammalian cell, a herpes simplex virus genome (FIG. 1A) is modified to inactivate the immediate early genes ICP0, ICP4, and ICP27, while the immediate early gene ICP22 is modified to include a heterologous, inducible promoter. This decreases the toxicity of the genome in mammalian cells. Next, a cassette is inserted into the modified herpes virus genome by restriction cloning. The cassette contains a heterologous promoter capable of expressing a transgene in a target mammalian cell. The promoter is operably linked to the nucleic acid sequence encoding a Collagen alpha-1 (VII)

chain polypeptide, as well as downstream regulatory elements (FIG. 1B) ensuring proper production of the mRNA. Alternatively, the cassette includes two transgenes, each of which has its own heterologous promoter operably linked to the nucleic acid encoding either a Collagen alpha-1 (VII) chain polypeptide or a Lysyl hydroxylase 3 polypeptide. The transgenes are encoded either on the same strand of DNA (FIG. 1C), or on opposite strands of DNA in an antisense orientation (FIG. 1D). Linking each transgene with its own promoter and regulatory elements allows for independent expression of each coding sequence on separate mRNA transcripts. Expressing the transgenes from distinct promoters allows for the ability to operably link the coding sequences to different promoter types, which can drive expression of the transgenes at different levels, at different times in the cell cycle, in different cell types, or under the control of different inducers or repressors.

A modified herpes virus genome is also constructed that includes a cassette expressing a single mRNA encoding a Collagen alpha-1 (VII) chain polypeptide and a Lysyl hydroxylase 3 polypeptide separated by an internal ribosomal entry site (FIG. 1E). This allows for approximately equimolar production of each polypeptide when expressed in a target cell. Finally, a modified herpes virus genome is constructed that includes a cassette expressing a chimeric polypeptide. This chimeric polypeptide includes, from N-terminus to C-terminus, a Collagen alpha-1 (VII) chain polypeptide, a cleavable peptide linker, and a Lysyl hydroxylase 3 polypeptide (FIG. 1F).

Additional modified herpes virus genomes are constructed that include two cassettes, each expressing Collagen alpha-1 (VII) chain polypeptides, where each cassette is inserted into a copy of the ICP4 gene locus (FIGS. 2B-2G) of the wild-type herpes simplex virus genome (FIG. 2A). These additional recombinant herpes virus genomes are constructed with various combinations of herpes virus gene deletions/modifications.

A recombinant herpes virus genome is constructed which contains deletions of the coding sequences of both copies of the ICP4 gene, as well as deletions of the coding sequences of the ICP27 and UL55 genes. These recombinant viruses are further modified to contain inactivating mutations in the promoter regions of the ICP22 and ICP47 genes such that the ICP22 and ICP47 genes are not expressed with normal kinetics (FIG. 2B).

Further recombinant herpes simplex viruses are constructed which incorporate expression cassettes for Collagen alpha-1 (VII) chain polypeptides into both loci of the herpes ICP4 genes. These recombinant viruses include: viruses containing deletions of the coding sequences of the ICP22 gene and both copies of the ICP4 gene (FIG. 2C); deletions of the coding sequences of the ICP0 gene and both copies of the ICP4 gene (FIG. 2D); deletions of the coding sequences of the ICP0 and ICP22 genes, and both copies of the ICP4 gene (FIG. 2E); deletions of the coding sequences of the ICP0, ICP22, and ICP27 genes, and both copies of the ICP4 gene (FIG. 2F); and deletions of the coding sequences of the ICP0, ICP22, ICP27, and UL55 genes, and both copies of the ICP4 gene (FIG. 2G). Additional vectors are constructed based upon the vectors shown in FIGS. 2C-2G which further comprise one or more transgenes encoding one or more additional effectors (e.g., LH3, KRT17) in the ICP0 and/or UL41 loci.

These modified herpes simplex virus genome vectors are transfected into engineered Vero cells that are modified to express herpes virus genes. These engineered Vero cells secrete replication-defective herpes simplex virus with the modified genomes packaged within into the supernatant. The supernatant is then collected, concentrated, and sterile filtered through a 5 μm filter.

Example 2: Rescuing Col7 Expression with Replication Defective HSV-1

The following example describes the construction of a replication defective herpes simplex type-1 virus modified to express the human COL7A1 gene, and use of such a viral vector to rescue several defects observed in cells isolated from RDEB patients.

Methods

Cells and Cell Culture

Normal and RDEB human dermal fibroblasts and keratinocytes were isolated as described previously (NG, Y. Z. et al. (2012) *Cancer Res.* 72: 3522-3534; Rheinwald, J. G. and Green, H. (1975) *Cell* 6: 331-42). Cells were cultured according to standard techniques.

Construction of KB103

The KB103 vector was generated from D3GFP, a replication-defective HSV-1 vector backbone harboring GFP in place of the viral ICP4. The sequence of the GFP in D3GFP was replaced with the coding sequence of human COL7A1 using a transfer plasmid by cloning COL7A1 into the EcoRI site of the ICP4 recombination plasmid pSASB3. A mixed transfection/infection of the COL7A1 containing transfer plasmid and D3GFP vector was performed on VeroD cells. Resulting plaques which did not express GFP were isolated and tested by western blot for Col7 protein expression.

Virus Purification

KB103 virus was purified according to standard techniques (See Diefenbach, R. and Fraefel, C. *Herpes Simplex Virus*. New York: Humana Press, 2014).

Viral Infections

Cells were seeded in duplicates or triplicates in six-well plates at approximately 50% confluency one day prior to viral infection. An additional well was seeded in parallel for cell counting and MOI determination. 24 hours after cell seeding, cells from one well were trypsinized and counted to calculate the MOI, and viral stocks were thawed and diluted in cell culture medium to achieve the desired MOI. Culture medium was aspirated from each well to be infected, and 500 μL of KB103-containing medium (or control medium) was added to each well. Plates were incubated at 37° C. with 5-7.5% $CO_2$ for 1.5-2 hours with intermittent rocking every 15-20 minutes, then 1.5-2 mL of complete cell culture medium was added to each well, and the plates were incubated for 24-72 hours at 37° C. After incubation, the cells and supernatants were harvested and processed for analysis.

mRNA Quantification

Col7 transcripts were amplified from RNA isolated from primary RDEB keratinocytes after infection using a SYBR PCR assay (Sybr Select Master Mix, Life Technologies) according to the manufacturer's protocol. Col7 transcript levels were normalized to β-actin transcript levels.

Western Blot Analysis

Cell lysates were generated from cells 48 hours post-infection, and western blots were carried out according to standard techniques using the following antibodies: rabbit anti-human Col7 polyclonal antibody (Sigma, Cat. #HPA042420), mouse anti-human GAPDH antibody (Santa Cruz Biotechnology, Cat. #sc-365062), rabbit anti-LH3 antibody (Protein Tech, Cat. #11027-1-AP), and mouse anti-TSP1 antibody (Santa Cruz Biotechnology, Cat. #sc-59887).

Immunofluorescence

Cells were plated on cover slips prior to infection, fixed 48 hours post-infection, and stained with a primary rabbit anti-human Col7 polyclonal antibody (Sigma, Cat. #HPA042420), washed, and further stained with a fluorescently labelled anti-rabbit secondary antibody (Invitrogen, Cat. 3 A11012). Cell nuclei were stained with DAPI using standard techniques.

Cellular Adhesion 96-well plates were coated with 10, 20, or 50 µg/mL rat tail Collagen 1 (Marathon Laboratory Supply) or human fibronectin (Sigma-Aldrich) in 100 µL reaction volume at 4° C. overnight, then washed with PBS, and blocked with PBS+0.1% BSA for 1 hour at 37° C. Mock (control) infected or KB103 infected RDEB keratinocytes ($2.4*10^4$ cells in 100 µL of DMEM/HamF12+0.1% BSA) were added to the plates and incubated at 37° C. for 40-90 minutes. Wells were washed three times with PBS to remove any unbound cells, and adherent cells were fixed with PFE for 20 minutes. The fixed cells were then treated with 70% ethanol, stained with crystal violet, resolved in 100% ethanol, and were quantified by measuring absorbance at 630 nm.

Skin Equivalent (SE) Organotypic Cultures

A skin equivalent organotypic culture composed of RDEB fibroblasts and keratinocytes was used to evaluate the expression of Col7 at the basement membrane zone (BMZ). Briefly, RDEB fibroblasts ($2*10^5$ cells per well) were embedded in fibrin gel matrix in six-well plates and incubated in DMEM+10% serum containing ascorbic acid and aprotinin for 24 hours at 37° C. and 5% $CO_2$. RDEB keratinocytes ($1*10^6$ cells per well) were then seeded on the matrix, grown to confluence in DMEM/F-12 keratinocyte medium containing 50 mg/mL of ascorbic acid, and raised at the air-liquid interface. Two days post raising, KB103 virus was added to the cultures (at an MOI of 3) and incubated for 1.5 hours. Following incubation, cultures were washed and incubated for 5-14 days to favor stratification and differentiation into an epithelium. Skin equivalents (SEs) were manually detached from the plates and embedded in optimal cutting temperature compound, frozen in liquid nitrogen, and cut into 6 mm sections for immunofluorescence staining with a monoclonal anti-Col7 antibody.

Results

KB103 Pharmacology in Normal and RDEB Cells

A number of ex vivo approaches have been undertaken to deliver the human COL7A1 gene to primary cells isolated from RDEB patients in an attempt to correct Col7 deficiencies (Ortiz-Urda, S. et al. (2003) *J. Clin. Invest.* 111(2) 251-5; Woodley, D. T. et al. (2003) *J. Invest. Dematol.* 121(5) 1021-8). Although successful in achieving durable correction of key disease features, an ex vivo gene delivery strategy for treating epidermolysis bullosa has a number of key disadvantages, including high cost, poor graft takes, surgical debridement, complex bandaging and wound care, and the high potential for post-surgical infection. An attractive alternate route for gene therapy is the use of viral or non-viral vectors to deliver gene products. However, non-viral vectors using plasmid DNA suffer from very low gene transfer efficiency when injected or topically administered, while the most widely used viral vectors in human gene therapy trials (retroviral vectors) do not infect non-dividing cells. This is problematic for gene delivery to the skin, as manipulation of the tissue (such as wounding) to create an adequate population of dividing cells would be required for retroviral gene therapy. Large-capacity adenoviral vectors can deliver genome-sized transcription units and survive in transduced cells for long periods of time, but the toxicity and immunogenicity of adenoviral particles, as well as the requirements for helper virus during vector production, remain as significant hurdles for their use in human gene therapy strategies. While replication-defective HSV vectors have been employed as delivery vehicles in a number of pre-clinical studies, no pre-clinical evidence supporting the use of HSV-based viral vectors for epidermolysis bullosa or other dermatological applications has been reported.

To this end, a replication defective herpes simplex type-1 virus (HSV-1) encoding the human COL7A1 gene was developed as a novel vector useful for gene therapy treatment of DEB patients. An HSV-1 virus was modified to harbor complete deletions of the viral ICP4, ICP27, and UL55 genes, with the ICP4 deletion resulting in the removal of the upstream promoter sequences driving the transcription of the immediate early viral genes ICP22 and ICP47. The virus was further modified to include a human cytomegalovirus (HCMV) immediate early promoter-driven human COL7A1 expression cassette encoded within both copies of the deleted ICP4 loci, resulting in a replication-defective HSV-1 vector, termed KB103, suitable for delivering human COL7A1 to target cells (FIG. 3).

To test the ability of KB103 to deliver and express Col7 in human cells, and to rescue Col7 deficiencies in RDEB patients, patient-derived human dermal fibroblasts and keratinocytes were isolated from healthy individuals, as well as individuals suffering from RDEB, and these primary cells were infected with KB103 at various MOIs. 24-72 hours post infection, COL7A1 gene expression was measured by real-time PCR in transduced cells, while Col7 protein expression was analyzed in parallel by both western blot and immunofluorescence analysis.

Figure 4A:
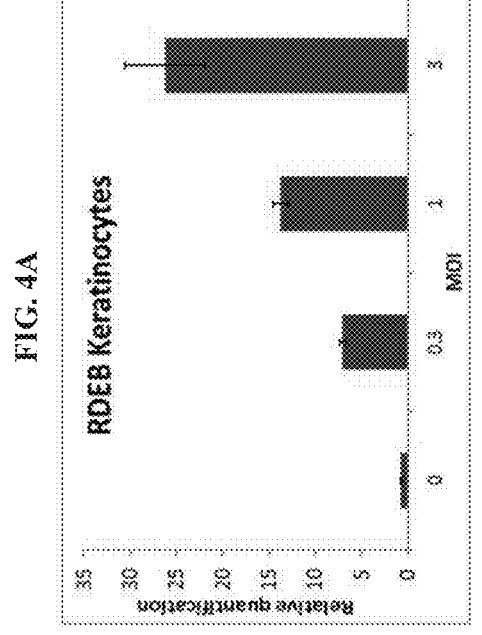
FIGS. 4A-4B show dose-dependent increases in COL7 transcript levels from KB103-infeted RDEB human dermal keratinocytes (FIG. 4A) and RDEB human dermal fibroblasts (FIG. 4B). Transcripts were quantified relative to 3-actin levels and normalized to expression in uninfected cells.
Figure 4B:
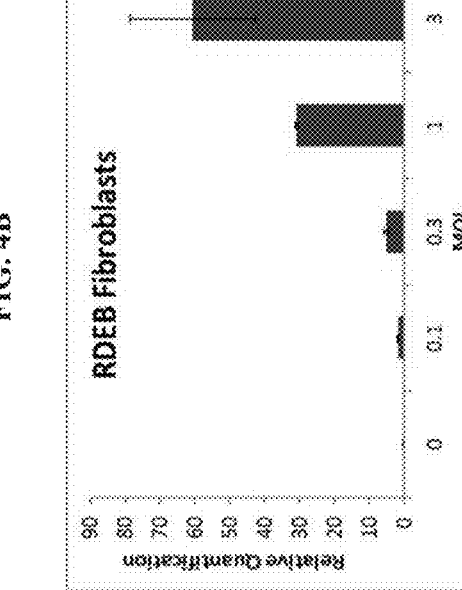

Dose-dependent increases in COL7A1 gene expression were observed in RDEB keratinocytes (FIG. 4A) and fibroblasts (FIG. 4B) infected with KB103. KB103 infection increased COL7A1 gene expression by approximately 7.5 fold, 12.5 fold, and 25 fold in RDEB keratinocytes infected at an MOI of 0.3, 1, and 3, respectively (FIG. 4A). Surprisingly, even more drastic changes in COL7A1 gene expression was observed in infected RDEB fibroblasts. While infections at an MOI of 0.1 and 0.3 showed moderate increases in COL7A1 gene expression, an approximate 30 fold increase in COL7A1 gene expression was measured for RDEB fibroblasts infected at an MOI of 1, while a 60 fold increase was observed in this cell type infected at an MOI of 3. This data showed that COL7A1 gene expression was massively upregulated in RDEB primary cells after infection with KB103.

Figures 5A, 5B:
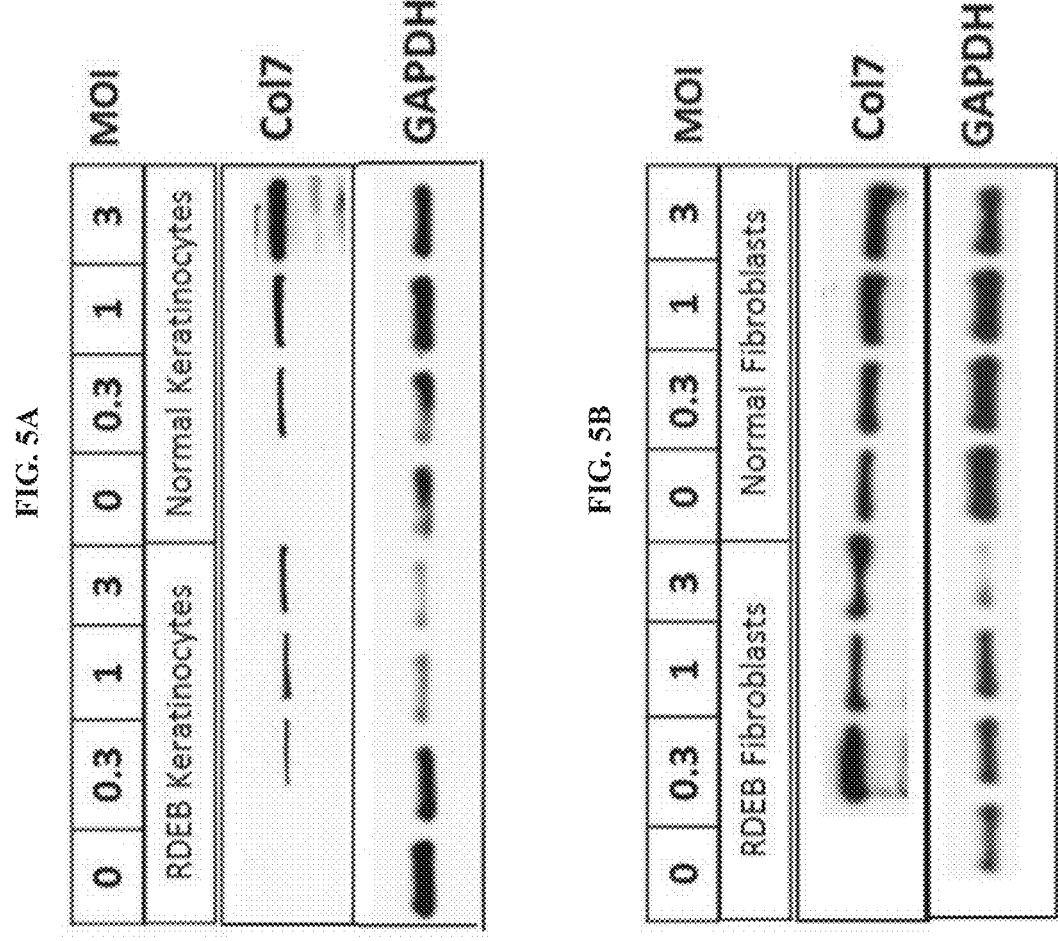
FIGS. 5A-5B show human Col7 protein expression detected in KB103-infected cells.

Consequently, robust Col7 protein expression was also observed in cells infected with KB103. Col7 protein expression was detected in both normal and RDEB keratinocytes (FIG. 5A) and fibroblasts (FIG. 5B) 48 hours after infection with KB103 at an MOI of 0.3, 1, and 3, with an apparent dose-dependent increase in Col7 protein expression observed at higher viral titers. Expression of Col7 was observed in both the supernatants and cell lysates from infected cells. Surprisingly, RDEB fibroblasts infected at an MOI of 0.3 showed higher levels of Col7 than was observed in uninfected normal fibroblasts (FIG. 5B), suggesting complete rescue of Col7 expression in RDEB fibroblasts using KB103, even at low viral titers. No obvious effects on cell morphology using high viral doses (MOI of 3) were observed. Additionally, no negative impacts on fibroblast or keratinocyte cell proliferation using high doses of KB103 were indicated in these experiments, as determined by GAPDH expression.

Figure 6:
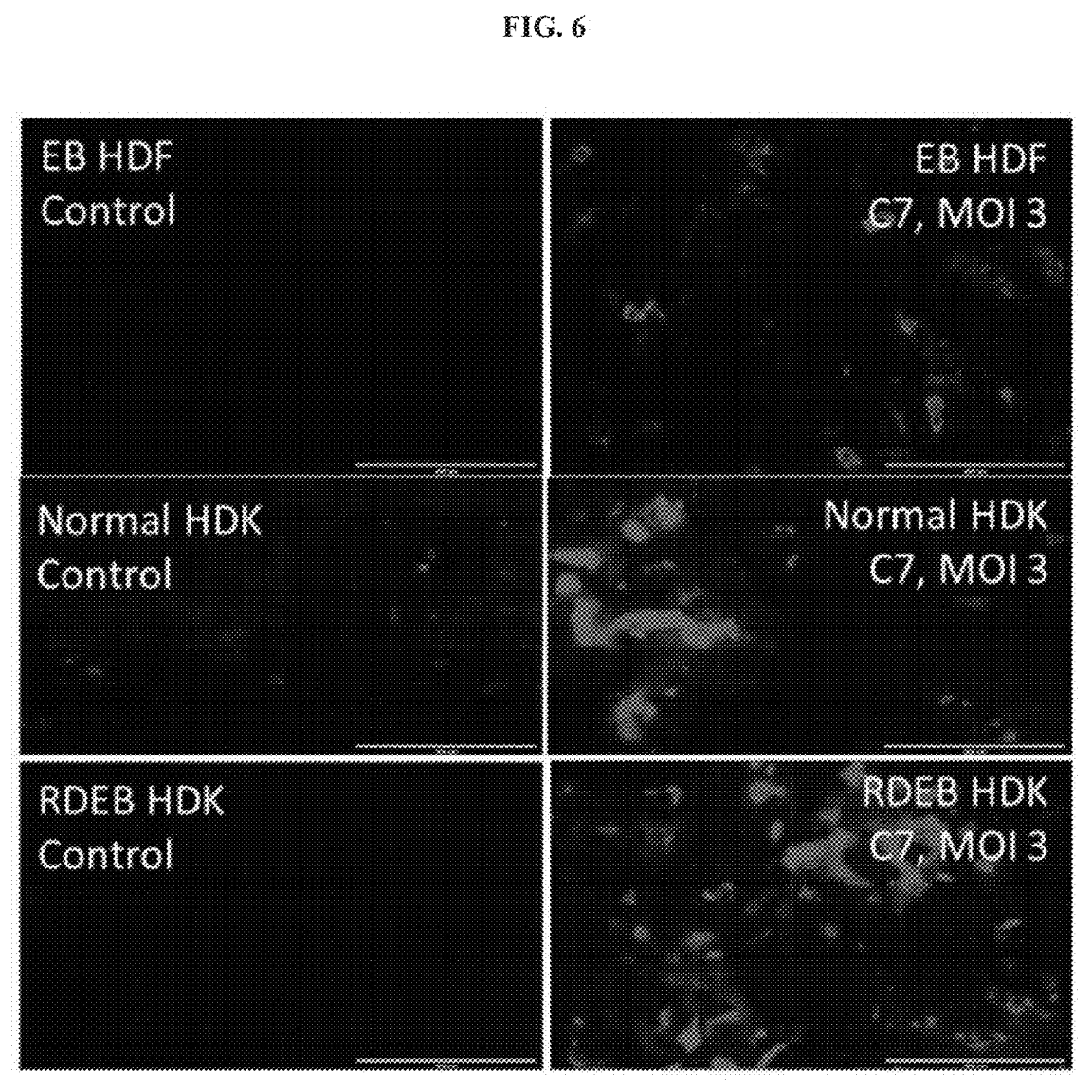

In agreement with the above experiments, a robust and dose-dependent increase in Col7 protein expression was confirmed in normal and RDEB cells infected with KB103, as demonstrated by immunofluorescent detection of Col7 protein expression (FIG. 6). As expected, no Col7 protein was detected in uninfected RDEB human dermal fibroblasts or keratinocytes; limited Col7 protein was detected in uninfected normal keratinocytes and fibroblasts. However, infection with KB103 was capable of rescuing Col7 protein expression in RDEB fibroblasts and keratinocytes at or above the levels observed in uninfected normal cells. Furthermore, infection efficiency of KB103 (at an MOI of 3) was calculated to be >95% based on an assessment of three or more independent panels for each infected replicate, showing that KB103 efficiently delivered and expressed the COL7A1 expression cassette. Taken together, this data suggested that KB103 was capable of delivering and expressing COL7A1 in normal and RDEB primary cells, and that KB103 was well tolerated by both human dermal fibroblasts and keratinocytes.

Functional Assessment of KB103 in RDEB Cells

Figure 7:
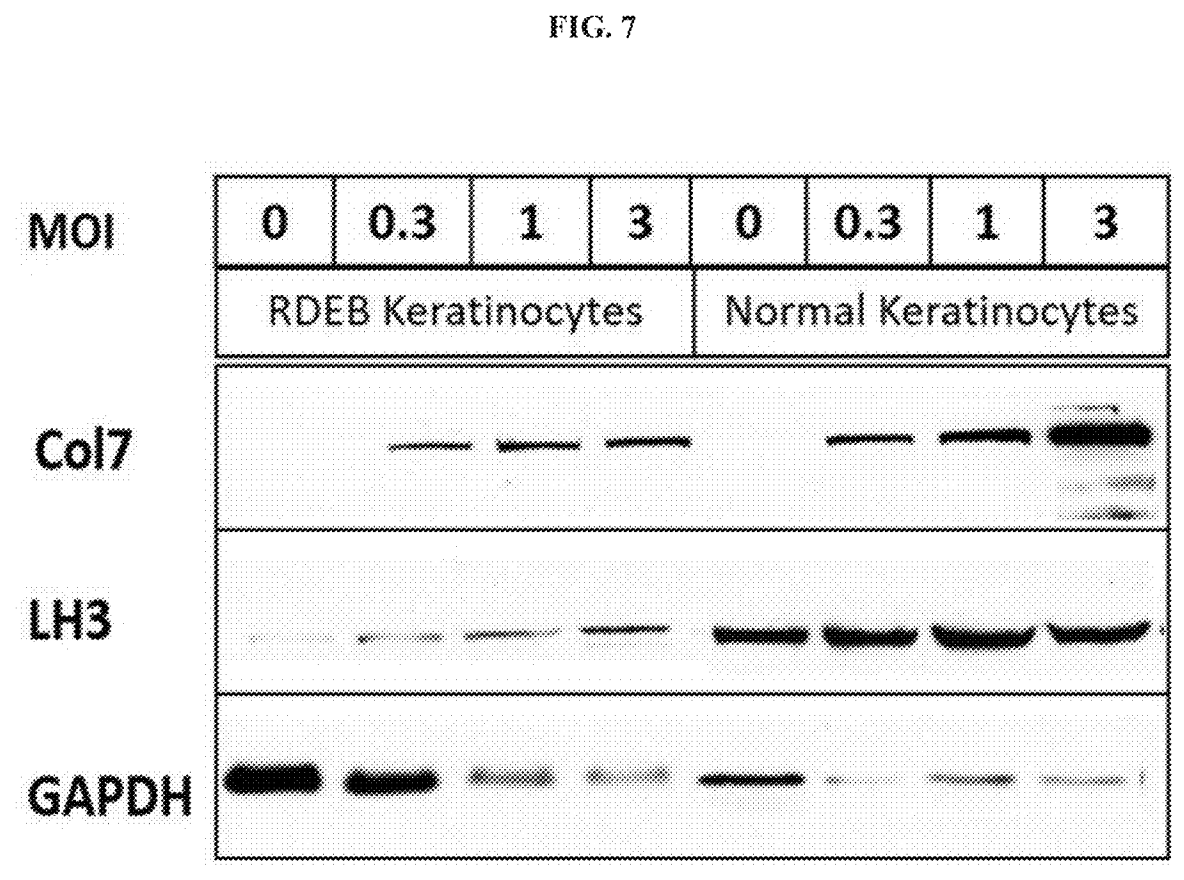

The functionality of the human Col7 protein expressed from KB103 was next investigated in human dermal fibroblasts and keratinocytes. First, the effect of Col7 expression on the levels of lysyl hydroxylase 3 was tested in KB103-infected cells. LH3 is required for the deposition and organization of extracellular matrix, and it has been reported that LH3 levels are reduced in RDEB skin (Watt, S. A. et al. (2015) *PLoS One* 10(9): p. e0137639). Little to no LH3 was observed in uninfected RDEB keratinocytes relative to normal keratinocytes (FIG. 7, lanes 1 vs. 5), in agreement with previous studies. However, unexpectedly, a dose-dependent increase in LH3 levels, concomitant with increased Col7 protein expression, was observed in RDEB keratinocytes infected with KB103 (FIG. 7), suggesting that KB103 was capable of rescuing not only Col7 protein expression, but also LH3 expression in RDEB cells.

Figure 8:
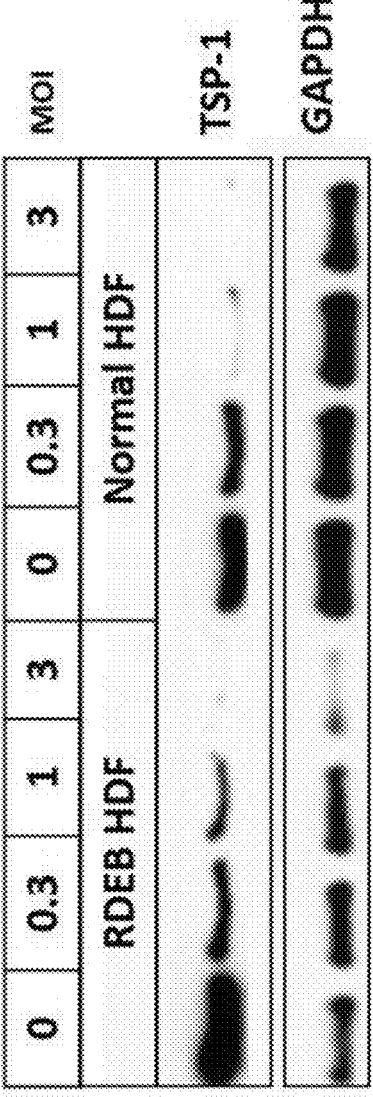
FIG. 8 shows human TSP-1 protein expression in uninfected normal and RDEB human dermal fibroblasts, as well as fibroblasts infected with KB103 at the indicated MOI. Human GAPDH protein expression is shown as a loading control.

Next, the effect of Col7 expression on TSP-1 levels was tested. TSP-1 is a negative regulator of angiogenesis, and has been reported to be increased in RDEB fibroblasts (Ng, Y. Z. et al. (2012) *Cancer Res.* 72(14): p. 3522-34). In agreement with previous studies, higher levels of TSP-1 were observed in uninfected RDEB vs. normal human dermal fibroblasts (FIG. 8, lanes 1 and 4). Surprisingly, TSP-1 protein expression was robustly inhibited upon infection of either normal or RDEB fibroblasts infected with KB103 (FIG. 8). This data suggested that KB103 may not only increase Col7 and LH3 levels in infected cells, but may also promote angiogenesis by inhibiting the negative regulator TSP-1.

Figures 9A, 9B:
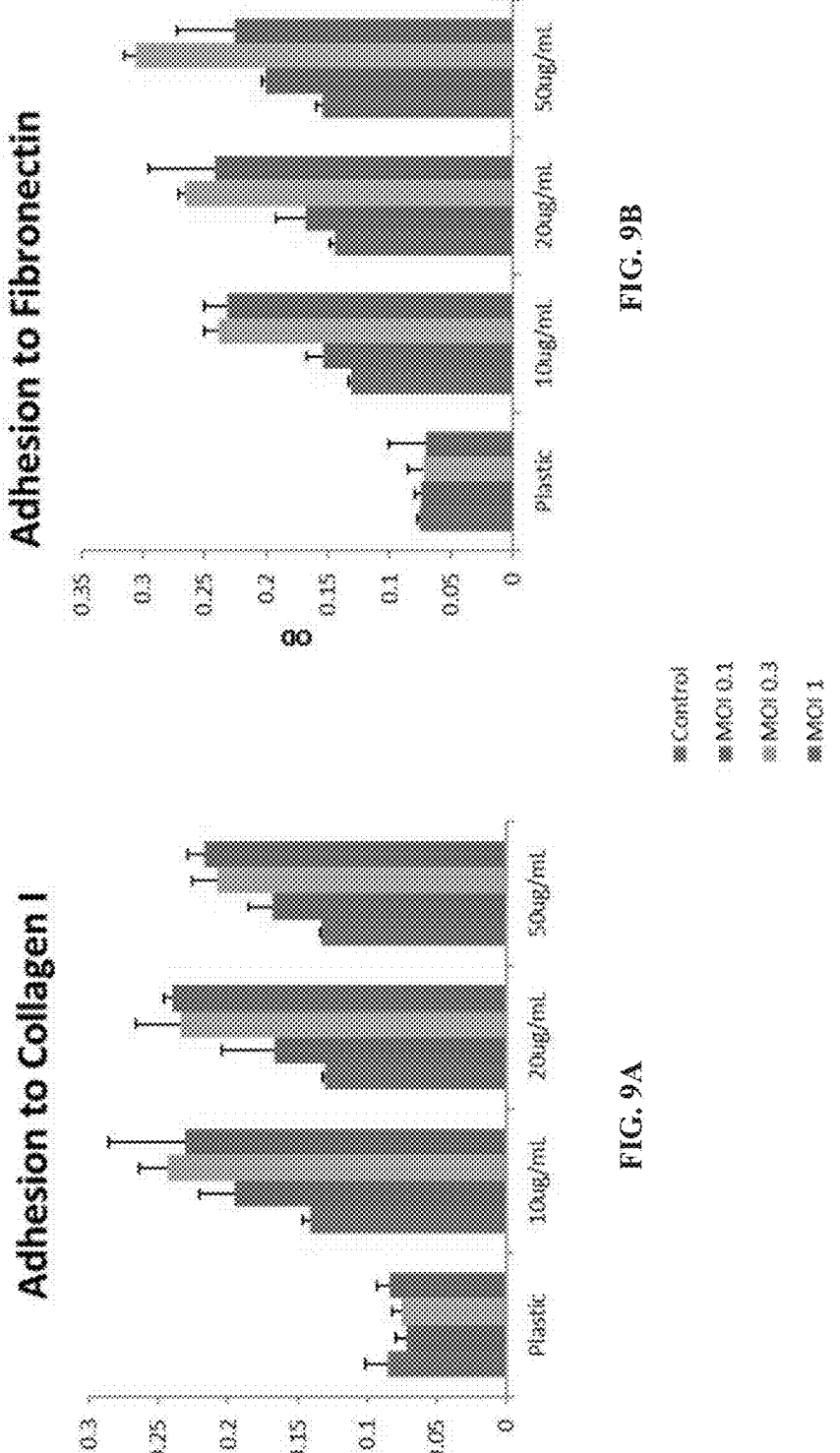
FIGS. 9A-9B show cellular adhesion of uninfected (control) RDEB human dermal keratinocytes, and keratinocytes infected with KB103 at the indicated MOIs, to wells treated with increasing concentration of rat tail Collagen 1 (FIG. 9A) and human Fibronectin (FIG. 9B)

Finally, the ability of KB103 to increase cellular adherence of RDEB keratinocytes to either Collagen 1 or Fibronectin was tested. A dose-dependent increase in cellular adherence to both Collagen 1 and Fibronectin was observed in RDEB keratinocytes infected with KB103 at various MOIs (FIGS. 9A and 9B). Infection of RDEB keratinocytes at all MOIs tested showed higher adhesion to wells treated with all concentrations of both substrates relative to uninfected (control) cells. Taken together, this data indicated that the human Col7 protein expressed from KB103 was functional in the transduced cells. Functionality of this protein was indicated by its ability to increase LH3 protein levels, decrease TSP-1 protein levels, and improve cellular adherence to both Collagen 1 and Fibronectin relative to mock-infected samples.

KB103 Pharmacology and Toxicity in RDEB Organotypic Cultures

Figure 10:
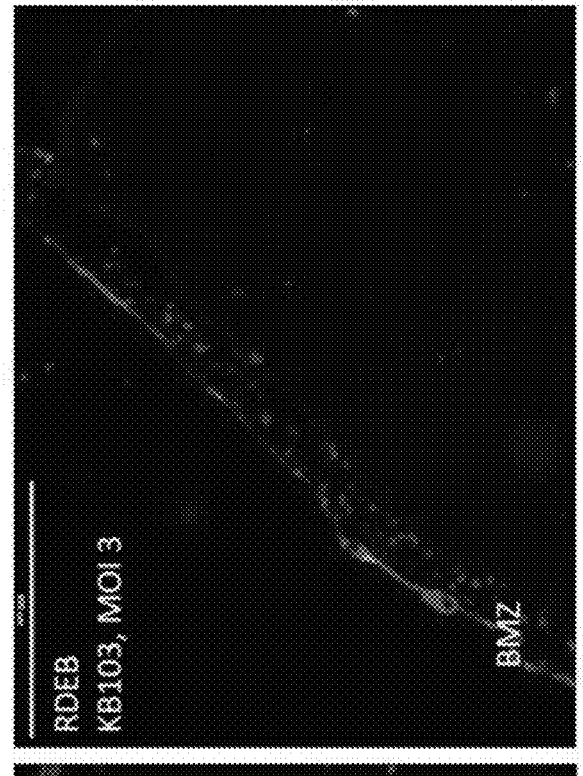
FIG. 10 shows Col7 deposition at the basement membrane zone (BMZ) in KB103 infected skin-equivalent organotypic cultures by immunofluorescence.
Figure 10:
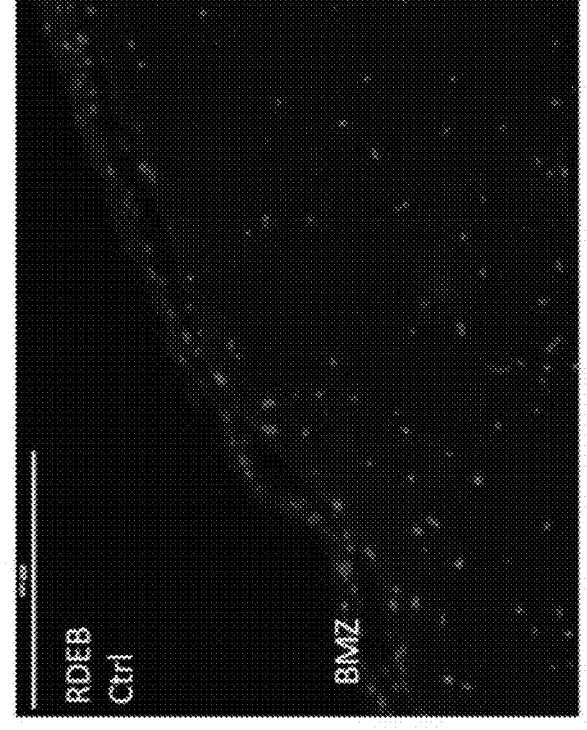

A skin equivalent (SE) organotypic culture composed of RDEB fibroblasts and keratinocytes was used to evaluate the expression of Col7 protein expressed from KB103 at the Basement Membrane Zone (BMZ). RDEB fibroblasts and keratinocytes were mock infected or infected with KB103 at an MOI of 3, and incubated for 5 days to favor stratification and differentiation into epithelium. The resulting skin equivalents (SEs) were isolated, sectioned, and stained for immunofluorescence to detect Col7 protein expression. Col7 expression was detected in these organotypic cultures from cells infected with KB103, and the initiation of Col7 protein deposition at the BMZ was observed relative to mock-infected controls (FIG. 10). This data suggested that not only could KB103 deliver COL7A1 and express Col7 protein efficiently, but the Col7 protein began to organize in organotypic cultures similar to the pattern of organization expected for Col7 protein in vivo.

Taken as whole, these experiments revealed, for the first time, that a replication-defective HSV-1 vector may be employed as a vehicle for delivering a COL7A1 expression cassette into primary cells isolated from epidermolysis bullosa patients. Moreover, these data revealed that Col7 protein could be expressed at high levels from this expression cassette in two different human cell types from healthy individuals, as well as individuals suffering from a dermatological disorder. Finally, the Col7 protein was shown to be functional, as it was capable of increasing expression of LH3, decreasing expression of TSP-1, increasing cellular adherence to Collagen 1 and Fibronectin, and could organize in organotypic cultures in a pattern similar to the organization of Col7 in vivo. Without wishing to be bound by theory, the data presented herein suggests that KB103 and other HSV-1 vectors may be useful as novel in vivo treatment strategies for epidermolysis bullosa and/or other dermatological applications.

Example 3: In Vivo Col7 Expression Using Replication Defective HSV-1

The following example describes the use of a replication defective herpes simplex type-1 virus (modified to contain a human COL7A1 transgene) as a delivery vehicle for expression of human Col7 protein in vivo.

Methods

Construction and Purification of KB103

The KB103 virus was constructed and purified as described in Example 2 above.

Viral Infections

KB103 virus was delivered to wild-type Balb/c or skh1-elite mice by intradermal injection as follows: each animal was injected once at 2-4 sites within the flank region of the animal with $1 \times 10^8$ plaque forming units (PFU) of virus/site in a volume of 50 μL. Animals were sacrificed 48 hours post KB103 administration, and the inject sites were harvested and processed for either real time qPCR or immunofluorescence analysis.

For qPCR analysis, skin tissue was dissected down to the fascia using a 6 mm punch biopsy tool. The biopsy was bisected into two pieces, and each piece was snap frozen using liquid nitrogen. Total RNA and DNA were isolated from one half of the biopsy using the Qiagen AllPrep DNA/RNA kit.

For immunofluorescence analysis, a circular area approximately one cm in diameter was excised from skin at the injection site, cut in half, and mounted in OCT so that the central portion of the circular area was facing upward. The prepared samples were freeze plunged into liquid nitrogen cooled isopentane, and stored at −80° C.

mRNA Quantification

Col7 transcripts were amplified from RNA isolated from mouse dermal tissue after KB103 injection using a 2-step protocol: 1) cDNA synthesis was carried out using the superscript III First Strand Synthesis kit (Thermofisher, Cat. #18-080-051), and 2) qPCR amplification was performed using the Quantitect Probe PCR kit (Qiagen, Cat. #204345) according to the manufacturer's protocol. 100 ng of cDNA was used in each reaction. Col7 transcript levels were normalized to GAPDH transcript levels.

Genome Copy Quantification

The copy number of KB103 viral genomes in the KB103 injected mice was quantified by qPCR amplification using the Quantitect Probe PCR kit (Qiagen Cat. #204345). 100 ng of mouse genomic DNA was used in each reaction, and mouse genomic GAPDH was used as a control.

Immunofluorescence

Tissue sections from mice injected with KB103 were fixed, and subsequently stained with a primary rabbit anti-human Col7 polyclonal antibody (Sigma, Cat. #HPA042420), washed, and further stained with a fluorescently labelled anti-rabbit secondary antibody (Invitrogen, Cat. 3 A11012). Cell nuclei were stained with DAPI using standard techniques.

Results

Figure 11:
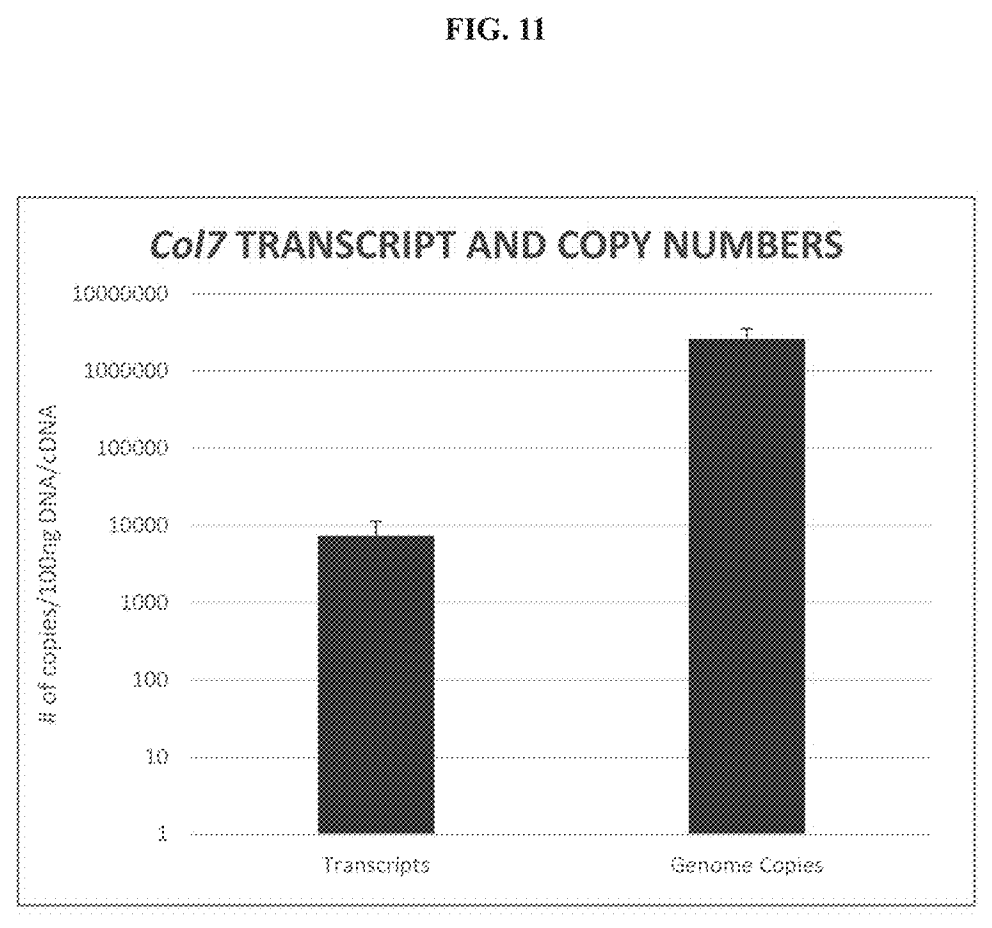
Figure 12:
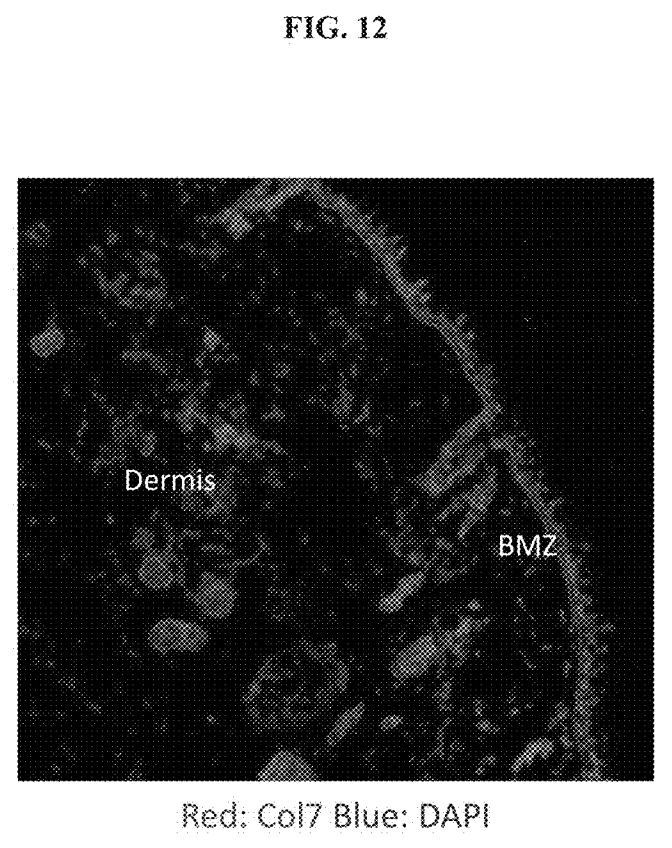

To test the ability of KB103 to successfully deliver and express human Col7 protein in vivo, mice were intradermally administered the KB103 virus. Viral genome copy number in infected mouse tissue was assessed, and delivery of high levels (>1,000,000 viral genome copies/100 ng mouse DNA) of the KB103 viral genome was observed in the mice (FIG. 11). Next, the ability of the ability of the virus to express human Col7 in vivo was examined. Quantification of human Col7 transcripts in KB103-infected mice were measured and assessed compared to expression of a control mouse housekeeping gene. High levels of human Col7 transcript were observed in the infected mouse tissue (FIG. 11), suggesting that the delivered viral genomes were capable of successfully expressing their human gene cargo. Finally, the ability of KB103 to express Col7 protein was tested in the infected mice. Mouse dermal tissue was excised from mice after infection, and Col7 protein expression was assessed by immunohistochemical staining of the mouse tissue. High levels of human Col7 protein were detected after tissue staining (FIG. 12). Surprisingly, not only was human Col7 protein expressed from the KB103 virus in mouse dermis, but the initiation of deposition of human Col7 at the Basement Membrane Zone in KB103-infected mice was observed (FIG. 12). Without wishing to be bound by theory, this data suggests that: 1) the KB103 virus can successfully infect relevant tissue in vivo, delivering high genome copy numbers to these tissues tissue, 2) delivery of the KB103 virus to relevant tissue results in significant expression of the encoded human genes on this virus, and 3) KB103 not only successfully expresses human Col7 protein in vivo, but this protein is capable of beginning to organize (e.g. at the Basement Membrane Zone) in a way suggesting its ability to rescue endogenous Col7 defects in affected individuals.

40

The invention claimed is:

1. A kit, comprising:
   a) a pharmaceutical composition comprising,
      (i) a replication-defective herpes simplex virus (HSV) comprising a recombinant herpes simplex virus genome, wherein the recombinant herpes simplex virus genome comprises one or more polynucleotides encoding a transgene, and
      (ii) a pharmaceutically acceptable carrier; and
   b) a package insert comprising instructions for administering the pharmaceutical composition,
   wherein the recombinant herpes simplex virus genome comprises an inactivating mutation in one or both copies of the ICP4 herpes simplex virus gene,
   wherein the pharmaceutical composition is topically or transdermally administered to a subject,
   wherein the pharmaceutical composition is administered to one or more areas of the subject affected by a wound, disorder, or disease of the skin,
   wherein the pharmaceutically acceptable carrier comprises glycerol, and
   wherein the one or more polynucleotides encoding the transgene does not comprise a miRNA binding site.

2. The kit of claim 1, wherein the pharmaceutical composition comprises an ointment, paste, cream, suspension, emulsion, fatty ointment, gel, powder, lotion, solution, spray, patch, or microneedle array.

3. The kit of claim 1, wherein the inactivating mutation in one or both copies of the ICP4 herpes simplex virus gene is a deletion of at least a portion of the coding sequence of the ICP4 herpes simplex virus gene.

4. The kit of claim 1, wherein the recombinant herpes simplex virus genome further comprises an inactivating mutation in one or both copies of an ICP0 herpes simplex virus gene, an ICP22 herpes simplex virus gene, an ICP27 herpes simplex virus gene, an ICP47 herpes simplex virus gene, a tk herpes simplex virus gene, an UL41 herpes simplex virus gene, or an UL55 herpes simplex virus gene.

5. The kit of claim 1, wherein the replication-defective HSV has reduced cytotoxicity when compared to its wild-type counterpart.

6. The kit of claim 1, wherein the pharmaceutical composition is suitable for delivery to a subject.

7. The kit of claim 6, wherein the replication-defective HSV is suitable for delivering to and expressing the one or more polynucleotides encoding the transgene in one or more target cells of the subject.

8. The kit of claim 1, wherein the one or more polynucleotides encoding the transgene is in one or both of the ICP4 viral gene loci.

9. The kit of claim 1, wherein the recombinant herpes simplex virus genome is a recombinant HSV-1 genome.

US 12,582,684 B2

139

140

10. A kit, comprising:
a) a pharmaceutical composition comprising,
  (i) a replication-defective herpes simplex virus (HSV) comprising a recombinant herpes simplex virus genome, wherein the recombinant herpes simplex virus genome comprises one or more polynucleotides encoding a transgene, and
  (ii) a pharmaceutically acceptable carrier; and
b) a package insert comprising instructions for administering the pharmaceutical composition,
wherein the recombinant herpes simplex virus genome comprises an inactivating mutation in one or both copies of the ICP4 herpes simplex virus gene,
wherein the pharmaceutical composition comprises an ointment, paste, cream, suspension, emulsion, fatty ointment, gel, powder, lotion, solution, spray, patch, or microneedle array,
wherein the pharmaceutical composition is administered to one or more areas of a subject affected by a wound, disorder, or disease of the skin,
wherein the pharmaceutically acceptable carrier comprises glycerol, and
wherein the one or more polynucleotides encoding the transgene does not comprise a miRNA binding site.

11. The kit of claim 10, wherein the inactivating mutation in one or both copies of the ICP4 herpes simplex virus gene is a deletion of at least a portion of the coding sequence of the ICP4 herpes simplex virus gene.

12. The kit of claim 10, wherein the recombinant herpes simplex virus genome further comprises an inactivating mutation in an ICP0 herpes simplex virus gene, an ICP22 herpes simplex virus gene, an ICP27 herpes simplex virus gene, an ICP47 herpes simplex virus gene, a tk herpes simplex virus gene, an UL41 herpes simplex virus gene, or an UL55 herpes simplex virus gene.

13. The kit of claim 10, wherein the replication-defective HSV is suitable for delivering to and expressing the one or more polynucleotides encoding the transgene in one or more target cells of the subject.

14. The kit of claim 10, wherein the one or more polynucleotides encoding the transgene is in one or both of the ICP4 viral gene loci.

15. The kit of claim 10, wherein the recombinant herpes simplex virus genome is a recombinant HSV-1 genome.

16. The kit of claim 12, wherein the inactivating mutation in the ICP22 herpes simplex virus gene is a deletion of at least a portion of the coding sequence of the ICP22 herpes simplex virus gene.

17. The kit of claim 10, wherein the pharmaceutical composition is administered topically, transdermally, subcutaneously, or intradermally to the subject.

18. The kit of claim 10, wherein the pharmaceutical composition comprises hydroxypropyl methylcellulose.

* * * * *